US008383886B2

(12) United States Patent
Chen et al.

(10) Patent No.: US 8,383,886 B2
(45) Date of Patent: Feb. 26, 2013

(54) GENES ENCODING A NOVEL TYPE OF LYSOPHOPHATIDYLCHOLINE ACYLTRANSFERASES AND THEIR USE TO INCREASE TRIACYLGLYCEROL PRODUCTION AND/OR MODIFY FATTY ACID COMPOSITION

(75) Inventors: Qilin Chen, Saskatoon (CA); Jitao Zou, Saskatoon (CA); Zhifu Zheng, Zionsville, IN (US); Jingyu Xu, Saskatoon (CA)

(73) Assignees: National Research Council of Canada, Ottawa, Ontario (CA); Dow Agrosciences LLC, Indianapolis, IN (US)

( * ) Notice: Subject to any disclaimer, the term of this patent is extended or adjusted under 35 U.S.C. 154(b) by 569 days.

(21) Appl. No.: 12/448,061

(22) PCT Filed: Dec. 13, 2007

(86) PCT No.: PCT/US2007/025650
§ 371 (c)(1),
(2), (4) Date: Oct. 1, 2009

(87) PCT Pub. No.: WO2008/076377
PCT Pub. Date: Jun. 26, 2008

(65) Prior Publication Data
US 2010/0016431 A1 Jan. 21, 2010

Related U.S. Application Data

(60) Provisional application No. 60/874,497, filed on Dec. 13, 2006.

(51) Int. Cl.
*A01H 1/00* (2006.01)
*A01H 5/00* (2006.01)
*A01H 5/10* (2006.01)
*C12N 5/04* (2006.01)

(52) U.S. Cl. ......... 800/278; 800/281; 435/419; 435/468

(58) Field of Classification Search .................. None
See application file for complete search history.

(56) References Cited

U.S. PATENT DOCUMENTS

| 6,265,636 | B1 | 7/2001 | Randall et al. |
| 6,500,670 | B1 | 12/2002 | Zou et al. |
| 7,015,373 | B1 | 3/2006 | Zou et al. |
| 7,112,724 | B1 | 9/2006 | Zou et al. |
| 7,214,859 | B2 | 5/2007 | Marillia |
| 7,732,155 | B2 | 6/2010 | Zou et al. |
| 7,741,532 | B2 * | 6/2010 | Lardizabal et al. ........... 800/281 |
| 2005/0208558 | A1 | 9/2005 | Venter et al. |
| 2006/0046253 | A1 | 3/2006 | Nakao et al. |
| 2010/0281574 | A1 | 11/2010 | Zheng et al. |
| 2011/0061130 | A1 | 3/2011 | Zou et al. |
| 2011/0093983 | A1 | 4/2011 | Zou et al. |
| 2011/0167515 | A1 | 7/2011 | Zheng et al. |

FOREIGN PATENT DOCUMENTS

| WO | WO 92/18634 | 10/1992 |
| WO | WO0185946 A2 * | 11/2001 |
| WO | WO 2008/076377 A2 | 6/2008 |

OTHER PUBLICATIONS

BLAST Results with SEQ ID No. 4—LOCUS NP_172724 Definition MBOAT (membrane bound O-acyl transferase)-like protein [Arabidopsis], Jan. 10, 2002.*
Inze et al, WO200185946-A2, Nov. 15, 2011.*
Benghezal et al., SLC1 ad SLC4 Encode Partially Redundant Acyl-Coenzyme A 1-Acylglycerol-3-phosphate O-Acyltransferases of Budding Yeast, Journal of Biological Chemistry, Oct. 19, 2007, pp. 30845-30855, vol. 282, No. 42.
Chen et al., Identification and characterization of a lysophosphatidylcholine acyltransferase in alveolar type II cells, PNAS, Aug. 1, 2006, pp. 11724-11729, vol. 103, No. 31.
Chen et al., The yeast acylglycerol acyltransferase LCA1 is a key component of Lands cycle for phosphatidylcholine turnover, FEBS Letters, Nov. 8, 2007, pp. 5511-5516.
Chica et al., Curr. Opin. Biotechnol. Aug. 2005, pp. 378-384, vol. 16, No. 4.
Furukawa-Stoffer et al., Properties of Lysophosphatidylcholine Acyltransferase from *Brassica napus* Cultures, Lipids, 2003, pp. 651-656, vol. 38, No. 6.
Hishikawa et al., Discovery of a lysophospholipid acyltransferase family essential for membrane asymmetry and diversity, PNAS, Feb. 26, 2008, pp. 2830-2835, vol. 105, No. 8.
Jain et al., Identification of a Novel Lysophospholipid Acyltransferase in *Saccharomyces cerevisiae*, Journal of Biological Chemistry, Oct. 19, 2007, pp. 30562-30569, vol. 282, No. 42.
Kazachkov et al., Substrate Preferences of a Lysophosphatidylcholine Acyltransferase Highlight Its Role in Phospholipid Remodeling, Lipids, 2008, pp. 895-902, vol. 43.
Nakanishi et al., Cloning and Characterization of Mouse Lung-type Acyl-CoA:Lysophosphatidylcholine Acyltransferase I (LPCAT1), Journal of Biological Chemistry, Jul. 21, 2006, pp. 20140-20147, vol. 281, No. 29.
Neville et al., The activities of monocyte lysophosphatidylcholine acyltransferase and coenzyme A-independent transacylase are changed by the inflammatory cytokines tumor necrosis factor alpha and interferon gamma, Biochimica et Biophysica Acta, 2005, pp. 232-38, vol. 1733.
Riekhof et al., Identification and Characterization of the Major Lysophosphatidylethanolamine Acyltransferase in *Saccharomyces cerevisiae*, The Journal of Biological Chemistry, Sep. 28, 2007, pp. 28344-28352, vol. 282, No. 39.
Stahl et al., A family of eukaryotic lysophospholipid acyltransferases with broad specificity, FEB Letters, 2008, pp. 305-309, vol. 582.
Tamaki et al., LPT1 Encodes a Membrane-bound O-Acyltransferase Involved in the Acylation of Lysophospholipids in the Yeast *Saccharomyces cerevisiae*, The Journal of Biological Chemistry, Nov. 23, 2007, pp. 34288-34298, vol. 282, No. 47.

(Continued)

*Primary Examiner* — Eileen B O Hara
(74) *Attorney, Agent, or Firm* — TraskBritt

(57) ABSTRACT

Described nucleic acid molecules (and corresponding peptides) encode lyso-phosphatidylcholine (LPC) acyltransferases. Over-expression of the LPC acyltransferases in a cell may lead to enhanced production of PUFA, or other unusual fatty acids, and/or to increased oil content in the cell.

8 Claims, 19 Drawing Sheets

OTHER PUBLICATIONS

Zhao et al., Identification and Characterization of a Major liver Lysophosphatidylcholine Acyltransferase, The Journal of Biological Chemistry, Mar. 28, 2008, pp. 8258-8265, vol. 283, No. 13.

PCT International Preliminary Report on Patentability, PCT/US07/025650 dated Jul. 27, 2011.

PCT International Search Report, PCT/US2007/025650, dated Jan. 5, 2009.

U.S. Appl. No. 11/122,943, filed May 4, 2005, Zou et al., Methods of Producing and Growing Plants Having Improved Phosphorus Utilization.

U.S. Appl. No. 11/820,014, filed Jun. 15, 2007, Zou et al., Genes Encoding a Novel Type of Lysophophatidylcholine Acyltransferases and Their Use to Increase Triacylglycerol Production and/or Modify Fatty Acid Composition.

U.S. Appl. No. 61/168,532, filed Apr. 10, 2009, Zheng et al., Plant SNF1-Related Protein Kinase Gene.

PCT/US2007/025650, Dec. 13, 2007, Chen et al., Genes Encoding a Novel Type of Lysophophatidylcholine Acyltransferases and Their Use to Increase Triacylglycerol Production and/or Modify Fatty Acid Composition.

PCT/US2008/013811, Dec. 16, 2008, Zou et al., Diacylglycerol Acyltransferase 2 Genes and Proteins Encoded Thereby From Algae.

PCT/US2009/001912, Mar. 26, 2009, Zou et al., Identification of Glycerol-3-Phosphate Acyltransferase.

* cited by examiner

```
SEQ ID NO:50  (1)  ---------------------------------MLPYVDLKLIASFLLSYPLAALLKR
SEQ ID NO:51  (1)  ---------------------MAYLIDIPFEYFSSFLGVHPDQLKLFCFLSAYPFAGLLKR
SEQ ID NO:52  (1)  ---------------------MYNPVDAVLTKIITNYGIDSFTLRYAICLLGSYPLNALLKR
SEQ ID NO:53  (1)  MRLYLQFNLSINDYCHFFTVPSFVKEGVESLSASTGQDVETLEYLLGMLICYPLGMIMLA
SEQ ID NO:54  (1)  ------------------------MDMSSMAGSICVSVALRFLLCFVATIPVSFACRI
SEQ ID NO:55  (1)  -----------------------MELLDMNSMAASIGVSVALRFLLCFVATIPISFLWRF
SEQ ID NO:56  (1)  -----------------------MGLEMEGMAAAIGVSVPVLRFLLCFAATIPTGLMWRA
SEQ ID NO:57  (1)  -----------------------------------------------------------
SEQ ID NO:58  (1)  ----MLEPPKFIENDCYNGSRTFTWLADMVGLSVDLVNFLICQLSALFLASLFRSMLHPS
SEQ ID NO:59  (1)  ----------------------MKCCFHHIIPRVNFVVCQLFALLAAIWFRTYLHSS
SEQ ID NO:60  (1)  -----------MATTSTTGSTLLQPLSNAVQLPIDQVNFVVCQLFALLAAIWFRTYLHSS
SEQ ID NO:61  (1)  -----------MATTSTTGSTLLQPLSNAVQLPIDQVNFVVCQLFALLAAVWFRTYLHSS
SEQ ID NO:62  (1)  ----MAARPPASLSYRTTGSTCLHPLSQLLGIPLDQVNFVACQLFALSAAFWFRIYLHPG
SEQ ID NO:63  (1)  ---------------MAEFEEDLPHNGLMDGIASGVGVPVEALRLLLTILAGYPVAALYQK

(27)  IPDAQP--WKKNAFIIAVSLFYLVGLFDLWDGLRTLAYSAAGIYALAYYIDGSLMPWIGF
             (42)  LPSAP---WIRNLFSISIGLFYLIGVHHLYDGVLVLLFDALFTYFVAAFYRSSRMPWIIF
             (42)  LPEKRI--GLKCCFIISMSMFYLFGVLNLVSGFRTLFISTMFTYLISRFYRSKFMPHLNF
             (61)  LPYG----KVKFLPSFILGAFLLQFTIGIQW--IHHLISSMIAVMFLVLPAKFAKTAVP
             (36)  VPSR----LGKHLYAAASGAFLSYLSFGFSS--NLHFLVPMTIGYASMALYRPKCGILTF
             (39)  LPSR----LGKHLYSAASGAFLSYLSFGFSS--NLHFLVPMTIGYASMALYRPLSGFITF
             (38)  VPGA----AGRHLYAGLTGAALSYLSFGATS--NLLFVVPMAFGYIAMLLCRRLAGLVTF
              (1)  -----------------------------------------------------------
             (57)  KVSS----KLRHTEALSIGLAFGYFCFGQQA--IHLAGLPAICYIVIRTQDPRIVQRAVL
             (36)  KTSS----FIRHVVATLLGLYIALFCFGWYA--LHFLVQSGISYCLMIILGVENMHNYCF
             (50)  KTSS----FIRHVVATLLGLYIALFCFGWYA--LHFLVQSGISYCLMIILGVENMHNYCF
             (50)  KTSS----FIRHVVATLLGLYIAEFCFGWYA--LHFLVQSGISYCLMIIAGVESMQQCCF
             (57)  KASP----EVRHTLATILGIYFVVFCFGWYA--MHIFLVLMCYGVMMSASVSNLHRYSF
             (47)  FISVIADKTVHIMEFAGCGAGLCYFNYGLDTYHSLIALLTTYFLVILRKKTQIFLALNE

Motif 1
                                          _____
             (85)  LELMGHMSLSHIYR--QIIDDAHVTDIIGAQMVLVMKLSSFCWNVIDGRLS----QEQLS
             (99)  IVILGHTFSSMIR---YILPSENTDITASSQMVLCMKLTAFAWSYMDGRLP----SSELS
            (100)  MFVMGHEALNLTHAQFLNEQTQTTVDITSSQMVLAMKLTSFAWSYMDGSCTSESDFKDLT
            (115)  VFAMIYITAGHLHR-QYINYLGWDMDFTGBQMVLTMKLYMLAYNLADGDLLKKGKFDRAA
             (90)  FLGFAYLIGCHVFYMSGDAWKEGGIDSTGALMVLTLKVISCSMYNDGMLK----EEGLR
             (93)  FLGFAYLIGCHVFYMSGDAWKEGGIDSTGALMVLTLKVISCOINYNDGMLK----EEGLR
             (92)  LGAFGELIACHMYYMSGDAWKEGGIDATGALMVLTLKIISCAINYSDGMLK----EEGLR
              (1)  ---------MYYMSGDAWKEGGIDATGALMVLTLKIISCAINYSDGMLK----EEGLR
            (111)  LVAMSYLLCVHIMR-QLYDYGSYALDITGPLMITQKVTSLAFSTHDGFVRG---DEELT
             (90)  VFALGYLTVCQVTRVYIFDYGQYSADFSGPMMITQKITSLACEIHDGMFRK---DEELT
            (104)  VFALGYLTVCQVTRVYIFDGQYSADFSGPMMITQKITSLACEIDCMFRK---DEELT
            (104)  VFALGYISVCQITRVYIFDGQYSADFSGPMMITQKITSLAYEIDGMFRK---DEELT
            (111)  FVAMGYLTICHSRIYIFHYGILTTDFSGPLMIVQKITLAFQVHDGLGRK---AEDLS
            (107)  VEHMSYLLLGMFYT----SSNDYDILWIMPHCLLVLRMIGYGEDITDGLKE----ESELS (139)  DPQKYAAIKDFPGILDYLGVVLFFPSLFAGPSREYVDYRRWIDTTLFDVPPGTDPSKVPP
            (152)  SYQKDRALRKIPNILYLGYVFFPPSLLVGPAFDYVGEREFTLS---------MFKPLA
            (160)  EHQKSRAVRGHPPLIKPLAYAFFYSTLFTGPSEDYADFDSWLNCEMFRDLPESKKPMRRH
            (174)  KKCADVAISSVLGTTEYLGTFCLASVLAGPAFEYKFMADACDGSLLYDK----SGKPKG
            (146)  EAQKKNRLIQMPSLTEYFGYCLCCGSHFAGPVWEMKDYLEWTE-G---------KGIWDT
            (149)  EAQKKNRLIQMPSLTEYFGYCLCCGSHFAGPVWEMKDYLEWTE-E---------KGIWAV
            (148)  DAQKKYRLAKLPSLIEYFGYCLCCGSHFAGPVWEMKDYEYTE-R---------KGLWAS
```

FIG. 2A

```
 (46) DAQKKYRLAKLPSLIEYFGYCLCCGSHFAGPVYEMKDYLEYTE-R---------KGLWAS
(167) KAQQYHAIRKMPSALEYFSYVWHEQSILAGPLVFYKDYIEFVEGYNLLSTPPG-NGNLDS
(147) SSQRDLAVRRMPSLLEYLSYNCNEMGILAGPLCSYKDYITFIEGRSYHITQSGENGKEET
(161) SSQRDLAVRRMPSLLEYLSYNCNEMGILAGPLCSYKDYITFIEGRSYHITQSGENGKEET
(161) PSQRGLAVRRMPSLLEYVSYTCNEMGILAGPLCSYKDYIAFIEGRASHVAQPSENGK-DE
(168) AEQHRLAVKAKPSLLEYLSYHLNEMSVIAGPCNNEKDYIAFIEGRHIHMKLLEVNWTQRG
(159) KDQKETALKKPPSLLELLAFSYFPSGFIVGPQEPERRYKAFVDGEFR-------------

(199) TRK-KRKIERSGTPAAKKALAGLGWILAFLQLGSLMNQELVLDETEMQYS----------
(203) DPYEKQITEHSLEPALGRCWRGLLWLILFITGSSIMELKFLLTEKEASSP----------
(220) HPGERRQIPKNGKLALWKVVQGLAWMILSTLGMKHEPVKYVLDKDGFPTRS---------
(230) K------IPSQVWPTLRPLFGSLICLGLFVVGTGMYELLDPNDEQNATPIPLTPEMLAKP
(196) TEK--RKKPSFYGATIRAILQAAICMALYLYLVPQYPLTRFTEPVYQEWG----------
(199) SEK--GKRPSFYGAMIRAVFQAAICMALYLYLVPQFPLTRFTEPVYQEWG----------
(198) P------TPSPLLPTLRALVQAGACMGLYLYLSPQFPLSRFSEPLYYEWG----------
 (96) P------TPSPLLPTLRALVQAGACMGLYLYLSPQFPLSRFSEPLYYEWG----------
(226) SKREVVLEPSPTKAVIRKVVGSLVCAFIFMKFVKIMPVKDMKEDDFMNNTS---------
(207) QYE--RTEPSPNTAVVQKLLVCGLSLLFHLTICTTLEVEYNIDEHEQATAS---------
(221) QYE--RTEPSPNTAVVQKLLVCGLSLLFHLTICTTLEVEYNIDEHEQATAS---------
(220) QHG--KADPSPNAAVTEKLLVCGLSLLFHLTISNMLEVEYNIDEHEQATAS---------
(228) FQS--LPEPSPTGAVIQKLCVTLMSLLLFLTLSKSEPVTELLDDWEVHKAN---------
(206) ------QHEGNVEAGVRRFGAGAFYLIVCQVGLRYLBDSMFLTEEHAQVS----------
```

Motif 2
```
(248) FVQRVWILHMLGFTARLKYYGVWYLTEGACVLSGMGYNGEDPKSG-KVFWNRLENVDPWS
(253) ILLKYGYVCITAFVARMKYYGAWELSDGACILSGLGYNGLDSSK--HPRWDRVKNIDPIK
(271) EIFRIHYLFLLGFIHREKYYAAWTISEGSCIILCGLGYNGYDSKT-QKIRWDRVRNIDIWT
(284) AYARYAYSWLALFFIREKYYFAWMNAEGASNIWYAGFEGEDASGN-PKGWIVSNNIDVIQ
(244) FLRKFSYQYMAGFTARWKYYEIWSISEASIILSGLGFSGWTDDASPKPKWDRAKNVDILG
(247) FLKRFGYQYMAGFTARWKYYEIWSISEASIILSGLGFSGWTDETQTKAKWDRAKNVDILG
(242) FWHRLFYQYMSGFTARWKYYEIWSISEAAIILSGLGFSGWSDSSPPKAKWDRAKNVDLLG
(140) FWHRLFYQYMSGFTARWKYYEIWSISEAAIILSGLGFSGWSDSSPPKAKWDRAKNVDLLG
(277) MDYKYWYAMMATTCIREKYYHAWLLADAICNNSGLGFTGYDKDG--NSKWDLLISNINVLS
(256) WPTKIIYLYISLLAARPKYYFAWILADAINNAAGFGERGYDENG--AARWDLISNLRLQQ
(270) WPTKIIYLYISLLAARPKYYFAWILADAINNAAGFGERGYDENG--AARWDLISNLRLQQ
(269) WPTKATYLYVSLLAARPKYYFAWILADAINNAAGFGERGYDKNG--VARWDLISNLRLQQ
(277) FLSRLWYLYVVMQAAKPKYYFAWILADAVHNAAGFGFNGMDTDG--KSRWDLLSNLNIWK
(250) FVKRIYLLGFWAKFSLMKYISCWLLTEGALLCIGLTYKGEDKNG--QPDWSGCSNVKLKL
```

Motif 3                            Motif 4
```
(307) LETAQNSHGYLGSWNKNTNHWLRNYVYLRVTPKGKKPGERASLATFVTSAFWHGFYEGYY
(311) FEFADNIKCALEEAWNMNTNKWLRNYVYLRVAKKGKRPGFKSILSTFTVSAMWHGVSAGYY
(330) VETAQNTREMLEAWNMNTNKWLKYSVYLRVTKKGKKPGFRSILFTFLTSAFWHGTREGYY
(343) FETAPNLKTLSAAWNKKIANWLAKYVYIRTG--------GSLFATYGMSAFWHGFYEGYY
(304) VELAKSAVQIPLVVWNIQVSTWLRHYVYERIVQNGKKAGFFQLLATQTVSAVWHGLYEGYM
(307) VELAKSAVQIPLFWNIQVSTWLRHYVYERIVKPGKKAGFFQLLATQTVSAVWHGLYEGYI
(302) VELATSAVQLPLMWNIQVSTWLRYYVYERLVQKGKKPGFLQLLGTQTVSAVWHGLYEGYI
(200) VELATSAVQLPLMWNIQVSTWLRYYVYERLVQKGKKPGFLQLLGTQTVSAVWHGLYEGYI
(335) FEFSTNMRDAIINNWNCGINRWLRTLVYERVP------QQYGTILTEALSAWHGFYEGYY
(314) IEMSTSFKMFLDNWNIQTALWLKRVCYERTS-------FSPTIQTFILSAIWHGVYEGYY
(328) IEMSTSFKMFLDNWNIQTALWLKRVCYERTS-------FSPTIQTFILSAIWHGVYEGYY
```

FIG. 2B

```
(327) IEMSTSFKMFIDNWNTQTALWLKRVCYERAT-------ESPTIQTEFLSAIWHGVYPGYY
(335) IETATSFKMYLENWNTQTSTWLKCVCYERVS-------WYPTVLTELLSALWHGVYPGYY
(308) LETGNIMEHYVQSENVNTNQWVGQYIYKRLKFLNN--RTISYGAALGFLAVWHGYHSGYY
```

Motif 4

```
(371) LTFVLGSFIQTVAKNFRRHVRPFEITPDGSRPTAYKKYYDIASYVVQLTLSEAVME---
(390) LTFVSAAFIQTVAKYTRRHVRPFELKPDMETPGPFKRVYDVIGMVAINLSLSYLIIS---
(395) LTFAIGALYQTCGKIYRRNERPIELREDGVTPLPSKKIYDLVGIYAIKLAFGYMVQP---
(364) MFIVQSALMIAGSRVIYRWQQAISPK-----MAMLRNIMVFINFLYIVVVLNYSAVG---
(367) IFFVQSALMIDGSKAIYRWQQAIPPK-----MAMLRNVLVGINFLYIVVVLNYSSVG---
(362) IFFVQSALMINGSKVIYRWQQAVS-------NPVFHAILVFVNESYTLMVLNYSCIG---
(260) IFFVQSALMINGSKVIYRWQQAVS-------NPVFHAILVFVNESYTLMVLNYSCIGFQF
(389) LTFAIGAVVTAARTGRRLFRHREQS-----TQVTRMFYDTLTCLIITRVLGVATFE---
(367) LTFLTGVLMTLAARAMRNNERHYFIE-----PSQLKLFYDVITWIVTQVALSYTVVP---
(381) LTFLTGVLMTLAARAMRNNERHYEIE-----PSQLKLFYDVITWIVTQVALSYTVVP---
(380) LTFLTGVLMTLAARAVRNNERHYELE-----PPQLKLFYDLITWVAIQITLSYTVVP---
(388) FTFLTGVPVTLAARAVRNNYRHHFLS-----SKARKIAYDVATWAVTQLAVSYTAAE---
(366) MTFIMEYMVVSTEKQITRFYTKVVLPQWG--HILNNSDIYKLLYFITLKSYNVVYMGWCL
```

```
(424) ---------FIFLSFGDSIKVWHSVYFYGIVGNIVSLAFFVSPARGLLLKKLKARNKPH
(428) ---------FLLLNLKESIHVWKELYFIVHIYILTALAVFNSPIRSKLDNKIRSRVNSY
(447) ---------FIILDLKPSLMVWGSVYFYVHILIVAFSFFLFRGPYAKQVTEFFKSKQPKE
(446) ---------FQLLAFDWAWENWSSYYIAGHIVCVWFYLVVSNMPT---------PKTKE
(416) ---------FMVLSLHETLTAYGSVYYIGTTIPVGLILLSYWVP-----AKPSRPKPRK
(419) ---------FMVLSLHETLVAHKSVYYIGTVIPIAVLLISYLVP-----VKPVRPKTRK
(412) ---------EQVLSFKETLASYQSVYYIGTIVPIVVVLLGYVIKP----ARPVKPKARK
(313) VFTMLYTLRFLQVLSFKETLASYQSVYYIGTIVPIVVVLLGYVIKP----ARPVKPKARK
(441) ---------FVLLEFMGSIKLYLRFYLCHIISLVTIFILPKFIRGERRLRTSNGNGNV
(419) ---------FVLLSIKPSLTFYSSWYYCLHILGILVLLLLPVKKT----QRRKNTHENI
(433) ---------FVLLSIKPSLTFYSSWYYCLHILGILVLLLLPVKKT----QRRKNTHENI
(432) ---------FVLLSIKPSFTFYSSWYYCLHVCSILVLLLPVKKS----QRRTSTQENV
(440) ---------FVMLAVEPIISLYKSVFIFLHLICLLITLFLPIKPH----QPQR--QSRS
(424) TA-------FMFLKYERWIVVLGAVSYYGFTFLVLWAAFYHTFNHFFRSSSRKLAGEDQ
```

```
(474) VPRAVSSENIRQPTLGLPNDAIQEFDDAVQEIRAEIESRQRRGSLAHMPIGDELKAAVED
(478) KLKSYEQSMKSTSDTDMLNMSVPKREDFENDE---------------------------
(497) IFIRQKKLEKDISASSPNLGGILKAKIEHEKGKTAEEEEMNLGIPPIELEKWDNAKEDW
(487) T----------------------------------------------------------
(461) EE---------------------------------------------------------
(464) EE---------------------------------------------------------
(458) AE---------------------------------------------------------
(369) AE---------------------------------------------------------
(491) RLSGSGNTKDAVTTSVESTAALTAGNDLNEDKEEDKHAQCKVHTPTQQQPAAGPHKTTVE
(465) QLSQSKKFDEGENSLGQNSFSTTNNVCNQNQEIASRHSSLKQ------------------
(479) QLSQSRKFDEGENSLGQNSFSTTNNVCNQNQEIASRHSSLKQ------------------
(478) HLSQAKKFDERDNPLGQNSFSTMNNVCNQNRDTGSRHSSLTQ------------------
(484) PNSVKKKAD--------------------------------------------------
(476) KLQDSNTDKLVEEKKPEDKKSE-------------------------------------
```

FIG. 2C

```
(534) KIGRGH----------------------------------------------------
(510) ----------------------------------------------------------
(557) EDFCKDYKEWRNKNGLEIEEENLSKAFERFKQEFSNAASGSGERVRKMSFSGYSPKPISK
(488) ----------------------------------------------------------
(463) ----------------------------------------------------------
(466) ----------------------------------------------------------
(460) ----------------------------------------------------------
(371) ----------------------------------------------------------
(551) QPTEQPNNVNLRSRPQQQQPHLEKKAMPPTCARDAVSVPHDQCEMDQLSSKLKEKIEAET
(507) ----------------------------------------------------------
(521) ----------------------------------------------------------
(520) ----------------------------------------------------------
(493) ----------------------------------------------------------
(498) ----------------------------------------------------------

(540) ----------------------------------------------------------
(510) ----------------------------------------------------------
(617) KEE-------------------------------------------------------
(488) ----------------------------------------------------------
(463) ----------------------------------------------------------
(466) ----------------------------------------------------------
(460) ----------------------------------------------------------
(371) ----------------------------------------------------------
(611) KNIEEFIDKTVTETVSGIVEFKNDLMRDIEFPKLKLPGSNGAISLDSSNGGGLRKRNISS
(507) ----------------------------------------------------------
(521) ----------------------------------------------------------
(520) ----------------------------------------------------------
(493) ----------------------------------------------------------
(498) ----------------------------------------------------------

(540) ----------------------------------------------------------
(510) ----------------------------------------------------------
(620) ----------------------------------------------------------
(488) ----------------------------------------------------------
(463) ----------------------------------------------------------
(466) ----------------------------------------------------------
(460) ----------------------------------------------------------
(371) ----------------------------------------------------------
(671) VHDNGTDPGHATADLHPPLEENGAAFLKKEIEVINAVVQQAVPAVLSNGHAK
(507) ----------------------------------------------------------
(521) ----------------------------------------------------------
(520) ----------------------------------------------------------
(493) ----------------------------------------------------------
(498) ----------------------------------------------------------
```

FIG. 2D

```
SEQ ID NO:64   (1) ------------------------------------------------
SEQ ID NO:65   (1) ------------------------------------------------
SEQ ID NO:66   (1) ------------------------------------------------
SEQ ID NO:67   (1) ------------------------------------------------
SEQ ID NO:68   (1) ------------------------------------------------
SEQ ID NO:69   (1) ------------------------------------------------
SEQ ID NO:70   (1) -MGLEMEGMAAAIGVSVPVLRFLLCFAATIPTGLMWRAVPGAAGRHLYAG
SEQ ID NO:71   (1) ------------------------------------------------
SEQ ID NO:72   (1) ------------------------------------------------
SEQ ID NO:73   (1) ------------------------------------------------
SEQ ID NO:74   (1) ---MDMSSMAGSIGVSVAVLRFLLCFVATIPVSFACRIVPSRLGKHLYAA
SEQ ID NO:75   (1) MELLDMNSMAASIGVSVAVLRFLLCFVATIPISFLWRFIPSRLGKHIYSA
SEQ ID NO:76   (1) ------------------------------------------------
SEQ ID NO:77   (1) ------------------------------------------------
SEQ ID NO:78   (1) ------------------------------------------------
SEQ ID NO:79   (1) ------------------------------------------------
SEQ ID NO:80   (1) ------------------------------------------------

(1) ------------------------------------------------
               (1) ------------------------------------------------
               (1) ------------------------------------------------
               (1) ------------------------------------------------
               (1) ------------------------------------------------
               (1) ------------------------------------------------
              (50) LTGAALSYLSFGATSNLLFVVPMAFGYLAMLLCRRLAGLVTFLGAFGFLI
               (1) ------------------------------------------------
               (1) ------------SSNLHFLVPMLLGYAAMLLCRRCGVITFFLGFGYLI
               (1) ------------------------------------------------
              (48) ASGAFLSYLSFGFSSNLHFLVPMTIGYASMAIYRPKCGIITFFLGFAYLI
              (51) ASGAFLSYLSFGFSSNLHFLVPMTIGYASMAIYRPLSGFITFFLGFAYLI
               (1) ------------------------------------------------
               (1) ------------------------------------------------
               (1) ------------------------------------------------
               (1) ------------------------------------------------
               (1) ------------------------------------------------

(1) ------------------------------------------------
               (1) ------------------------------------------------
               (1) ------------------------------------------------
               (1) ------------------------------------------------
               (1) ------------------------------------------------
               (1) ----------------------------ISCLINYSDGILKEEGLRDA
               (1) ------------------------------------------------
             (100) ACHMYYMSGDAWKEGGIDATGALMVLTLKIISCAINYSDGMLKEEGLRDA
               (1) ---MYYMSGDAWKEGGIDATGALMVLTLKIISCAINYSDGMLKEEGLRDA
              (38) GCHVYYMSGDAWKEGGIDATGALMVLTLKVISCAMNYNDGLLKEDGLREA
               (1) ------------------------------------------------
              (98) GCHVFYMSGDAWKEGGIDSTGALMVLTLKVISCSMNYNDGMLKEEGLREA
             (101) GCHVFYMSGDAWKEGGIDSTGALMVLTLKVISCSINYNDGMLKEEGLREA
               (1) ------------------------------------------------
               (1) ------------------------------------------------
               (1) ------------------------------INYNDGLLKKEDLREP
               (1) ------------------------------------------------
               (1) ------------------------------------------------

```
  (1)  --------------------HFAGPVYEMKDYLEWTERKGIWAGST
 (21)  QIKHRLTKLPSLIEYFGYCLCCGSHFAGPVYEMKDYLEWTERKGIWASPT
  (1)  --------------------------------------------------
(150)  QKKYRLAKLPSLIEYFGYCLCCGSHFAGPVYEMKDYLEYTERKGIWASPT
 (48)  QKKYRLAKLPSLIEYFGYCLCCGSHFAGPVYEMKDYLEYTERKGIWASPT
 (88)  QKKNRLLKLPSLIEYFGYCLCCGSHFAGPVYEIKDYLEWTERKGIWAKSE
  (1)  --------------------------------------------------
(148)  QKKNRLIQMPSLIEYFGYCLCCGSHFAGPVYEMKDYLEWTEGKGIWDTTE
(151)  QKKNRLIQMPSLIEYFGYCLCCGSHFAGPVYEMKDYLEWTEPKGIWAVSE
  (1)  --------------------------------------------------
  (1)  --------------------------------------------------
 (17)  QKKNRLLKMPSLLEYIGYCLCCGSHFAGPVYEMKDYLEWTERKGIWQHTT
  (1)  --------------------------------------------------
  (1)  --ENRILKLPSLIEYVGYCLCCGSHFAGPVYEIKDYLDWTERKGIWTKSE
  (1)  --------------------------RRPKFPLSRFTEPLYQEWGFWKR
  (1)  --------------------------------------------------
  (1)  --------------------------------------------------
 (27)  PS----PLLPTLRALVQAGICMGLYLYLSPMPHS-YRGSLNRERGFWHR
 (71)  PS----PLLPTLRALVQAGICMGLYLYLSPKFPLSRFSEPLYYEWGFWHR
  (1)  ----------------------------TRLSRFSEPLYYEWGFWHR
(200)  PS----PLLPTLRALVQAGACMGLYLYLSPQFPLSRFSEPLYYEWGFWHR
 (98)  PS----PLLPTLRALVQAGACMGLYLYLSPQFPLSRFSEPLYYEWGFWHR
(138)  KGPPPSPYGATIRALIQAAFCMGLYVYLVPHDPLIIETDPVYQEWGFWKR
  (1)  --------------------------------------------------G
(198)  KRKKPSPYGATIRAILQAAICMALYLYLVPQYPLTRFTEPVYQEWGFLRK
(201)  KGKRPSPYGAMIRAVFQAAICMALYLYLVPQFPLTRFTEPVYQEWGFLKR
  (1)  ------------------------------------------HEKR
  (1)  -------------------GMGLYLYLVPQFPLSRFTESVYHEWGFFKR
 (67)  KGPKPSPYWATLRAILQAAICMGLYLYLVPHYPLSRFTEPEYQEWGFWKR
  (1)  ----------------------IHLYLVPHYPLSRFTDPVYQEWGFWKR
 (49)  KG-TPSPFLPTLRAILQAGFCMGLYLYLSPSYPLSRFSEPLYQEWGFVKR
                                Motif 5              Motif 6

(24)  LFYQYMSGFTARWKYYFIWSISEASIILSGLGFSGWIESSPPKPRWDRAK
  (1)  ------------KYYFIWSISEASIILSGLGFTGWIESSPPKPRWDRAK
  (1)  ----------------------EAAIILSGLGFTGWSDSSPPKAKWDRAI
 (72)  LFRQYMSGFTARWKYYFIWSVSEAAIILSGLGFTGWSDSSPPKAKWDRAI
(117)  LFYQYMSGFTARWKYYFIWSISEASIILSGLGFTGWSESSPPKAKWDRAK
 (20)  LFYQYMSGFTARWKYYFIWSISEASIILSGLGFTGWSESSPPKAKWDRAK
(246)  LFYQYMSGFTARWKYYFIWSLSEAAIILSGLGFSGWSDSSPPKAKWDRAK
(144)  LFYQYMSGFTARWKYYFIWSLSEAAIILSGLGFSGWSDSSPPKAKWDRAK
(188)  LGYQYMCGFTARWKYYFIWSISEAAVILSGLGFSGWIESSPPKPKWDRAK
  (2)  LGYQYMAGFTARWKYYFIWSISEASIILSGLGFSGWIDSSPPKPKWDRAK
(248)  FSYQYMAGFTARWKYYFIWSISEASIILSGLGFSGWIDDASPKPKWDRAK
(251)  FGYQYMAGFTARWKYYFIWSISEASIILSGLGFSGWIDETQTKAKWDRAK
  (5)  LGYQYMAGFTARWKYYFIWSISEAAIILSGLGFSGWIDSSPPKPRWDRAK
 (31)  LGYQYMAGFTARWKYYFIWSISEASIILSGLGFSGWINSSPPKPRWDRAK
(117)  LSYQYMSGFTARWKYYFIWSISEASIILSGLGFSGWIDSDPPKALWDRAK
 (28)  LTYQYMSGLTARWKYYFIWSISEASIILSGLGFSGWIDTSPPKPQWDRAR
 (98)  LTVQYMSGFTARWKYYFIWSISEASIILSGFGFSGWIDSSPPKARWDRAK
                                        Motif 7              Motif 8

(74)  NVDILGVEFAKSSVQLPLVWNIQVSTWLRHYVYDRLVKPGKKPGFFQLLA
 (38)  NVDILGVEFAKSSVQLPLVWNIQVSTWLRHYVYERLVKPGKKAGFFQLLT
 (29)  NVDILGVELAGSSAAQLPLKWNIQVSTWLRMYVYERLIQKGKKPGFLQLLG
(122)  NVDILGVELAGSSAAQLPLKWNIQVSTWLRMYVYERLIQKGKKPGFLQLLG
(167)  NVDVLGVELAGSSVQLPLVWNIQVSTWLRMYVYERLIQKGKKPGFLQLLG
 (70)  NVDVLGVELAGSAVQLPLVWNIQVSTWLRMYVYERLIQKGKKPGFLQLLG
```

FIG. 3B

```
(296) NVDVLGVELATSAVQLPLMWNIQVSTWLRMYVYERLVQKGKKPGFLQLLG
(194) NVDVLGVELATSAVQLPLMWNIQVSTWLRMYVYERLVQKGKKPGFLQLLG
(238) NVDILGVELAKSAVTLPLVWNIQVSTWLRMYVYERLTQNGKKPGFEQLLA
 (52) NVDILRVEFAKTAAQIPLAWNIQVSTWLRHYVYERLVQKGKKPGFEQLLA
(298) NVDILGVELAKSAVQIPLVWNIQVSTWLRHYVYERLVQNGKKAGFEQLLA
(301) NVDILGVELAKSAVQIPLFWNIQVSTWLRHYVYERLVKPGKKAGFEQLLA
 (55) NVDVLGVELAKSSVQLPAVWNIQVSTWLRHYVYERLIQKGRKPGFEQLLA
 (81) NVDVLGVELAKSSVQLPLVWNIQVSTWLRHYVYERLVQKGRKPGFEQLLA
(167) NVDVLGVELAKSSVQLPLVWNIQVSTWLKHYVYERLVQKGKKPGFEQLLA
 (78) NVDILGVEFAKSAAELPLVWNIQVSTWLRHYVYDRLVPKGKKAGFLQLLA
(148) NVDVLGVEFAKSSVELPLVWNIQVSTWLRHYVYDRLVQKGKKPGFEQLLA
              Motif 8

(124) TQTVSAVWHGLYPGYLIFFVQSALMIAGSRVIYRWQQAVPPTMDVVKKIL
 (88) TQTVSAVWHGLYPGYLIFFVQSALMIAGSRVIYRWQQAVPQNMDAVKNIL
 (79) TQTVSAIWHGLYPGYMIFFVQSALMINGSKVIYRWQQAVKQ--FRPPHYP
(172) TQTVSAIWHGLYPGYMFFFVQSALMINGSKVIYRWQQAVSN--PGLRTIL
(217) TQTVSAIWHGLYPGYLIFFFSSALMXNGSRVIYRWQQAASS--SFLSGIL
(120) TQTVSAIWHGLYPGYLIFFVQSALMINGSRVIYRWQQAVSS--SFLRGIL
(346) TQTVSAVWHGLYPGYLIFFVQSALMINGSKVIYRWQQAVSN--PVFHAIL
(244) TQTVSAVWHGLYPGYLIFFVQSALMINGSKVIYRWQQAVSN--PVFHAIL
(288) TQTVSAVWHGLYPGYLIFFVQSALM------------------------
(102) TQTVSAVWHGLYPGYLIFFVQSALMIAGSRVIYRWQQAVPPKMDLVKKVF
(348) TQTVSAVWHGLYPGYMMFFVQSALMIAGSRVIYRWQQAISPKMAMLRNIM
(351) TQTVSAVWHGLYPGYLIFFVQSALMIDGSKALYRWQQAIPPKMAMLRNVL
(105) TQTVSAVWHGLYPGYLIFFVQSALMIAGSRVIYRWQQAKG--SMFEKIL
(131) TQTVSAVWHGLYPGYLIFFVQSALMIAGSRVIYRWQQATKG--TMFEKIL
(217) TQTVSAVWHGLYPGYLIFF------------------------------
(128) TQTTSAVWHGLYPGYLIFFVQSALMIAGSKVIYRWQQAIPSNKALEKKIL
(198) TQTVSAVWHGLYPGYLIFFVQSALMISGSRAIYRWQQAVPP---TVKKFL (174) VFINFAYTVLVLNYSCVG------------FLVLSLRETLASYGSVHF-
(138) VFINFAYTLLVLNYSCVG------------FLVLSLRETLASYGSVHFI
(127) VFTKLLHIP----------------------------------------
(220) SLLNCAYTMMVLNYSCIG------------FQVLSFQETLASYKSVYYV
(265) ALLILLYIAGAY-YSCIG------------VQVLSF-------------
(168) AFLNFAYTLLVLNYSCIG------------FLVLSFKETLASYQSVYYV
(394) VFVNFSYTLMVLNYSCIG------------FQVLSFKETLASYQSVYYI
(292) VFVNFSYTLMVLNYSCIGFQFVFTMLYTLRFLQVLSFKETLASYQSVYYI
(313) -------------------------------------------------
(152) VLLNFAYTVLVLNYSSVG------------FMVLSHETIVAYGSVYSL
(398) VFINFLYTVLVLNYSAVG------------FMVLSHETLTAYGSVYYI
(401) VLINFLYIWVLNYSSVG------------FMVLSHETLVAEKSVYYI
(153) VAMNFAYTLLVLNYSAVG------------FMVLSHETLTAYGSVYYV
(179) IAMNFAYTLLVLNYSAVG------------FMVLSHETLTAYGSVYYI
(236) -------------------------------------------------
(178) VFMNFAYTVLVLNYSCVG------------FMVLSHETIAAYGSVYFI
(245) MLMNFAYTLLVLNYSCIG------------FMVLSHETLAAYGSVYYV (210) -------------------------------------------------
(175) GTLLPIALILLSYVIKPPRPARSKARKEE---------
(136) -------------------------------------------------
(257) GTIVPILCVLLGYVVKPTRPVKP--------------
(288) -------------------------------------------------
(205) GTIVPIVFLLLGN------------------------
(431) GTIVPIVVVLLGYVIKPARPVKPKARKAE---------
(342) GTIVPIVVVLLGYVIKPARPVKPKARKAE---------
```

FIG. 3C

```
(313)  ------------------------------------
(189)  EPLFRYL-----------------------------
(435)  GTIIPVGLILLSYWPAKPSRPKPRKEE---------
(438)  GTVIPIAVLLLSYLVPVKPVRPKTRKEE--------
(190)  GTIIPIALILLSKVIKPPRPCTSK------------
(216)  GTIVPILLILLSKVIKPPRPATSKARKAE-------
(236)  ------------------------------------
(215)  GTIVPVVFFLLGFIIKPARPSRSKHGTMSEVETVFLLL
(282)  GNIIPVA-----------------------------
```

Figure 3 Alignment of LPCAT sequences from different plant species.

Motif 5 (SEQ ID NO:81): E A φ φ I I(L) S G φ G F S(T) G W;
Motif 6 (SEQ ID NO:82): W D R A φ N V D;
Motif 7 (SEQ ID NO:83): W N I Q V S T W L φ φ Y V Y;
Motif 8 (SEQ ID NO:84): G F φ Q L L φ T Q T φ S A φ W H G L Y P G Y

FIG. 3D

| 1 | 2 | 3 | 4 | 5 | 6 | 7 | 8 | 9 | 10 | 11 | 12 | 13 | 14 |
14:0   16:0   16:1   18:0   18:1   18:2   22:6

… # GENES ENCODING A NOVEL TYPE OF LYSOPHOPHATIDYLCHOLINE ACYLTRANSFERASES AND THEIR USE TO INCREASE TRIACYLGLYCEROL PRODUCTION AND/OR MODIFY FATTY ACID COMPOSITION

CROSS-REFERENCE TO RELATED APPLICATIONS

This patent application is the national entry of PCT International Patent Application PCT/US2007/025650, filed on Dec. 13, 2007 designating the United States of America, published in English as WO2008/076377 on Jun. 26, 2008, and claims priority under 35 U.S.C. §119(e) to U.S. Provisional patent Application U.S. Ser. No. 60/874,497, filed on Dec. 13, 2006, and priority, under the Paris Convention, to U.S. Ser. No. 11/820,014, filed on Jun. 15, 2007, now U.S. Pat. No. 7,732,155 (Jun. 19, 2008), the contents of the entirety of both of which are incorporated herein by this reference.

TECHNICAL FIELD

The invention relates generally to biotechnology, and, more particularly, to lyso-phosphatidylcholine (LPC) acyltransferase, polynucleotides that encode LPC acyltransferases, and associated means and methods.

BACKGROUND

Phosphatidylcholine (PC) serves not only as a major component of cellular membranes, but also as a major source of fatty acyl donors for triacylglycerol biosynthesis in eukaryotic organisms. At least three pathways through which PC is generated exist: (i) the CDP-choline pathway where diacylglycerol (DAG) is a direct precursor; (ii) a pathway where CDP-DAG is a direct precursor, involving phosphatidylserine formation and decarboxylation and phosphatidylethanolamine methylation (Zheng and Zou, 2001); and (iii) a pathway with LPC as substrate. The third pathway is exerted by LPC acyltransferases (LPCAT).

LPCAT enzymes catalyze the acylation of LPC molecules to form PC and play a pivotal role in membrane biogenesis. They can also exert a reversible reaction to release the fatty acyl chain esterified to the sn-2 position of PC, thereby contributing to a continuous remodeling of fatty acyl-CoA and PC pools.

The significance of LPCAT in glycerolipid metabolism of eukaryotic systems has been noted for many years. For genetic engineering of plant-based production of very long chain polyunsaturated fatty acid (PUFA), this enzyme is believed to represent a bottleneck for acyl exchange between the fatty acyl elongation and de-saturation systems. In higher plants, the function of this enzyme is largely unknown, but it has been proposed that the enzyme is involved in the selective incorporation of fatty acids into a storage pool.

Although LPCAT relating to the synthesis of surfactant lipid located on the surface of (pulmonary) cells have been reported in mammalian systems (X. Chen et al., PNAS 2006 103:11724-11729; H. Nakanishi et al., JBC 2006 281:20140-20147), an LPC acyltransferase involved in membrane or storage lipid synthesis has not been reported.

Recently, a mitochondrial acyl-CoA independent LPCAT from *Saccharomyces cerevisiae* has been identified. This enzyme has been shown to function in cardiolipin metabolism (Testet et al. 2005). In addition, Shindou et al. (2007) reported that aceyl-CoA:lyso-PAF (platelet-activating factor) acetyltransferase possesses LPCAT activity.

SUMMARY OF THE INVENTION

Novel types of LPCAT enzymes whose sequences are unrelated to any known LPCAT enzymes have been identified. Known domains for other sn-2 acyltransferases such as the mammalian LPC acyltransferases are not identifiable in the LPC acyltransferase assay disclosed herein.

Previously reported LPCAT enzymes share a substantial sequence homology to glycerol-3-phosphate acyltransferase and lysophosphatidic acyltransferase. In contrast, the LPCAT sequences disclosed herein are unrelated to any known LPCAT sequences, and belong to a new class of LPCAT. Four conserved motifs were identified in this novel class of LPCAT enzymes. The identified motifs are different from previously reported LPCAT, which contain motifs having a high degree of similarity to those in other known acyltransferases employing glycerol-3-phosphate and lysophosphatidic acid as substrates. In contrast, sequence information of the motifs identified herein is novel, and can lead to the identification of new class of LPCAT genes from a broad spectrum of species.

Thus, in certain embodiments, a lyso-phosphatidylcholine acyltransferase gene or class of genes is identified. The LPC acyltransferase gene may be expressed or overexpressed in a cell and used to modify glycerolipid biosynthesis in a cell. Such an LPC acyltransferase gene may be expressed or overexpressed in a cell and used to modulate or enhance production of fatty acids, especially polyunsaturated fatty acids (PUFA) or other unusual fatty acids, and/or to increased oil content in the cell. The LPC acyltransferase gene may be expressed or overexpressed in planta in order to modify glycerolipid biosynthesis in a plant. In certain embodiments, the LPC acyltransferase gene is expressed or overexpressed, in planta, in order to enhance the production of fatty acids in a plant.

In certain embodiments, a vector is provided having an LPC acyltransferase gene of the invention. The vector may be used to transform a cell, thus producing a recombinant cell having the LPC acyltransferase gene. The cell may comprise, for example, a bacterial cell, a yeast cell, or a plant cell. In certain embodiments, a plant, plant seed or progeny thereof includes a cell having a recombinant LPC acyltransferase gene.

In other embodiments, knock-out mutants disrupted in LPC acyltransferase gene of yeast and plants are identified.

In certain embodiments, a recombinant cell expresses an LPC acyltransferase gene and produces an LPC acyltransferase polypeptide that may be isolated or purified from the cell.

In certain embodiments, nucleotide and deduced amino acid sequences associated with an LPC acyltransferase gene are disclosed. The sequence, or a portion thereof, may be used to identify genes from other species that encode polypeptides with LPC acyltransferase activity.

In certain embodiments, a process for producing fatty acids includes transforming a cell with an LPC acyltransferase gene. The transformed cell expresses the fatty acid acyltransferase gene and produces fatty acids. The fatty acids may be isolated or purified from the recombinant cell or culture media in which the cell grows, and subsequently incorporated into a composition.

In certain embodiments, a peptide comprising one or more of the four motifs identified herein may be used as an LPC Acyltransferase. Similarly, a nucleotide sequence encoding a peptide comprising one or more of the four motifs may be used as an LPC Acyltransferase.

Provided is an isolated or recombinant nucleic acid molecule encoding an LPC acyltransferase, and a cell transformed with the isolated or recombinant nucleic acid molecule as described herein. Also provided is a process for increasing fatty acid production in a cell, the process comprising: transforming a cell with a nucleic acid molecule encoding an LPC acyltransferase; and, growing the cell under conditions wherein the LPC acyltransferase is expressed. Also provided is a use of an isolated or recombinant nucleic acid molecule encoding an LPC acyltransferase for producing an LPC acyltransferase in a cell. Also provided is a purified or an isolated LPC acyltransferase.

LPCAT enzymes play a critical role in remodeling fatty acid and PC pools as well as PC synthesis. The remodeled fatty acyl chains in the form of acyl-CoA or esterified at the sn-2 position of PC can be used for triacylglycerol synthesis. Thus, this novel type of LPCAT isolated from the organisms where very-long-chain polyunsaturated fatty acids (VLCPUFA) are present at a high level can be used to increase the production of VLCPUFA. As well, this novel type of LPCAT isolated from species containing high amount of unusual fatty acids can be used to increase the production of unusual fatty acids. For instance, LPCAT enzymes isolated from castor bean are useful in increasing the production of hydroxyl fatty acids in oil seeds.

The enzyme activity described herein provides support that the motif-based gene searching is a useful approach.

BRIEF DESCRIPTION OF THE DRAWINGS

FIG. 2 is an alignment of LPCAT sequences from different species that revealing, among other things, four conserved motifs unique for this type of LPCAT enzymes.

FIG. 3 is another alignment of LPCAT sequences from different plant species that revealed four conserved motifs (SEQ ID NOS:81-84).

DESCRIPTION OF THE PREFERRED EMBODIMENTS

Figure 1:
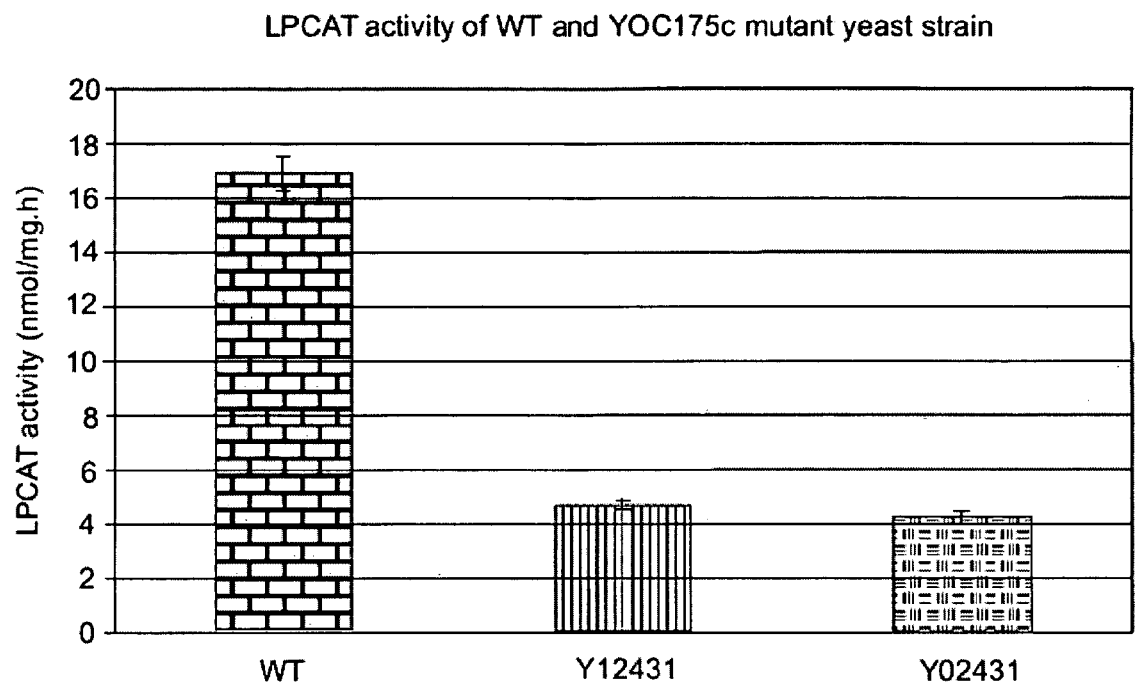
FIG. 1 is a graph of LPCAT activity (nmol/mg·h) of wild type (WT) and YOC175c mutant yeast strains.

Preferably, the nucleic acid molecule encoding the LPC acyltransferase is derived from yeast, plant, or mammalian species. Yeast species include, for example, species of the genus *Saccharomyces*, for example, *Saccharomyces cerevisiae*. Plant species include, for example, species of the family Brassicaceae. Of the family Brassicaceae, species of genus *Brassica* and genus *Arabidopsis* are of particular note, for example, *Arabidopsis thaliana*. Mammalian species include mouse and human.

In particular, provided are a nucleic acid molecule encoding an LPC acyltransferase from *S. cerevisiae* and two nucleic acid molecules encoding two different isoforms of LPC acyltransferase from *A. thaliana*. There is also provided the LPC acyltransferases encoded by the herein described nucleic acid molecules.

Provided herein is an isolated or recombinant nucleic acid molecule having a nucleotide sequence encoding an LPC acyltransferase such as amino acid sequence comprising SEQ ID NO:2, SEQ ID NO:4, SEQ ID NO:6, SEQ ID NO:8, SEQ ID NO:10, SEQ ID NO:11; SEQ ID NO:13, SEQ ID NO:15, SEQ ID NO:17; SEQ ID NO:19, SEQ ID NO:21, SEQ ID NO:25, SEQ ID NO:27, SEQ ID NO:29, SEQ ID NO:31, SEQ ID NO:33, SEQ ID NO:35, SEQ ID NO:36, SEQ ID NO:37, SEQ ID NO:38, SEQ ID NO:39; SEQ ID NO:40, SEQ ID NO:41, SEQ ID NO:42, SEQ ID NO:43, SEQ ID NO:44, SEQ ID NO:45, SEQ ID NO:85, SEQ ID NO:86, SEQ ID NO:87, or SEQ ID NO:88. In particular, there is provided an isolated or recombinant nucleic acid molecule having a nucleotide sequence comprising SEQ ID NO:1, SEQ ID NO:3, SEQ ID NO:5, SEQ ID NO:7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34. Preferably, the LPC acyltransferase encoded by a nucleic acid molecule comprises an amino acid sequence comprises an amino acid sequence having at least 60% homology to the aforementioned sequences. Homology is more preferably at least 70%, 80%, 90%, or 95%. It will be appreciated that this disclosure embraces the degeneracy of codon usage as would be understood by one of ordinary skill in the art.

Homologs of the LPC acyltransferase genes described herein obtained from other organisms, for example, plants, may be obtained by screening appropriate libraries that include the homologs, wherein the screening is performed with the nucleotide sequence of the specific LPC acyltransferase genes of the instant invention or portions or probes thereof, or identified by sequence homology search using sequence alignment search programs such as BLAST, FASTA.

Further included are nucleic acid molecules that hybridize to the above disclosed sequences. Hybridization conditions may be stringent in that hybridization will occur if there is at least a 90%, 95% or 97% identity with the nucleic acid molecule that encodes the LPC acyltransferase of the instant invention. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001), incorporated herein in its entirety by this reference.

Nucleic acid molecules that code for an LPC acyltransferase may be transformed into an organism, for example, a plant. As known in the art, there are a number of ways by which genes and gene constructs can be introduced into organisms, for example, plants, and a combination of transformation and tissue culture techniques have been successfully integrated into effective strategies for creating transgenic organisms, for example, crop plants. These methods, which can be used in the invention, have been described elsewhere (Potrykus, 1991; Vasil, 1994; Walden and Wingender, 1995; Songstad et al., 1995), and are well known to persons skilled in the art. For example, one skilled in the art will certainly be aware that, in addition to *Agrobacterium*-mediated transformation of *Arabidopsis* by vacuum infiltration (Bechtold et al., 1993) or wound inoculation (Katavic et al., 1994), it is equally possible to transform other plant and crop species, using *Agrobacterium* Ti-plasmid-mediated transformation (e.g., hypocotyl (DeBlock et al., 1989) or cotyledonary petiole (Moloney et al., 1989) wound infection), particle bombardment/biolistic methods (Sanford et al., 1987; Nehra et al., 1994; Becker et al., 1994) or polyethylene glycol-assisted, protoplast transformation (Rhodes et al., 1988; Shimamoto et al., 1989) methods.

As will also be apparent to persons skilled in the art, and as described elsewhere (Meyer, 1995; Dada et al., 1997), it is possible to utilize plant promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use herein may be inducible, constitutive, or tissue-specific or have various combinations of such characteristics. Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter).

It may be desirable to use a tissue-specific or developmentally regulated promoter instead of a constitutive promoter in certain circumstances. A tissue-specific promoter allows for overexpression in certain tissues without affecting expression in other tissues. By way of illustration, a preferred promoter used in overexpression of enzymes in seed tissue is an ACP promoter as described in PCT International Publication WO 92/18634, published Oct. 29, 1992, the disclosure of which is herein incorporated by reference.

The promoter and termination regulatory regions will be functional in the host plant cell and may be heterologous (that is, not naturally occurring) or homologous (derived from the plant host species) to the plant cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via *Agrobacterium* and screening for increased isoprenoid levels.

Suitably, the nucleotide sequences for the genes may be extracted from, for instance, the GenBank® (a registered trademark of the U.S. Department of Health and Human Services) nucleotide database and searched for restriction enzymes that do not cut. These restriction sites may be added to the genes by conventional methods such as incorporating these sites in PCR primers or by sub-cloning.

Preferably, a DNA construct for use herein is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al., *Cloning Vectors, A Laboratory Manual*, Elsevier, Amsterdam (1986). Particularly suitable vectors include the Ti plasmid vectors.

Transformation techniques for introducing the DNA constructs into host cells are well known in the art and include such methods as micro-injection, using polyethylene glycol, electroporation, or high velocity ballistic penetration. A preferred method relies on *Agrobacterium*-mediated transformation. After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved isoprenoid levels may be propagated and self-pollinated to produce homozygous lines. Such plants produce seeds containing the genes for the introduced trait and can be grown to produce plants that will produce the selected phenotype.

Plants that may be modified or used for fatty acid production according to the instant invention include, without limitation, borage (*Borago* spp.), Canola, castor (*Ricinus communis*); cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oeanothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the *Gramineae*. It will further be apparent to those of ordinary skill in the art that genomic or sequence libraries of each of these plants may be screened with the nucleotide or amino acid sequences described herein (e.g., for one or more of the hereinafter identified conserved motifs (SEQ ID NO:46 through SEQ ID NO:49) for other sequences that encode or are homologous to sequences associated with the LPC acyltransferase of the instant invention.

Plants transformed with a nucleotide sequence of the instant invention that codes for an LPC acyltransferase may be grown. Seeds of the transgenic plants are harvested and fatty acids of the seeds are extracted. The extracted fatty acids are used for subsequent incorporation into a composition, for example, a pharmaceutical composition, a nutraceutical composition or a food composition.

In certain embodiments, a peptide comprising one or more of the four motifs may be used as an LPC Acyltransferase. Similarly, a nucleotide sequence encoding a peptide comprising one or more of the four motifs may be used as an LPC Acyltransferase.

Further described herein is a lyso-PAF sensitivity screen to identify novel LPCAT. This is detailed in FIGS. 12 and 16. For example, a method of screening for an LPCAT, wherein the method comprises expressing a candidate gene in a yeast LPCAT mutant, plating the yeast on to lyso-PAF plates, and detecting yeast colonies showing higher tolerance to the lyso-PAF, wherein the colonies showing higher tolerance indicate that the candidate gene is a LPCAT gene hereof. The candidate gene may be identified by screening a gene to determine the presence of one of more of nucleic acid sequences encoding at least one motif selected from the group consisting of SEQ ID NO:46, SEQ ID NO:47, SEQ ID NO:48, SEQ ID NO:49, SEQ ID NO:81, SEQ ID NO:82, SEQ ID NO:83, SEQ ID NO:84, and any combination thereof.

In certain embodiments, other methods of enhancing or altering oil production may also be used with the plant to be transformed (e.g., incorporating, for expression in the plant, a nucleic acid sequence selected from the group consisting of a nucleic acid sequence encoding a peptide having, for example, *Brassica* pyruvate dehydrogenase kinase activity (see, e.g., U.S. Pat. No. 7,214,859 to Marilla et al. (May 8, 2007), U.S. Pat. No. 6,500,670 to Zou et al. (December 2002), and U.S. Pat. No. 6,256,636 6,265,636 to Randall et al. (July 2001), the contents of the entirety of each of which is incorporated herein by this reference), a nucleic acid sequence encoding a peptide having diacylglycerol acyltransferase activity (see, e.g., U.S. Pat. No. 7,015,373 and U.S. Pat. No. 6,500,670 to Zou et al. (December 2002), the contents of the entirety of each of which is incorporated herein by this reference), a nucleic acid sequence encoding a peptide having glycerol-3-phosphate dehydrogenase activity (see, e.g., U.S. Pat. No. 7,112,724, the contents of the entirety of which is incorporated herein by this reference), and combinations thereof).

Also described is a method of transforming a cell or a plant, the method comprising introducing the isolated, purified or recombinant nucleic acid into the cell or plant. A process for producing a genetically transformed plant seed comprises introducing the nucleic acid into the plant seed.

Also described is a vector comprising SEQ ID NO:1, SEQ ID NO:3, SEQ ID NO:5, SEQ ID NO:7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, and/or SEQ ID NO:34.

Also described is a vector comprising a nucleic acid sequence encoding a polypeptide having lyso-phosphatidylcholine acyltransferase activity, wherein the nucleic acid sequence comprises SEQ ID NO:1, SEQ ID NO:3, SEQ ID NO:5, SEQ ID NO:7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34, or a fragment of SEQ ID NO:1, SEQ ID NO:3, SEQ ID NO:5, SEQ ID NO:7, SEQ ID NO:9, SEQ BD NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ BD NO:32, or SEQ ID NO:34, or having 90% identity with SEQ ID NO:1, SEQ ID NO:3, SEQ ID NO:5, SEQ ID NO:7, SEQ ID NO:9, SEQ ID NO:12, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32, or SEQ ID NO:34, wherein the fragment encodes the polypeptide having the lyso-phosphatidylcholine acyltransferase activity.

Also described is a method for increasing fatty acid production in a cell, the method comprising transforming a cell with a nucleic acid molecule encoding a lyso-phosphatidylcholine acyltransferase; and growing the cell under conditions wherein the lyso-phosphatidylcholine acyltransferase is expressed. The method can further comprise isolating the fatty acid. In such a method, the lyso-phosphatidylcholine acyltransferase preferably comprises at least one motif selected from the group consisting of SEQ ID NO:46, SEQ ID NO:47, SEQ ID NO:48, SEQ ID NO:49, and any combination thereof.

Also described is a method of altering oil content in a plant comprising screening for a peptide encoded by a nucleotide sequence for at least one motif selected from the group consisting of SEQ ID NO:46, SEQ BD NO:47, SEQ ID NO:48, and SEQ ID NO:49; selecting the peptide based upon the presence of at least one of the four motifs; and expressing the nucleotide sequence encoding the peptide in the plant to alter the oil content of the plant.

Also described is a method of changing the oil content of a plant or plant seed, the method comprising introducing a nucleic acid construct comprising a nucleic acid sequence encoding a polypeptide selected from the group consisting of SEQ ID NO:2, SEQ ID NO:4, SEQ ID NO:6, SEQ ID NO:8, SEQ ID NO:10, SEQ ID NO:11; SEQ ID NO:13, SEQ ID NO:15, SEQ ID NO:17; SEQ ID NO:19, SEQ ID NO:21, SEQ ID NO:25, SEQ ID NO:27, SEQ ID NO:29, SEQ ID NO:31, SEQ ID NO:33, SEQ ID NO:35, and an amino acid sequence having at least 60% homology to any thereof having lyso-phosphatidylcholine acyltransferase activity into a plant transformation vector; transforming a genome of a plant or plant seed with the plant transformation vector; expressing the nucleic acid sequence; growing the plant or plant seed; and extracting the oil from the plant seed.

The methods can further comprise incorporating, for expression in the plant, a nucleic acid sequence selected from the group consisting of a nucleic acid sequence encoding a peptide having pyruvate dehydrogenase kinase activity, a nucleic acid sequence encoding a peptide having diacylglycerol acyltransferase activity, a nucleic acid sequence encoding a peptide having glycerol-3-phosphate dehydrogenase activity, and any combination thereof.

The invention is further described with the aid of the following illustrative Examples.

EXAMPLES

Example 1

Identification of Yeast LPC Acyltransferase Gene

Nucleotide sequences of nucleic acid molecules of the invention were identified through yeast genetic and functional screening. Yeast (*S. cerevisiae*) LPC acyltransferase gene was identified based on enzyme assays of yeast mutant strains in which the gene, YOR175c, was knocked out. The enzyme activity was assessed using 14C-labeled acyl-CoA and lyso-phosphatidylcholine. The reaction product of the lyso-phosphatidylcholine and radio-labeled acyl-CoA was separated through TLC and measured through scintillation counting. Deletion of the YOR175c gene in yeast resulted in a 90% reduction of LPC acyltransferase activity (FIG. 1). Therefore, YOR175c encodes LPC acyltransferase. Details are given below for the In Vitro Assay protocol for LPCAT (lyso-phosphatidylcholine (LPC) acyltransferase) activity.

We designate YOR175c as LCA1 in following description.

Gene expression vector construction: For TOPO TA-cloning and yeast complementation, *Saccharomyces cerevisiae* YOR175c ORF was PCR-amplified with primers FP: 5' GGTGATTCTAGACTGCTGCTGATCGCTT 3' (SEQ ID NO:91) and RP: 5' GCATCTGTCGTTTTTGGAGCTCTACTCTT 3' (SEQ ID NO:92), and cloned into pYES2.1 vector (Invitrogen). Correctly oriented plasmids were identified by DNA sequencing and subsequently introduced into YOR175c mutant yeast strain Y02431.

Microsomal preparation: Yeast strains were first grown in 15 ml of SC-Leu-His-Ura medium containing 2% glucose. Protein expression induction was carried out as described in Invitrogen manufacturer manual for yeast expression vector pYFS2.1. After 24 hours of growth in SC+2% galactose+1% raffinose induction conditions, the cells were washed, first with distilled water and then with wall-breaking buffer (50 mM Tris-HCl, 1 mM EDTA, 0.6 M sorbitol, pH 7.4, 1 mM DTT). After centrifugation at 4,000 rpm (Eppendorf Centrifuge 5145C), the cells were resuspended in 1 ml wall-breaking buffer with 10 µl yeast protease cocktail (Sigma), and shaken vigorously in the presence of acid-washed glass beads (diameter 0.5 mm). The resultant homogenate was centrifuged at 12,000 rpm for ten minutes at 4° C. The decanted supernatant was further centrifuged at 100,000×g for 90-120 minutes at 4° C. The supernatant was discarded, and the pellet was suspended in homogenization buffer containing 20% glycerol and frozen at −80° C. until use. Protein concentration was measured using Bio-Rad Protein Assay Kit for final enzyme activity calculation.

In Vitro Assay of LPCAT activity: LPCAT substrate specificity was determined by measuring incorporation of [$^{14}$C] lysophosphatidylcholine or [$^{14}$C] palmitoyl-CoA into phosphatidylcholine. All assays were performed at least twice. For lysophospholipid substrate specificity assessment, 400 µl HEPES buffer contained 3 µg microsomal protein, 50 µM of lysophospholipid substrates and 112.5 µM [$^{14}$C] palmitoyl-CoA (5.5 nCi/nmol). For acyl-CoA substrate selectivity analysis, 400 µl HEPES reaction buffer (pH7.4, 0.1 M) contained 3 µg microsomal protein, 50 µM acyl-CoA and 112.5 µM [$^{14}$C] palmitoyl-PC (1.35 nCi/nmol). Reaction was allowed for 2 minutes at 30° C. with 100 rpm shaking. The reaction products were extracted with chloroform/methanol (2/1, v/v) and separated with Merck silica G60 TLC plates. Spots corresponding to different phospholipid species products were scraped off and $^{14}$C incorporation were scintillation counted. Different concentrations of $ZnCl_2$ were added in to reactions for $Zn^{2+}$ inhibitory effect assay.

TABLE 1

Inhibitory effect of $Zn^{2+}$ on LCA1 activity

| $ZnCl_2$ concentration | LPCAT activity (% control) |
|---|---|
| 0 mM (control) | 100 ± 7.9 |
| 20 mM | 6 ± 2.0 |
| 0.1 mM | 35 ± 22.4 |
| 25 μM | 149.7 ± 12.0 |
| 10 μM | 136.8 ± 3.9 |
| 5 μM | 98 ± 5.9 |

Results are expressed as means ± S.D. The lca1Δ over-expressing LCA1 was used to assess $Zn^{2+}$ effect. The reactions contained 5.6 μM palmitoyl-LPC (1.35 nCi/nmol), 1.5 μg microsomal proteins, 0.1M HEPES (pH 7.4), 11.25 μM stearyl-CoA and indicated concentration of $ZnCl_2$. The reaction was stopped after two minutes by adding 2 ml of chloroform/methanol solution (2:1).

TABLE 2

Phosphatidylcholine turnover in lca1Δ, slc1Δ and BY4741 (WT) strains

| | | 28° C. | | | 37° C. | | |
|---|---|---|---|---|---|---|---|
| Chase time (h): | | 0 | 1 | 2 | 0 | 1 | 2 |
| lca1Δ | Medium | 12.1 ± 1.7 | 16.2 ± 1.1 | 17.4 ± 2.7 | 12.1 ± 1.7 | 13.2 ± 3.5 | 13.3 ± 1.5 |
| | Intracellular | 41.1 ± 3.2 | 47.8 ± 2.8 | 53.6 ± 1.5 | 41.1 ± 3.2 | 67.9 ± 2.7 | 73.5 ± 2.5 |
| | Membrane | 46.8 ± 2.8 | 36.0 ± 2.3 | 28.9 ± 1.5 | 46.8 ± 2.8 | 18.9 ± 3.4 | 13.2 ± 2.3 |
| slc1Δ | Medium | 14.5 ± 1.1 | 16.1 ± 1.3 | 17.2 ± 1.6 | 14.5 ± 0.3 | 18.3 ± 2.3 | 19.7 ± 0.7 |
| | Intracellular | 37.4 ± 2.1 | 40.1 ± 2.2 | 42.1 ± 3.3 | 37.4 ± 1.5 | 49.1 ± 1.9 | 57.4 ± 4.1 |
| | Membrane | 48.1 ± 1.7 | 43.8 ± 2.6 | 40.7 ± 1.7 | 48.1 ± 0.9 | 32.6 ± 2.8 | 22.9 ± 1.3 |
| WT | Medium | 14.1 ± 0.8 | 16.1 ± 2.8 | 17.1 ± 3.1 | 14.1 ± 0.8 | 14.9 ± 1.5 | 15.3 ± 0.5 |
| | Intracellular | 36.5 ± 0.2 | 37.1 ± 1.6 | 41.6 ± 0.1 | 36.5 ± 0.2 | 55.9 ± 2.1 | 60.7 ± 4.3 |
| | Membrane | 49.4 ± 0.8 | 46.9 ± 1.2 | 41.3 ± 3.2 | 49.4 ± 0.8 | 29.2 ± 0.6 | 24.1 ± 2.7 |

Yeast cells were labeled at starting OD600 = 1.5 for five hours in chemically defined synthetic medium containing 0.15 μCi/ml. The cells were then washed twice, cultured in medium containing 10 mM non-radioactive choline at 28° C. and 37° C. One microliter culture aliquot was removed, separated into three factions then scintillation counted. The data were presented as mean of three analyses.

Lyso-PAF sensitivity: Yeast strains Y02431 over-expressing LCA1 or harboring empty vector were first grown in 15 ml of SC-ura medium containing 2% glucose then transferred to SC-ura+2% galactose and 1% raffinose. After 12 hours LCA1 expression induction, the culture was diluted to correspond to $OD_{600}$ value of 0.5, 1, 2, 3, 4. Five μl of each dilution was spotted to a YPD plate supplemented with varying concentrations of Lyso-PAF. The plates were incubated at 28° C. for two days.

PC turnover analysis: PC turnover analysis was performed according to previously described method [13] with slight modification. Briefly, Y02431 and BY4741 yeast cells were grown overnight in chemically defined synthetic media without inositol and choline. Yeast at $OD_{600}$=1.5 were used to inoculate fresh chemically defined synthetic media containing 0.15 μCi/ml [$^{14}$C]choline chloride (20 μM). Cells were harvested through centrifugation after 5 hours labeling, washed twice in fresh non-radioactive medium, and then inoculated into in medium containing 10 mM non-radioactive choline. At different time points, 1 ml aliquots were removed and centrifuged. The supernatant was saved as the "medium" fraction. The cell pellet was suspended in 0.5 ml 5% trichloroacetic acid (TCA) and incubated on ice with frequent vortexing. Following centrifugation at 14,000 rpm (Eppendorf), the TCA-containing supernatant was decanted as "intracellular water-soluble fraction", and neutralized by adding 1 M Tris-HCl (pH 8.0) to avoid acid-induced luminescence in scintillation counting. The pellet was saved as the "membrane" fraction. The labeling of each fraction was measured and presented as percentage of total counts in all the three fractions. To confirm that the majority of choline-containing compounds in TCA fraction are glycerophosphorylcholine (GroPC), the fractions from WT and lca1Δ yeast cells chased for two hours at 37° C. were applied to Merck silica G60 gel and developed in solvent system methanol/0.5% NaCl/$NH_3.H_2O$ (50/50/1, v/v/v)[14]. After drying, choline-containing chemicals on the plate were detected with scanner (Bioscan, Inc.) and only one major [$^{14}$C]-labeled spot was clearly detected. The spot was scraped off and re-extracted into distilled water then concentrated with a vacuum refrigerator. The purified TCA fractions were spotted on Merck silica G60 plate with soluble choline-containing compound standards including GroPC, phosphocholine, CDP-choline, [$^{14}$C] choline and 16:1-LPC, loaded on parallel lanes. The TLC plate was developed in the above-mentioned solvent system. [$^{14}$C] choline and [$^{14}$C] choline containing compound in TCA fractions were detected with scanner (Bioscan, Inc.), LPC was stained by iodine exposure, and other choline-containing standards were visualized by spraying molybdenum blue, which is specific to phosphorus present in GroPC, phosphocholine and CDP-choline [15].

Yeast culture: One colony each of wild-type (strain BY4741) and LPCAT mutants (YOR175c deletion strains Y12431, Y02431) are inoculated in 10 ml YPD media and grown overnight. After 24 hours, another 20 ml YPD media is added and growth is continued for another 24 hours.

Protein extraction: Yeast cultures are spun at 2800 rpm at 4° C. for 20 minutes. The supernatant is discarded and the yeast pellet washed with 10 ml of ice cold IB buffer (80 mM HEPES, 320 mM sucrose, 5 mM EDTA pH 8, 10 mM KCl, 2 mM DTT). The pellets are spun again and re-suspend in 500 μl of IB buffer. Yeast cells are divided and transferred into two tubes appropriate for a mini-bead beater. 0.5 mm cold glass beads are added to fill completely the tube. To break the yeast cell, three 60-second pulses of the mini-bead beater are used. The mixtures are spun again to remove unbroken cells and debris.

Protein assay conditions: A reaction is conducted using the recipe for fatty-CoA substrate specificity, as listed in Table 3.

TABLE 3

| Solution | Volume added |
|---|---|
| 450 μM lyso-PC (18:1) | 50 μl |
| 180 μM $^{14}$C 18:1-CoA (10 nCi/nmol) | 50 μl |

TABLE 3-continued

| Solution | Volume added |
|---|---|
| Microsome | 400 µg protein |
| pH 7.4 HEPES | to make fine volume 0.5 ml |

The reaction mixture is allowed to sit in a water bath at 30° C. and stirred at 100 rpm for 30 minutes. The reaction is then terminated by adding 2 ml of $CH_2Cl_2$:Isopropanol (1:2). The mixture is allowed to sit at room temperature for 15-30 minutes with occasional vortexing. Phases are separated by adding 2 ml $CH_2Cl_2$ followed by 2 ml 1M KCl in $H_3PO_4$. The lower layer is transferred to a clean tube and the upper aqueous phase is backwashed twice with $CH_2Cl_2$ and centrifuged, saving the organic phase each time. Organic phases are combined and dried under nitrogen. Dried material is taken up in 200 µl $CH_2Cl_2$:MeOH (2:1) and protein is separated by thin layer chromatography (TLC) using silica G (250 µm) commercial plate. Plates are developed to within 2 cm of top in ethyl acetate:isooctane:acetic acid (45:15:10, V/V/V), then dried and scraped. The phosphatidyl choline region is counted in 4 ml Aquasol-2 by a scintillation counter.

The YOR175c gene from *S. cerevisiae* has been identified as encoding an LPC acyltransferase. The coding sequence of this yeast LPC acyltransferase gene is SEQ ID NO:1:

```
ATGTACAATCCTGTGGACGCTGTTTTAACAAAGATAATTACCAACTATGG
GATTGATAGTTTTACACTGCGATATGCTATCTGCTTATTGGGATCGTTCC
CACTGAATGCTATTTTGAAGAGAATTCCCGAGAAGCGTATAGGTTTAAAA
TGTTGTTTTATCATTTCTATGTCGATGTTTTACTTATTCGGTGTGCTGAA
TCTAGTAAGTGGATTCAGGACCCTGTTTATTAGTACCATGTTTACTTACT
TGATCTCAAGATTTTACCGTTCCAAGTTTATGCCACACTTGAATTTCATG
TTTGTTATGGGTCATTTGGCAATAAATCATATACACGCCCAATTCCTTAA
CGAACAGACTCAAACTACCGTTGACATTACAAGTTCACAAATGGTTTTAG
CCATGAAACTAACTTCTTTTGCATGGTCGTACTATGATGGTTCATGCACT
AGCGAAAGCGATTTCAAAGATTTGACTGAGCATCAAAAATCTCGTGCTGT
CAGAGGTCATCCACCCTTATTAAAGTTCCTGGCATATGCATTTTTCTATT
CAACGTTGCTAACTGGCCCAAGTTTCGATTATGCCGATTTTGACAGCTGG
TTGAATTGTGAGATGTTCCGTGACTTGCCTGAAAGCAAAAAGCCTATGAG
AAGACACCACCCTGGTGAAAGAAGACAGATTCCAAAGAATGGTAAACTTG
CATTATGGAAAGTTGTTCAAGGTCTTGCTTGGATGATTTTAAGTACACTA
GGAATGAAGCACTTCCCCGTAAAATACGTTTTGGACAAAGATGGCTTCCC
AACGAGATCTTTTATATTCAGAATCCATTACTTATTCTTGCTTGGTTTCA
TCCATAGATTCAAGTACTACGCTGCCTGGACTATTTCGGAAGGATCTTGT
ATTTTGTGCGGTTTGGGTTATAATGGTTATGATTCAAAGACACAAAAGAT
CAGATGGGATCGTGTCAGAAATATTGACATTTGGACCGTAGAAACGGCGC
AGAATACGCGTGAAATGTTGGAAGCATGGAATATGAATACTAACAAGTGG
CTAAAATACTCTGTTTATTTACGTGTCACAAAGAAGGGCAAAAAACCTGG
TTTCCGCTCAACTTTGTTTACTTTCCTAACTTCCGCATTTTGGCATGGTA
CCAGACCTGGGTACTATCTGACTTTTGCGACAGGGGCTTTGTACCAAACA
TGTGGTAAAATCTACAGACGCAATTTTAGACCAATTTTCTTGCGAGAAGA
TGGTGTCACTCCTTTGCCTTCTAAAAAAATCTACGATTTAGTTGGCATAT
ATGCAATTAAACTAGCATTTGGTTACATGGTGCAACCATTTATTATCTT
GATTTGAAGCCATCTTTAATGGTATGGGGCTCTGTTTATTTCTATGTTCA
TATTATTGTTGCTTTCTCATTTTTCCTATTCAGAGGACCATATGCTAAAC
AAGTTACTGAATTTTTTAAATCCAAACAACCTAAAGAAATATTCATTACA
AAACAAAAGAAGTTGGAAAAAGATATTTCTGCAAGCTCTCCAAACTTGGG
TGGTATATTGAAGGCAAAGATTGAACATGAAAAGGGAAAGACAGCAGAAG
AAGAAGAAATGAACTTAGGTATTCCACCAATTGAGTTAGAAAAGTGGGAC
AATGCTAAGGAAGATTGGGAAGATTTCTGCAAAGATTACAAAGAATGGAG
AAATAAAAATGGTCTTGAAATAGAAGAGGAAAACCTTTCTAAAGCTTTTG
AAAGATTCAAGCAGGAATTTTCTAACGCTGCAAGTGGATCAGGTGAACGT
GTGAGAAAAATGAGTTTTAGTGGTTACTCACCAAAGCCTATTTCAAAAAA
GGAAGAGTAG
```

The deduced amino acid sequence of the yeast LPC acyltransferase encoded by the gene is SEQ ID NO:2:

```
MYNPVDAVLTKIITNYGIDSFTLRYAICLLGSFPLNAILKRIPEKRIGLK
CCFIISMSMFYLFGVLNLVSGFRTLFISTMFTYLISRFYRSKFMPHLNFM
FVMGHLAINHIHAQFLNEQTQTTVDITSSQMVLAMKLTSFAWSYYDGSCT
SESDFKDLTEHQKSRAVRGHPPLLKFLAYAFFYSTLLTGPSFDYADFDSW
LNCEMFRDLPESKKPMRRHHPGERRQIPKNGKLALWKVVQGLAWMILSTL
ILCGLGYNGYDSKTQKIRWDRVRNIDIWTVETAQNTREMLEAWNMNTNKW
LKYSVYLRVTKKGKKPGFRSTLFTFLTSAFWHGTRPGYYLTFATGALYQT
CGKIYRRNFRPIFLREDGVTPLPSKKIYDLVGIYAIKLAFGYMVQPFIIL
DLKPSLMVWGSVYFYVHIIVAFSFFLFRGPYAKQVTEFFKSKQPKEIFIR
KQKKLEKDISASSPNLGGILKAKIEHEKGKTAEEEEMNLGIPPIELEKWD
NAKEDWEDFCKDYKEWRNKNGLEIEEENLSKAFERFKQEFSNAASGSGER
VRKMSFSGYSPKPISKKEE
```

Figure 9:
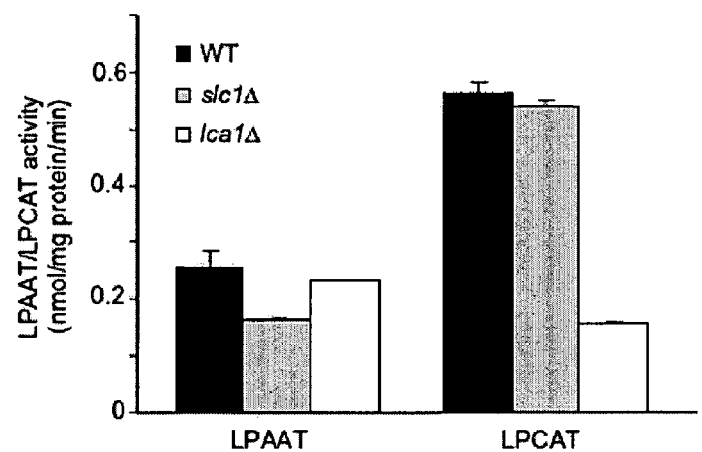
FIG. 9 is a graph comparing LPAAT and LPCAT activity of slc1Δ, lca1Δ, and congenic WT yeast strain. Cell lysates equivalent to 200 μg protein were assayed for acylation of oleoyl-LPA and oleoyl-LPC with [$^{14}$C] oleoyl-CoA. The reaction mixture contained 45 μM 18:1-LPA or 18:1-LPC, 18 μM (10 nCi/nmol) 18:1-CoA. The results are presented as a mean of three assays.
Figure 10:
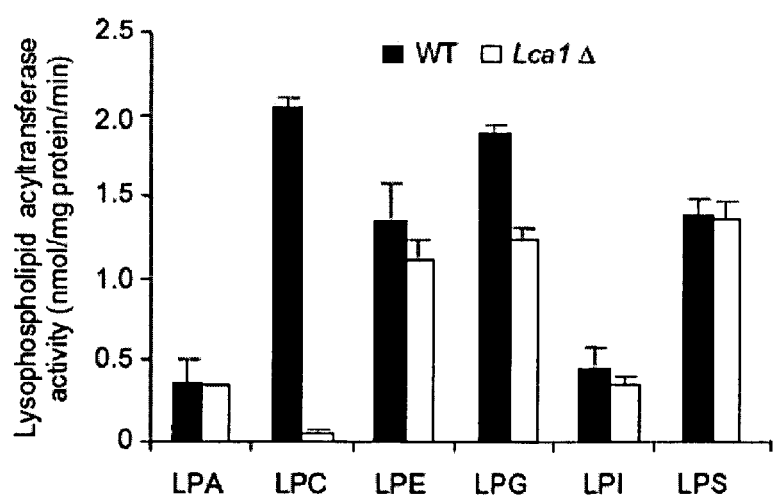
FIG. 10 is graph depicting lysophospholipid acyltransferase activity in lca1Δ and its congenic WT yeast strains. Microsomal preparations were assayed for acylation of palmitoyl-LPA, LPC, LPE, LPG, LPI, and LPS with [$^{14}$C] palmitoyl-CoA. The reaction mixture contained 45 μM lysophospholipid, 27 μM (10 nCi/nmol) 16:1-CoA and 50 μg protein. The results are presented as a mean of three assays.

Deletion of YOR175 cp leads to reduced lysophosphatidylcholine acyltransferase (LPCAT) activity: YOR175c is a MBOAT family protein, and was shown to be localized in endoplasm reticulum. In a preliminary experiment, we first examined if disruption of YOR175c would have any impact on lysophosphatidic acid acyltransferase (LPAAT) and LPCAT activities using both the parental strain and slc1Δ mutant as controls. When lysophosphatidic acid (18:1) was supplied as acyl acceptor, the cell lysate of slc1Δ mutant had a LPAAT level reduced to 63% of the parental strain, but we detected no significant LPAAT reduction in the yor175cΔ mutant. In marked contrast, when LPC was provided as acyl acceptor, our in vitro assay showed acyltransferase activity reduction in yor175cΔ to a level approximately 28% of the parental strain. The slc1Δ displayed no significant decrease in LPCAT activity as compared with WT strain (FIG. 9). We further investigated sn-2 lysophospholipid acyl transferase activity in yor175cΔ by using microsomal enriched fractions with different lysophospholipid acyl acceptors and palmitoyl-CoA (16:0-CoA). In keeping with the results of total cell lysate, microsomal fractions of the yor175cΔ strain showed a striking decrease in LPCAT activity. LPE and LPG acyltransferase were also slightly decreased, but to a much lesser degree (FIG. 10).

Figure 11:
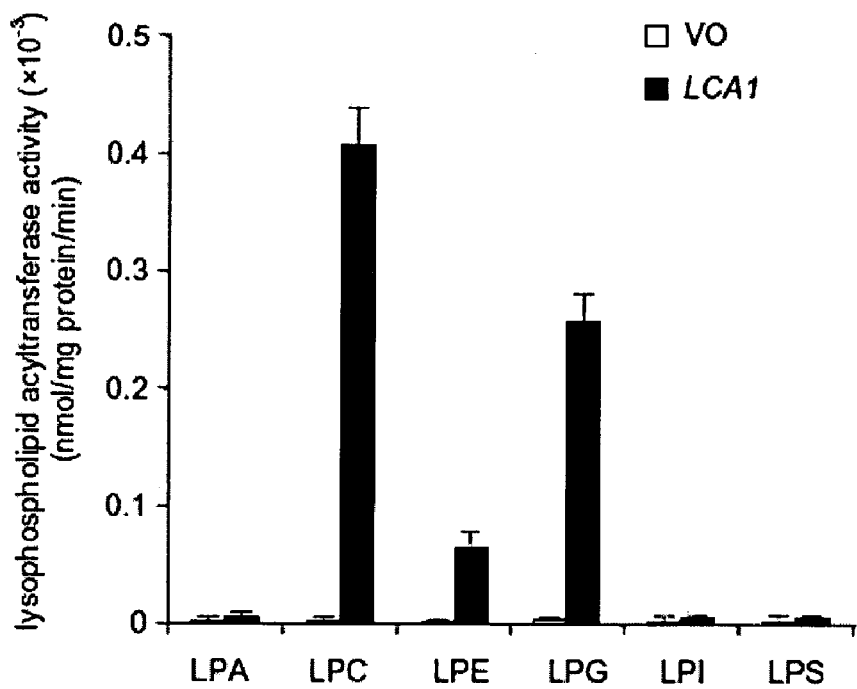
FIG. 11 is a graph showing the substrate specificity of LCA1. The assays were performed with 3 μg microsomal protein from lca1Δ harboring an empty vector (V0) and lca1Δ expressing LCA1. The reaction contained 112.5 μM [$^{14}$C] palmitoyl-CoA (5.5 nCi/nmol) and 50 μM lysophospholipid substrate (LPA, LPC, LPE, LPG, LPI, and LPS). Reaction was allowed for two minutes with 100 rpm shaking. The results are presented as a mean of three assays.

YOR175 cp displays in vitro acyltransferase activity with preference for LPC: Microsomal preparations of lca1Δ mutant expressing YOR175c and lca1Δ harboring the empty vector (VO) were used to perform acyltransferase assays with [$^{14}$C] palmitoyl-CoA and various lysophospholipids substrates including LPA, LPC, LPE, LPG, LPI and LPS. As shown in FIG. 11, the highest activity was found with LPC as substrate. The activity of LPC acylation was linear at 30° C. for 20 minutes, and the conversion of LPC to PC is negligible in the absence of 16:0-CoA (data not shown). Over-expression of YOR175c also caused substantial increases in the acylation of LPG and LPE. But the rates of LPG and LPE acylation were at a level approximately 60% and 20%, respectively, of the activity registered for LPC. Activities for LPA, LPS and LPI, were all less than 1% of the activity of LPCAT. Thus, YOR175c appeared capable of accepting several major lysophospholipid classes, but under our assay conditions it exhibited the highest activity with LPC.

Figure 12:
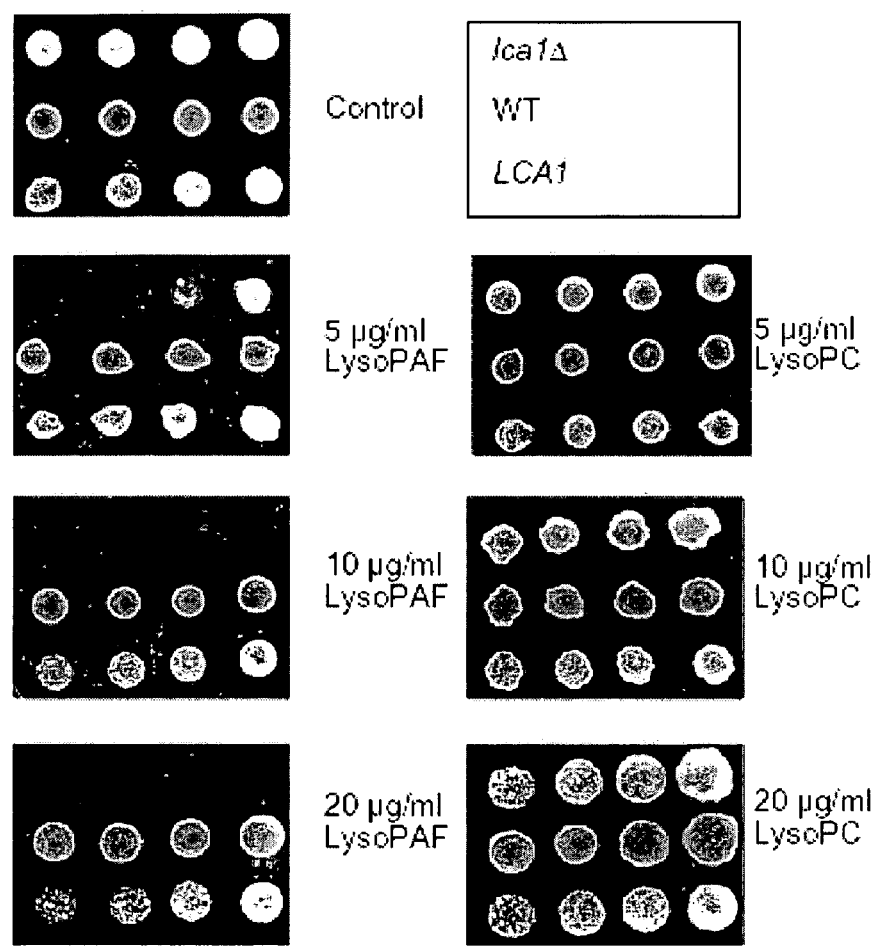
FIG. 12 shows the lyso-PAF and lyso-PC Sensitivity test lca1Δ, WT and lca1 delta over-expressing LCA1. Cells were frown first in SC-URA+2% glucose media overnight then in protein expression induction media for six hours. Cultures were diluted to $OD_{600}$ value of $OD_{600}$ 0.5, 1, 2, 3, respectively, from which 5 μl were inoculated (from left to right) onto YPD plate containing lyso-PAF or lyso-PC. The plates were incubated at 28° C. for 36 hours.

Correlation of YOR175c LPCAT activity with Lyso-PAF sensitivity: Although not an endogenous acyl acceptor, ether-linked glycerolipid, lyso-PAF, can be acylated in yeast, and the reaction was attributed to a LPCAT. When lyso-PAF was used as acyl acceptor, the lca1Δ strain had a rate of lyso-PAF acylation reduced to 31.1% of WT strain. Conversely, over-expression of LCA1 resulted in 86.3-fold increase in lyso-PAF acyltransferase activity. It was established previously that high lyso-PAF level exerts toxic effect on yeast cells. Consistent with in vitro results; LCA1 mediating Lyso-PAF acylation was also evident in a plate assay (FIG. 12). In our study, both the parental strain and the lca1Δ were capable of tolerating LPC at a level up to 20 µg/ml, but the lca1Δ mutant displayed hypersensitivity to lyso-PAF at a concentration above 5 µg/ml. Moreover, its sensitivity to lyso-PAF was ameliorated by the expression of LCA1. In contrast, slc1Δ strain could survive and grew well on lyso-PAF plate without any apparent difference from WT cells, indicating SLC1 disruption did not affect lyso-PAF acylation.

$Zn^{2+}$ inhibitory effect on LPCAT activity: $Zn^{2+}$ caused significant reduction of LPCAT activity of LCA1 in a range between 0.1 mM to 20 mM (Table 1). Our results also suggested that a lower (10-25 µM) concentration of $Zn^{2+}$ enhanced LPCAT activity. The maximum increase was observed with 25 µM $ZnCl_2$. We did not detect significant effect of $Mg^{2+}$ on LPCAT activity of LCA1, in a concentration ranging from 5 to 40 µM (data not shown).

Figure 13:
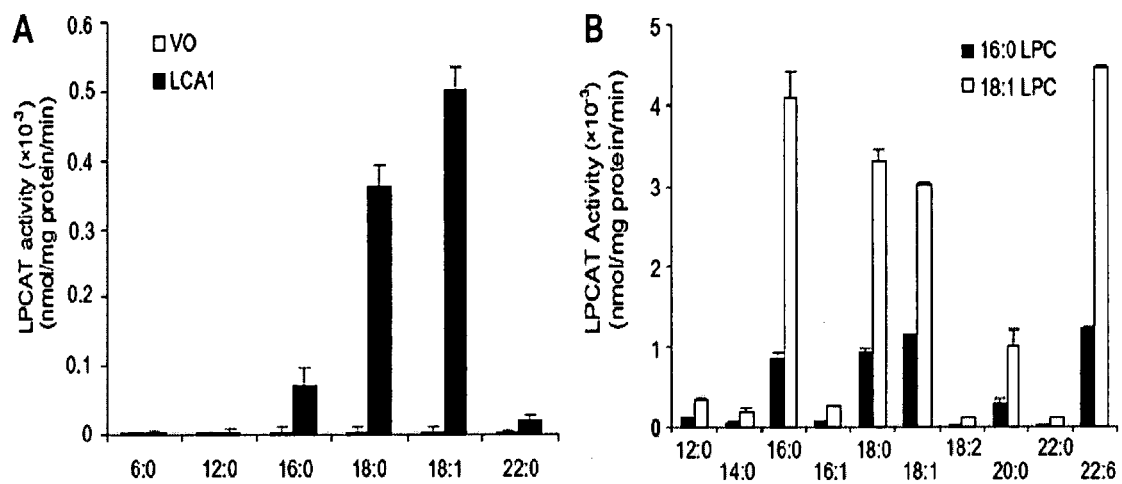
FIG. 13 depicts two graphs showing substrate preference of LCA1. A. Acyl-CoA substrate preference. Assays were performed with 3 μg microsomal protein from lca1Δ harboring an empty vector (V0) and lca1Δ expressing LCA1, with 112.5 μM [$^{14}$C] palmitoyl-CoA (1.35 nCi/nmol) and 50 μM acyl-CoA species. B. LPC substrate preference. Assays were performed with 3 μg microsomal protein, 112.5 μM [$^{14}$C] palmitoyl-CoA (5.5 nCi/nmol) and 50 μM lysophospholipid species. The values for lca1Δ are not shown. The results are presented as a mean of three assays.

Kinetic parameters of LCA1: Kinetics constants based on Lineweaver-Burk double-reciprocal plot analysis showed that LCA1 had an apparent Km for acyl-CoA at 0.89±0.25 µM and a Vmax of 524 pmol/min/µg protein. PC molecules are distinguished by fatty acid chain length. As shown in FIG. 13 (in graph A), LCA1 exhibited a LPC substrate preference in the order of oleic (18:1)-LPC>stearic (18:0)-LPC>palmitic (16:0)-LPC. The fatty acid substrate specificity of the LCA1 was also assessed using acyl-CoA with chain lengths ranging from 14 to 22 carbons. Based on assays using 50 µM acyl-CoAs, LCA1 could use a broad range of acyl-CoAs (FIG. 13, in graph B), but it displayed particularly high activities with 16:0-CoA, 18:0-CoA and 18:1-CoA, regardless whether 18:1-LPC or 16:0-LPC was used as acyl acceptor. Interestingly, LCA1 could also efficiently mediate LPC acylation using very long chain fatty acyl-CoAs, such as 20:0-CoA and 22:6-CoA. LPC (16:0) at concentrations above 75 µM, and acyl-CoA at higher than 10 µM, exerted inhibitory effects on LPCAT activity (data not shown).

Figure 14:
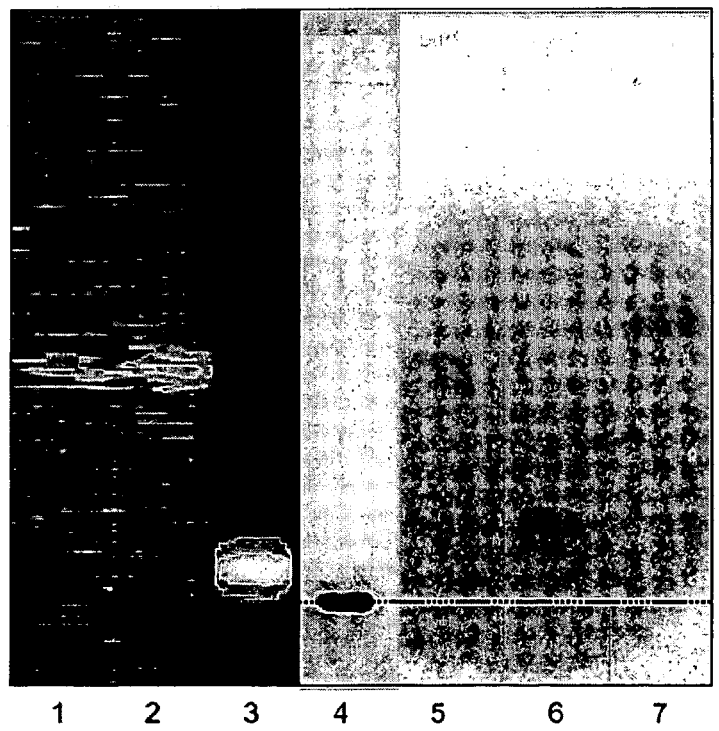
FIG. 14 depicts a TLC pattern of choline-containing compounds in the TCA fraction for PC turnover assessment. Samples were chromatographed and visualized on MERCK® Silica Gel G60 plate as described herein. Lane 1, TCA fraction of WT yeast; lane 2, TCA fraction of lca1Δ yeast; lane 3, [14C] choline; lane 4, palmitoleoyl-LPC; lane 5, GroPC; lane 6, phosphocholine; and lane 7, CDP-choline. Dashed line indicated sample origin.

LCA1 is involved in PC turnover: We studied PC turnover by following an established protocol [13]. We included a slc1Δ strain in the PC turnover analysis in order to differentiate the involvement of SLC1 and LCA1. The yeast cells were cultured and labeled in chemically defined synthetic medium containing [$^{14}C$] choline at 28° C. Because higher growth temperature particularly accelerates the deacylation process [13], [$^{14}C$] choline was subsequently chased by 10 mM exogenously added choline at 28° C. and 37° C., respectively. The $^{14}C$ labels in the membrane fraction, intracellular non-membrane fraction, and in the medium were monitored at different time points. There was no significant difference with regard to the dynamics of membrane-associated labels between slc1Δ and WT. Each lost about 8% at 28° C., and 25% at 37° C. of labeling, in the membrane fraction over the course of 2 hours. In contrast, the lca1Δ strain lost 18% at 28° C., and 33% at 37° C., over the same period of time. The label was rising in the intracellular, non-membrane fraction, which was suggested to be of mainly glycerophosphorylcholine (GroPC) [13, 24], a product of PC deacylation. We attempted to separate the compounds in TCA fraction on Merck silica G60 plate and found only one [$^{14}C$]-choline band detected. We then purified the choline-containing compound in TCA fractions and developed on the same TLC plate with commercial choline-containing chemical standards. The compound clearly showed the same migration rate as GroPC (FIG. 14). Since an increased GroPC level was observed in both 28° C. and 37° C., these results suggested that the metabolic impact was independent of PC deacylation, therefore strongly suggesting that lca1Δ was compromised in the reacylation process of the Lands' cycle. That slc1Δ had a similar PC turnover rate to that of the WT strain indicated that, although being a major sn-2 acyltransferase, SLC1 did not appear to play a significant role in PC turnover.

Example 2

Identification of Plant Nucleotide Sequences Encoding LPC Acyltransferase

The nucleotide sequence of the yeast LPC acyltransferase gene was used to search for homologous sequences using computer programs designed to search for homologous sequences. For instance, readily commercially available computer programs that may be used for such searches include without limitation, BLASTN, BLASTX and TBLASTX which may be used to search for nucleotide sequences, and BLASTP and TBLASTN which may be used to search for amino acid sequences. Such computer programs are readily accessible at the web-site WorldWideWeb.ncbi.nlm.nih.gov.

Two plant (A. thaliana) homologs were identified through sequence alignment searching using BLAST. The two homologs are cDNA sequences that encode two different isoforms of LPC acyltransferase.

```
Arabidopsis LPC acyltransferase 1
Nucleotide sequence of Arabidopsis LPC acyltransferase 1
cDNA is SEQ ID NO: 3:
    1 ACCAACAACC ACACGACACG ACACGACCGA TCTATAGATT CGGCGAGATC
   51 AGAAGAAAGC TTCCCGGAGC AACTCGGTCG TTGTGACTCA TTCCGAGTTA
  101 AAAAAAACGG GTTTTCGACA CCATGGATAT GAGTTCAATG GCTGGTTCAA
  151 TCGGAGTTTC GGTAGCCGTA CTCCGATTCC TCCTCTGTTT CGTTGCCACG
  201 ATCCCTGTTT CATTCGCTTG TCGAATCGTC CCGAGTAGAC TCGGTAAACA
  251 CTTGTATGCC GCTGCTTCAG GTGCTTTCCT CTCTTACCTC TCCTTTGGCT
  301 TCTCCTCCAA CCTTCACTTC CTTGTTCCGA TGACGATCGG ATATGCTTCA
  351 ATGGCGATTT ATAGACCCAA GTGTGGAATC ATCACTTTCT TCCTCGGTTT
  401 CGCTTATCTT ATTGGCTGTC ATGTGTTTTA TATGAGTGGT GATGCGTGGA
  451 AAGAAGGAGG AATCGATTCT ACTGGAGCGT TAATGGTGTT GACGCTGAAA
  501 GTCATCTCAT GTTCAATGAA TTACAATGAT GGGATGTTGA AGGAGGAAGG
  551 TCTACGTGAA GCTCAGAAGA AAAACAGATT GATTCAGATG CCGTCTTTGA
  601 TTGAGTACTT TGGTTACTGC CTTTGTTGTG GTAGCCATTT TGCTGGTCCT
  651 GTTTATGAAA TGAAAGATTA TCTTGAATGG ACCGAAGGGA AAGGGATTTG
  701 GGATACTACT GAGAAAAGAA AGAAGCCATC GCCTTATGGA GCTACAATCC
  751 GAGCTATTTT GCAAGCTGCG ATTTGCATGG CTCTGTATCT CTATTTAGTG
  801 CCTCAATATC CGTTAACTCG GTTCACAGAA CCAGTGTATC AAGAATGGGG
  851 ATTCTTGAGA AAATTTAGTT ACCAATACAT GGCTGGATTC ACGGCTCGTT
  901 GGAAGTATTA CTTCATCTGG TCAATTTCAG AGGCTTCTAT TATCATCTCT
  951 GGTTTGGGTT TCAGTGGTTG GACTGATGAT GCTTCACCAA AGCCCAAATG
 1001 GGACCGTGCC AAGAACGTAG ATATTCTCGG TGTTGAACTA GCTAAGAGCG
 1051 CGGTTCAGAT TCCACTTGTG TGGAACATAC AAGTCAGCAC GTGGCTCCGT
 1101 CACTATGTGT ATGAGAGACT TGTGCAGAAC GGAAAGAAAG CGGGTTTCTT
 1151 CCAGTTACTA GCTACACAAA CCGTCAGCGC GGTTTGGCAT GGACTGTATC
 1201 CTGGATATAT GATGTTCTTT GTTCAGTCAG CTTTGATGAT CGCAGGCTCA
 1251 CGGGTTATTT ACCGGTGGCA ACAAGCGATC AGTCCGAAAA TGGCAATGCT
 1301 GAGAAATATA ATGGTCTTCA TCAACTTCCT TTACACTGTT TTGGTTCTCA
```

-continued
```
1351 ACTACTCAGC CGTCGGTTTC ATGGTGTTAA GCTTGCACGA AAACACTTACC
1401 GCCTACGGAA GCGTATATTA CATTGGAACA ATCATACCTG TTGGATTGAT
1451 TCTCCTCAGT TACGTTGTGC CTGCAAAACC TTCAAGACCA AAACCGCGTA
1501 AAGAAGAATA AGCAGTTATC TTCTTCTCTT AACGGTAAGT AAGTTTCCCG
1551 CGCTTGCCAG CTTCTTCTTC TTCTTCTGTA ACATTTGGAA ACAAACCGAT
1601 CCGGTTCTTG TTTCTCTCTG ATTTTTTAGC ACCGATATTT TTTTTGTATT
1651 TGTTGCTTAT AAATCTTATT TTTCACACTT CTTTTTTTTA ATTAGTATTG
1701 GATTTGCAAT TATATAGACA ATAAGTATAA ATATGTAACT GTAAATTGCA
1751 AATGGGAAAA AATAGTAGTG TTTATGTTTG The deduced amino acid sequence of Arabidopsis LPC
acyltransferase 1 is SEQ ID NO: 4:
  1 MDMSSMAGSI GVSVAVLRFL LCFVATIPVS FACRIVPSRL GKHLYAAASG
 51 AFLSYLSFGF SSNLHFLVPM TIGYASMAIY RPKCGIITFF LGFAYLIGCH
101 VFYMSGDAWK EGGIDSTGAL MVLTLKVISC SMNYNDGMLK EEGLREAQKK
151 NRLIQMPSLI EYFGYCLCCG SHFAGPVYEM KDYLEWTEGK GIWDTTEKRK
201 KPSPYGATIR AILQAAICMA LYLYLVPQYP LTRFTEPVYQ EWGFLRKFSY
251 QYMAGFTARW KYYFIWSISE ASIIISGLGF SGWTDDASPK PKWDRAKNVD
301 ILGVELAKSA VQIPLVWNIQ VSTWLRHYVY ERLVQNGKKA GFFQLLATQT
351 VSAVWHGLYP GYMMFFVQSA LMIAGSRVIY RWQQAISPKM AMLRNIMVFI
401 NFLYTVLVLN YSAVGFMVLS LHETLTAYGS VYYIGTIIPV GLILLSYVVP
451 AKPSRPKPRK EE Arabidopsis LPC acyltransferase 2
Nucleotide sequence of Arabidopsis LPC acyltransferase 2
cDNA is SEQ ID NO: 5:
   1 AGATGTCCGA ACTGTGAGAG TCGTCGTCGT CGTCGTAACT CAGTCCGAGT
  51 TGACACAATC TTCCACTTCA CGCAAGATAC AACCATGGAA TTGCTTGACA
 101 TGAACTCAAT GGCTGCCTCA ATCGGCGTCT CCGTCGCCGT TCTCCGTTTC
 151 CTCCTCTGTT TCGTCGCAAC GATACCAATC TCATTTTTAT GGCGATTCAT
 201 CCCGAGTCGA CTCGGTAAAC ACATATACTC AGCTGCTTCT GGAGCTTTCC
 251 TCTCTTATCT CTCCTTTGGC TTCTCCTCAA ATCTTCACTT CCTTGTCCCA
 301 ATGACGATTG GTTACGCTTC AATGGCGATT TATCGACCCT TGTCTGGATT
 351 CATTACTTTC TTCCTAGGCT TCGCTTATCT CATTGGCTGT CATGTGTTTT
 401 ATATGAGTGG TGATGCTTGG AAAGAAGGAG GAATTGATTC TACTGGAGCT
 451 TTGATGGTAT TAACACTGAA AGTGATTTCG TGTTCGATAA ACTACAACGA
 501 TGGAATGTTG AAAGAAGAAG GTCTACGTGA GGCTCAGAAG AAGAACCGTT
 551 TGATTCAGAT GCCTTCTCTT ATTGAGTACT TTGGTTATTG CCTCTGTTGT
 601 GGAAGCCATT TCGCTGGCCC GGTTTTCGAA ATGAAAGATT ATCTCGAATG
 651 GACTGAAGAG AAAGGAATTT GGGCTGTTTC TGAAAAGGA AAGAGACCAT
 701 CGCCTTATGG AGCAATGATT CGAGCTGTGT TCAAGCTGC GATTTGTATG
 751 GCTCTCTATC TCTATTTAGT ACCTCAGTTT CCGTTAACTC GGTTCACTGA
 801 ACCAGTGTAC CAAGAATGGG GATTCTTGAA GAGATTTGGT TACCAATACA
 851 TGGCGGGTTT CACGGCTCGT TGGAAGTATT ACTTTATATG GTCTATCTCA
 901 GAGGCTTCTA TTATTATCTC TGGTTTGGGT TTCAGTGGTT GGACTGATGA
 951 AACTCAGACA AAGGCTAAAT GGGACCGCGC TAAGAATGTC GATATTTTGG
1001 GGGTTGAGCT TGCCAAGAGT GCGGTTCAGA TTCCGCTTTT CTGGAACATA
1051 CAAGTCAGCA CATGGCTCCG TCACTACGTA TATGAGAGAA TTGTGAAGCC
1101 CGGGAAGAAA GCGGGTTTCT TCCAATTGCT AGCTACGCAA ACCGTCAGTG
1151 CTGTCTGGCA TGGACTGTAT CCTGGATACA TTATATTCTT TGTGCAATCA
1201 GCATTGATGA TCGATGGTTC GAAAGCTATT TACCGGTGGC AACAAGCAAT
1251 ACCTCCGAAA ATGGCAATGC TGAGAAATGT TTTGGTTCTC ATCAATTTCC
1301 TCTACACAGT AGTGGTTCTC AATTACTCAT CCGTCGGTTT CATGGTTTTA
1351 AGCTTGCACG AAACACTAGT CGCCTTCAAG AGTGTATATT ACATTGGAAC
1401 AGTTATACCT ATCGCTGTGC TTCTTCTCAG CTACTTAGTT CCTGTGAAGC
1451 CTGTTAGACC AAAGACCAGA AAAGAAGAAT AATGTTGTCT TTTTAAAAAA
1501 TCAACAACAT TTTGGTTCTT TTCTTTTTTT CCACTTGGAC CGTTTTATGT
1551 AAAACAAGAG AAATCAAGAT TTGAGGTTTT ATTCTTCTTC TCCTTCCCAA
1601 TTTTCGAAAA TGATTTTATT TTTTCTGATA TATATCTAAG CTAGTCCAAA
1651 GTCAACTCG The deduced amino acid sequence of Arabidopsis LPC
acyltransferase 2 is SEQ ID NO: 6:
  1 MELLDMNSMA ASIGVSVAVL RFLLCFVATI PISFLWRFIP SRLGKHIYSA
 51 ASGAFLSYLS FGFSSNLHFL VPMTIGYASM AIYRPLSGFI TFFLGFAYLI
101 GCHVFYMSGD AWKEGGIDST GALMVLTLKV ISCSINYNDG MLKEEGLREA
151 QKKNRLIQMP SLIEYFGYCL CCGSHFAGPV FEMKDYLEWT EEKGIWAVSE
201 KGKRPSPYGA MIRAVFQAAI CMALYLYLVP QFPLTRFTEP VYQEWGFLKR
251 FGYQYMAGFT ARWKYYFIWS ISEASIIISG LGFSGWTDET QTKAKWDRAK
301 NVDILGVELA KSAVQIPLFW NIQVSTWLRH YVYERIVKPG KKAGFFQLLA
351 TQTVSAVWHG LYPGYIIFFV QSALMIDGSK AIYRWQQAIP PKMAMLRNVL
401 VLINFLYTVV VLNYSSVGFM VLSLHETLVA FKSVYYIGTV IPIAVLLLSY
451 LVPVKPVRPK TRKEE
```

Figure 15:
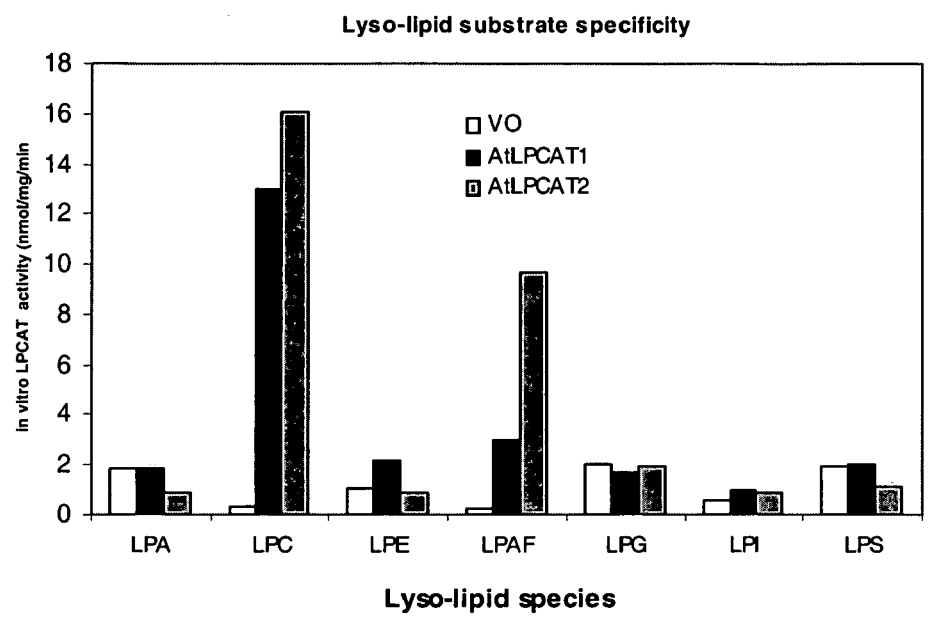
FIG. 15 is a graph illustrating lyso-lipid substrate specificity of AtLPCATs expressed in lca1Δ. The assays were preformed with 3 μg microsomal protein from lca1Δ harboring an empty vector (VO) and lca1Δ expressing AtLPCAT1 and AtLPCAT2. The reaction contained 45 μM [$^{14}$C] palmitoyl-CoA (5.5 nCi/nmol) and 45 μM Lysophospholipid substrate (LPA, LPC, LPE, LPG, LPI and LPS). The reaction was allowed for ten minutes with 100 rpm shaking. The results were presented as a mean of three assays.
Figure 16:
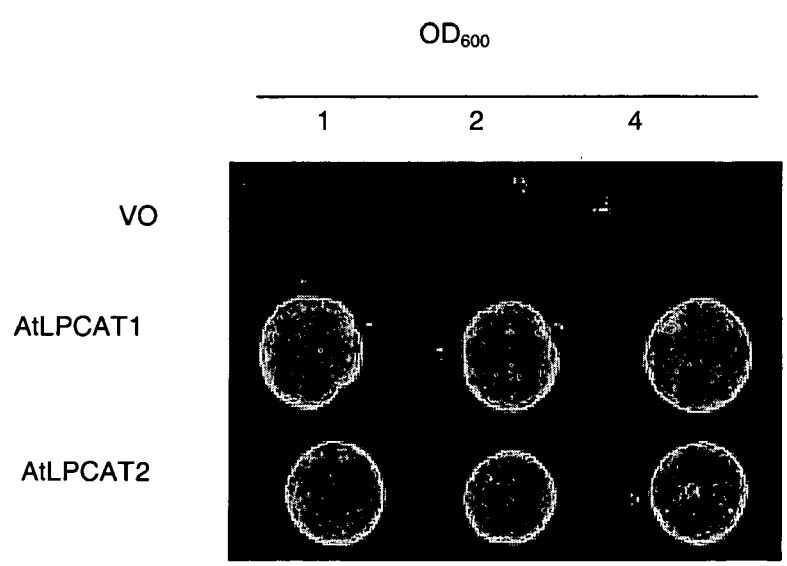
FIG. 16 depicts plates showing LysoPAF Sensitivity test of a yor175c mutant strain transformed with empty pYES2.1, pYES2.1::AtLPCAT1 and pYES2.1::LPCAT2. Cells were grown first in SC-URA+2% glucose media overnight then in protein expression induction media for six hours. Cultures were diluted to $OD_{600}$ value of $OD_{600}$=1, 2, 4, respectively, from which 5 μl was inoculated (from left to right) onto YPD plate containing Lyso-PAF or Lyso-PC. The plates were incubated at 28° C. for 36 hours.

AtLPCAT1 and AtLPCAT2 lysophospholipid acyltransferase activity was in vitro assessed with various lysophospholipid including lysophosphatidic acid ("LPA"), lysophosphatidylcholine ("LPC"), lysophosphatidylethanolamine ("LPE"), lysophosphatidylinositol ("LPI"), lysophosphatidylglycerol ("LPG"), lyso-platelet-activating factor as acyl group acceptor and [$^{14}$C]-palmitoyl-CoA as acyl group donor. Results clearly showed that lysophosphatidylcholine and lyso-platelet-activating factor were the most preferred lysophospholipid substrates (FIG. 15). Preference of LPCAT1 and LPCAT2 towards lyso-platelet-activating factor was also evidenced by lyso-PAF plate test (FIG. 16).

Figure 17:
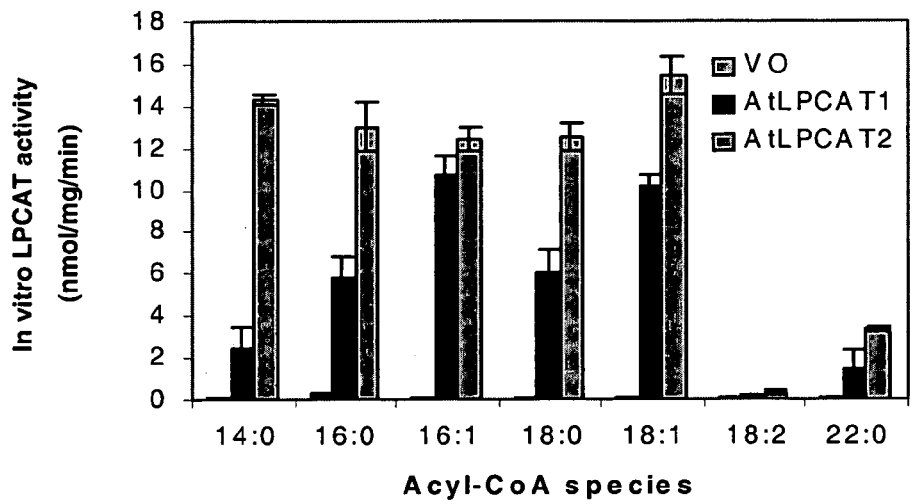
FIG. 17 is a graph depicting the Acyl-CoA preference assessment of AtLPCATs expressed in lca1Δ. Assays were preformed with 20 μg microsomal protein from lca1Δ harboring an empty vector (VO) and lca1Δ expressing AtLPCAT1 and AtLPCAT2, with 45 μM [$^{14}$C]palmitoyl-LPC (1.35 nCi/nmol) and 45 μM acyl-CoA species.

Acyl-CoA preference of AtLPCAT1 and AtLPCAT2 was assessed in vitro with various acyl-CoA species as acyl-group donor and [$^{16}$C]-palmitoyl-sn2-lysophosphatidylcholine as acyl-group acceptor. AtLPCAT1 preferred monounsaturated 16:1 and 18:1-acyl-CoA followed by 16:0 and 18:0-acyl-CoA. AtLPCAT2 similarly preferred 16:0, 16:1, 18:0 and 18:1-CoA. Comparatively, both AtLPCATs discriminated against 18:2 acyl-CoA as acyl group donor (FIG. 17).

Figure 18:
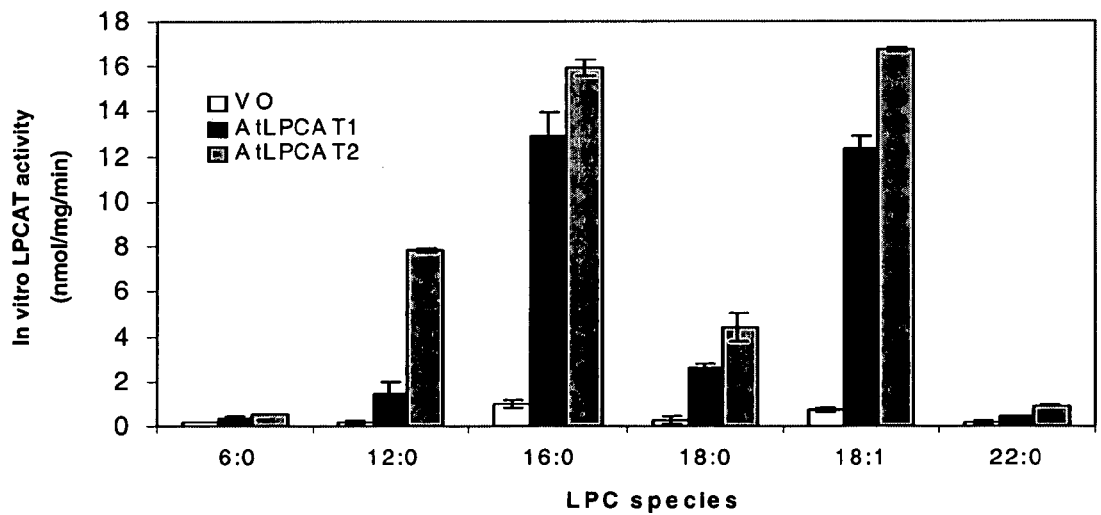
FIG. 18 is a graph depicting the LPC substrate preference of AtLPCATs expressed in lca1Δ. Assays were preformed with 20 μg microsomal protein, 45 μM [$^{14}$C]palmitoyl-CoA (5.5 nCi/nmol), 45 μM LPC species. The results were presented as a mean of three assays.

AtLPCAT1 and AtLPCAT2 preferences towards LPC species of different chain length were in vitro assessed with lysophosphatidylcholine of various chain lengths as acyl-group acceptor and [$^{14}$C]-palmitoyl-CoA as acyl-group donor. AtLPCAT1 and AtLPCAT2 both preferred 16:0 and 18:1-lysophosphatidylcholine (FIG. 18).

Figure 19:
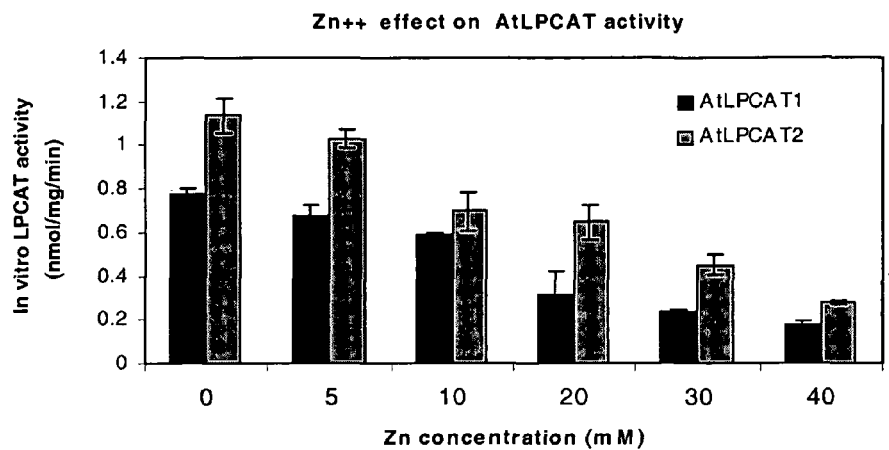
FIG. 19 is a graph depicting the inhibitory effect of $Zn^{2+}$ on AtLPCATs activity. The lca1Δ over-expressing AtLPCATs was used to assess $Zn^{2+}$ effect. The reactions contained 25 μM palmitoyl-LPC (1.35 nCi/nmol), 20 μg microsomal proteins, 0.1 M HEPES (pH 7.4), 25 μM stearyl-CoA and indicated concentration of $ZnCl_2$.

$Zn^{2+}$ sensitivity of AtLPCATs was investigated, activities of both AtLPCATs decreased with increasing concentration of $Zn^{2+}$ added into in vitro assay reactions (FIG. 19).

Example 3

Transformation of a Plant with LPC Acyltransferase Gene

Transformation protocol is adapted from that described by Bechtold et al. (1993). Plants are grown in moist soil at a density of 10-12 plants per pot, in 4-inch square pots, and are covered with a nylon screen fixed in place with an elastic band. When the plants reach the stage at which bolts emerge, plants are watered, the bolts and some of the leaves are clipped, and the plants are infiltrated in *Agrobacterium* suspension as outlined below.

*Agrobacterium* transformed with the LPC acyltransferase gene of the instant invention is grown in a 25 mL suspension in LB medium containing kanamycin at a concentration of 50 µg/mL. The *Agrobacterium* is cultured for two to three days. The day before infiltration, this "seed culture" is added to 400 mL of LB medium containing 50 µg/mL kanamycin. When the absorbance at 600 nm is >2.0, the cells are harvested by centrifugation (5,000 times g, ten minutes in a GSA rotor at room temperature) and are re-suspended in 3 volumes of infiltration medium (one times Murashige and Skoog salts, one times, B5 vitamins, 5.0% sucrose, 0.044 µM benzylaminopurine) to an optical density at 600 nm of 0.8. The *Agrobacterium* suspension is poured into a beaker and the potted plants are inverted into the beaker so that the bolts and entire rosettes are submerged. The beaker is placed into a large Bell jar and a vacuum is drawn using a vacuum pump, until bubbles form on the leaf and stem surfaces and the solution starts to bubble a bit, and the vacuum is rapidly released. The necessary time and pressure vanes from one lab setup to the next; but good infiltration is visibly apparent as uniformly darkened, water-soaked tissue. Pots are removed from the beaker, are laid on their side in a plastic tray and are covered with a plastic dome, to maintain humidity. The following day, the plants are uncovered, set upright and are allowed to grow for approximately four weeks in a growth chamber under continuous light conditions as described by Katavic et al. (1995). When the siliques are mature and dry, seeds are harvested and selected for positive transformants.

Example 4

Selection of Putative Transformants (Transgenic Plants) and Growth and Analysis of Transgenic Plants Seeds are harvested from vacuum-infiltration transformation procedures, and are sterilized by treating for one minute in ethanol and five minutes in 50% bleach/0.05% Tween™ 20™ in sterile distilled water. The seeds are rinsed several times with sterile distilled water. Seeds are plated by re-suspending them in sterile 0.1% agarose at room temperature (about 1 mL agarose for every 500-1000 seeds), and applying a volume equivalent to about 2,000-4,000 seeds onto 150×15 mm selection plates (½×Murashige and Skoog salts, 0.8% agar, autoclave, cool and add 1×B5 vitamins and kanamycin at a final concentration of 50 µg/mL). The plates are dried in a laminar flow hood until seed no longer flows when the plates are tipped. The plates are vernalized for two nights at 4° C. in the dark, and are moved to a growth chamber (conditions as described by Katavic et al., 1995). After seven to ten days, transformants are clearly identifiable as dark green plants with healthy green secondary leaves and roots that extend over and into the selective medium.

Seedlings are transplanted to soil, plants are grown to maturity and mature seeds ($T_2$ generation as defined in Katavic et al., 1994) are collected and analyzed. $T_2$ seeds are propagated. The vegetative growth patterns are monitored by measuring shoot tissue dry weights, and/or by counting the number of rosette leaves present by the time plants began to enter the generative (flower initiation) stage. Floral initiation (beginning of generative phase of growth) is analyzed by recording, on a daily basis, the percentage of plants in which a flower bud first appears and/or the percentage of plants that are bolting (as described by Zhang et al., 1997). Data are reported in terms of percentage of plants flowering/bolting on a given day after planting (d.a.p.).

Example 5

Analysis of Fatty Acids

Cells or plants transformed with the LPC acyltransferase gene of the instant invention are grown to maturity and mature seeds are harvested. Fatty acids are extracted from the cells or plants transformed with the LPC acyltransferase gene. Normal-phase HPLC analysis is used to assay for the production of fatty acids in the transformed cells or plants.

Example 6

Analysis of LPCAT from Various Species (1) Identification of LPCAT from the Alga *Thalassiosira pseudonana*

We made use of the sequence information of LPCAT from *S. cerevisiae* (SEQ ID NO: 1) and identified a sequence coding for LPCAT from the alga *T. pseudonana*. This algal LPCAT shows 27% identity at the amino acid to the yeast LPCAT which is encoded by YOR175c.

The nucleotide and amino acid sequences of LPCAT from *T. pseudonana*

(a) The nucleotide sequence of LPCAT from the alga *T. pseudonana*

```
                                              (SEQ ID NO: 7)
ATGCGATTGTATTTGCAATTCAACTTATCCATCAATGATTATTGTCACTT
CTTCACAGTACCATCCTTTGTCAAAGAGGGCGTCGAGTCTCTCTGCATCC
ACCGGACAAGACGTCGAGACTCTCGAGTACCTCCTTGGTATGCTCATCTG
CTACCCCCTCGGAATGATCATGCTCGCTCTACCCTACGGAAAAGTAAAAC
ATCTCTTCTCCTTCATCCTCGGAGCCTTCCTACTTCAATTCACCATTGGT
ATCCAGTGGATTCATCACTTAATCTCCTCAATGATTGCCTACGTCATGTT
CCTCGTCCTTCCTGCCAAATTTGCCAAAACGGCAGTGCCTGTGTTTGCCA
TGATCTACATCACCGCGGGACATTTGCATCGTCAATACATCAATTATCTT
GGGTGGGATATGGACTTCACGGGGCCTCAGATGGTGCTTACGATGAAACT
```

-continued
CTACATGCTTGCTTACAACCTTGCGGATGGGGACTTGCTCAAGAAGGGAA
AGGAGGATAGGGCTGCAAAGAAGTGTGCGGATGTCGCTATTTCGTCTGTT
CCCGGAATCATTGAGTACTTGGGCTACACGTTCTGCTTTGCCAGTGTTTT
AGCAGGCCCTGCTTTTGAGTACAAATTCTACGCCGATGCATGCGACGGAT
CACTCTTGTACGACAAATCTGGCAAACCCAAAGGAAAGATCCCCAGTCAG
GTGTGGCCTACATTGCGTCCTCTTTTTGGAAGTCTCTTGTGTCTCGGCAT
CTTTGTTGTGGGAACTGGAATGTATCCTCTTTTGGATCCCAACGATCCTC
AGAATGCCACTCCTATCCCTCTCACTCCAGAGATGTTGGCCAAACCAGCC
TATGCTCGATACGCTTACTCGTGGCTTGCACTCTTTTTCATCCGATTTAA
GTATTACTTTGCTTGGATGAACGCCGAAGGAGCAAGCAACATTTGGTATG
CTGGATTTGAGGGATTTGATGCCAGCGGCAACCCCAAAGGATGGGAGGTA
TCCAATAACATTGACGTAATTCAGTTCAGACTGCACCCAATCTCAAGAC
TTTGAGTGCTGCTTGGAATAAGAAGACTGCGAACTGGTTGGCGAAGTATG
TGTACATTCGCACGGGTGGTTCTCTCTTTGCGACGTACGGAATGAGTGCT
TTCTGGCATGGCTTGTACCCTGGATACTACCTCTTCTTCATGTCGGTACC
CATGATGGCTTTCTGTGAGAGGATTGGAAGGAAGAAACTTACACCTCGTT
TCGGAAATGGAAAGAAGTGGAGTCCTTATGGCATTGTGTGCATTATCGCC
ACATCGTTGATGACGGAATACATGATTCAGCCATTCCAACTACTTGCGTT
TGATTGGGCCTGGGAGAACTGGAGCAGCTACTACTTTGCTGGACACATTG
TTTGTGTTGTGTTTTACCTCGTTGTGTCCAACATGCCTACACCAAAGACG
AAGGAGACTTAA (b) The amino acid sequence of LPCAT from *T. pseud-
onana*

(SEQ ID NO: 8)
MRLYLQFNLSINDYCHFFTVPSFVKEGVESLSASTGQDVETLEYLLGMLI
CYPLGMIMLALPYGKVKHLFSFILGAFLLQFTIGIQWIHHLISSMIAYVM
FLVLPAKFAKTAVPVFAMIYITAGHLHRQYINYLGWDMDFTGPQMVLTMK
LYMLAYNLADGDLLKKGKEDRAAKKCADVAISSVPGIIEYLGYTFCFASV
LAGPAFEYKFYADACDGSLLYDKSGKPKGKIPSQVWPTLRPLFGSLLCLG
IFVVGTGMYPLLDPNDPQNATPIPLTPEMLAKPAYARYAYSWLALFFIRF
KYYFAWMNAEGASNIWYAGFEGFDASGNPKGWEVSNNIDVIQFETAPNLK
TLSAAWNKKTANWLAKYVYIRTGGSLFATYGMSAFWHGFYPGYYLFFMSV
PMMAFCERIGRKKLTPRFGNGKKWSPYGIVCIIATSLMTEYMIQPFQLLA
FDWAWENWSSYYFAGHIVCVVFYLVVSNMPTPKTKET (2) Identification of LPCAT from Diverse Plant Species Taking the same approach as described above, identified were the full-length or partial sequences of LPCAT from various plant species, including apple, barley, *Capsicum annuum*, castor bean, grapevine, maize, peach, rice, tomato, snapdragon, *sorghum*, sunflower, *vaccinium corymbosum* and wheat as well as *Arabidopsis*.

(a) The partial nucleotide sequence of LPCAT from apple (SEQ ID NO: 9)
TCAGGAGGCCCAAATTTCCTTTGTCAAGATTTACTGAGCCCATATACCAA
GAATGGGGGTTTTGGAAACGACTTTTCTACCAGTATATGTCTGGATTCAC
AGCAAGGTGGAAATATTATTTCATTTGGTCAATATCAGAGGCTTCTATCA
TTCTTTCTGGCCTCGGTTTCAGTGGCTGGACAGAGTCCTCACCACCAAA
CCTCGATGGGATCGTGCAAAAAATGTTGATATTATAGGCGTTGAGTTTGC
AAAGAGTTCAGTTCAGTTACCACTTGTTTGGAACATACAAGTCAGCACCT
GGCTTCGCCATTATGTTTATGATAGGCTTGTTAAACCTGGAAAGAAGCCT
GGTTTCTTCCAGTTGCTGGCTACACAGACCGTCAGTGCTGTTTGGCATGG
CCTCTATCCTGGCTACATCATATTCTTTGTTCAGTCAGCGTTGATGATTG
CTGGATCAAGAGTGATTTACCGATGGCAGCAAGCTGTACCTCCAACTATG
GATGTTGTTAAGAAGATATTGGTGTTCATCAACTTTGCTTACACTGTCTT
GGTTCTGAACTACTCCTGTGTTGGTTTCATTGTATTAAGCCTTCGTGAAA
CACTGGCCTCGTATGGAAGCGTGCATTTC The partial amino acid sequence of LPCAT from apple (SEQ ID NO: 10)
RRPKFPLSRFTEPIYQEWGFWKRLFYQYMSGFTARWKYYFIWSISEASII
LSGLGFSGWTESSPPKPRWDRAKNVDIIGVEFAKSSVQLPLVWNIQVSTW
LRHYVYDRLVKPGKKPGFFQLLATQTVSAVWHGLYPGYIIFFVQSALMIA
GSRVIYRWQQAVPPTMDVVKKILVFINFAYTVLVLNYSCVGFIVLSLRET
LASYGSVHF (b) The partial amino acid sequence of LPCAT from barley (SEQ ID NO: 11)
EAAIIISGLGFTGWSDSSPPKAKWDRAINVDILGVELAGSAAQLPLKWNI
QVSTWLRYYVYERLIQKGKKPGFLQLLGTQTVSAIWHGLYPGYMIFFVQS
ALMINGSKVIYRWQQAVKQFRPPHYPVFTKLLHTP (c) The partial nucleotide sequence of LPCAT from *Capsicum annuum*

(SEQ ID NO: 12)
GGCACGAGAAACGGTTGGGTTACCAATATATGGCTGGCTTTACTGCCCGG
TGGAAGTATTATTTTATCTGGTCAATCTCTGAAGCTGCTATAATCATATC
TGGACTGGGTTTCAGTGGTTGGACAGACTCTTCTCCGCCAAAACCACGTT
GGGACCGTGCAAAAAATGTTGATGTATTGGGTGTTGAGTTAGCAAAGAGC
TGGGTTCAGTTGCCTGCTGTCTGGAACATTCAAGTCAGCACATGGCTGCG
GCATTATGTATATGAAAGGCTCATACAAAAGGGAAGGAAGCCTGGTTTCT
TCCAGTTACTGGCTACCCAAACTGTCAGTGCCGTATGGCATGGATTATAT
CCTGGGTATATCATATTCTTTGTACAGTCCGCTTTGATGATTGCTGGATC
AAGAGTCCTTTACAGATGGCAGCAAGCTGCTAAAGGTTCTATGTTTGAGA
AGATACTGGTAGCAATGAATTTTGCATACACACTGCTGGTTCTAAATTAC
TCCGCTGTTGGGTTCATGGTATTAAGCCTGCATGAAACTCTTACTGCTTA
TGGAAGTGTATACTATGTTGGAACAATTATACCAATTGCTCTCATCCTGC
TCAGTAAAGTAATTAAGCCTCCAAGACCCTGCACATCTAAAG

The partial amino acid sequence of LPCAT from *Capsicum annuum*

(SEQ ID NO: 13)
HEKRLGYQYMAGFTARWKYYFIWSISEAAIIISGLGFSGWTDSSPPKPRW
DRAKNVDVLGVELAKSSVQLPAVWNIQVSTWLRHYVYERLIQKGRKPGFF
QLLATQTVSAVWHGLYPGYIIFFVQSALMIAGSRVLYRWQQAAKGSMFEK
ILVAMNFAYTLLVLNYSAVGFMVLSLHETLTAYGSVYYVGTIIPIALILL
SKVIKPPRPCTSK (d) The partial nucleotide sequence of LPCAT from castor bean (SEQ ID NO: 14)
ATTCATTTATACTTGGTGCCCCACTATCCTTTATCCCGGTTCACTGATCC
TGTGTACCAAGAATGGGGCTTCTGGAAACGATTAACTTATCAGTATATGT
CAGGTTTAACAGCACGTTGGAAATACTACTTCATCTGGTCAATTTCCGAG
GCCTCCATTATTATCTCTGGATTGGGTTTCAGTGGTTGGACAGATACTTC
TCCACCAAAGCCACAGTGGGATCGCGCTAGAAACGTTGACATTCTAGGTG
TTGAGTTTGCAAAGAGTGCAGCTGAGTTGCCACTTGTGTGGAACATACAA
GTCAGCACATGGCTTCGCCACTATGTTTATGATCGACTTGTTCCAAAGGG
AAAGAAAGCTGGTTTCCTTCAGTTGTTGGCCACTCAGACTACCAGTGCTG
TTTGGCATGGATTATATCCTGGATACATTATATTCTTTGTCCAGTCAGCA
TTAATGATTGCAGGTTCGAAAGTCATATACAGATGGCAACAAGCTATACC
TTCAAATAAGGCTCTTGAAAAGAAGATACTAGTGTTTATGAACTTTGCTT
ACACAGTTTTGGTTCTAAATTACTCCTGTGTTGGTTTCATGGTTTTAAGC
TTGCATGAAACGATTGCAGCATATGGAAGTGTATATTTTATTGGCACCAT
AGTGCCCGTTGTATTTTTCCTCCTTGGCTTCATTATTAAACCAGCAAGGC
CTTCCAGGTCTAAACACGGAACGATGAGTGAGGTAGAAACTGTTTTTCTT
CTCCTT The partial amino acid sequence of LPCAT from castor bean (SEQ ID NO: 15)
IHLYLVPHYPLSRFTDPVYQEWGFWKRLTYQYMSGLTARWKYYFIWSISE
ASIIISGLGFSGWTDTSPPKYQWDRARNVDILGVEFAKSAAELPLVWNIQ
VSTWLRHYVYRLVPKGKKAGFLQLLATQTTSAVWHGLYPGYIIFFVQSAL
MIAGSKVIYRWQQAIPSNKALEKKILVFMFAYTVLVLNYSCVGFMVLSLH
ETIAAYGSVYFIGTIVPVVFFLLGFIIKPARPSRSKHGTMSEVETVFLLL (e) The partial nucleotide sequence of LPCAT from grapevine (SEQ ID NO: 16)
CTCGTCCAATCTCCACTTCCTCGTTCCCATGCTTCTTGGCTACGCGGCTA
TGCTTCTCTGTCGCCGTCGATGCGGTGTGATCACCTTTTTCTTGGGATTC

```
GGCTACCTCATTGGCTGCCATGTATACTACATGAGTGGGGATGCATGGAA
GGAAGGGGGTATTGATGCTACTGGAGCTCTAATGGTTTTAACATTGAAAG
TCATTTCATGTGCAATGAATTATAATGATGGATTGTTAAAAGAAGACGGT
TTGCGTGAGGCACAGAAGAAAAACCGATTGCTTAAGTTACCATCATTGAT
CGAGTACTTTGGTTATTGTCTCTGCTGTGGAAGTCACTTTGCTGGACCAG
TTTATGAAATAAAGGATTATCTTGAATGGACAGAAAGAAAAGGGATTTGG
GCCAAATCAGAGAAAGGGCCACCACCATCACCTTATGGGGCAACGATTCG
AGCTCTTATCCAAGCTGCCTTTTGCATGGGCTTGTATGTGTATCTAGTAC
CCCATTTTCCCTTGACCATATTTACTGATCCTGTATATCAAGAATGGGGC
TTCTGGAAACGGTTGGGATACCAATATATGTGTGGCTTTACAGCACGCTG
GAAATACTATTTCATCTGGTCAATCTCTGAGGCAGCTGTCATTATTTCTG
GCCTGGGATTCAGTGGGTGGACAGAATCTTCCCCACCAAAACCAAAATGG
GACCGTGCAAAGAATGTTGACATTTTAGGTGTTGAGTTGGCAAAGAGTGC
AGTAACACTGCCACTTGTTTGGAACATACAAGTCAGCACCTGGCTACGTT
ATTATGTTTATGAGAGGCTCATTCAAAATGGGAAGAAACCTGGTTTCTTC
CAGTTGCTGGCTACACAAACTGTCAGTGCTGTTTGGCATGGATTATATCC
TGGATACATCATATTCTTTGTTCAGTCTGCACTGATG
```

The partial amino acid sequence of LPCAT from grapevine (SEQ ID NO: 17)
SSNLHFLVPMLLGYAAMLLCRRRCGVITFFLGFGYLIGCHVYYMSGDAWK
EGGIDATGALMVLTLKVISCAMNYNDGLLKEDGLREAQKKNRLLKLPSLI
EYFGYCLCCGSHFAGPVYEIKDYLEWTERKGIWAKSEKGPPPSPYGATIR
ALIQAAFCMGLYVYLVPHFPLTIFTDPVYQEWGFWKRLGYQYMCGFTARW
KYYFIWSISEEAAVIISGLGFSGWTESSPPKPKWDRAKNVDILGVELAKSA
VTLPLVWNIQVSTWLRYYVYERLIQNGKKPGFFQLLATQTVSAVWHGLYP
GYIIFFVQSALM (f) The partial nucleotide sequence of LPCAT from maize (SEQ ID NO: 18)
```
CATTTCGTGTCTCATAAACTACAGTGATGGTATCTTGAAGGAAGAGGGTT
TACGCGATGCTCAGATTAAACACCGATTGACTAAGCTTCCTTCTCTAATT
GAATATTTTGGGTACTGTCTCTGTTGTGGGAGCCACTTTGCTGGACCGGT
ATATGAGATGAAAGATTATCTTGAATGGACTGAAAGGAAAGGAATATGGG
CTAGCCCAACTCCTTCGCCATTGTTACCTACTTTGCGTGCTCTAGTTCAG
GCTGGTATATGCATGGGGTTATATTTATACCTGTCACCTAAATTTCCACT
CTCACGGTTTAGTGAGCCCTATATTATGAATGGGGTTTTTGGCACCGAC
TCTTCTATCAGTACATGTCAGGCTTTACCGCTCGTTGGAAATATTACTTT
ATATGGTCAATTTCAGAAGCCTCAATTATCATATCTGGTCTAGGCTTTAC
TGGTTGGTCGGAATCTTCTCCCCCAAAAGCCAAATGGGATCGTGCAAAA
ATGTTGATGTATTAGGTGTTGAATTAGCTGGAAGTTCAGTTCAATTGCCC
CTTGTGTGGAATATTCAAGTGAGCACATGGCTACGATACTATGTCTATGA
GAGGTTAATTCAGAAAGGAAAGAAACCAGGTTTCCTTCAATTGTTGGGTA
CACAGACAGTCAGTGCCATCTGGCATGGACTATATCCTGGATATATCATA
TTCTTTTTTTTCATCAGCATTGATGATNAATGGTTCACGAGTTATATACAG
ATGGCAGCAAGCAGCGAGCAGTTCATTCCTGAGCGGTATCCTGGCCCTTC
TAATTTTGCTATACATTGCTGGGGCTTACTACTCCTGCATCGGGGTCCAG
GTACTGAGCTTCAA
```

The partial amino acid sequence of LPCAT from maize (SEQ ID NO: 19)
ISCLINYSDGILKEEGLRDAQIKHRLTKLPSLIEYFGYCLCCGSHFAGPV
YEMKDYLEWTERKGIWASPTPSPLLPTLRALVQAGICMGLYLYLSPKFPL
SRFSEPLYYEWGFWHRLFYQYMSGFTARWKYYFIWSISEASIIISGLGFT
GWSESSPPKAKWDRAKNVDVLGVELAGSSVQLPLVWNIQVSTWLRYYVYE
RLIQKGKKPGFLQLLGTQTVSAIWHGLYPGYIIFFFSSALMXNGSRVIYR
WQQAASSSFLSGILALLILLYIAGAYYSCIGVQVLSF (g) The partial nucleotide sequence of LPCAT from peach (SEQ ID NO: 20)
```
AAATATTATTTCATCTGGTCAATTTCAGAGGCTTCTATCATTCTTTCTGG
TTTGGGTTTCACTGGCTGGACAGAATCTTCACCACCAAAGCCGCGATGGG
ATCGTGCAAAAAATGTTGATATTCTAGGCGTTGAGTTTGCAAAGAGTTCA
GTTCAGTTACCACTTGTTTGGAACATACAAGTCAGCACCTGGCTACGTCA
TTATGTTTATGAAAGGCTTGTTAAACCTGGCAAGAAGGCTGGTTTCTTCC
AGTTGCTGACTACACAGACCGTCAGTGCGGTTTGGCATGGACTCTATCCT
GGGTACATCATATTCTTTGTTCAGTCAGCATTGATGATTGCTGGTTCAAG
AGTGATTTACAGATGGCAACAAGCTGTACCTCAAAACATGGATGCTGTTA
AGAACATACTGGTGTTCATAAACTTTGCTTACACTCTCTTGGTTCTGAAC
TACTCCTGCGTTGGTTTCATTGTATTAAGCCTTCGTGAAACACTTGCCTC
ATATGGGAGCGTGCATTTCATCGGAACCATTCTTCCGATAGCATTGATAC
TACTGAGTTACGTAATAAAACCTCCAAGGCCTGCAAGATCAAAGGCTCGG
AAGGAAGAGTGAGGTTGTCANCCGCAACAGCATTTTTAACG
```

The partial amino acid sequence of LPCAT from peach (SEQ ID NO: 21)
KYYFIWSISEASIILSGLGFTGWTESSPPKPRWDRAKNVDILGVEFAKSS
VQLPLVWNIQVSTWLRHYVYERLVKPGKKAGFFQLLTTQTVSAVWHGLYP
GYIIFFVQSALMIAGSRVIYRWQQAVPQNMDAVKNILVFINFAYTLLVLN
YSCVGFIVLSLRETLASYGSVHFIGTILPIALILLSYVIKPPRPARSKAR
KEE (h) The full-length or partial amino acid sequence of LPCAT from rice Sequence 1 (accession number Os02g0676000
(SEQ ID NO: 22))
MGLEMEGMAAAIGVSVPVLRFLLCFAATIPTGLMWRAVPGAAGRHLYAGL
TGAALSYLSFGATSNLLFVVPMAFGYLAMLLCRRLAGLVTFLGAFGFLIA
CHMYYMSGDAWKEGGIDATGALMVLTLKIISCAINYSDGMLKEEGLRDAQ
KKYRLAKLPSLIEYFGYCLCCGSHFAGPVYEMKDYLEYTERKGLWASPTP
SPLLPTLRALVQAGACMGLYLYLSPQFPLSRFSEPLYYEWGFWHRLFYQY
MSGFTARWKYYFIWSLSEAAIIISGLGFSGWSDSSPPKAKWDRAKNVDVL
GVELATSAVQLPLMWNIQVSTWLRYYVYERLVQKGKKPGFLQLLGTQTVS
AVWHGLYPGYIIFFVQSALMINGSKVIYRWQQAVSNPVFHAILVFVNFSY
TLMVLNYSCIGFQVLSFKETLASYQSVYYIGTIVPIVVVLLGYVIKPARP
VKPKARKAE Sequence 2 (accession number EAY87053
(SEQ ID NO: 23))
MYYMSGDAWKEGGIDATGALMVLTLKIISCAINYSDGMLKEEGLRDAQKK
YRLAKLPSLIEYFGYCLCCGSHFAGPVYEMKDYLEYTERKGLWASPTPSP
LLPTLRALVQAGACMGLYLYLSPQFPLSRFSEPLYYEWGFWHRLFYQYMS
GFTARWKYYFIWSLSEAAIIISGLGFSGWSDSSPPKAKWDRAKNVDVLGV
ELATSAVQLPLMWNIQVSTWLRYYVYERLVQKGKKPGFLQLLGTQTVSAV
WHGLYPGYIIFFVQSALMINGSKVIYRWQQAVSNPVFHAILVFVNFSYTL
MVLNYSCIGFQVFTMLYTLRFLQVLSFKETLASYQSVYYIGTIVPIVVV
LLGYVIKPARPVKPKARKAE (i) The partial nucleotide sequence of LPCAT from snapdragon (SEQ ID NO: 24)
```
GCATTAATTACAACGATGGATTACTTAAAAAGGAAGATCTACGTGAGCCA
CAAAAGAAAAACCGCTTGCTCAAGATGCCATCATTACTTGAGTACATTGG
TTACTGTTTGTGTTGTGGAAGTCACTTTGCTGGTCCTGTGTATGAAATGA
AAGATTATCTTGAATGGACTGAGAGGAAAGGGATCTGGCAACATACAACC
AAGGGACCGAAACCTTCTCCGTATTGGGCGACTCTCAGGGCTATTTGCA
AGCTGCCATCTGTATGGGCTTGTATCTATATCTTGTACCACATTACCCAC
TTTCCAGATTCACGGAGCCAGAATACCAAGAGTATGGGTTCTGGAAACGG
TTAAGTTACCAGTACATGTCAGGCTTCACCGCTCGTTGGAAGTACTATTT
CATTTGGTCTATCTCAGAAGCTTCCATAATTATTTCTGGCCTGGGGTTCA
GTGGCTGGACAGATTCTGATCCACCCAAAGCACTGTGGGATCGTGCAAAA
AATGTTGATGTATTAGGTGTTGAGTTGGCAAAGAGTTCTGTGCAGTTACC
ACTTGTATGGAATATTCAAGTTAGCACCTGGCTTAAACACTATGTCTATG
AGAGGCTGGTTCAGAAAGGTAAGAAACCAGGCTTCTTCCAGTTGCTGGCT
ACCCAGACCGTGAGTGCAGTGTGGCATGGATTGTACCCTGGGTACATCAT
ATTCTTT
```

The partial amino acid sequence of LPCAT from snapdragon (SEQ ID NO: 25)
INYNDGLLKKEDLREPQKKNRLLKMPSLLEYIGYCLCCGSHFAGPVYEMK
DYLEWTERKGIWQHTTKGPKPSPYWATLRAILQAAICMGLYLYLVPHYPL
SRFTEPEYQEYGFWKRLSYQYMSGFTARWKYYFIWSISEASIIISGLGFS
GWTDSDPPKALWDRAKNVDVLGVELAKSSVQLPLVWNIQVSTWLKHYVYE
RLVQKGKKPGFFQLLATQTVSAVWHGLYPGYIIFF (j) The partial nucleotide sequence of LPCAT from sorghum (SEQ ID NO: 26)
GCACGAGGCTCTCACGGTTTAGTGAGCCCTTATATTATGAATGGGGTTTC
TGGCACCGACTCTTCTATCAGTACATGTCAGGCTTCACTGCTCGTTGGAA
ATATTACTTTATATGGTCAATTTCAGAAGCCTCAATTATCATATCTGGTC
TGGGCTTTACTGGTTGGTCAGAATCTTCTCCCCCGAAAGCCAAATGGGAT
CGTGCGAAAATGTTGATGTATTAGGTGTTGAATTAGCTGGAAGTGCAGT
TCAAATTCCCCTTGTGTGGAATATTCAAGTGAGCACATGGTTACGATACT
ATGTCTATGAGAGGCTAATTCAGAAAGGAAAGAAACCAGGTTTCCTTCAG
TTGTTGGGTACACAGACAGTCAGCGCCATCTGGCATGGACTGTATCCTGG
ATATATCATATTCTTTGTTCAGTCAGCATTGATGATAAATGGTTCACGAG
TTATATACAGATGGCAGCAAGCAGTGAGCAGTTCATTCCTCCGCGGTATC
CTGGCTTTTCTAAATTTTGCTTATACATTGCTGGTGCTTAACTACTCCTG
CATCGGGTTCCTGGTACTGAGCTTCAAAGAAACCTTGGCGTCCTACCAGA
GCGTATATTATGTTGGCACAATTGTTCCCATTGTGTTTCTCCTGCTGGGC
AAT The partial amino acid sequence of LPCAT from sorghum (SEQ ID NO: 27)
TRLSRFSEPLYYEWGFWHRLFYQYMSGFTARWKYYFIWSISEASIIISGL
GFTGWSESSPPKAKWDRAKNVDVLGVELAGSAVQIPLVWNIQVSTWLRYY
VYERLIQKGKKPGFLQLLGTQTVSAIWHGLYPGYIIFFVQSALMINGSRV
IYRWQQAVSSSFLRGILAFLNFAYTLLVLNYSCIGFLVLSFKETLASYQS
VYYVGTIVPIVFLLLGN (k) The partial nucleotide sequence of LPCAT from sunflower (SEQ ID NO: 28)
GAAAACCGCATACTTAAGTTGCCATCTTTAATCGAGTATGTGGGATATTG
CTTATGCTGCGGAAGTCACTTTGCTGGTCCGGTTTACGAAATCAAAGATT
ATTTGGATTGGACCGAAAGAAAGGGGATTTGGACAAGATCCGAGAAAGGC
ACACCATCACCATTTTTGCCAACACTACGAGCGATTCTCCAAGCGGGTTT
CTGTATGGGTTTGTATTTATATCTATCGCCTTCGTATCCGCTTTCAAGAT
TCAGTGAGCCGATATATCAAGAATGGGGATTTGTGAAACGTCTGACCGTC
CAATACATGTCGGGCTTCACCGCGCGTTGGAAATACTATTTCATTTGGTC
TATCTCAGAAGCTTCTATCATTATTTCGGGCTTCGGTTTCAGTGGCTGGA
CTGATTCTTCTCCACCAAAAGCCCGATGGGACCGTGCGAAAAACGTTGAC
GTTTTGGGTGTTGAGTTTGCAAAGAGTTCAGTTGAGTTACCACTCGTGTG
GAATATCCAAGTCAGCACATGGCTTCGTCACTATGTTTATGACAGACTTG
TTCAAAAGGGAAAGAAGCCTGGCTTTTTCCAATTGTTAGCAACACAGACT
GTTAGCGCTGTCTGGCATGGATTATATCCTGGGTACTTGATATTCTTTGT
TCAATCTGCTTTGATGATTTCCGGGTCAAGAGCCATTTACAGATGGCAGC
AGGCGGTTCCGCCAACCGTTAAGAAGTTTTTGATGCTCATGAACTTTGCT
TACACGCTTCTTGTTCTTAACTACTCCTGCATAGGTTTTATGGTATTAAG
CCTACACGAAACACTGGCTGCATACGGAAGTGTATACTACGTTGGAAACA
TCATTCCAGTGGCGT The partial amino acid sequence of LPCAT from sunflower (SEQ ID NO: 29)
ENRILKLPSLIEYVGYCLCCGSHFAGPVYEIKDYLDWTERKGIWTKSEKG
TPSPFLPTLRAILQAGFCMGLYLYLSPSYPLSRFSEPIYQEWGFVKRLTV
QYMSGFTARWKYYFIWSISEASIIISGFGFSGWTDSSPPKARWDRAKNVD
VLGVEFAKSSVELPLVWNIQVSTWLRHYVYDRLVQKGKKPGFFQLLATQT
VSAVWHGLYPGYLIFFVQSALMISGSRAIYRWQQAVPPTVKKFLMLMNFA
YTLLVLNYSCIGFMVLSHETLAAYGSVYYVGNIIPVA (l) The partial nucleotide sequence of LPCAT from tomato (SEQ ID NO: 30)
GGTATGGGGTTGTATCTCTATCTGGTGCCTCAGTTCCCACTTTCCAGGTT
CACTGAGTCAGTATACCACGAATGGGGTTTCTTCAAACGACTGGGTTACC
AATATATGGCTGGCTTTACTGCCCGGTGGAAATATTATTTTATTTGGTCA
ATCTCTGAAGCTTCTATAATCATATCTGGACTGGGTTTCAGTGGTTGGAC
AAACTCTTCTCCGCCAAAACCACGTTGGGACCGAGCAAAAAATGTTGATG
TATTGGGTGTTGAGTTAGCAAAGAGCTCGGTTCAGTTACCACTAGTATGG
AACATTCAAGTCAGCACATGGCTGCGGCATTATGTGTATGAAGGCTCGT
ACAGAAGGGAAGGAAGCCTGGTTTCTTCCAGTTGCTGGCTACCCAAACTG
TCAGTGCCGTTTGGCATGGATTATATCCTGGATACATCATATTCTTTGTT
CAGTCCGCTTTGATGATTGCTGGATCAAGAGTCATTTACAGATGGCAGCA AGCTACAAAAGGTACTATGTTTGAGAAGATACTGATAGCAATGAATTTTG
CATACACACTGCTGGTTCTAAACTACTCCGCTGTTGGATTCATGGTATTA
AGTCTGCATGAAACTCTTACTGCTTATGGAAGTGTATACTATATTGGAAC
AATTGTACCAATTCTTCTCATCCTGCTTAGTAAAGTGATTAAGCCTCCAA
GACCTGCGACGTCTAAAGCTAGGAAAGCAGAGTAAATCCAAGTCAGTT The partial amino acid sequence of LPCAT from tomato (SEQ ID NO: 31)
GMGLYLYLVPQFPLSRFTESVYHEWGFFKRLGYQYMAGFTARWKYYFIWS
ISEASIIISGLGFSGWTNSSPPKPRWDRAKNVDVLGVELAKSSWQLPLVW
NIQVSTWLRHYVYERLVQKGRKPGFFQLLATQTVSAVWHGLYPGYIIFFV
QSALMIAGSRVIYRWQQATKGTMFEKILIAMNFAYTLLVLNYSAVGFMVL
SLHETLTASYGSVYYWIGTIVPILLILLSKVIKPPRPATSKARKAE (m) The partial nucleotide sequence of LPCAT from Vaccinium corymbosum (SEQ ID NO: 32)
GGGGTTGGGTTACCAGTACATGGCTGGCTTTACAGCACGGTGGAAGTATT
ATTTCATTTGGTCAATCTCAGAAGCTTCCATCATCATTTCTGGCCTGGGG
TTCAGTGGTTGGACAGATTCTTCTCCACCAAAACCAAAATGGGACCGTGC
AAAGAATGTAGATATTTTGCGGGTTGAGTTTGCAAAGACTGCAGCTCAGA
TTCCACTTGCATGGAACATTCAAGTCAGCACCTGGCTACGCCATTATGTT
TATGAGAGGCTCGTGCAGAAGGGAAAGAAACCTGGTTTCTTTCAGTTGTT
GGCTACCCAGACTGTCAGTGCTGTTTGGCATGGTTTATATCCTGGATACA
TCATATTCTTTGTGCAGTCAGCATTGATGATTGCTGGTTCAAGAGTTATT
TATAGATGGCAGCAAGCTGTTCCTCCTAAAATGGATCTGGTGAAGAAAGT
ATTCGTACTTTTAAACTTTGCTTACACAGTTCTGGTGTTGAACTACTCCT
CTGTCGGTTTCATGGTACTAAGCCTACATGAAACAATTGTTGCATACGGG
AGCGTGTATTCGTTGGAACCATTGTTCCCATACTTGTAATCCTCCTTGGT
TACGTAATT The partial amino acid sequence of LPCAT from Vaccinium corymbosum (SEQ ID NO: 33)
GLGYQYMAGFTARWKYYFIWSISEASIIISGLGFSGWTDSSPPKPKWDRA
KNVDILRVEFAKTAAQIPLAWNIQVSTWLRHYVYERLVQKGKKPGFFQLL
ATQTVSAVWHGLYPGYIIFFVQSALMIAGSRVIYRWQQAVPPKMDLVKKV
FVLLNFAYTVLVLNYSSVGFMVLSHETIVAYGSVYSLEPLFPYL (n) The partial nucleotide sequence of LPCAT from wheat (SEQ ID NO: 34)
CACTTTGCTGGACCAGTATATGAGATGAAAGATTATCTTGAATGGACTGA
AAGGAAAGGAATATGGGCGGCTCAACTCCTTCACCATTATTACCTACTC
TGCGTGCTCTAGTTCAGGCTGGAATATGCATGGGGTTATATTTGTATCTG
TCACCTATGTTTCCCCATTCATAATATAGAGGTTCACTAAATCGTGAAAG
GGGTTTCTGGCACCGGCTCTTCTTTCAATACATGTCAGGATTTACTGCTC
GATGGAAATACTACTTTTATATGGTCAGTCTCAGAAGCTGCAATTATTATA
TCTGGCCTGGGTTTCACTGGTTGGTCTGATTCTTCTCCCCCAAAAGCCAA
ATGGGACCGTGCTATAAATGTTGATATTCTGGGCGTCGAGCTAGCTGGAA
GTGCAGCTCAATTGCCACTTAAGTGGAATATTCAAGTGAGCACATGGCTA
AGATACTATGTGTATGAGAGGTTAATTCAGAAAGGGAAGAAGCCTGGTTT
CCTTCAGTTGTTGGGTACACAGACAGTCAGTGCTATCTGGCATGGACTGT
ATCCAGGATATATGTTTTTCTTTGTTCAGTCAGCGTTGATGATAAATGGT
TCAAAAGTTATATACAGATGGCAACAAGCTGTGAGCAATCCAGGCCTCCG
CACTATCCTGTCTTTACTAAATTGTGCATACACCATGATGGTGCTTAACT
ACTCATGCATTGGCTTCCAGGTACTGAGCTTCCAGGAGACCTTAGCATCC
TACAAGAGCGTGTATTATGTCGGCACAATCGTTCCTATTCTATGTGTCTT
GCTGGGCTATGTCGTCAAGCCCACGAGACCTGTGAAGCCGA The partial amino acid sequence of LPCAT from wheat (SEQ ID NO: 35)
HFAGPVYEMKDYLEWTERKGIWAGSTPSPLLPTLRALVQAGICMGLYLYL
SPMFPHS*YRGSLNRERGFWHRLFFQYMSGFTARWKYYFIWSVSEAAII
SGLGFTGWSDSSPPKAKWDRAINVDILGVELAGSAAQLPLKWNIQVSTWL

```
RYYVYERLIQKGKKPGFLQLLGTQTVSAIWHGLYPGYMFFFVQSALMING
SKVIYRWQQAVSNPGLRTILSLLNCAYTMMVLNYSCIGFQVLSFQETLAS
YKSVYYVGTIVPILCVLLGYVVKPTRPVKP
```

(o) The amino acid sequences of LPCAT from *A. thaliana*

```
Sequence (accession number At1g12640
(SEQ ID NO: 36))
MDMSSMAGSIGVSVAVLRFLLCFVATIPVSFACRIVPSRLGKHLYAAASG
AFLSYLSFGFSSNLHFLVPMTIGYASMAIYRPKCGIITFFLGFAYLIGCH
VFYMSGDAWKEGGIDSTGALMVLTLKVISCSMNYNDGMLKEEGLREAQKK
NRLIQMPSLIEYFGYCLCCGSHFAGPVYEMKDYLEWTEGKGIWDTTEKRK
KPSPYGATIRAILQAAICMALYLYLVPQYPLTRFTEPVYQEWGFLRKFSY
QYMAGFTARWKYYFIWSISEASIIISGLGFSGWTDDASPKPKWDRAKNVD
ILGVELAKSAVQIPLVWNIQVSTWLRHYVYERLVQNGKKAGFFQLLATQT
VSAVVWHGLYPGYMMFFVQSALMIAGSRVIYRWQQAISPKMAMLRNIMVFI
NFLYTVLVLNYSAVGFMVLSLHETLTAYGSVYYIGTIIPVGLILLSYVVP
AKPSRPKPRKEE Sequence (accession number At1g63050
(SEQ ID NO: 37))
MELLDMNSMAASIGVSVAVLRFLLCFVATIPISFLWRFIPSRLGKHIYSA
ASGAFLSYLSFGFSSNLHFLVPMTIGYASMAIYRPLSGFITFFLGFAYLI
GCHVFYMSGDAWKEGGIDSTGALMVLTLKVISCSINYNDGMLKEEGLREA
QKKNRLIQMPSLIEYFGYCLCCGSHFAGPVFEMKDYLEWTEEKGIWAVSE
KGKRPSPYGAMIRAVFQAAICMALYLYLVPQFPLTRFTEPVYQEWGFLKR
FGYQYMAGFTARWKYYFIWSISEASIIISGLGFSGWTDETQTKAKWDRAK
NVDILGVELAKSAVQIPLFWNIQVSTWLRHYVYERIVKPGKKAGFFQLLA
TQTVSAVWHGLYPGYIIFFVQSALMIDGSKAIYRWQQAIPPKMAMLRNVL
VLINFLYTVVVLNYSSVGFMVLSLHETLVAFKSVYYIGTVIPIAVLLLSY
LVPVKPVRPKTRKEE
```

The amino acid sequences of LCPAT from fruit fly, human, mouse, *S. pombe*, and *Aspergillus oryzae*.

(1) The amino acid sequences of LCPAT from fruit fly

```
Sequence 1 (accession number AAR99097
(SEQ ID NO: 38))
MLEPPKFIENDCYNGSRTFTWLADMVGLSVDLVNFLICQISALFLASLFR
SMLHPSKVSSKLRHTFALSIGLAFGYFCFGQQAIHIAGLPAICYIVIRTQ
DPRIVQRAVLLVAMSYLLCVHLMRQLYDYGSYALDITGPLMIITQKVTSL
AFSIHDGFVRGDEELTKAQQYHAIRKMPSALEYFSYVWHFQSILAAGPLV
FYKDYIEFVEGYNLLSTPPGNGNLDSSKREVVLEPSPTKAVIRKVVGSLV
CAFIFMKFVKIYPVKDMKEDDFMNNTSMVYKYWYAMMATTCIRFKYYHAW
LLADAICNNSGLGFTGYDKDGNSKWDLISNINVLSFEFSTNMRDAINNWN
CGTNRWLRTLVYERVPQQYGTLLTFALSAVWHGFYPGYIFTFFATGAVVVT
AARTGRRLFRHRFQSTQVTRMFYDILTCLITRVVLGYARFPFVLLEFMGS
IKLYLRPFYLCLHIISLVTIFILPKFIRGERRLRTSNGNGNVRLSGSGNTK
DAVTTSVESTAALTAGNDLNEDKEEDKHAQCKVHTPTQQQPAAGPHKTTV
EQPTEQPNNVNLRSRPQQQQPHLEKKAMPPTCARDAVSVPHDQCEMDQLS
SKLKEKIEAETKNIEEFIDKTVTETVSGIVEFKNDLMRDIEFPKLKLPGS
NGAISLDSSNGGGLRKRNISSVHDNGTDPGHATADLHPPLEENGAAFLKK
EIEVINAVVQQAVPAVLSNGHAK Sequence 2 (accession number AAO41223
(SEQ ID NO: 39))
MAEFEEDLPHNGLMDGIASGVGVPVEALRLLLTILAGYPVAALYQKFISV
IADKTVHHMFFAGCGAGLCYFNYGLDTYHSLIAILTTYFLVLLLRKKTQI
FLAINFVFHMSYLLLGYFYTSSNDYDILWTMPHCILVLRMIGYGFDITDG
LKEESELSKDQKETALKKPPSLLELLAFSYFPSGFLVGPQFPFRRYKAFV
DGEFRQHEGNVEAGVRRFGAGAFYLIVCQVGLRYLPDSYFLTPEFAQVSF
VKRIYLLGFWAKFSLYKYISCWLLTEGALICIGLTYKGEDKNGQPDWSGC
SNVKLKLLETGNTMEHYVQSFNVNTNQWVGQYIYKRLKRLNNRTISYGAA
LGFLAVWHGYHSGYYMTFLMEYMVVSTEKQITRFYTKVVLPQWGHILNNS
DIYKLLYFITLKSYNVVYMGWCLTAFVFLKYERWIVVYGAVSYYGFTFLV
LWAAFYHTFNHFFRSSSRKLAGEDQKLQDSNTDKLVEEKKPEDKKSE
```

(2) The amino acid sequences of LCPAT from human

```
Sequence 1 (accession number EAX01013
(SEQ ID NO: 40))
MKCCFHHIIPRVNFVVCQLFALLAAIWFRTYLHSSKTSSFIRHVVATLLG
LYLALFCFGWYALHFLVQSGISYCIMIIIGVENMHNYCFVFALGYLTVCQ
VTRVYIFDYGQYSADFSGPMMIITQKITSLACEIHDGMFRKDEELTSSQR
DLAVRRMPSLLEYLSYNCNFMGILAGPLCSYKDYITFIEGRSYHITQSGE
NGKEETQYERTEPSPNTAVVQKLLVCGLSLLFHLTICTTLPVEYNIDEHF
QATASWPTKIIYLYISLLAARPKYYFAWTLADAINNAAGFGFRGYDENGA
ARWDLISNLRIQQIEMSTSFKMFLDNWNIQTALWLKRVCYERTSFSPTIQ
TFILSAIWHGVYPGYYLTFLTGVLMTLAARAMRNNFRHYFIEPSQLKLFY
DVITWIVTQVAISYTVVPFVLLSIKPSLTFYSSWYYCLHILGILVLLLLP
VKKTQRRKNTHENIQLSQSKKFDEGENSLGQNSFSTTNNVCNQNQEIASR
HSSLKQ Sequence 2 (accession number Q6ZWT7
(SEQ ID NO: 41))
MATTSTTGSTLLQPLSNAVQLPIDQVNFVVCQLFALLAAIWFRTYLHSSK
TSSFIRHVVATLLGLYLALFCFGWYALHFLVQSGISYCIMIIIGVENMHN
YCFVFALGYLTVCQVTRVYIFDYGQYSADFSGPMMIITQKITSLACEIHD
GMFRKDEELTSSQRDLAVRRMPSLLEYLSYNCNFMGILAGPLCSYKDYIT
FIEGRSYHITQSGENGKEETQYERTEPSPNTAVVQKLLVCGLSLLFHLTI
CTTLPVEYNIDEHFQATASWPTKIIYLYISLLAARPKYYFAWTLADAINN
AAGFGFRGYDENGAARWDLISNLRIQQIEMSTSFKMFLDNWNIQTALWLK
RVCYERTSFSPTIQTFILSAIWHGVYPGYYLTFLTGVLMTLAARAMRNNF
RHYFIEPSQLKLFYDVITWIVTQVAISYTVVPFVLLSIKPSLTFYSSWYY
CLHILGILVLLLLPVKKTQRRKNTHENIQLSQSRKFDEGENSLGQNSFST
TNNVCNQNQEIASRHSSLKQ Sequence 3 (accession number Q6P1A2
(SEQ ID NO: 85))
MASSAEGDEGTVVALAGVLQSGFQELSLNKLATSLGASEQALRLIISIFL
GYPFALFYRHYLFYKETYLIHLFHTFTGLSIAYFNFGNQLYHSLLCIVLQ
FLILRLMGRTITAVLTTFCFQMAYLLAGYYYTATGNYDIKWTMPHCVLTL
KLIGLAVDYFDGGKDQNSLSSEQQKYAIRGVPSLLEVAGFSYFYGAFLVG
PQFSMNHYMKLVQGELIDIPGKIPNSSIPALKRLSLGLFYLVGYTLLSPH
ITEDYLLTEDYDNHPFWFRCMYMLIWGKFVLYKYVTCWLVTEGVCILTGL
GFNGPEEKGKAKWDACANMKVWLFETNPRFTGTIASFNINTNAWVARYIF
KRLKFLGNKELSQGLSLLFLALWHGLHSGYLVCFQMEFLIVIVERQAARL
IQESPTLSKLAAITVLQPPFYYLVQQTIHWLFMGYSMTAFCLFTWDKWLKV
YKSIYFLGHIFFLSLLFILPYIHKAMVPRKEKLKKME Sequence 4 (accession number Q6ZNC8
(SEQ ID NO: 86))
MAAEPQPSSLSYRTTGSTYLHPLSELLGIPLDQVNFVVCQLVALFAAFWF
RIYLRPGTTSSDVRHAVATIFGIYPVIFCFGWYSVHLFVLVLMCYAIMVT
ASVSNIHRYSFFVAMGYLTICHISRIYIFHYGILTTDFSGPLMIVTQKIT
TLAFQVHDGLGRRAEDLSAEQHRLAIKVKPSFLEYLSYLLNFMSVIAGPC
NNFKDYIAFIEGKHIHMKLLEVNWKRKGFHSLPEPSPTGAVIHKLGITLV
SLLLFLTLTKTFPVTCLVDDWFVHKASFPARLCYLYVVMQASKPKYYFAW
TLADAVNNAAGFGFSGVDKNGNFCWDLLSNLNIWKIETATSFKMYLENWN
IQTATWLKCVCYQRVPWYPTVLTFILSALWHGVYPGYYFTFLTGILVTLA
ARAVRNNYRHYFLSSRALKAVDAGTWAVTQLAVSYTVAPFVMLAVEPTI
SLYKSMYFYLHIISLLIILFLPMKPQAHTQRRPQTLNSINKRKTD Sequence 5 (accession number XP_001129292
(SEQ ID NO: 87))
MVMMMMMKVLLLLMKQRGAGLPAPAGVEPRPSSHHPKARVRLQGDESVRP
RGCSQLWAFTRHSPRQRGFSARSLFWFVVLPAPTFVPNFPWRWLGGVPHI
VPPAATPGPFVVCRLSQRGVGGRDIPGRRNRGVRGKDALPCSHPRSAPHD
AGQPGSGDARHPRAEREVGRALLPATAPGEGGRMGVRVCMRSLPFAAAAL
GSSGGRVPEQPPVRMDRVVERVRKAALWGAWRGAACPARASERPPERLMHG
SGDGLLGFSFVRASLTVFGEEAGPSFLLAVLCAVVWGGRGEDVVSDVQAC
PAEQGFLLAEPSVFGVNFVVCQLFALLAAIWFRTYLHSSKTSSFIRHVVA
TLLGLYLALFCFGWYALHFLVQSGISYCIMIIIGVENMHNYCFVFALGYL
TVCQVTRVYIFDYGQYSADFSGPMMIITQKITSLACEIHDGMFRKDEELT
SSQRDLAVRRMPSLLEYLSYNCNFMGILAGPLCSYKDYITFIEGRSYHIT
QSGENGKEETQYERTEPSPNTAVVQKLLVCGLSLLFHLTICTTLPVEYNI
DEHFQATASWPTKIIYLYISLLAARPKYYFAWTLADAINNAAGFGFRGYD
ENGAARWDLISNLRIQQIEMSTSFKMFLDNWNIQTALWLKRVCYERTSFS
PTIQTFILSAIWHGVYPGYYLTFLTGVLMTLAARAMRNNFRHYFIEPSQL
KLFYDVITWIVTQVAISYTVVPFVLLSIKPSLTFYSSWYYCLHILGILVL
LLLPVKKTQRRKNTHENIQLSQSKKFDEGENSLGQNSFSTTNNVCNQNQE
IASRHSSLKQ Sequence 6 (accession number XP_001131044
(SEQ ID NO: 88))
MVNFVVCQLVALFAAFWFRIYLRPGTTSSDVRHAVATIFGIYPVIFCFGW
YSVHLFVLVLMCYAIMVTASVSNIHRYSFFVAMGYLTICHISRIYIFHYG
ILTTDFSGPLMIVTQKITTLAFQVHDGLGRRAEDLSAEQHRLAIKVKPSF
LEYLSYLLNFMSVIAGPCNNFKDYIAFIEGKHIHMKLLEVNWKRKGFHSL
PEPSPTGAVIHKLGITLVSLLLFLTLTKTFPVTCLVDDWFVHKASFPARL
CYLYVVMQASKPKYYFAWTLADAVNNAAGFGFSGVDKNGNFCWDLLSNLN
IWKIETATSFKMYLENWNIQTATWLKCVCYQRVPWYPTVLTFILSALWHG
VYPGYYFTFLTGILVTLAARAVRNNYRHYFLSSRALKAVDAGTWAVTQL
AVSYTVAPFVMLAVEPTISLYKSMYFYLHIISLLIILFLPMKPQAHTQRR
PQTLNSINKRKTD
```

(3) The amino acid sequences of LCPAT from mouse

Sequence 1 (accession number AAH24653
(SEQ ID NO: 42))
MAARPPASLSYRTTGSTCLHPLSQLLGIPLDQVNFVACQLFALSAAFWFR
IYLHPGKASPEVRHTLATILGIYFVVFCFGWYAVHLFVLVLMCYGVMVSA
SVSNIHRYSPFVAMGYLTICHISRIYIFHYGILTTDFSGPLMIVTQKITT
LAFQVHDGLGRKAEDLSAEQHRLAVKAKPSLLEYLSYHLNFMSVIAGPCN
NFKDYVAFIEGRHIHMKLLEVNWTQRGFQSLPEPSPTGAVIQKLCVTLMS
LLLFLTLSKSFPVTFLIDDWFVHKANFLSRLWYLYVVMQAAKPKYYFAWT
LADAVHNAAGFGFNGMDTDGKSRWDLLSNLNIWKIETATSFKMYLENWNI
QTSTWLKCVCYERVSWYPTVLTFLLSALWHGVYPGYYFTFLTGVPVTLAA
RAVRNNYRHHFLSSKARKIAYDVVTWAVTQLAVSYTAAPFVMLAVEPTIS
LYKSVFFFLHIICLLIILFLPIKPHQPQRQSRSPNSVKKKAD Sequence 2 (accession number AAH25429
(SEQ ID NO: 43))
MATTSTTGSTLLQPLSNAVQLPIDQVNFVVCQLFALLAAVWFRTYLHSSK
TSSFIRHVVATLLGLYLAFFCFGWYALHFLVQSGISYCIMIIAGVESMQQ
CCFVFALGYLSVCQITRVYIFDYGQYSADFSGPMMIITQKITSLAYEIHD
GMFRKDEELTPSQRGLAVRRMPSLLEYVSYTCNFMGILAGPLCSYKDYIA
FIEGRASHVAQPSENGKDEQHGKADPSPNAAVTEKLLVCGLSLLFHLTIS
NMLPVEYNIDEHFQATASWPTKATYLYVSLLAARPKYYFAWTLADAINNA
AGFGFGYDKNGVARWDLSINLRIQQIEMSTSFKMFLDNWNIQTALWLKRV
CYERATFSPTIQTFFLSAIWHGVYPGYYLTFLTGVLMTLAARAVRNNFRH
YFLEPPQLKLFYDLITWVATQITISYTVVPFVLLSIKPSFTFYSSWYYCL
HVCSILVLLLLPVKKSQRRTSTQENVHLSQAKKFDERDNPLGQNSFSTMN
NVCNQNRDTGSRHSSLTQ (4) The amino acid sequences of LCPAT from *S. pombe*

Sequence (accession number CAA16861
(SEQ ID NO: 85))
MAYLIDIPFEYFSSFLGVHPDQLKLLFCFLSAYPFAGILKRLPSAPWIRN
LFSISIGLFYLIGVHHLYDGVLVLLFDALFTYFVAAFYRSSRMPWIIFIV
ILGHTFSSHVIRYIYPSENTDITASQMVLCMKLTAFAWSVYDGRLPSSEL
SSYQKDRALRKIPNILYFLGYVFFFPSLLVGPAFDYVDYERFITLSMFKP
LADPYEKQITPHSLEPALGRCWRGLLWLILFITGSSIYPLKFLLTPKFAS
SPILLKYGYVCITAFVARMKYYGAWELSDGACILSGIGYNGLDSSKHPRW
DRVKNIDPIKFEFADNIKCALEAWNMNTNKWLRNYVYLRVAKKGKRPGFK
STLSTFTVSAMWHGVSAGYYLTFVSAAFIQTVAKYTRRHVRPPFFLKPDME
TPGPFKRVYDVIGMVATNLSLSYLIISFLLLNLKESIHVWKELYFIVHIY
ILIALAVFNSPIRSKLDNKIRSRVNSYKLKSYEQSMKSTSDTDMLNMSVP
KREDFENDE (5) The amino acid sequences of LCPAT from *Aspergillus oryzae*

Sequence (accession number BAE61812
(SEQ ID NO: 45))
MLPYVDLLKLIASFLLSYPLAALLKRIPDAQPWKKNAFIIAVSLFYLVGL
FDLWDGLRTLAYSAAGIYAIAYYIDGSLMPWIGFIFLMGHMSISHIYRQI
IDDAHVTDITGAQMVLVMKLSSFCWNVHDGRLSQEQLSDPQKYAAIKDFP
GILDYLGYVLFFPSLFAGPSFEYVDYRRWIDTTLFDVPPGTDPSKVPPTR
KKRKIPRSGTPAAKKALAGLGWILAFLQLGSLYNQELVLDERFMQYSFVQ
RVWILHMLGFTARLKYYGVWYLTEGACVLSGMGYNGFDPKSGKVFWNRLE
NVDPWSLETAQNSHGYLGSWNKNTNHWLRNYVYLRVTPKGKKPGFRASLA
TFVTSAFWHGFYPGYYLTFVLGSFIQTVAKNFRRHVRPFFLTPDGSRPTA
YKKYYDIASYVVTQLTLSFAVMPFIFLSFGDSIKVWHSVYFYGIVGNIVS
LAFFVSPARGLLLKKLKARNKPHVPRAVSSENIRQPTLGLPNDAIQEFDD
AVQEIRAEIESRQRRGSLAHMPIGDELKAAVEDKIGRGH Alignment of the LPCAT sequences from different species that reveals four conserved motifs unique for this novel type of LPCAT enzymes (FIG. 2). They are not present in the previously identified glycerol-3-phosphate acyltransferases, lyso-phosphatidic acid acyltransferases, and known LPCAT enzymes. The sequences of these motifs are as follows. The letter φ represents a certain amino acid.

Motif 1: M V(I) L(I) φ φ K L(V,I) φ φ φ φ φ φ D G (or Met Xaa Xaa Xaa Xaa Lys Xaa Xaa Xaa Xaa Xaa Xaa Xaa Asp Gly (SEQ ID NO:46), wherein the Xaa at position 2 can be Val or Ile, the Xaa at position 3 can be Leu or Ile, the Xaa at position 7 can be Leu, Val, or Ile, while the other Xaa's in the motif may be any amino acid.

Motif 2: R φ K Y Y φ φ W φ φ φ E(D) A(G) φ φ φ φ φ G φ G F(Y) φ G (or Arg Xaa Lys Tyr Tyr Xaa Xaa Trp Xaa Xaa Xaa Xaa Xaa Xaa Xaa Xaa Xaa Gly Xaa Gly Xaa Xaa Gly (SEQ ID NO:47), wherein the Xaa at position 12 is Glu or Asp, wherein the Xaa at position 13 is Ala or Gly, wherein the Xaa at position 22 is Phe or Tyr, while the other Xaa's in the motif may be any amino acid.

Motif 3: E φ φ φ φ φ φ φ φ φ φ φ W N φ φ T(V) φ φ W (or Glu Xaa Xaa Xaa Xaa Xaa Xaa Xaa Xaa Xaa Xaa Xaa Trp Asn Xaa Xaa Xaa Xaa Xaa Trp (SEQ ID NO:48) wherein the Xaa at position 17 is Thr or Val, while the other Xaa's in the motif may be any amino acid.

Motif 4: S A φ W H G φ φ P G Y (T(F)F (or Ser Ala Xaa Trp His Gly Xaa Xaa Pro Gly Tyr Xaa Xaa Xaa Phe (SEQ ID NO:49) wherein Xaa at position 14 is Thr or Phe, while the other Xaa's in the motif may be any amino acid.

FIG. 3 depicts another alignment of LPCAT sequences from different plant species that revealed the following motifs:

Motif 5 (SEQ ID NO: 81):
E A φ φ I I(L) S G φ G F S(T) G W;

Motif 6 (SEQ ID NO: 82):
W D R A φ N V D;

Motif 7 (SEQ ID NO: 83):
W N I Q V S T W L φ φ Y V Y;
and

Motif 8 (SEQ ID NO: 84):
G F φ Q L L φ T Q T φ S A φ W W H G L Y P G Y.

Example 7

Analysis of LPCAT from the Alga *Thalassiosira pseudonana*

Materials and Methods

Isolation of the LPCAT cDNA from *T. pseudonana*: PCR primers were designed for nucleotide sequence of the putative TpLPCAT obtained by a BLAST search of the sequenced *T. pseudonana* genome using the yeast LPCAT sequence. Plasmid from a cDNA library of *T. pseudonana* was used as template. A 50 µl PCR reaction contained 50 ng of plasmid DNA, 20 pM of each primer: 5'-GGTATGCTCATCTGC-TACCCCCTC-3' (SEQ ID NO:89) and 5'-TTAAGTCTCCT-TCGTCTTTGGTGTAG-3' (SEQ ID NO:90) and 1 µl of BD Advantage™ 2 Polymerase Mix (Clontech Laboratories, Inc.), and was amplified in a thermocycler during 30 cycles of the following program: 94° C. for 30 seconds, 58° C. for 30 seconds, and 72° C. for one minute 30 seconds. The PCR product was purified, and subsequently cloned into the pYES2.1/V5-His-TOPO expression vector (Invitrogen).

Expression of TpLPCAT in yeast: The TpLPCAT in pYES2.1/V5-His-TOPO plasmid was transformed into yeast lpcat mutant By02431 using the method provided by the producer's manual (Invitrogen). Yeast cells transformed with pYES2.1/V5-His-TOPO plasmid only were used as a control. Transformants were selected by growth on synthetic complete medium lacking uracil (SC-ura), supplemented with 2% (w/v) glucose. The colonies were transferred into liquid SC-ura with 2% (w/v) glucose and grown at 28° C. overnight. The overnight cultures were diluted to an OD 0.4 in induction medium (SC-ura+2% Galactose+1% Raffinose), and were induced by incubating at 28° C. for 24 hours. The yeast cells were collected and broken using glass beads. The protein concentrations in the lysates were normalized using the Biorad assay (Bradford 1976) and then assayed for LPCAT activity.

Identification of LPCAT from the Algae *Thalassiosira pseudonana*

Isolation of the LPCAT cDNA from *T. pseudonana* A full-length *T. pseudonana* LPCAT cDNA clone was amplified by PCR from an algae cDNA library. The nucleotide sequence had an open reading frame of 1,323 bp encoding a polypeptide of 440 amino acids with a calculated molecular mass of 49.75 kD.

Figure 4:
FIG. 4 depicts that the expression of the TpLCAT in an lpcat mutant was able to complement the sensitivity of the lpcat mutant to Lyso-PAF.

Expression of TpLPCAT in Yeast: To confirm the function of the protein encoded by the TpLPCAT, the full-length coding region of TpLPCAT was cloned into a yeast expression vector pYES2.1/V5-His-TOPO under the control of the galactose-inducible GAL1 promoter, and the construct was used to transform a LPCAT-deficient yeast strain By02431 (a yeast lpcat strain). Yeast cells harboring an empty pYES2.1 vector plasmid were used as a control. We also discovered that the yeast lpcat strain is hypersensitive to lyso-PAF (lyso-Platelet-activating factor, 1-O-alkyl-sn-glycero-3-phosphocholine). Expression of the TpLPCAT in yeast lpcat mutant was able to overcome lyso-PAF the sensitivity of the lpcat mutant (FIG. 4).

Figure 5:
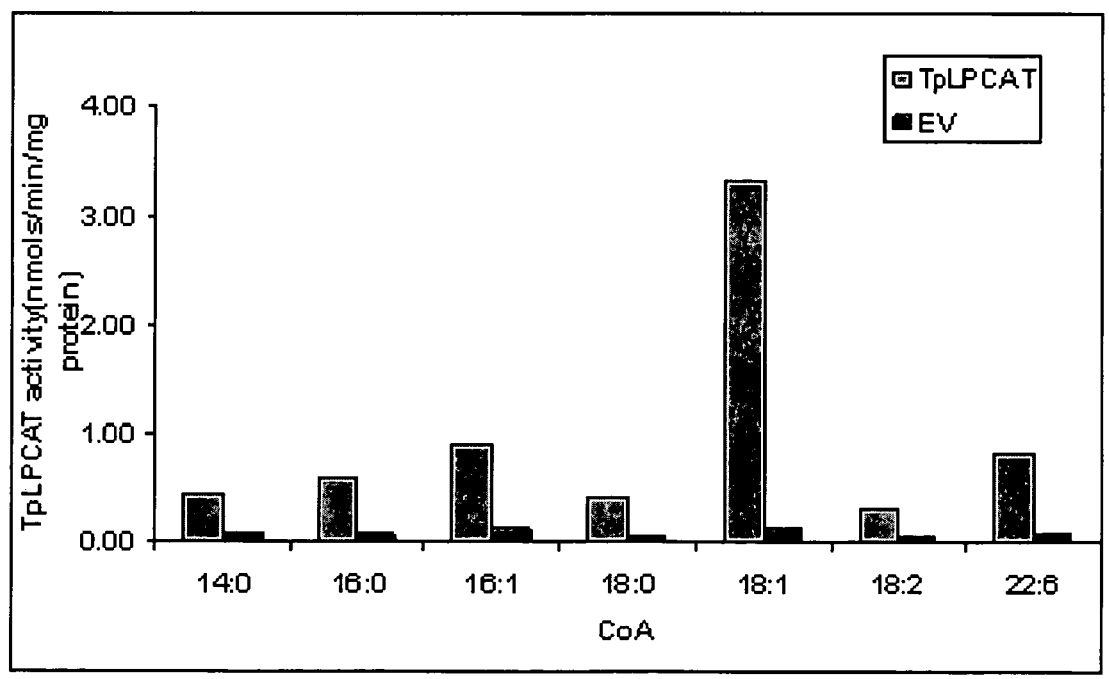
FIG. 5 is a graph showing the expression of TpLPCAT in yeast. LPCAT assays were performed on cell lysates of yeast lpcat mutant strain By02431 transformed with TpLPCAT/pYES2.1 and pYes2.1/V5-His-TOPO plasmid only (control) in the presence of $^{14}$C-Lyso-PC and different acyl-CoAs.
Figure 6:
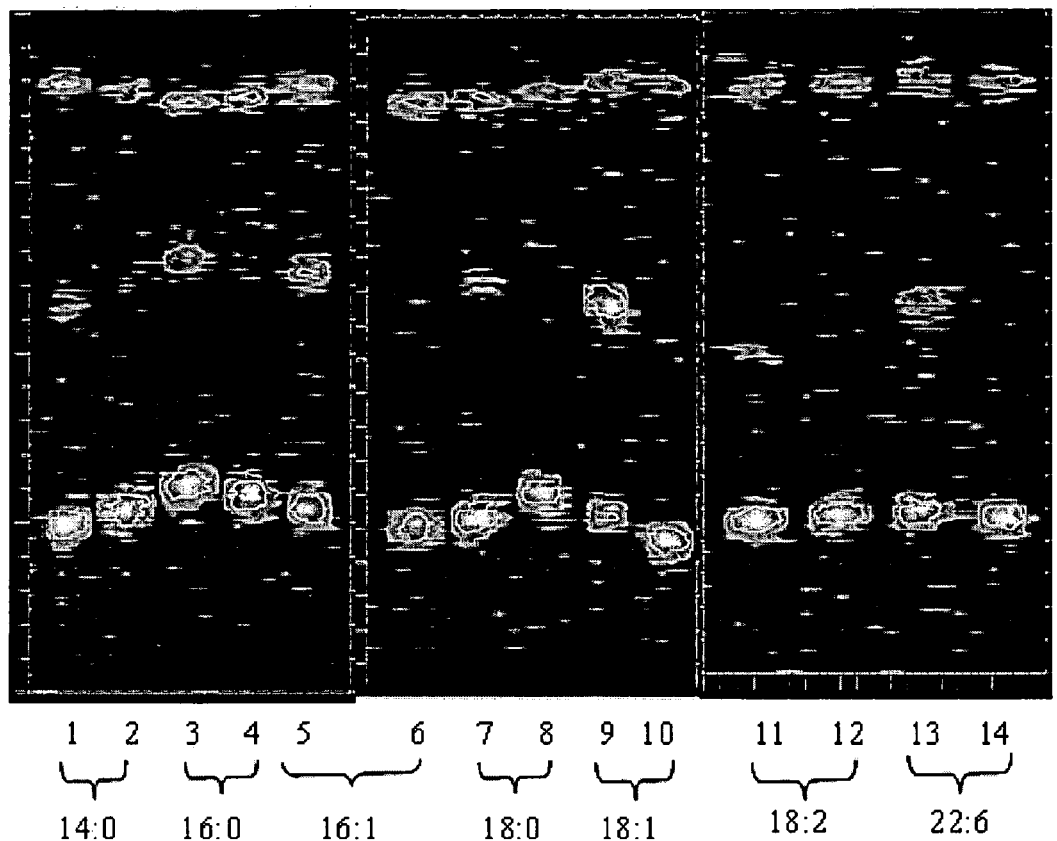
FIG. 6 comprises TLC plates of LPCAT assays on cell lysates of yeast lpcat mutant strain By02431 transformed with TpLPCAT/pYES2.1 and pYes2.1/V5-His-TOPO plasmid only (control) in the presence of $^{14}$C-Lyso-PC and different acyl-CoAs. 1, 3, 5, 7, 9, 11, and 13-TpLPCAT; 2, 4, 6, 8, 10, 12, and 14-empty vector.

The microsomal membrane fractions prepared from lysates of the induced yeast cells were assayed for LPCAT activity using 14C-labelled Lyso-PC as acceptor, and different unlabeled acyl-CoAs as acyl donors. Under our assay conditions, expression of the TpLPCAT in yeast lpcat mutant resulted in a restoration of LPCAT function and produced a recombinant LPCAT protein capable of incorporating a range of different acyl-CoAs into PC including 14:0-, 16:0-, 16:1-, 18:0-, 18:1-, 18:2-, and 22:6(DHA)-, with the most preference of 18:1-CoA, and efficiently utilization of the very long chain polyunsaturated fatty acid—22:6-CoA(DHA) (FIGS. 5 and 6).

Example 8

*Arabidopsis* Gene Assays

Experimental Procedure:

TA-cloning and yeast complementation: Total RNA was prepared from *Arabidopsis* seedlings using RNeasy Plant Mini Kit (Qiagen). RT-PCR of the ORFs of *Arabidopsis* At1g12460, At1g63050 was performed with primer pairs designed based on sequences of gene annotation available at TAIR (The *Arabidopsis* Information Resources). The cDNA was cloned into vector pYES2.1 using pYES2.1 TOPO TA Cloning Kit according to the manufacturer's protocol (Invitrogen). Correctly-oriented positive colonies were identified through double digestion with restriction enzyme, followed by verification through DNA sequencing. The construct was introduced into yeast strain YOR175c, BY02431. Yeast extract, Yeast Nitrogen Base, Bacto-peptone, and Bacto-agar were purchased from DIFCO™, D-glucose, D-galactose and D-raffinose were from Sigma. SC minimal medium and plates was prepared according to Invitrogen's recipe described for the pYES2.1 TOPO TA Cloning Kit.

Lyso-PAF sensitivity: Yeast strains BY02431 carrying pYES 2.1-AtLPCATs or the empty vector were first grown in 15 ml of SC-Leu-His-ura medium containing 2% glucose. Yeast transformant strains of AtLPCATs were first grown in YPD overnight. Protein expression induction were carried out by protocol described in Invitrogen manufacturer manual for yeast expression vector pYES2.1. After 12 hours induction, 5 µl cultures were inoculated onto YPD plate with 10 µg/ml lysoPAF. The plates were incubated at 28° C. for two days. The final lysoPAF is 10 µg/ml.

In vitro assay: Yeast strains BY02431 carrying pYES 2.1-AtLPCATs (or the empty vector) were first grown in 15 ml of SC-Leu-His-ura medium containing 2% glucose. Yeast transformant strains of AtLPCATs were first grown in YPD overnight. Protein expression induction was carried out by protocol described in Invitrogen manufacturer manual for yeast expression vector pYES2.1. After 24 hours of growth in the galactose induction conditions, the cells were washed first with distilled water and then with wall-breaking buffer (50 mM sodium phosphate, pH7.4; 1 mM EDTA; 1 mM PMSF; 5% glycerol) and spun down at 4,000 rpm (Eppendorf Centrifuge 5145C) to re-pellet cells. The cells, resuspended in 1 ml cell wall-breaking buffer, were shaken vigorously in the presence of acid-washed glass beads (diameter 0.5 mm) in a mini-bead beater at 5,000 rpm for three 1-minute intervals. The resultant homogenate was centrifuged at 1,500 g for five minutes at 4° C. The supernatant was decanted for in vitro assay. Protein concentration was measured using Bio-Rad Protein Assay Kit for final AtSAT1 activity calculation.

AtLPCAT substrate specificity was determined by counting incorporation of 14C-labeled lysophosphatidylcholine or 14C-labled palmitoyl-CoA into phosphatidylcholine. All assays were performed at least twice. 200 ml reaction mixture contained 50 mg microsomal protein, 50 mM acyl-CoA and 45 mM palmitoyl-PC, pH7.4. 14C-lysophosphatidylcholine (1.4 nCi/nmol) or 14C-palmityl-CoA (5.5 nCi/nmol) was used to assess fatty-CoA or lyso-lipid substrate specificity. Reaction was allowed for ten minutes at 30° C. All radiolabel chemicals for these assays were purchased from ARC, Inc.

Figure 7:
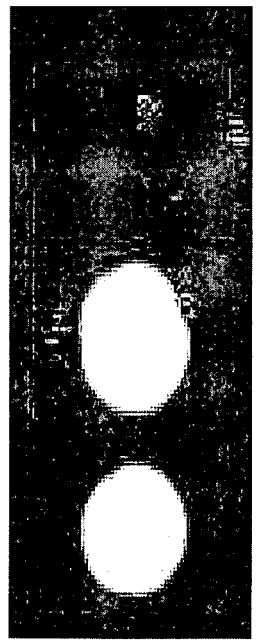
FIG. 7 shows a LysoPAF sensitivity test of YOR175c mutant, AtLPCATs transformant, wherein A is VO/BY02431, B is AtLPCAT1/BY02431, and C is AtLPCAT2/BY02431.

Lyso-PAF sensitivity test (FIG. 7): The yeast lpcat strain is deficient in its endogenous LPCAT and hypersensitive to lyso-PAF (lyso-Platelet-activating factor, 1-O-alkyl-sn-glycero-3-phosphocholine). The lpcat yeast mutant is incapable of growth in the presence of 10 ug/ml lyso-PAF (lyso-Platelet-activating factor, 1-O-alkyl-sn-glycero-3-phosphocholine). However, when the *Arabidopsis* LPCAT genes, At1g12640 and At1g63050, were introduced into the yeast mutant, the transformants could survive on lyso-PAF-containing YPD plate. These results indicated that the *Arabidopsis* genes encode for LPCAT.

In vitro enzyme characterization with the yeast cell free lysate expressing the *Arabidopsis* LPCATs was further conducted.

Figure 8:
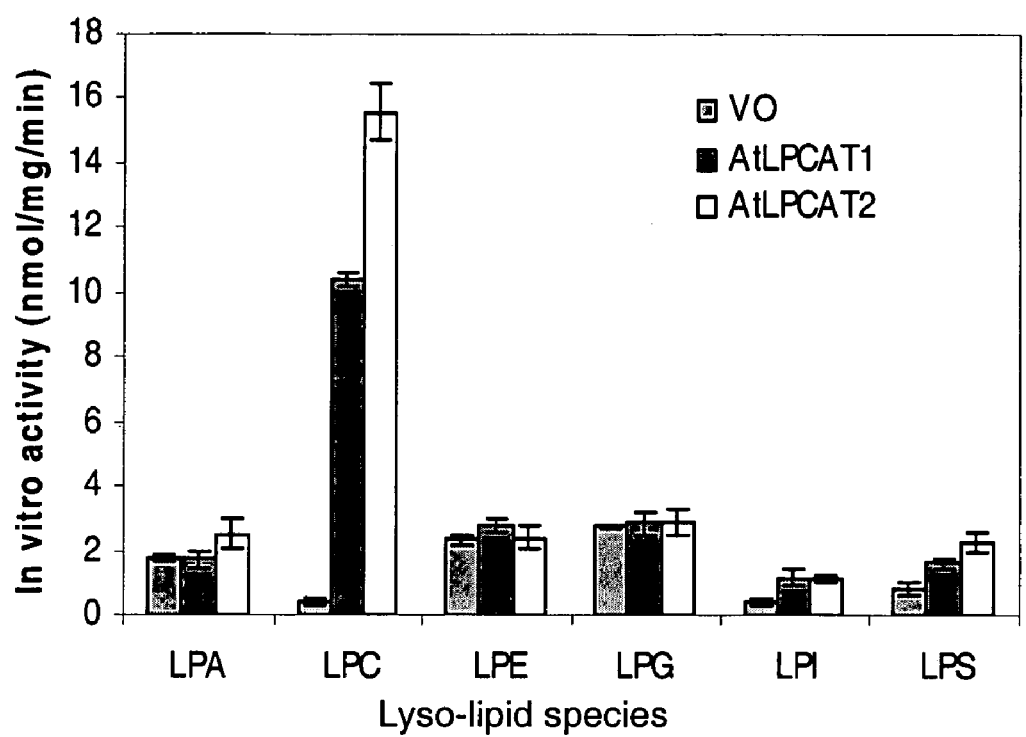
FIG. 8 is a graph showing the Lyso-lipid substrate specificity of *Arabidopsis* LPCATs.

Lyso-lipid substrate specificity (FIG. 8): LPA (lysophosphatidic acid), LPC (lysophosphatidic choline), LPE (lysophosphatidylethanolamine), LPG (lysophosphatidylglycerol), LPI (lysophosphatidyl inositol) and LPS (lysophosphatidyl serine) were first tested as substrates to compare their acyltransferase activity. The results clearly showed that At1g12640 and At1g63050 both exhibited high activity towards LPC (FIG. 8).

Example 9

By NCBI-BLASTp search with default Algorithm parameters (expect threshold=10; word size=3; matrix=BLOSUM62; gap costs=existence: 11 Extension: 1; compositional adjustments=composition-based statistics) following sequences (E value<5e18) from various organisms including human and mouse were identified as YOR175 cp homologs.

SEQ ID NO:87: Human_XP_001129292 protein sequence, PREDICTED: similar to O-acyltransferase (membrane bound) domain containing 2 [*Homo sapiens*].

SEQ ID NO: 93: Human_XP_001129292 CDS sequence
ATGGTGATGATGATGATGATGAAGGTGCTGCTGCTGCTGATGAAGCAAAG
GGGAGCCGGTCTCCCTGCGCCCGCGGGCGTCGAACCCAGGCCCAGCTCTC
ACCACCCAAAGGCCCGGGTGCGGCTGCAGGGTGACGAAAGCGTCAGACCC
CGGGGCTGCTCTCAGCTTTGGGCTTTCACCCGGCACTCTCCCAGACAAAG
GGGCTTCTCAGCCAGGTCGCTGTTTTGGTTTGTCGTCCTCCCAGCCCCCA
CCTTCGTCCCCAACTTCCCCTGGCGCTGGCTCGGCGGCGTCCTCACATC
GTCCCTCCGGCCGCCACCCCGGGCCCCTTTGTTGTCTGCCGTCTCTCCCA
GAGAGGGGTGGGGGGCCGCGACATTCCAGGGAGGGAGAAACCGAGGAGTGA
GGGGCAAAGACGCTCTTCCATGCTCTCACCCGAGGAGCGCGCCCCACGAC
GCTGGCCAGCCGTTCTCCGGCGACGCCCGCCATCCCCGGGCCGAGCGGGA
GGTGGGCCGGGCGTTGTTGCCGGCGACAGCCCCCGGGGAGGGTGGTCGTA
TGGGCGTGCGGGTGTGCATGCGGTCCCTGCCCTTCGCGGCAGCGGCGCTC
GGATCCGTGGTCGGGTCCCGGAGCAGCCCCCGTGCGCATGGACCGGGT
GTGGAAAGGGTGCGGAAGGCTGCGCTTTGGGGAGCCTGGCGTGGTGCTGC
CTGCCCCGCGCGCGCCTCTGAGCGACCCCCGGAGAGGCTGATGCATGGGT
CTGGGGATGGGCTGCTTGGCTTCTCATTTGTCAGAGCAAGCTTGACAGTG
TTTGGAGGAGGAAGCAGGCCCATCCTTTCTATTGGCAGTTCTCTGTCGT
TGTCTGGGGAGGAAGAGGAGAGGATGTGTGTCTGATGTACAGGCTTGTC
CTGCAGAACAGGGCTTCTTGCTGGCTGAACCAGTGTATTGGTGTCAAC
TTTGTAGTGTGCCAACTCTTTGCCTTGCTAGCAGCCATTTGGTTTCGAAC
TTATCTACATTCAAGCAAAACTAGCTCTTTTATAAGACATGTAGTTGCTA
CCCTTTTGGGCCTTTATCTTGCACTTTTTGCTTTGGATGGTATGCCTTA
CACTTTCTTGTACAAAGTGGAATTTCCTACTGTATCATGATCATCATAGG
AGTGGAGAACATGCACAATTACTGCTTTGTGTTTGCTCTGGGATACCTCA
CAGTGTGCCAAGTTACTCGAGTCTATATCTTTGACTATGGACAATATTCT
GCTGATTTTTCAGGCCCAATGATGATCATTACTCAGAAGATCACTAGTTT
GGCTTGCGAAATTCATGATGGGATGTTCGGAAGGATGAAGAACTGACTT
CCTCACAGAGGGATTTAGCTGTAAGGCGCATGCCAAGCTTACTGGAGTAT
TTGAGTTACAACTGTAACTTCATGGGGATCCTGGCAGGCCCACTTTGCTC
TTACAAAGACTACATTACTTTCATTGAAGGCAGATCATACCATATCACAC
AATCTGGTGAAAATGGAAAGAAGAGACACAGTATGAAAGAACAGAGCCA
TCTCCAAATACTGCGGTTGTTCAGAAGCTCTTAGTTTGTGGGCTGTCCTT
GTTATTTCACTTGACCATCTGTACAACATTACCTGTGGAGTACAACATTG
ATGAGCATTTTCAAGCTACAGCTTCGTGGCCAACAAAGATTATCTATCTG
TATATCTCTCTTTTGGCTGCCAGACCCAAATACTATTTTGCATGGACGCT
AGCTGATGCCATTAATAATGCTGCAGGCTTTGGTTTCAGAGGGTATGACG
AAAATGGAGCAGCTCGCTGGGACTTAATTTCCAATTTGAGAATTCAACAA
ATAGAGATGTCAACAAGTTTCAAGATGTTTCTTGATAATTGGAATATTCA
GACAGCTCTTTGGCTCAAAAGGGTGTGTTATGAACGAACCTCCTTCAGTC
CAACTATCCAGACGTTCATTCTCTGCCATTTGGCACGGGTATACCCA
GGATATTATCTAACGTTTCTAACAGGGGTGTTAATGACATTAGCAGCAAG
AGCTATGAGAAATAACTTTAGACATTATTTCATTGAACCTTCCAACTGA
AATTATTTTATGATGTTATAACATGGATAGTAACTCAAGTAGCAATAAGT
TACACAGTTGTGCCATTTGTGCTTCTTTTCTATAAAACCATCACTCACGTT
TTACAGCTCCTGGTATTATTGCCTGCACATTCTTGGTATCTTAGTATTAT
TGTTGTTGCCAGTGAAAAAAACTCAAAGAAGAAAGAATACACATGAAAA
ATTCAGCTCTCACAATCCAAAAAGTTTGATGAAGGAGAAATTCTTTGGG
ACAGAACAGTTTTTCTACAACAAACAATGTTTGCAATCAGAATCAAGAAA
TAGCCTCGAGACATTCATCACTAAAGCAGTGA SEQ ID NO: 85: Human_NP_005759 protein sequence,
O-acyltransferase (membrane bound) domain
containing 5 [Homo sapiens]:
MASSAEGDEGTVVALAGVLQSGFQELSLNKLATSLGASEQALRLIISIFL
GYPFALFYRHYLFYKETYLIHLFHTFTGLSIAYFNFGNQLYHSLLCIVLQ
FLILRLMGRTITAVLTTFCFQMAYLLAGYYYTATGNYDIKWTMPHCVLTL
KLIGLAVDYFDGGKDQNSLSSEQQKYAIRGVPSLLEVAGFSYFYGAFLVG
PQFSMNHYMKLVQGELIDIPGKIPNSIIPALKRLSLGLFLVGYTLLGPH
ITEDYLLTEDYDNHPFWFRCMYMLIWGKFVLYKYVTCWLVTEGVCILTGL
GFNGFEEKGKAKWDACANMKVWLFETNPRFTGTAISFNINTNAWVARYIF
KRLKFLGNKELSQGLSLLFLALWHGLHSGYLVCFQMEFLIVIVERQAARL
IQESPTLSKLAAITVLQPFYYLVQQTIHWLFMGYSMTAFCLFTWDKWLKV
YKSIYFLGHIFFLSLLFILPYIHKAMVPRKEKLKKME SEQ ID NO: 94: Human_NP_005759 cDNA sequence
ATGGCGTCCTCAGCGGAGGGGACGAGGGGACTGTGGTGGCGCTGGCGGG
GGTTCTGCAGTCGGGTTTCCAGGAGCTGAGCCTTAACAAGTTGGCGACTT
CCCTGGGCGCGTCAGAACAGGCGCTGCGGCTGATCATCTCCATCTTCCTG
GGTTACCCCTTTGCTTTGTTTTATCGGCATTACCTTTTCTACAAGGAGAC
CTACCTCATCCACCTCTTCCATACCTTTACAGGCCTCTCAATTGCTTATT
TTAACTTTGGAAACCAGCTCTACCACTCCCTGCTGTGTATTGTCCTTCAG
TTCCTCATCCTTCGACTAATGGGCCGCACCATCACTGCCGTCCTCACTAC
CTTTTGCTTCCAGATGGCCTACCTTCTGGCTGGATACTATTACACTGCCA
CCGGCAACTACGATATCAAGTGGACAATGCCACATTGTGTTCTGACTTTG
AAGCTAATTGGTTGGCTGTTGACTATTTTGACGGAGGGAAAGATCAGAA
TTCCTTGTCCTCTGAGCAACAGAAATATGCCATACGTGGTGTTCCTTCCC
TGCTGGAAGTTGCTGGTTTCTCCTACTTCTATGGGGCCTTCTTGGTAGGG
CCCCAGTTCTCAATGAATCACTACATGAAGCTGGTGCAGGGAGAGCTGAT
TGACATACCAGGAAAGATACCAAACAGCATCATTCCTGCTCTCAAGCGCC
TGAGTCTGGGCCTTTTCTACCTAGTGGGCTACACACTGCTCAGCCCCCAC ATCACAGAAGACTATCTCCTCACTGAAGACTATGACAACCACCCCTTCTG
GTTCCGCTGCATGTACATGCTGATCTGGGGCAAGTTTGTGCTGTACAAAT
ATGTCACCTGTTGGCTGGTCACAGAAGGAGTATGCATTTTGACGGGCCTG
GGCTTCAATGGCTTTGAAGAAAAGGGCAAGGCAAAGTGGGATGCCTGTGC
CAACATGAAGGTGTGGCTCTTTGAAACAAACCCCCGCTTCACTGGCACCA
TTGCCTCATTCAACATCAACACCAACGCCTGGGTGGCCGCTACATCTTC
AAACGACTCAAGTTCCTTGGAAATAAAGAACTCTCTCAGGGTCTCTCGTT
GCTATTCCTGGCCCTCTGGCACGGCCTGCACTCAGGATACCTGGTCTGCT
TCCAGATGGAATTCCTCATTGTTATTGTGGAAAGACAGGCTGCCAGGCTC
ATTCAAGAGAGCCCCACCCTGAGCAAGCTGGCCGCCATTACTGTCCTCCA
GCCCTTCTACTATTTGGTGCAACAGACCATCCACTGGCTCTTCATGGGTT
ACTCCATGACTGCCTTCTGCCTCTTCACGTGGGACAAATGGCTTAAGGTG
TATAAATCCATCTATTTCCTTGGCCACATCTTCTTCCTGAGCCTACTATT
CATATTGCCTTATATTCACAAAGCAATGGTGCCAAGGAAAGAGAAGTTAA
AGAAGATGGAATAA SEQ ID NO: 95: Human_NP_077274 protein sequence,
leukocyte receptor cluster (LRC) member 4 protein
[Homo sapiens]:
MSPEEWTYLVVLLISIPIGFLFKKAGPGLKRWGAAAVGLGLTLFTCGPHT
LHSLVTILGTWALIQAQPCPCHALALAWTFSYLLFFRALSLLGLPTPTPF
TNAVQLLLTLKLVSLASEVQDLHLAQRKEMASGFSKGPTLGLLPDVPSLM
ETLSYSYCYVGIMTGPFFRYRTYLDWLEQPFPGAVPSLRPLLRRAWPAPL
FGLLFLLSSHLFPLEAVREDAFYARPLPARLFYMIPVFFARFMRFYVAWI
AAECGCIAAGFGAYPVAAKARAGGGPTLQCPPPSSPEKAASLEYDYETIR
NIDCYSTDFCVRVRDGMRYWNMTVQWWLAQYIYKSAPARSYVLRSAWTML
LSAYWHGLHPGYYSLFLTIPLCLAAEGRLESALRGRLSPGGQKAWDWVHW
FLKMRAYDYMCMGFVLLSLADTLRYWASIYFCIHFLALAALGLGLALGGG
SPSRRKAASQPTSLAPEKLREE SEQ ID NO: 96: Human_NP_077274 cDNA sequence
ATGTCGCCTGAAGAATGGACGTATCTAGTGGTTCTTCTTATCTCCATCCC
CATCGGCTTCCTCTTTAAGAAAGCCGGTCCTGGGCTGAAGAGATGGGGAG
CAGCCGCTGTGGGCCTGGGGCTCACCCTGTTCACCTGTGGCCCCCACACT
TTGCATTCCTCGGTCACCATCCTCGGGACCTGGGCCCTCATTCAGGCCCA
GCCCTGCCCCTGCCACGCCCTGGCTCTGGCCTGGACTTTCTCCTATCTCC
TGTTCTTCCGAGCCCTCAGCCTCCTGGGCCTGCCCACTCCCACGCCCTTC
ACCAATGCCGTCCAGCTGCTGCTGACGCTGAAGCTGGTGAGCCTGGCCAG
TGAAGTCCAGGACCTGCATCTGGCCCAGAGGAAGGAAATGGCCTCAGGCT
TCAGCAAGGGGCCCACCCTGGGGCTGCTGCCCGACGTGCCTTCCCTGATG
GAGACACTCAGCTACAGCTACTGCTACGTGGGAATCATGACAGGCCCGTT
CTTCCGCTACCGCACCTACCTGGACTGGCTGGAGCAGCCCTTCCCCGGGG
CAGTGCCCAGCCTGCGGCCCCTGCTGCGCCGCGCTGGCCGGCCCCGCCT
TTCGGGCTGCTGTTCCTGCTCTCCTCACCTCTTCCCGCTGGAGGCCGT
GCGCGAGGACGCCTTCTACGCCCGCCCGCTGCCCGCCCGCCTCTTCTACA
TGATCCCCGTCTTCTTCGCCTTCCGCATGCGCTTCTACGTGGCCTGGATT
GCCGCCGAGTGCGGCTGCATTGCCGCCGGCTTTGGGGCCTACCCCGTGGC
CGCCAAGGCCCGGGCCGGAGGCGGCCCCACCCTCCAATGCCCACCCCCCA
GCAGTCCGGAGAAGGCGGCTTCCTTGGAGTATGACTATGAGACCATCCGC
AACATCGACTGCTACAGCACAGATTTCTGCGTGCGGGTGCGCGATGGCAT
GCGGTACTGGAACATGACGGTGCAGTGGTGGCTGGCCAGTATATCTACA
AGAGCGCCACCTGCCCGTTCCTATGTCCTGCGGAGCGCCTGGACCATGCTG
CTGAGCGCCTACTGGCACGGCCTCCACCCGGGCTACTACCTGAGCTTCCT
GACCATCCCGCTGTGCCTGGCTGCCGAGGGCCGGCTGGAGTCAGCCCTGC
GGGGCGGCCTGAGCCCAGGGGGCCAGAAGGCCTGGGATTGGGTGCATTGG
TTCCTGAAGATGCGCGCCTATGACTACATGTGCATGGGCTTCGTGCTGCT
CTCCTTGGCCGACACCCTTCGGTACTGGGCCTCCATCTACTTCTGTATCC
ACTTCCTGGCCCTGGCAGCCCTGGGGCTGGGGCTGGCTTTAGGTGGGGGC
AGCCCCAGCCGGCGGAAGGCAGCATCCCAGCCCACCAGCCTTGCCCCGGA
GAAGCTCCGGGAGGAGTAA SEQ ID NO: 97: Human_NP_620154 protein sequence,
O-acyltransferase (membrane bound) domain
containing 2[Homo sapiens]:
MATTSTTGSTLLQPLSNAVQLIPDQVNFVVCQLFALLAAIWFRTYLHSSK
TSSFIRHVVSTLLGLYLALFCFGWYALHPLVQSGISYCIMIIIGVENMHN
YCFVFALGYLTVCQVTRVYIFDYGQYSADFSGPMMIITQKITSLACEIHD
GMFRKDEELTSSQRDLAVRRMPSLLEYLSYNCNFMGILAGPLCSYKDYIT
FIEGRSYHITQSGENGKEETQYERTEPSPNTAVVQKLLVCGLSLLFHLTI
CTTLPVEYNIDEHFQATASWPTKIIYLYISLLAARPKYYFAWTLADAINN
AAGFGFRGYDENGAARWDLSINLRIQQIEMSTSFKMFLDNWNIQTALWLK
RVCYERTSFSPTIQTFILSAIWHGVYPGYYLTFLTGVLMTLAARAMRNNF
RHYFIEPSQLKLFYDVITWIVTQVAISYTVVPFVLLSIKPSLTFYSSWYY
CLHILGILVLLLLPVKKTQRRKNTHENIQLSQSKKFDEGENSLGQNSFST
TNNVCNQNQEIAARHSSLKQ SEQ ID NO: 98: Human_NP_620154 cDNA sequence
ATGGCCACCACCAGCACCACGGGCTCCACCCTGCTGCAGCCCCTCAGCAA
CGCCGTGCAGCTGCCCATCGACCAGGTCAACTTTGTAGTGTGCCAACTCT
TTGCCTTGCTAGCAGCCATTTGGTTTCGAACTTATCTACATTCAAGCAAA
ACTAGCTCTTTTTATAAGACATGTAGTTGCTACCCTTTTGGGCCTTTATCT

```
TGCACTTTTTTGCTTTGGATGGTATGCCTTACACTTTCTTGTACAAAGTG
GAATTTCCTACTGTATCATGATCATCATAGGAGTGGAGAACATGCACAAT
TACTGCTTTGTGTTTGCTCTGGGATACCTCACAGTGTGCCAAGTTACTCG
AGTCTATATCTTTGACTATGGACAATATTCTGCTGATTTTTCAGGCCCAA
TGATGATCATTACTCAGAAGATCACTAGTTTGGCTTGCAGAAATTCATGAT
GGGATGTTTCGGAAGGATGAAGAACTGACTTCCTCACAGAGGGATTTAGC
TGTAAGGCGCATGCCAAGCTTACTGGAGTATTTGAGTTACAACTGTAACT
TCATGGGATCCTGGCAGGCCCACTTTGCTCTTACAAAGACTACATTACT
TTCATTGAAGGCAGATCATACCATATCACACAATCTGGTGAAAATGAAA
AGAAGAGACACAGTATGAAGAACAGAGCCATCTCCAAATACTGCGGTTG
TTCAGAAGCTCTTAGTTTGTGGGCTGTCCTTGTTATTTCACTTGACCATC
TGTACAACATTACCTGTGGAGTACAACATTGATGAGCATTTTCAAGCTAC
AGCTTCGTGGCCAACAAAGATTATCTATCTGTATATCTCTCTTTTGGCTG
CCAGACCCAAATACTATTTTGCATGGACGCTAGCTGATGCCATTAATAAT
GCTGCAGGCTTTGGTTTCAGAGGGTATGACGAAAATGGAGCAGCTCGCTG
GGACTTAATTTCCAATTTGAGAATTCAACAATAGAGATGTCAACAAGTT
TCAAGATGTTTCTTGATAATTGGAATATTCAGACAGCTCTTTGGCTCAAA
AGGGTGTGTTATGAACGAACCTCCTTCAGTCCAACTATCCAGACGTTCAT
TCTCTCTGCCATTTGGCACGGGGTATACCCAGGATATTATCTAACGTTTC
TAACAGGGGTGTTAATGACATTAGCAGCAAGAGCTATGAGAAATAACTTT
AGACATTATTTCATTGAACCTTCCCAACTGAAATTATTTTATGATGTTAT
AACATGGATAACATCCAAGTAGCAATAAGTTACACAGTTGTGCCATTG
TGCTTCTTTCTATAAAACCATCACTCACGTTTTACAGTCCTGGTATTAT
TGCCTGCACATTCTTGGTATCTTAGTATTATTGTTGTTGCCAGTGAAAAA
AACTCAAAGAAGAAAGAATACACATGAAAACATTCAGCTCTCACAATCCA
AAAAGTTTGATGAAGGAGAAAATTCTTTGGGACAGAACAGTTTTTCTACA
ACAAACAATGTTTGCAATCAGAATCAAGAAATAGCCTCGAGACATTCATC
ACTAAAGCAGTGA

SEQ ID NO: 88: Human_XP_001131044 protein
sequence, PREDICTED: similar to O-acyltransferase
(membrane bound) domain containing 1 isoform 1
SEQ ID NO: 99: Human_XP_001131044 cDNA sequence
ATGGTGAATTTTGTGGTATGCCAGCTTGTTGCTCTGTTTGCTTTCTGG
TTTCGCATCTACTTACGTCCTGGTACAACAGCTCTGATGTCCGGCATGC
GGTTGCCACCATTTTTGGCATCTATTTTGTCATCTTTTGTTTCGGCTGGT
ACTCTGTGCATCTTTTTGTGCTGGTGTTAATGTGCTATGCAATCATGGTC
ACTGCTAGTGTATCCAATATTCACAGTATTCCTTTTTGTAGCAATGGGA
TATCTTACAATATGCCACATCAGCCGAATATCATCTTCCACTATGGAAT
TCTCACTACGGATTTTTCTGGGCCTCTGATGATTGTCACTCAGAAGATCA
CAACCTTGGCATTCCAGGTTCATGATGGATTAGGTCGAAGAGCTGAAGAC
CTTTCTGCTGAACAACATCGACTTGCTATCAAAGTGAAACCCTCTTTTTT
GGAATACTTAAGTTACCTTCTCAATTTCATGAGTGTCATAGCTGGTCTT
GTAACAATTTCAAGGACTACATAGCCTTCATTGAGGGGAAGCATATACAC
ATGAAGTTGCTGGAGGTGAACTGGAAGCGAAAAGGTTTCCACAGCTTGCC
AGAACCTTCTCCCACAGGAGCTGTGATACACAAGTTGGGCATCACCTTGG
TGTCTCTCCTTTTGTTTTTGCTGTAACGAAGACCTTTCCTGTCGACTCTG
CTTGTGGATGACTGGTTTGTCCATAAGCAAGCCTTTCCGGCTCGACTCTG
CTACTTATATGTTGTCATGCAAGCCTAAAGCCCAAGTATTACTTTGCAT
GGACATTAGCTGATGCAGTGAATAACGCAGCTGGCTTTGGGTTCAGCGGA
GTGGATAAGAATGGGAATTTCTGTTGGGATCTGCTTTCAGAACATGAACAT
CTGGAAATTGAGACTGCCACAAGTTTCAAAATGTACTTGGAAAACTGGA
ATATTCAGACAGCTACTTGGCTAAAGTGTGTGTGCTATCAGCGGGTTCCA
TGGTACCCCACGGTGCTAACCTTCATCCTGTCTGCTTTGTGGCATGGTGT
CTACCCTGGATACTATTTTACCTTCTTAACTGGAATTCTTGCACATTAG
CAGCTAGACGGTCAGGAACAACTACAGACATTACTTCCTTCTTCAAGA
GCTCTCAAGGCTGTGTATGATGCAGGCACCTGGGCCGTCACTCAGCTGGC
TGTCTCTTACACGTAGCACCCTTTGTGATGTTGGCAGTTGAACCGACCA
TCAGCTTATACAAGTCCATGTACTTTATTTGCACATCATAAGTCTCCTG
ATAATACTATTTCTGCCAATGAAACCACAAGCTCATACGCAAAGGCGCC
TCAGACTCTGAACTCTATTAATAAGAGAAAAACAGATTGA SEQ ID NO: 88: Human_XP_001125855 protein
sequence, PREDICTED: similar to O-acyltransferase
(membrane bound) domain containing 2
[Homo sapiens]
MVNFVVCQLVALFAAFWFRIYLRPGTTSSDVRHAVATIFGIYFVIFCFGW
YSVHLFVLVLMCYAIMVTASVSNIHRYSFFVAMGYLTICHISRIYIFHYG
ILTTDFSGPLMIVTQKITTLAFQVHDGLGRRAEDLSAEQHRLAIKVKPSF
LEYLSYLLNFMSVIAGPCNNFKDYIAPIEGKHIHMKLLEVNWKRKGFHSL
PEPSPTGAVIHKLGITLVSLLLFLTLTKTFPVTCLVDDWFVHKASFPARL
CYLYVVMQASKPKYYFAWTLADAVNNAAGFGFSGVDKNGNFCWDLLSNLN
IWKIETATSFKMYLENWNIQTATWLKCVCYQRVPWYPTVLTFILSALWHG
VYPGYYFTFLTGILVLTAARAVRNNYRHYFLSSRALKAVYDAGTWAVTQL
AVSYTVAPFVMLAVEPTISLYKSMYFYLHIISLLIILFLPMKPQAHTQRR
PQTLNSINKRKTD SEQ ID NO: 100: Human_XP_001125855 cDNA sequence
ATGTTCTTTAAAAAATTATCTTGCAGGTTCTGCATCACTCTTTCTTCT
CATGCTCTTGACCCAGAGGGTCACGTCCCTCTCTCTGGACATTTGTGAGG
GGAAAGTGAAGGCAGCATCTGGAGGCTTCAGGAGCAGGAGCTCTTGTCT
```

```
GAGCATGTGTGTAAGGCACTGCCCTATTTCAGCTACTTGCTCTTTTTCCC
TGCTCTCCTGGGAGGCTCTCTGTGCTCCTTCCAGCGATTTCAGGCTCGTG
TTCAAGGGTCCAGTGCTTTGCATCCCAGACACTCTTTCTGGGCTCTGAGC
TGGAGGGGTCTGCAGATTCTTGGACTAGAATGCCTAAACGTGGCAGTGAG
CAGGGTGGTGGATGCAGGAGCGGGACTGACTGATTGCCAGCAATTCGAGT
GCATCTATGTCGTGTGACCACAGCTGGGCTTTTCAAGCTCACCTTACTAC
TCCCACTGGATCCTGGACGACTCCCTCCTCCACGCAGCGGGCTTTGGGCC
TGAGCTTGGTCAGAGCCCTGGAGAGGAGGGATATGTCCCCGATGCAGACA
TCTGGACCCTGGAAAGAACCCCACAGGATATCTGTGTTCTCAAGAAAGTGG
AACCAAAGCACAGCTCGATGGCTCCGACGGCTTGTATTCCAGCACAGCAG
GGCTTGGCCGTTGTTGCAGACATTTGCCTTCTCTGCCTGGTGGCATGGAG
TCCATCCAGGACAGGTGTTTGGTTTCGTTTGCTGGGCCGTGATGGTGGAA
GCTGACTACCTGATTCACTCCTTTGCCAATGAGTTTATCAGATCCTGGCC
GATGAGGCTGTTCTATAGAACCCTCACCTGGGCCCACACCCAGTTGATCA
TTGCCTACATCATGCTGGCTGTGGAGGTCAGGAGTCTCCCTCTCTCTGG
TTGCTCTGTAATTCGTACAACAGTGTCTTTCCCATGGTGTACTGTATTCT
GCTTTTGCTATTGGCAAGAGAAAGCACAAATGTAACTGA

SEQ ID NO: 43: Mouse_NP_080313 deduced protein
sequence, O-acyltransferase (membrane bound)
domain containing 2 isoform a [Mus musculus]
MATTSTTGSTLLQPLSNAVQLPIDQVNFVVCQLFALLAAVWFRTYLHSSK
TSSFIRHVVATLLGLYAFFCFGWYALHFLVQSGISYCIMIIAGVESMQQC
CFVFALGYLSVCQITRVYIFDYGQYSADGSGPMMIITQKITSLAYEIHDG
MFRKDEELTPSQRGLAVRRMPSLLEYVSYTCNFMGILAGPLCSYKDYIAF
IEGRASHVAQPSENGKDEQHGKADPSPNAAVTEKLLVCGLSLLFHLTISN
MLPVEYNIDEHFQATASWPTKATYLYVSLLAARPKYYFAWTLADAINNAA
GFGFRGYDKNGVARWDLISNLRIQQIEMSTSFKMPLDNWNIQTALWLKRV
CYERATFSPTIQTFFLSAIWHGVYPGYYLTFLTGVLMTLAARAVRNNFRH
YFLEPPQLKLFYDLITWVATQITISYTVVPFVLLSIKPSFTFYSSWYYCL
HVCSILVLLLLPVKKSQRRTSTQENVHLSQAKKFDERDNPLGQNSFSTMN
NVCNQNRDTGSRHSSLTQ SEQ ID NO: 111: Mouse_NP_080313 cDNA sequence
ATGGCCACCACCAGCACCACGGGCTCCACCCTGCTGCAGCCCCTCAGCAA
CGCCGTGCAACTGCCCATCGATCAGGTCAACTTTGTAGTGTGCCAGCTCT
TTGCCTTGTTAGCAGCCGTTTGGTTTCGAACTTATCTACACTCAAGCAAA
ACTAGCTCTTTATCAGACACGTAGTTGCTACCCTTTTGGGCCTTTATCTT
GCATTTTTTGCTTTGGATGGTATGCCTTACACTTTCTTGTACAAAGTGG
GATTTCCTACTGCATGATCATAGGAGTGGAGAACATGCAGCAGR
GTTGCTTTGTGTTTGCTTTGGATACCTCTCAGTGTCAGATTACTAGA
GTCTATATCTTTGATTATGGACAATATTCTGCTGATTTTTCAGGCCCAAT
GATGATCATTACGCAGAAGATCACTAGTTTGGCTTGCAGAAATTCACGATG
GGATGTTTCGGAAGGATGAAGAACTGACTCCGTCGCAGAGGGGATTAGC
GTGAGGCGCATGCCAAGTCTCCTGGAGTATGTAAGTTATACCTGCAACTT
CATGGGCATCCTGGCAGGCCCACTGTGCTCCTACAAAGACTACATTGCCT
TCATTGAAGGCAGATCCCCGTGCACAACGAGCAGTTACGGAAGATG
GACGAGCAGCATGGGAAAGCAGATCCCATCCAAATGACAGCAGTTACGGA
GAAGCTCCTGGTCTGTGGACTCTCCTTATTATTCCACCTGACCATCTCCA
ACATGCTACCCGTGGAGTACAACATCGATGAGCATTTCCAAGCCACTGCG
TCGTGGCCGACTAAAGCCACCTATCTGTACGTCTCCTCTTTGGCTGCCAG
ACCTACTATTTTGCATGGACTTAGCTGACGCCATTAACAATGCTG
CGGGCTTCGGTTTCAGAGGATACGACAAGAATGGAGTGGCTCGCTGGGAC
TTAATTTCCAACTTGAGAATTCAGCAAATAGAGATGTCAACAAGTTTTAA
GATGTTTCTGATAACTGGAATATCCAGACAGCTCTTTGGCTCAAAAGGG
TGTGCTATGAAGAGCAACCTTCAGTCCGACAATCCAGACATTCTTTCTC
TCTGCCATTTGGCATGGGGTCTACCCAGGATATTATCTGACATTCCTAAC
GGGAGTGCTAATGACGTTAGCAGCTCGGGCTGTGAGAAATAACTTTAGGC
ACTATTTCCTGGAGCCCCCTCAACTTAAGTTATTTTATGACCTCATAACC
TGGGTGGCCACCCAGATAACAATAAGTTACACAGTTGTTCCGTTTGTGCT
CCTCTCCATAAAACCGTCGTTCACGTTTTACAGCTCCTGGTATTACTGCC
TTCACGTCTGTAGTATCTTGGTGTTGCTGTTGCTGCCTGTGAAAAAGTCT
CAAAGAAGAACGAGCCACACAGGAAATGTTCATCTCTCACAGGCCAAAA
GTTTGACGAAAGGGACAATCCTCTGGGACAGAACAGTTTTTCCACGATGA
ATAACGTTTGCAATCAGAACCGAGACACTGGCTCCAGACACTCGTCACTA
ACACAGTGA SEQ ID NO: 101: Mouse_NP_084210 deduced protein
sequence, leukocyte recpetor cluster (LRC) member
4 [Mus musculus]
MTPEEWTYLMVLLISIPVGFLGKKAGPGLKRWGAAAVGLGLTLFTCGPHS
LHSLITILGTWALIQAQPCSCHALALAWTFSYLLFFRALSLLGLPTPTPF
TNAVQLLLTLKLVSLASEVQDLHLAQRKEIASGFHKEPTLGLLPEVPSLM
ETLSYSYCYVGIMTGPFFRYRTYLDWLEQPFPEAVPSLRPLLRRAWPAPL
FGLLFLLSSHLFPLEAVREDAFYARPLPTRLFYMIPVFFAFRMRFYVAWI
AAECGCIAAGFGAYPVAAKARAGGGPTLQCPPPSSPEIAASLEYDYETIR
NIDCYGTDFCVRVRDGMRYWNMTVQWWLAQYIYKSAPFRSYVLRSAWTML
LSAYWHGLHPGYYLSFMTIPLCLAAEGYLESALRRHLSPGGQKAWDWVHH
FLKMRAYDYMCMGGVLLSMADTLRYWASIYFWVHFLALACLGLGLVLGGG
SPSKRKTPSQATSSQAKEKLREE
```

SEQ ID NO: 102: Mouse_NP_084210 deduced cDNA
sequence
ATGACACCCGAAGAATGGACATATCTAATGGTCCTTCTTATCTCCATCCC
TGTTGGCTTCCTCTTTAAGAAAGCTGGACCTGGGCTGAAGAGATGGGGGG
CAGCAGCTGTGGGCCTGGGGCTCACCTTATTCACCTGTGGCCCCCACAGT
TTGCATTCTCTGATCACCATCTTGGGAACCTGGGCCCTCATTCAGGCCCA
GCCCTGCTCCTGCCATGCCCTGGCTCTTGCCTGGACCTTCTCCTATCTCC
TCTTCTTCCGAGCCCTCAGCCTGCTGGGCCTGCCCACTCCCACGCCCTTC
ACCAATGCTGTCCAGCTGCTGCTGTTGACACTGGAGTTGGTGAGTCTAGC TAG
TGAAGTCCAGGATCTGCATCTGGCTCAGAGAAAGGAAATAGCCTCCGGCT
TCCACAAGGAGCCTACGCTGGGCCTCCTGCCTGAGGTCCCCTCTTTGATG
GAGACACTCAGCTATAGCTACTGTTACGTGGGAATCATGACAGGCCCATT
CTTCCGCTACCGCACCTACCTGGATTGGCTGGAACAGCCCTTCCCGGAAG
CCGTGCCCAGCCTGAGGCCCCTGCTGCGCCGCGCCTGGCCAGCCCCGCTC
TTTGGCCTGCTCTTCCTGCTGTCCTCCCATCTCTTCCCACTGGAAGCTGT
GCGTGAGGACGCCTTCTACGCCCGCCCGCTGCCCACCCGCCTCTTCTACA
TGATCCCGGTCTTCTTCGCCTTCCGCATGCGCTTCTACGTTGCCTGGATT
GCGGCCGAGTGCAGTTGCATTGCCGCGGGCTTCGGGGCTACCCTGGTGA
TGCCAAAGCCCGGGCCGGGGCGGCCCACCCTCCAATGCCACCCCCTA
GCAGTCGGAGATTGCAGCTTCCTGGAGTATGACTATGAGACCATCCGT
AACATCGACTGCTATGGCACAGACTTCTGCGTGCGTGTGCGGGATGGCAT
GCGATACTGGAACATGACCATGCGCTGGTGGCTGGCACAGTACATCTACA
AGAGCGCACCTTTCCGCTCCTACGTTTTGAGGAGTGCCTGGACCATGCTG
TTGAGTGCCTACTGGCATGGCCTCCACCCTGGTTACTACCTAAGCTTCAT
GACCATCCCGCTGTGCCTGGCTGCTGAGGGCTATTTGGAGTCAGCCTTGC
GGAGACACCTGGAGCCCCGGGGGCCAGAAGCCTGGGACTGGGTCCACTGG
TTCCTGAAGATGCGTCGCTACGACTACATGTGCATGGGCTTTGTGCTCCT
TTCCATGGCTGACACACTCCGGTACTGGGCCTCCATCTACTTCTGGGTCC
ACTTTCTAGCCCTGGCTTGCTTGGGGCTGGGGCTGGTTTTGGGTGGGGGC
AGCCCCAGCAAGAGGAAGACACCATCCCAGGCCACCAGCAGCCAAGCGAA
GGAAAAGCTCCGGGAAGAGTGA SEQ ID NO: 103: Mouse_NP_660112 deduced protein
sequence, membrane bound O-acyltransferase domain
containing 5 [Mus musculus]
MASTADGDMGETLEQMRGLWPGVEDLSLNKLATSLGASEQLARLIFSIFL
GYPLALFYRHYLFYKDSYLIHLFHTFTGLSIAYFNFGHQFYHSLLCVVLQ
FLILRLMGRTVTAVITTLCFQMAYLLAGYYYTATGDYDIKWTMPHCVLTL
KLIGLCIDYYDGGKDGNSLTSEQQKYAIRGVPSLLEVAGFSYFYGAFLVG
PQFSMNHYMKLVRGQLTDIPGKMPNSTIPALKRLSLGLVYLVGYTLLSPH
ITDDYLLTEDYDNRPFWFRCMYMLIWGKFVLYKYVTCWLVTEGVCILSGL
GFNGFDENGTVRWDACANMKVWLFETTPRFNGTIASFNINTNAWVARYIF
KRLKFLGNKELSQGLSLLFLALWHGLHSGYLICFQMEFLIVIVEKQVSSL
IRDSPALSSLASITALQPFYYLVQQTIHWLFMGYSMTAFCLFTWDKWLKV
YRSIYFLGHVFFLSLLFILPYIHKAMVPRKEKLKKRE SEQ ID NO: 104: Mouse_NP_660112 deduced cDNA
sequence
ATGGCGTCTACAGCGGACGGGGACATGGGAGAGACGCTGGAGCAGATGCG
GGGGCTGTGGCCGGGTGTCGAGGATCTCAGCCCTTAACAAGTTGGCGACGT
CTCTGGGCGCGTCGGAACAGGCGCTGCGGCTCATCTTCTCCATCTTCCTG
GGCTACCCGTTGGCTCTGTTTTACCGGCATTACCTTTTCTACAAGGACAG
CTACCTCATCCATCTCTTCCACACCTTCACGGGCCTCTCAATTGCTTATT
TCAACTTTGGCCACCAGTTCTACCACTCCTTGCTATGTGTCGTCTTCAG
TTCCTCATCCTGCGACTCATGGGCCGCACCGTCACTGCCGTTATTACTAC
CCTTTGCTTCCAGATGGCCTACCTTCTTGCCGGATATTACTACACAGCCA
CCGGTGACTACGATATCAAGTGGACAATGCCACATTGTGTCTTGACACTG
AAGCTAATTGGGCGTGTGTATTGACTACGATGGAGGCAAAGACGGGAA
TTCCTTGACCTCTGAGCAACAGAAATATGCCATACGGGGTGTCCCTTCAT
TGCTGGAAGTTGCTGGCTTCTCCTACTTCTATGGAGCCTTCTTGGTAGGG
CCCCAATTTTCAATGAACCACTACATGAAGCTGGTGCGGGGACAGCTGAC
TGACATACCAGGGAAGATGCCAAACAGCACCATACCTGCTCTCAAGCGCC
TGAGTCTGGGCCTTGTCTACCTGGTGGGCTACACCCTGCTGAGCCCCCAC
ATCACAGACGACTATCTCCTCACAGAAGCTATGATAACCGCCCTTCTG
GTTCCGCTGCATGTACATGCTGATCTGGGCAAATTTGTGCTGTACAAT
ACGTCACCTGCTGGCTGGTCACAGAAGGAGTGTGCATTCTGTCGGGCCTG
GGCTTTAATGGCTTCGATGAAAATGGGACCGTGAGATGGGATGCCTGTGC
CAACATGAAAGTGTGGCTCTTTGAAACCACCCCCTCGCTTCAATGGCACCA
TCGCCTCTTTCAACATCAATACCAATGCCTGGGTAGCCCGTTACATCTTC
AAACGCCTCAAGTTCCTTGGAAATAAAGAGCTCTCACAAGGTCTCTCCTT
GCTGTTCTTGGCCCTCTGGCATGGCCTACACTCAGGATACCTGATTTGCT
TCCAGATGGAATTCCTCATTGTTATCGTGGAAAAGCAGGTCAGCAGTCTA
ATTCGGGACAGCCCTGCCTTGAGCAGCCTGGCCTCCATCACTGCCCTACA
GCCCTTCTACTACTTGGTGCAACAGACCATCCACTGGCTGTTCATGGGTT
ACTCTATGACTGCCTTCTGCCTCTTCACATGGGACAAATGGCTTAAGGTG
TACAGATCCATCTATTTCCTTGGACATGTCTTCTTCTTGAGCCTACTATT
CATATTGCCTTATATCCACAAAGCAATGGTGCCAAGAAAAGAAAGTTAA
AAAAGAGGGAATGA SEQ ID NO: 105: Mouse_NP_705774 deduced protein
sequence, membrane bound O-acyltransferase domain
containing 1 [M. musculus]
MAARPPASLSYRTTGSTCLHPLSQLLGIPLDQVNFVACQLFALSAAFWFR
IYLHPGKASPEVRHTLATILGIYFVVFCFGWYAVHLFVLVLMCYGVMVTA
SVSNIHRYSFFVAMGYLTICHISRIYIFHYGILTTDFSGPLMIVTQKITT
LAFQVHDGLGRKAEDLSAEQHRLAVKAKPSLLEYLSYHLNFMSVIAGPCN
NFKDYVAFIEGRHIHMKLLEVNWTQRGFQSLPEPSPMGAVIQKLCVTLMS
LLLFLTLSKSFPVTFLIDDWFVHKANFLSRLWYLYVVMQAAKPKYYFAWT
LADAVHNAAGFGFNGMDTGKSRWDLLSNLNIWKIETATSFKMYLENWNI
QTSTWLKCVCYERVPWYPTVLTFLLSALWHGVYPGYYFTFLTGVPVTLAA
RAVRNNYRHHFLSSKARKIAYDVVTWAVTQLAVSYTAAPFVMLAVEPTIS
LYKSVFFFLHIICLLIILFLPIKPHQPQRQSRSPNSVKKKAD SEQ ID NO: 106: Mouse_NP_705774 cDNA sequence
ATGGCAGCACGGCCGCCCGCCAGCCTCTCTTACCGTACCACCGGCTCCAC
CTGCCTGCAACTGCCCATCAGCCAGCTCCTGGGCATCCCGCTGGATCAGGTTA
ACTTTGTGGCTTGCCAGCTCTTTGCCTTGTCTGCTGCTTTCTGGTTCAGA
ATCTACTTACATCCTGGTAAAGCCAGCCCTGAGGTCCGGCACACCTTGGC
CACCATTTTGGGCATCTATTTTGTTGTGTTTTGTTTTGGTTGGTATGCTG
TACATCTCTTTTGTGCTGGTTGATGTGTTTATGGGGTCATGGTCACTGCA
AGTGTATCCAATATTCACAGGTATTCCTTTTTGTAGCCATGGGCTACCT
TACGATATGCCACATCAGCCGCATTTACATCTTCCACTATGGAATTCTCA
CTACAGATTTTTCTGGGCCCCTGATGATTGTCACTCAGAAGATCACGACG
TTGGCTTTCCAAGTTCATGATGGATTGGGTCGAAAAGCTGAAGACCTTTC
TGCTGAGCAACACCGACTTGCTGTGAAAGCGAAGCCCTCGCTTCTGGAAT
ACTTAAGCTACCATCTCAACTTTATGAGTGTCATAGCCGGCCCTTGCAAC
AATTTCAAGGACTACGTAGCCTTCATCGAAGGGAGACATATACACATGAA
GTTGCTGGAAGTGAACTGGACGCAAAGGGGTTTCCAGAGTTTGCCAGAGC
CTTCTCCCATGGGAGCTGTGATCAGAAGTTGTGTGTGACCTTGATGTCT
CTCCTGTTGTTTTGACGCTCTCCAAGTCCTTTCCCGTCACCTTCCTTAT
TGATGACTGGTTTGTACATAAGGCCAACTTTCTGAGTCGTCTCTGGTACT
TATATGTCGTCATGCAAGCCGCAAAGCCCAAGTATTACTTTGCGTGGACA
TTAGCAGATGCGGTGCACAATGCAGCTGGATTCGGGTTCAATGGCATGGA
CACGGATGGGAAGTCTCGCTGGGATTTACTATCTAACCTGAACATCTGGA
AGATTGAGACTGCCACGAGTTTCAAAATGTACTTGGAAAACTGGAATATT
CAGACATCTACGTGGCTGAAATGTGTGTGCTATGAGCGGGTTCCCTGGTA
CCCCACAGTGCTTCACCTTCCTCCTGTCTGCTCTGTGGCACGGCGTCTACC
CTGGATACTACTTCACATTCCTAACTGGAGTCCCTGTCACATTGGCAGCC
AGAGCGGTGAGGAACAACTACAGACACCACTTCCTCTTCCAAAGCTCG
AAAGATTGCCTATGACGTGGTGACCTGGGCTGTCACTCAGTTGGCTGTCT
CTTACACGCCAGCGCCTTTCGTCATGTTGGCAGTCGAGCCAACCATCAGT
TTATACAAGTCCGTGTTCTTTTTTTTACACATCATATGTCTGCTGATAAT
CCTCTTTCTGCCAATCAAACCACACCAGCCTCAAAGGCAGTCTCGGAGTC
CAAATTCTGTAAAGAAGAAGGCAGACTGA SEQ ID NO: 107: Mouse_NP_001076810 deduced protein
sequence, O-acyltransferase (membrane bound)
domain containing 2 isoform b [M. musculus]
MATTSTTGSTLLQPLSNAVQLPIDQVNFVVCQLFALLAAVWFRTYLHSSK
TSSFIRHVVATLLGLYAFFCFGWYALHFLVQSGISYCIMIIAGVESMQHP
MMIITQKITSLAYEIHDGMFRKDEELTPSQRLGAVRRMPSLLEYVSYTCN
FMGILAGPLCSYKDYIAFIEGRASHVAQPSENGKDEQHGKADPSPNAAVT
EKLLVCGLSLLFHLTISNMLPVEYNIDEHFQATASWPTKATYLYVSLLAA
RPKYYFAWTLADAINNAAGFGFRGYDKNGVARWDLISNLRIQQIEMSTSF
KMFLDNWNIQTALWLKRVCYERATFSPTIQTFFLSAIWHGVYPGYYLTFL
TGVLMTLAARAVRNNFRHYFLEPPQLKLFYDLITWVATQITISYTVVPFV
LLSIKPSFTFYSSWYYCLHVCSILVLLLLPVKKSQRRTSTQENVHLSQAK
KFDERDNPLGQNSFSTMNNVCNQNRDTGSRHSSLTQ SEQ ID NO: 108: Mouse_NP_001076810 cDNA sequence
ATGGCCACCACCAGCACCACGGGCTTCCACCTGCTGCAGCCCCTCAGCAA
CGCCGTGCAACTGCCCATCGATCAGGTCAACTTTGTAGTGTGCCAGCTCT
TTGCCTTGTTAGCAGCCGTTTGGTTTCGAACTTATCTACACTCAAGCAAA
ACTAGCTCTTTTATCAGACACGTAGTTGCTACCCTTTTGGGCCTTTATCT
TGCATTTTTTTGCTTTGGATGGTATGCCTTACACTTTCTTGTACAAAGTG
GGATTTCCTACTGCATCATGATCATAGCAGGAGTGGAGAGCATGCAGCAC
CCAATGATGATCATTACGCAGAAGATCACTAGTTTGGCTTACGAAATTCA
CGACGGGATGTTTCGGAAGGATGAAGAACTGACTCCGTCGCAGAGGGGAT
TAGCTGTGAGGCGCATGCCAAGTCTCCTGGAGTATGTAAGTTATACCTGC
AACTTCATGGGCATCCTGGCAGGCCCACTGTGCTCCTACAAAGACTACAT
TGCCTTCATTGAAGGCAGAGCATCCACGTGGCACAGCCCAGTGAAAATG
GAAAAGACGAGCAGCATGGGAAAGACATCCATCTCCAAATGCAGCAGTT
ACGGAGAAGTCCTGGTCTGTGGACTCTCCTTATTATTCCACCTGACCAT
CTCCAACATGCTACCCGTGGAGTACAACATCGATGAGCACTTTCAGGCCA
CTGCGTCGTGGCCTAAAGCCACCTACCTCTATGTCTCTCTCTTGGCT
GCCAGACCTAAGTACTATTTTGCATGGACCTTAGCTGACGCCATTAACAA
TGCTGCGGGCTTCGGTTTCAGAGGATACGACAAGAATGGAGTGGCTCGCT
GGGACTTAATTTCCAACTTGAGAATTCAGCAAATAGAGATGTCAACAAGT
TTTAAGATGTTTCTTGATAACTGGAATATCCAGACAGCTCTTTGGCTCAA

```
                        -continued
AAGGGTGTGCTATGAACGAGCAACCTTCAGTCCGACAATCCAGACATTCT
TTCTCTCTGCCATTTGGCATGGGGTCTACCCAGGATACTATCTGACATTC
CTAACGGGAGTGCTAATGACGTTAGCAGCTCGGGCTGTGAGAAATAACTT
TAGGCACTATTTCCTGGAGCCCCCTCAACTTAAGTTATTTTATGACCTCA
TAACCTGGGTGGCCACCCAGATAACAATAAGTTACACAGTTGTTCCGTTT
GTGCTCCTCTCCATAAAACCGTCGTTCACGTTTTACAGCTCCTGGTATTA
CTGCCTTCACGTCTGTAGTATCTTGGTGTTGCTGTTGCTGCCTGTGAAAA
AGTCTCAAAGAAGAACGAGCACACAGGAAAATGTTCATCTCTCACAGGCC
AAAAAGTTTGACGAAAGGGACAATCCTCTGGGACAGAACAGTTTTTCCAC
GATGAATAACGTTTGCAATCAGAACCGAGACACTGGCTCCAGACACTCGT
CACTAACACAGTGA SEQ ID NO: 109: Mouse_XP_134120 deduced protein
sequence, PREDICTED: similar to O-acyltransferase
(membrane bound) domain containing 1
[M. musculus].
MPHCLQGTASESDFSVNTARGENACILWFPWLRPSVGKPTFTLLISSASI
SFCPAGLSTSYKKATESPVVTSLLQGHRLGTLGRTVGLTFRMDWLQLFFL
HPLSFYQGAAFPFALLFNYLCILDTFSTRARYLFLLAGGGVLAFAAMGPY
SLLIFIPALCAVALVSFLSPQEVHRLTFFFQMGWQTLCHLGLHYTEYYLG
EPPPVRFYITLSSLMLLTQRVTSLSLDICEGKVEAPRRGIRSKSSFSEHL
WDALPHFSYLLFFPALLGGSLCSFRRFQACVQRSSSLYPSISFRALTWRG
LQILGLECLKVALRSAVSAGAGLDDCQRLECIYLMWSTAWLFKLTYYSHW
ILDDSLLHAAGFGAEAGQGPGEEGYVPDVDIWTLETTHRISLFARQWNRS
TALWLRRLVFRKSRRWPLLQTFAFSAWWHGLHPGQVFGFLCWSVMVKADY
LIHTFANVCIRSWPLRLLYRALTWAHTQLIIAYIMLAVEGRSLSSLCQLC
CSYNSLFPVMYGLLLFLLAERKDKRNSAFSF SEQ ID NO: 110: Mouse_XP_134120 deduced cDNA
sequence
ATGCCACACTGCCTGCAAGGTACAGCCTCTGAGAGTGACTTTTCAGTAAA
CACTGCGAGGGGAGAGAATGCCTGCATACTTTGGTTTCCATGGGCTCCGC
CCCTCTGTTGGGAAGCCAACCTTTACATTGCTTATCTCCAGTGCTTCCAT
TTCATTTTGTCCGGCAGGCCTTTCTACATCCTATAAAAAGGCTACGGAGA
GCCCAGTTGTGACTTCCCTTTTACAAGGGCACCGCTTAGGGACTCTAGGA
AGGACAGTGGGCCTCACATTCAGGATGGATTGGCTCCAGCTCTTTTTCT
GCATCCTTTATCATTTTATCAAGGGGCTGCATTCCCCTTTGCGCTTCTGT
TTAATTATCTCTGCATCTTGGACACCTTTTCCACCCGGGCCAGGTACCTC
TTTCTCCTGGCTGGAGGAGGTGTCCTGGCTTTTGCTGCCATGGGTCCCTA
CTCTCTGCTCATCTTCATCCCTGCGCTCTGCGCTGTGGCTCTGGTCTCCT
TCCTCAGTCCACAGGAAGTCCATAGGCTGACCTTCTTCTTTCAGATGGGC
TGGCAGACCCTGTGCCATCTGGGTCTTCACTACACCGAATACTACCTGGG
TGAGCCTCCACCCGTGAGGTTCTACATCACTCTTTCTTCCCTCATGCTCT
TGACGCAGAGAGTCACATCCCTCTCACTGGACATTTGTGAAGGGAAGGTG
GAGGCCCCGAGGCGGGCATCAGGAGCAAGAGTTCTTTCTCTGAGCACCT
GTGGGATGCTCTACCTCATTTCAGCTACTTGCTCTTTTTCCCTGCTCTCC
TGGGAGGCTCCCTGTGTTCCTTCCGGAGGTTTCAGGCTTGCGTTCAAAGA
TCAAGCTCTTTGTATCCGAGTATCTCTTTTCGGGCTCTGACCTGGAGGGG
TCTGCAGATTCTCGGGCTGGAGTGCCTCAAGGTGGCGCTGAGGAGCGCGG
TGAGTGCTGGAGCTGGACTGGATGACTGCCAGCGGCTGGAGTGCATCTAC
CTCATGTGGCTCCACAGCCTGGCTCTTTAAACTCACCTATTACTCCCATTG
GATCCTGGACGACTCTCTCCTCCACGCGGCGGGCTTTGGCGCTGAGGCTG
GCCAGGGGCCTGGAGAGGAGGGATACGTCCCCGACGTGGACATTTGGACC
CTGGAAACTACCCACAGGATCTCCCTGTTCGCCAGGCAGTGGAACCGAAG
CACAGCTCTGTGGCTCAGGAGGCTCGTCTTCCGGAAGAGCCGGCGCTGGC
CCCTGCTGCAGACATTTGCCTTCTCTGCCTGGTGGCACGGGCTCCACCCA
GGTCAGGTGTTCGGCTTCCTGTGCTGGTCTGTAATGGTGAAAGCCGATTA
TCTGATTCACACTTTTGCCAACGTATGTATCAGATCCTGGCCCCTGCGGC
TGCTTTATAGAGCCCTCACTTGGGCTCATACCCAACTCATCATTGCCTAC
ATCATGCTGGCGGTGGAGGGCCGGAGCCTTTCCTCTCTCTGCCAACTGTG
CTGTTCTTACAACAGTCTCTTCCCTGTGATGTACGGTCTTTTGCTTTTTC
TGTTAGCGGAGAGAAAAGACAAACGTAACTGA
```

Figure 20:
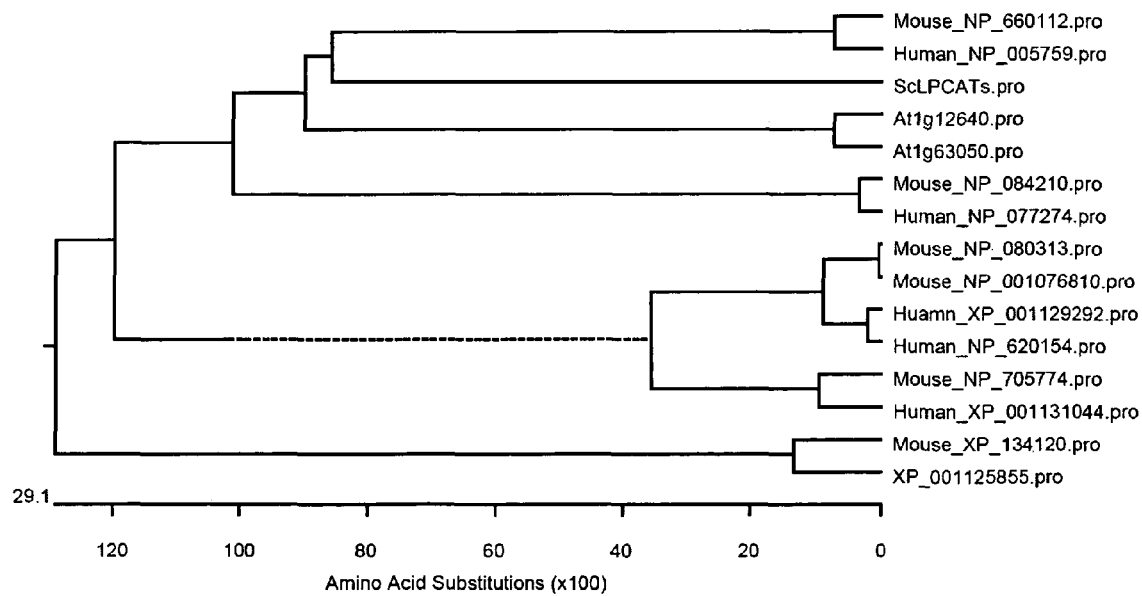
FIG. 20 is a sequence alignment of YOR175c with its selected human and mouse homologs. Alignment was performed with CLUSTALV from the DNASTAR package run with default multiple alignment parameters (gap opening penalty: 10; gap extension penalty: 10).

All of the above human and mouse YOR175cp homologs were aligned with YOR175cp sequence with MegAlign program of Lasergene7.0 software package (FIG. 20). Mouse proteins NP_660112 and NP_084210, human proteins NP_005759 and NP_077274 were characterized.

REFERENCES

The contents of the following references are incorporated herein in their entirety.

Abbadi A., F. Domergue, J. Bauer, J. A. Napier, R. Welti, U. Zähinger, P. Cirpus, and E. Heinz (2004). Biosynthesis of very-long-chain polyunsaturated fatty acids in transgenic oilseeds: constraints on their accumulation. *Plant Cell* 16:2734-2748.

Bechtold N., J. Ellis, and G. Pellefer (1993). In planta *Agrobacterium*-mediated gene transfer by infiltration of adult *Arabidopsis thaliana* plants. *C.R. Acad. Sci. Ser. III Sci. Vie*, 316:1194-1199.

Becker D., R. Brettschneider, and H. Lorz (1994). Fertile transgenic wheat from microprojectile bombardment of scutellar tissue. *Plant J.* 5:299-307.

Chen X., B. A. Hyatt, M. L. Mucenski, R. J. Mason, and J. M. Shannon (2006). Identification and characterization of a lysophosphatidylcholine acyltransferase in alveolar type II cells. *Proc. Natl. Acad. Sci. USA* 103:11724-11729.

Datla R, J. W. Anderson, and G. Selvaraj (1997). Plant promoters for transgene expression. *Biotechnology Annual Review* 3:269-296.

DeBlock M., D. DeBrouwer, and P. Tenning (1989). Transformation of *Brassica napus* and *Brassica oleracea* using *Agrobacterium tumefaciens* and the expression of the bar and neo genes in the transgenic plants. *Plant Physiol.* 91:694-701.

Domergue F., A. Abbadi, and E. Heinz (2005). Relief for fish stocks: oceanic fatty acids in transgenic oilseeds. *Trend Plant Sci.* 10:112-116.

Galván E. M., H. Chen, and D. M. Schifferli (2007). The Psa fimbriae of *Yersinia pestis* interact with phosphatidylcholine on alveolar epithelial cells and pulmonary surfactant. *Infect. Immun.* 75:1272-1279.

Huang Y. S., S. L. Pereira, and A. E. Leonard (2004). Enzymes for transgenic biosynthesis of long-chain polyunsaturated fatty acids. *Biochimie* 86:793-798.

Katavic Y., G. W. Haughn, D. Reed, M. Martin, and L. Kunst (1994). In planta transformation of *Arabidopsis thaliana*. *Mol. Gen. Genet.* 245:363-370. Meyer P. (1995). Understanding and controlling transgene expression. *Trends in Biotechnology* 13:332-337.

Moloney M. M., J. M. Walker, and K. K. Sharma (1989). High efficiency transformation of *Brassica napus* using *Agrobacterium* vectors. *Plant Cell Rep.* 8:238-242.

Napier J. A., F. Beaudoin, L. V. Michaelson, and O, Sayanova (2004). The production of long chain polyunsaturated fatty acids in transgenic plants by reverse-engineering. *Biochimic* 86:785-793.

Nehra N. S., R. N. Chibbar, N. Leung, K. Caswell, C. Mallard, L. Steinhauer, M. Baga, and K. K. Kartha (1994). Self-fertile transgenic wheat plants regenerated from isolated. scutellar tissues following microprojectile bombardment with two distinct gene constructs. *Plant J.* 5:285-297.

Potrykus L. (1991). Gene transfer to plants: Assessment of publish approaches and results. *Annu. Rev. Plant Physiol. Plant Mol. Biol.* 42:205-225.

Pouwels et al., *Cloning Vectors*. A laboratory manual, Elsevier, Amsterdam (1986).

Qi B., T. Fraser, S. Mugford, G. Dobson, O. Sayanova, J. Butler, J. A. Napier, A. K. Stobart, and C. M. Lazarus (2004). Production of very long chain polyunsaturated omega-3 and omega-6 fatty acids in plants. *Nat. Biotechnol.* 22:739-745.

Rhodes C. A., D. A. Pierce, I. J. Mettler, D. Mascarenhas, and J. J. Detmer (1988). Genetically transformed maize plants from protoplasts. *Science* 240:204-207.

Sanford J. C., T. M. Klein, E. D. Wolf, and N. Allen (1987). Delivery of substances into cells and tissues using a particle bombardment process. *J. Part. Sci. Technol.* 5:27-37.

Shimamoto K., R. Terada, T. Izawa, and H. Fujimoto (1989). Fertile transgenic rice plants regenerated from transformed protoplasts. *Nature* 335:274-276.

Shindou H., D. Hishikawa, H. Nakanishi, T. Harayama, S. Ishii, R. Taguchi, and T. Shimizu (2007). A single enzyme catalyzes both platelet-activating factor production and membrane biogenesis of inflammatory cells: Cloning and characterization of acetyl-CoA: lyso-PAF acetyltransferase. *J Biol Chem.* 282:6532-6539.

Songstad D. D., D. A. Somers, and R. J. Griesbach (1995). Advances in alternative DNA delivery techniques. *Plant Cell, Tissue and Organ Culture* 40:1-15.

Tamaki H., A. Shimada, Y. Ito, M. Ohya, J. Takase, M. Miyashita, H. Miyagawa, H. Nozaki, R. Nakayama, and H. Kumagai (2007). LPT1 encodes a membrane-bound O-acyltransferase involved in the acylation of lysophospholipids in the yeast *Saccharomyces cerevisiae*. *J. Biol. Chem.* [Epub ahead of print]

Testet E., J. Laroche-Traineau, A. Noubhani, D. Coulon, O. Bunoust, N. Camougrand, S. Manon, R. Lessire, and J. J. Bessoule (2005). Ypr140wp, "the yeast tafazzin," displays a mitochondrial lysophosphatidylcholine (lyso-PC) acyltransferase activity related to triacylglycerol and mitochondrial lipid synthesis. *Biochem. J.* 387:617-626.

Vasil I. K. (1994). Molecular improvement of cereals. *Plant Mol. Biol.* 5:925-937.

Walden R. and R. Wingender (1995). Gene-transfer and plant regeneration techniques. *Trends in Biotechnology* 13:324-331.

Wu G., M. Truksa, N. Datla, P. Vrinten, J. Bauer, T. Zank, P. Cirpus, E. Heinz, and X. Qiu (2005). Stepwise engineering to produce high yields of very long-chain polyunsaturated fatty acids in plants. *Nat. Biotechnol.* 23:1013-1017.

Yavin E. (1976). Regulation of phospholipids metabolism in differentiating cells from rat brain cerebral hemispheres in culture. Patterns of acetylcholine phosphocholine, and choline phosphoglycerides labeling from (methyl-$^{14}$C) choline. *J. Biol. Chem.* 251:1392-1397.

SEQUENCE LISTING

<160> NUMBER OF SEQ ID NOS: 90

<210> SEQ ID NO 1
<211> LENGTH: 1860
<212> TYPE: DNA
<213> ORGANISM: Saccharomyces cerevisiae

<400> SEQUENCE: 1

```
atgtacaatc ctgtggacgc tgttttaaca aagataatta ccaactatgg gattgatagt      60
tttacactgc gatatgctat ctgcttattg ggatcgttcc cactgaatgc tattttgaag     120
agaattcccg agaagcgtat aggtttaaaa tgttgtttta tcatttctat gtcgatgttt     180
tacttattcg gtgtgctgaa tctagtaagt ggattcagga ccctgtttat tagtaccatg     240
tttacttact tgatctcaag attttaccgt tccaagttta tgccacactt gaatttcatg     300
tttgttatgg gtcatttggc aataaatcat atacacgccc aattccttaa cgaacagact     360
caaactaccg ttgacattac aagttcacaa atggttttag ccatgaaact aacttctttt     420
gcatggtcgt actatgatgg ttcatgcact agcgaaagcg atttcaaaga tttgactgag     480
catcaaaaat ctcgtgctgt cagaggtcat ccacccttat taaagttcct ggcatatgca     540
tttttctatt caacgttgct aactggccca agtttcgatt atgccgattt tgacagctgg     600
ttgaattgtg agatgttccg tgacttgcct gaaagcaaaa agcctatgag aagacaccac     660
cctggtgaaa gaagacagat tccaaagaat ggtaaacttg cattatggaa agttgttcaa     720
ggtcttgctt ggatgatttt aagtacacta ggaatgaagc acttccccgt aaaatacgtt     780
ttggacaaag atggcttccc aacgagatct tttatattca gaatccatta cttattcttg     840
cttggtttca tccatagatt caagtactac gctgcctgga ctatttcgga aggatcttgt     900
attttgtgcg gtttgggtta taatggttat gattcaaaga cacaaaagat cagatgggat     960
cgtgtcagaa atattgacat ttggaccgta gaaacggcgc agaatacgcg tgaaatgttg    1020
gaagcatgga atatgaatac taacaagtgg ctaaaatact ctgtttattt acgtgtcaca    1080
aagaagggca aaaaacctgg tttccgctca actttgttta ctttcctaac ttccgcattt    1140
tggcatggta ccagacctgg gtactatctg acttttgcga caggggcttt gtaccaaaca    1200
tgtggtaaaa tctacagacg caatttaga ccaatttct tgcgagaaga tggtgtcact    1260
cctttgcctt ctaaaaaaat ctacgattta gttggcatat atgcaattaa actagcattt    1320
ggttacatgg tgcaaccatt tattatcctt gatttgaagc catctttaat ggtatggggc    1380
```

-continued

```
tctgtttatt tctatgttca tattattgtt gctttctcat ttttcctatt cagaggacca    1440
tatgctaaac aagttactga atttttaaa tccaaacaac ctaaagaaat attcattaga     1500
aaacaaaaga agttggaaaa agatatttct gcaagctctc caaacttggg tggtatattg    1560
aaggcaaaga ttgaacatga aagggaaag acagcagaag aagaagaaat gaacttaggt    1620
attccaccaa ttgagttaga aaagtgggac aatgctaagg aagattggga agatttctgc   1680
aaagattaca aagaatggag aaataaaaat ggtcttgaaa tagaagagga aaacctttct   1740 aaagctttg aaagattcaa gcaggaattt tctaacgctg caagtggatc aggtgaacgt    1800
gtgagaaaaa tgagttttag tggttactca ccaaagccta tttcaaaaaa ggaagagtag   1860
```

<210> SEQ ID NO 2
<211> LENGTH: 619
<212> TYPE: PRT
<213> ORGANISM: Saccharomyces cerevisiae

<400> SEQUENCE: 2

```
Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
            20                  25                  30

Phe Pro Leu Asn Ala Ile Leu Lys Arg Ile Pro Glu Lys Arg Ile Gly
        35                  40                  45

Leu Lys Cys Cys Phe Ile Ile Ser Met Ser Met Phe Tyr Leu Phe Gly
    50                  55                  60

Val Leu Asn Leu Val Ser Gly Phe Arg Thr Leu Phe Ile Ser Thr Met
65                  70                  75                  80

Phe Thr Tyr Leu Ile Ser Arg Phe Tyr Arg Ser Lys Phe Met Pro His
                85                  90                  95

Leu Asn Phe Met Phe Val Met Gly His Leu Ala Ile Asn His Ile His
            100                 105                 110

Ala Gln Phe Leu Asn Glu Gln Thr Gln Thr Thr Val Asp Ile Thr Ser
        115                 120                 125

Ser Gln Met Val Leu Ala Met Lys Leu Thr Ser Phe Ala Trp Ser Tyr
    130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Leu Leu Lys Phe
                165                 170                 175

Leu Ala Tyr Ala Phe Phe Tyr Ser Thr Leu Leu Thr Gly Pro Ser Phe
            180                 185                 190

Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
    210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
    290                 295                 300
```

```
Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
            325                 330                 335

Arg Glu Met Leu Glu Ala Trp Asn Met Asn Thr Asn Lys Trp Leu Lys
        340                 345                 350

Tyr Ser Val Tyr Leu Arg Val Thr Lys Gly Lys Lys Pro Gly Phe
    355                 360                 365

Arg Ser Thr Leu Phe Thr Phe Leu Thr Ser Ala Phe Trp His Gly Thr
370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
                405                 410                 415

Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
        435                 440                 445

Ile Leu Asp Leu Lys Pro Ser Leu Met Val Trp Gly Ser Val Tyr Phe
    450                 455                 460

Tyr Val His Ile Ile Val Ala Phe Ser Phe Leu Phe Arg Gly Pro
465                 470                 475                 480

Tyr Ala Lys Gln Val Thr Glu Phe Phe Lys Ser Lys Gln Pro Lys Glu
            485                 490                 495

Ile Phe Ile Arg Lys Gln Lys Lys Leu Glu Lys Asp Ile Ser Ala Ser
        500                 505                 510

Ser Pro Asn Leu Gly Gly Ile Leu Lys Ala Lys Ile Glu His Glu Lys
    515                 520                 525

Gly Lys Thr Ala Glu Glu Glu Met Asn Leu Gly Ile Pro Pro Ile
530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
            565                 570                 575

Glu Asn Leu Ser Lys Ala Phe Glu Arg Phe Lys Gln Gly Phe Ser Asn
        580                 585                 590

Ala Ala Ser Gly Ser Gly Glu Arg Val Arg Lys Met Ser Phe Ser Gly
    595                 600                 605

Tyr Ser Pro Lys Pro Ile Ser Lys Lys Glu Glu
610                 615
```

<210> SEQ ID NO 3
<211> LENGTH: 1780
<212> TYPE: DNA
<213> ORGANISM: Arabidopsis thaliana

<400> SEQUENCE: 3

| | | | | | |
|---|---|---|---|---|---|
| accaacaacc | acacgacacg | acacgaccga | tctatagatt | cggcgagatc | agaagaaagc | 60 |
| ttcccggagc | aactcggtcg | ttgtgactca | ttccgagtta | aaaaaaacgg | gttttcgaca | 120 |
| ccatggatat | gagttcaatg | gctggttcaa | tcggagtttc | ggtagccgta | ctccgattcc | 180 |
| tcctctgttt | cgttgccacg | atccctgttt | cattcgcttg | tcgaatcgtc | ccgagtagac | 240 |
| tcggtaaaca | cttgtatgcc | gctgcttcag | gtgcttcct | ctcttacctc | tcctttggct | 300 |
| tctcctccaa | ccttcacttc | cttgttccga | tgacgatcgg | atatgcttca | atggcgattt | 360 |

```
atagacccaa gtgtggaatc atcactttct tcctcggttt cgcttatctt attggctgtc    420
atgtgtttta tatgagtggt gatgcgtgga agaaggagg aatcgattct actggagcgt     480
taatggtgtt gacgctgaaa gtcatctcat gttcaatgaa ttacaatgat gggatgttga    540
aggaggaagg tctacgtgaa gctcagaaga aaaacagatt gattcagatg ccgtctttga    600
ttgagtactt tggttactgc ctttgttgtg gtagccattt tgctggtcct gtttatgaaa    660
tgaaagatta tcttgaatgg accgaaggga aagggatttg ggatactact gagaaaagaa    720
agaagccatc gccttatgga gctacaatcc gagctatttt gcaagctgcg atttgcatgg    780
ctctgtatct ctatttagtg cctcaatatc cgttaactcg gttcacagaa ccagtgtatc    840
aagaatgggg attcttgaga aaatttagtt accaatacat ggctggattc acggctcgtt    900
ggaagtatta cttcatctgg tcaatttcag aggcttctat tatcatctct ggtttgggtt    960
tcagtggttg gactgatgat gcttcaccaa agcccaaatg ggaccgtgcc aagaacgtag   1020
atattctcgg tgttgaacta gctaagagcg cggttcagat tccacttgtg tggaacatac   1080
aagtcagcac gtggctccgt cactatgtgt atgagagact tgtgcagaac ggaaagaaag   1140
cgggtttctt ccagttacta gctacacaaa ccgtcagcgc ggtttggcat ggactgtatc   1200
ctggatatat gatgttcttt gttcagtcag ctttgatgat cgcaggctca cgggttattt   1260
accggtggca acaagcgatc agtccgaaaa tggcaatgct gagaaatata atggtcttca   1320
tcaacttcct ttacactgtt ttggttctca actactcagc cgtcggtttc atggtgttaa   1380
gcttgcacga acacttacc gcctacgaa gcgtatatta cattggaaca atcatacctg    1440
ttggattgat tctcctcagt tacgttgtgc ctgcaaaacc ttcaagacca aaaccgcgta   1500
aagaagaata agcagttatc ttcttctctt aacggtaagt aagtttcccg cgcttgccag   1560
cttcttcttc ttcttctgta acatttggaa acaaaccgat ccggttcttg tttctctctg   1620
attttttagc accgatattt ttttttgtatt tgttgcttat aaatcttatt tttcacactt   1680
cttttttttta attagtattg gatttgcaat tatatagaca ataagtataa atatgtaact   1740
gtaaattgca aatgggaaaa aatagtagtg tttatgtttg                          1780
```

<210> SEQ ID NO 4
<211> LENGTH: 462
<212> TYPE: PRT
<213> ORGANISM: Arabidopsis thaliana

<400> SEQUENCE: 4

Met Asp Met Ser Ser Met Ala Gly Ser Ile Gly Val Ser Val Ala Val
1               5                   10                  15

Leu Arg Phe Leu Leu Cys Phe Val Ala Thr Ile Pro Val Ser Phe Ala
            20                  25                  30

Cys Arg Ile Val Pro Ser Arg Leu Gly Lys His Leu Tyr Ala Ala Ala
        35                  40                  45

Ser Gly Ala Phe Leu Ser Tyr Leu Ser Phe Gly Phe Ser Ser Asn Leu
    50                  55                  60

His Phe Leu Val Pro Met Thr Ile Gly Tyr Ala Ser Met Ala Ile Tyr
65                  70                  75                  80

Arg Pro Lys Cys Gly Ile Ile Thr Phe Phe Leu Gly Phe Ala Tyr Leu
                85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
        115                 120                 125

```
Ser Cys Ser Met Asn Tyr Asn Asp Gly Met Leu Lys Glu Glu Gly Leu
    130                 135                 140

Arg Glu Ala Gln Lys Lys Asn Arg Leu Ile Gln Met Pro Ser Leu Ile
145                 150                 155                 160

Glu Tyr Phe Gly Tyr Cys Leu Cys Cys Gly Ser His Phe Ala Gly Pro
                165                 170                 175

Val Tyr Glu Met Lys Asp Tyr Leu Glu Trp Thr Glu Gly Lys Gly Ile
            180                 185                 190

Trp Asp Thr Thr Glu Lys Arg Lys Pro Ser Pro Tyr Gly Ala Thr
        195                 200                 205

Ile Arg Ala Ile Leu Gln Ala Ala Ile Cys Met Ala Leu Tyr Leu Tyr
    210                 215                 220

Leu Val Pro Gln Tyr Pro Leu Thr Arg Phe Thr Glu Pro Val Tyr Gln
225                 230                 235                 240

Glu Trp Gly Phe Leu Arg Lys Phe Ser Tyr Gln Tyr Met Ala Gly Phe
                245                 250                 255

Thr Ala Arg Trp Lys Tyr Tyr Phe Ile Trp Ser Ile Ser Glu Ala Ser
                260                 265                 270

Ile Ile Ile Ser Gly Leu Gly Phe Ser Gly Trp Thr Asp Asp Ala Ser
            275                 280                 285

Pro Lys Pro Lys Trp Asp Arg Ala Lys Asn Val Asp Ile Leu Gly Val
        290                 295                 300

Glu Leu Ala Lys Ser Ala Val Gln Ile Pro Leu Val Trp Asn Ile Gln
305                 310                 315                 320

Val Ser Thr Trp Leu Arg His Tyr Val Tyr Glu Arg Leu Val Gln Asn
                325                 330                 335

Gly Lys Lys Ala Gly Phe Phe Gln Leu Leu Ala Thr Gln Thr Val Ser
                340                 345                 350

Ala Val Trp His Gly Leu Tyr Pro Gly Tyr Met Met Phe Phe Val Gln
            355                 360                 365

Ser Ala Leu Met Ile Ala Gly Ser Arg Val Ile Tyr Arg Trp Gln Gln
    370                 375                 380

Ala Ile Ser Pro Lys Met Ala Met Leu Arg Asn Ile Met Val Phe Ile
385                 390                 395                 400

Asn Phe Leu Tyr Thr Val Leu Val Leu Asn Tyr Ser Ala Val Gly Phe
                405                 410                 415

Met Val Leu Ser Leu His Glu Thr Leu Thr Ala Tyr Gly Ser Val Tyr
            420                 425                 430

Tyr Ile Gly Thr Ile Ile Pro Val Gly Leu Ile Leu Leu Ser Tyr Val
        435                 440                 445

Val Pro Ala Lys Pro Ser Arg Pro Lys Pro Arg Lys Glu Glu
    450                 455                 460

<210> SEQ ID NO 5
<211> LENGTH: 1659
<212> TYPE: DNA
<213> ORGANISM: Arabidopsis thaliana

<400> SEQUENCE: 5
agatgtccga actgtgagag tcgtcgtcgt cgtcgtaact cagtccgagt tgacacaatc    60
ttccacttca cgcaagatac aaccatggaa ttgcttgaca tgaactcaat ggctgcctca   120
atcggcgtct ccgtcgccgt tctccgtttc ctcctctgtt tcgtcgcaac gataccaatc   180
tcatttttat ggcgattcat cccgagtcga ctcggtaaac acatatactc agctgcttct   240
```

-continued

```
ggagctttcc tctcttatct ctcctttggc ttctcctcaa atcttcactt ccttgtccca    300
atgacgattg gttacgcttc aatggcgatt tatcgaccct tgtctggatt cattactttc    360
ttcctaggct tcgcttatct cattggctgt catgtgtttt atatgagtgg tgatgcttgg    420
aaagaaggag gaattgattc tactggagct ttgatggtat taacactgaa agtgatttcg    480
tgttcgataa actacaacga tggaatgttg aaagaagaag gtctacgtga ggctcagaag    540
aagaaccgtt tgattcagat gccttctctt attgagtact tggttattg cctctgttgt    600 ggaagccatt tcgctggccc ggttttcgaa atgaaagatt atctcgaatg gactgaagag    660
aaaggaattt gggctgtttc tgaaaaagga aagagaccat cgccttatgg agcaatgatt    720
cgagctgtgt ttcaagctgc gatttgtatg gctctctatc tctatttagt acctcagttt    780
ccgttaactc ggttcactga accagtgtac caagaatggg gattcttgaa gagatttggt    840
taccaataca tggcgggttt cacggctcgt tggaagtatt actttatatg gtctatctca    900
gaggcttcta ttattatctc tggtttgggt ttcagtggtt ggactgatga aactcagaca    960
aaggctaaat gggaccgcgc taagaatgtc gatattttgg gggttgagct tgccaagagt    1020
gcggttcaga ttccgctttt ctggaacata caagtcagca catggctccg tcactacgta    1080
tatgagagaa ttgtgaagcc cgggaagaaa gcgggtttct tccaattgct agctacgcaa    1140
accgtcagtg ctgtctggca tggactgtat cctggataca ttatattctt tgtgcaatca    1200
gcattgatga tcgatggttc gaaagctatt taccggtggc aacaagcaat acctccgaaa    1260
atggcaatgc tgagaaatgt tttggttctc atcaatttcc tctacacagt agtggttctc    1320
aattactcat ccgtcggttt catggtttta agcttgcacg aaacactagt cgccttcaag    1380
agtgtatatt acattggaac agttataccc atcgctgtgc ttcttctcag ctacttagtt    1440
cctgtgaagc ctgttagacc aaagaccaga aaagaagaat aatgttgtct ttttaaaaaa    1500
tcaacaacat tttggttctt ttcttttttt ccacttggac cgttttatgt aaaacaagag    1560
aaatcaagat ttgaggtttt attcttcttc tccttcccaa ttttcgaaaa tgatttattt    1620
ttttctgata tatatctaag ctagtccaaa gtcaactcg                          1659
```

<210> SEQ ID NO 6
<211> LENGTH: 465
<212> TYPE: PRT
<213> ORGANISM: Arabidopsis thaliana

<400> SEQUENCE: 6

```
Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
                20                  25                  30

Ser Phe Leu Trp Arg Phe Ile Pro Ser Arg Leu Gly Lys His Ile Tyr
            35                  40                  45

Ser Ala Ala Ser Gly Ala Phe Ser Tyr Leu Ser Phe Gly Phe Ser
        50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Leu Gly Phe
            85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125
```

Lys Val Ile Ser Cys Ser Ile Asn Tyr Asn Asp Gly Met Leu Lys Glu
130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
                180                 185                 190

Lys Gly Ile Trp Ala Val Ser Glu Lys Gly Lys Arg Pro Ser Pro Tyr
                195                 200                 205

Gly Ala Met Ile Arg Ala Val Phe Gln Ala Ala Ile Cys Met Ala Leu
210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                245                 250                 255

Ala Gly Phe Thr Ala Arg Trp Lys Tyr Tyr Phe Ile Trp Ser Ile Ser
                260                 265                 270

Glu Ala Ser Ile Ile Ile Ser Gly Leu Gly Phe Ser Gly Trp Thr Asp
                275                 280                 285

Glu Thr Gln Thr Lys Ala Lys Trp Asp Arg Ala Lys Asn Val Asp Ile
290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
                325                 330                 335

Val Lys Pro Gly Lys Lys Ala Gly Phe Phe Gln Leu Leu Ala Thr Gln
                340                 345                 350

Thr Val Ser Ala Val Trp His Gly Leu Tyr Pro Gly Tyr Ile Ile Phe
                355                 360                 365

Phe Val Gln Ser Ala Leu Met Ile Asp Gly Ser Lys Ala Ile Tyr Arg
370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
                405                 410                 415

Val Gly Phe Met Val Leu Ser Leu His Glu Thr Leu Val Ala Phe Lys
                420                 425                 430

Ser Val Tyr Tyr Ile Gly Thr Val Ile Pro Ile Ala Val Leu Leu Leu
                435                 440                 445

Ser Tyr Leu Val Pro Val Lys Pro Val Arg Pro Lys Thr Arg Lys Glu
450                 455                 460

Glu
465

<210> SEQ ID NO 7
<211> LENGTH: 1464
<212> TYPE: DNA
<213> ORGANISM: Thalassiosira pseudonana

<400> SEQUENCE: 7
atgcgattgt atttgcaatt caacttatcc atcaatgatt attgtcactt cttcacagta      60
ccatcctttg tcaaagaggg cgtcgagtct ctctctgcat ccaccggaca agacgtcgag     120
actctcgagt acctccttgg tatgctcatc tgctaccccc tcggaatgat catgctcgct     180

```
ctaccctacg gaaaagtaaa acatctcttc tccttcatcc tcggagcctt cctacttcaa    240
ttcaccattg gtatccagtg gattcatcac ttaatctcct caatgattgc ctacgtcatg    300
ttcctcgtcc ttcctgccaa atttgccaaa acggcagtgc ctgtgtttgc catgatctac    360
atcaccgcgg gacatttgca tcgtcaatac atcaattatc ttgggtggga tatggacttc    420
acggggcctc agatggtgct tacgatgaaa ctctacatgc ttgcttacaa ccttgcggat    480
ggggacttgc tcaagaaggg aaaggaggat agggctgcaa agaagtgtgc ggatgtcgct    540
atttcgtctg ttcccggaat cattgagtac ttgggctaca cgttctgctt tgccagtgtt    600
ttagcaggcc ctgcttttga gtacaaattc tacgccgatg catgcgacgg atcactcttg    660
tacgacaaat ctggcaaacc caaggaaag atccccagtc aggtgtggcc tacattgcgt    720
cctctttttg gaagtctctt gtgtctcggc atctttgttg tgggaactgg aatgtatcct    780
cttttggatc ccaacgatcc tcagaatgcc actcctatcc ctctcactcc agagatgttg    840
gccaaaccag cctatgctcg atacgcttac tcgtggcttg cactcttttt catccgattt    900
aagtattact ttgcttggat gaacgccgaa ggagcaagca acatttggta tgctggattt    960
gagggatttg atgccagcgg caaccccaaa ggatgggagg tatccaataa cattgacgta   1020
attcagttcg agactgcacc caatctcaag actttgagtg ctgcttggaa taagaagact   1080
gcgaactggt tggcgaagta tgtgtacatt cgcacgggtg gttctctctt tgcgacgtac   1140
ggaatgagtg ctttctggca tggcttctac cctggatact acctcttctt catgtcggta   1200
cccatgatgg ctttctgtga gaggattgga aggaagaaac ttacacctcg tttcggaaat   1260
ggaaagaagt ggagtcctta tggcattgtg tgcattatcg ccacatcgtt gatgacggaa   1320
tacatgattc agccattcca actacttgcg tttgattggg cctggagaa ctggagcagc   1380 tactactttg ctggacacat tgtttgtgtt gtgttttacc tcgttgtgtc caacatgcct   1440
acaccaaaga cgaaggagac ttaa                                          1464
```

<210> SEQ ID NO 8
<211> LENGTH: 487
<212> TYPE: PRT
<213> ORGANISM: Thalassiosira pseudonana

<400> SEQUENCE: 8

```
Met Arg Leu Tyr Leu Gln Phe Asn Leu Ser Ile Asn Asp Tyr Cys His
1               5                   10                  15

Phe Phe Thr Val Pro Ser Phe Val Lys Glu Gly Val Glu Ser Leu Ser
            20                  25                  30

Ala Ser Thr Gly Gln Asp Val Glu Thr Leu Glu Tyr Leu Leu Gly Met
        35                  40                  45

Leu Ile Cys Tyr Pro Leu Gly Met Ile Met Leu Ala Leu Pro Tyr Gly
    50                  55                  60

Lys Val Lys His Leu Phe Ser Phe Ile Leu Gly Ala Phe Leu Leu Gln
65                  70                  75                  80

Phe Thr Ile Gly Ile Gln Trp Ile His Leu Ile Ser Ser Met Ile
                85                  90                  95

Ala Tyr Val Met Phe Leu Val Leu Pro Ala Lys Phe Ala Lys Thr Ala
            100                 105                 110

Val Pro Val Phe Ala Met Ile Tyr Ile Thr Ala Gly His Leu His Arg
        115                 120                 125

Gln Tyr Ile Asn Tyr Leu Gly Trp Asp Met Asp Phe Thr Gly Pro Gln
    130                 135                 140

Met Val Leu Thr Met Lys Leu Tyr Met Leu Ala Tyr Asn Leu Ala Asp
```

```
            145                 150                 155                 160
Gly Asp Leu Leu Lys Lys Gly Lys Glu Asp Arg Ala Ala Lys Lys Cys
                165                 170                 175
Ala Asp Val Ala Ile Ser Ser Val Pro Gly Ile Ile Glu Tyr Leu Gly
            180                 185                 190
Tyr Thr Phe Cys Phe Ala Ser Val Leu Ala Gly Pro Ala Phe Glu Tyr
        195                 200                 205
Lys Phe Tyr Ala Asp Ala Cys Asp Gly Ser Leu Leu Tyr Asp Lys Ser
    210                 215                 220
Gly Lys Pro Lys Gly Lys Ile Pro Ser Gln Val Trp Pro Thr Leu Arg
225                 230                 235                 240
Pro Leu Phe Gly Ser Leu Leu Cys Leu Gly Ile Phe Val Val Gly Thr
                245                 250                 255
Gly Met Tyr Pro Leu Leu Asp Pro Asn Asp Pro Gln Asn Ala Thr Pro
            260                 265                 270
Ile Pro Leu Thr Pro Glu Met Leu Ala Lys Pro Ala Tyr Ala Arg Tyr
        275                 280                 285
Ala Tyr Ser Trp Leu Ala Leu Phe Phe Ile Arg Phe Lys Tyr Tyr Phe
    290                 295                 300
Ala Trp Met Asn Ala Glu Gly Ala Ser Asn Ile Trp Tyr Ala Gly Phe
305                 310                 315                 320
Glu Gly Phe Asp Ala Ser Gly Asn Pro Lys Gly Trp Glu Val Ser Asn
                325                 330                 335
Asn Ile Asp Val Ile Gln Phe Glu Thr Ala Pro Asn Leu Lys Thr Leu
            340                 345                 350
Ser Ala Ala Trp Asn Lys Lys Thr Ala Asn Trp Leu Ala Lys Tyr Val
        355                 360                 365
Tyr Ile Arg Thr Gly Gly Ser Leu Phe Ala Thr Tyr Gly Met Ser Ala
    370                 375                 380
Phe Trp His Gly Phe Tyr Pro Gly Tyr Tyr Leu Phe Phe Met Ser Val
385                 390                 395                 400
Pro Met Met Ala Phe Cys Glu Arg Ile Gly Arg Lys Lys Leu Thr Pro
                405                 410                 415
Arg Phe Gly Asn Gly Lys Lys Trp Ser Pro Tyr Gly Ile Val Cys Ile
            420                 425                 430
Ile Ala Thr Ser Leu Met Thr Glu Tyr Met Ile Gln Pro Phe Gln Leu
        435                 440                 445
Leu Ala Phe Asp Trp Ala Trp Glu Asn Trp Ser Ser Tyr Tyr Phe Ala
    450                 455                 460
Gly His Ile Val Cys Val Val Phe Tyr Leu Val Val Ser Asn Met Pro
465                 470                 475                 480
Thr Pro Lys Thr Lys Glu Thr
                485

<210> SEQ ID NO 9
<211> LENGTH: 629
<212> TYPE: DNA
<213> ORGANISM: Apple

<400> SEQUENCE: 9
tcaggaggcc caaatttcct ttgtcaagat ttactgagcc catataccaa gaatgggggt      60
tttggaaacg acttttctac cagtatatgt ctggattcac agcaaggtgg aaatattatt     120
tcatttggtc aatatcagag gcttctatca ttctttctgg cctcggtttc agtggctgga     180
cagagtcctc accaccaaaa cctcgatggg atcgtgcaaa aaatgttgat attataggcg     240
```

```
ttgagtttgc aaagagttca gttcagttac cacttgtttg gaacatacaa gtcagcacct      300
ggcttcgcca ttatgtttat gataggcttg ttaaacctgg aaagaagcct ggtttcttcc      360
agttgctggc tacacagacc gtcagtgctg tttggcatgg cctctatcct ggctacatca      420
tattctttgt tcagtcagcg ttgatgattg ctggatcaag agtgatttac cgatggcagc      480
aagctgtacc tccaactatg gatgttgtta agaagatatt ggtgttcatc aactttgctt      540
acactgtctt ggttctgaac tactcctgtg ttggtttcat tgtattaagc cttcgtgaaa      600
cactggcctc gtatggaagc gtgcatttc                                        629
```

```
<210> SEQ ID NO 10
<211> LENGTH: 209
<212> TYPE: PRT
<213> ORGANISM: Apple

<400> SEQUENCE: 10
```

Arg Arg Pro Lys Phe Pro Leu Ser Arg Phe Thr Glu Pro Ile Tyr Gln
1               5                   10                  15

Glu Trp Gly Phe Trp Lys Arg Leu Phe Tyr Gln Tyr Met Ser Gly Phe
            20                  25                  30

Thr Ala Arg Trp Lys Tyr Tyr Phe Ile Trp Ser Ile Ser Glu Ala Ser
        35                  40                  45

Ile Ile Leu Ser Gly Leu Gly Phe Ser Gly Trp Thr Glu Ser Ser Pro
    50                  55                  60

Pro Lys Pro Arg Trp Asp Arg Ala Lys Asn Val Asp Ile Ile Gly Val
65                  70                  75                  80

Glu Phe Ala Lys Ser Ser Val Gln Leu Pro Leu Val Trp Asn Ile Gln
                85                  90                  95

Val Ser Thr Trp Leu Arg His Tyr Val Tyr Asp Arg Leu Val Lys Pro
            100                 105                 110

Gly Lys Lys Pro Gly Phe Phe Gln Leu Leu Ala Thr Gln Thr Val Ser
        115                 120                 125

Ala Val Trp His Gly Leu Tyr Pro Gly Tyr Ile Ile Phe Phe Val Gln
    130                 135                 140

Ser Ala Leu Met Ile Ala Gly Ser Arg Val Ile Tyr Arg Trp Gln Gln
145                 150                 155                 160

Ala Val Pro Pro Thr Met Asp Val Val Lys Lys Ile Leu Val Phe Ile
                165                 170                 175

Asn Phe Ala Tyr Thr Val Leu Val Leu Asn Tyr Ser Cys Val Gly Phe
            180                 185                 190

Ile Val Leu Ser Leu Arg Glu Thr Leu Ala Ser Tyr Gly Ser Val His
        195                 200                 205

Phe

```
<210> SEQ ID NO 11
<211> LENGTH: 135
<212> TYPE: PRT
<213> ORGANISM: Barley

<400> SEQUENCE: 11
```

Glu Ala Ala Ile Ile Ile Ser Gly Leu Gly Phe Thr Gly Trp Ser Asp
1               5                   10                  15

Ser Ser Pro Pro Lys Ala Lys Trp Asp Arg Ala Ile Asn Val Asp Ile
            20                  25                  30

Leu Gly Val Glu Leu Ala Gly Ser Ala Ala Gln Leu Pro Leu Lys Trp
        35                  40                  45

Asn Ile Gln Val Ser Thr Trp Leu Arg Tyr Tyr Val Tyr Glu Arg Leu
    50                  55                  60

Ile Gln Lys Gly Lys Lys Pro Gly Phe Leu Gln Leu Leu Gly Thr Gln
65                  70                  75                  80

Thr Val Ser Ala Ile Trp His Gly Leu Tyr Pro Gly Tyr Met Ile Phe
                85                  90                  95

Phe Val Gln Ser Ala Leu Met Ile Asn Gly Ser Lys Val Ile Tyr Arg
                100                 105                 110

Trp Gln Gln Ala Val Lys Gln Phe Arg Pro Pro His Tyr Pro Val Phe
            115                 120                 125

Thr Lys Leu Leu His Thr Pro
            130             135

<210> SEQ ID NO 12
<211> LENGTH: 642
<212> TYPE: DNA
<213> ORGANISM: Capsicum annuum

<400> SEQUENCE: 12
ggcacgagaa acggttgggt taccaatata tggctggctt tactgcccgg tggaagtatt      60
attttatctg gtcaatctct gaagctgcta atcatatc tggactgggt ttcagtggtt      120
ggacagactc ttctccgcca aaaccacgtt gggaccgtgc aaaaaatgtt gatgtattgg     180
gtgttgagtt agcaaagagc tcggttcagt tgcctgctgt ctggaacatt caagtcagca     240
catggctgcg gcattatgta tatgaaaggc tcatacaaaa gggaaggaag cctggttcct     300
tccagttact ggctacccaa actgtcagtg ccgtatggca tggattatat cctgggtata     360
tcatattctt tgtacagtcc gctttgatga ttgctggatc aagagtcctt tacagatggc     420
agcaagctgc taaaggttct atgtttgaga agatactggt agcaatgaat tttgcataca     480
cactgctggt tctaaattac tccgctgttg ggttcatggt attaagcctg catgaaactc     540
ttactgctta tggaagtgta tactatgttt gaacaattat accaattgct ctcatcctgc     600
tcagtaaagt aattaagcct ccaagaccct gcacatctaa ag                         642

<210> SEQ ID NO 13
<211> LENGTH: 213
<212> TYPE: PRT
<213> ORGANISM: Capsicum annuum

<400> SEQUENCE: 13

His Glu Lys Arg Leu Gly Tyr Gln Tyr Met Ala Gly Phe Thr Ala Arg
1               5                   10                  15

Trp Lys Tyr Tyr Phe Ile Trp Ser Ile Ser Glu Ala Ala Ile Ile Ile
            20                  25                  30

Ser Gly Leu Gly Phe Ser Gly Trp Thr Asp Ser Ser Pro Lys Pro
        35                  40                  45

Arg Trp Asp Arg Ala Lys Asn Val Asp Val Leu Gly Val Glu Leu Ala
    50                  55                  60

Lys Ser Ser Val Gln Leu Pro Ala Val Trp Asn Ile Gln Val Ser Thr
65                  70                  75                  80

Trp Leu Arg His Tyr Val Tyr Glu Arg Leu Ile Gln Lys Gly Arg Lys
                85                  90                  95

Pro Gly Phe Phe Gln Leu Leu Ala Thr Gln Thr Val Ser Ala Val Trp
            100                 105                 110

His Gly Leu Tyr Pro Gly Tyr Ile Ile Phe Phe Val Gln Ser Ala Leu
        115                 120                 125

Met Ile Ala Gly Ser Arg Val Leu Tyr Arg Trp Gln Gln Ala Ala Lys
    130                 135                 140

Gly Ser Met Phe Glu Lys Ile Leu Val Ala Met Asn Phe Ala Tyr Thr
145                 150                 155                 160

Leu Leu Val Leu Asn Tyr Ser Ala Val Gly Phe Met Val Leu Ser Leu
                165                 170                 175

His Glu Thr Leu Thr Ala Tyr Gly Ser Val Tyr Val Gly Thr Ile
                180                 185                 190

Ile Pro Ile Ala Leu Ile Leu Leu Ser Lys Val Ile Lys Pro Pro Arg
    195                 200                 205

Pro Cys Thr Ser Lys
    210

<210> SEQ ID NO 14
<211> LENGTH: 756
<212> TYPE: DNA
<213> ORGANISM: Castor Bean

<400> SEQUENCE: 14

```
attcatttat acttggtgcc ccactatcct ttatcccggt tcactgatcc tgtgtaccaa      60
gaatggggct tctggaaacg attaacttat cagtatatgt caggtttaac agcacgttgg     120
aaatactact tcatctggtc aatttccgag gcctccatta ttatctctgg attgggtttc     180
agtggttgga cagatacttc tccaccaaag ccacagtggg atcgcgctag aaacgttgac     240
attctaggtg ttgagtttgc aaagagtgca gctgagttgc acttgtgtg aacatacaa      300
gtcagcacat ggcttcgcca ctatgtttat gatcgacttg ttccaaaggg aaagaaagct     360
ggtttccttc agttgttggc cactcagact accagtgctg tttggcatgg attatatcct     420
ggatacatta tattctttgt ccagtcagca ttaatgattg caggttcgaa agtcatatac     480
agatggcaac aagctatacc ttcaaataag gctcttgaaa agaagatact agtgtttatg     540
aactttgctt acacagtttt ggttctaaat tactcctgtg ttggtttcat ggttttaagc     600
ttgcatgaaa cgattgcagc atatggaagt gtatatttta ttggcaccat agtgcccgtt     660
gtatttttcc tccttggctt cattattaaa ccagcaaggc cttccaggtc taaacacgga     720
acgatgagtg aggtagaaac tgttttctt ctcctt                                756
```

<210> SEQ ID NO 15
<211> LENGTH: 252
<212> TYPE: PRT
<213> ORGANISM: Castor Bean

<400> SEQUENCE: 15

Ile His Leu Tyr Leu Val Pro His Tyr Pro Leu Ser Arg Phe Thr Asp
1               5                   10                  15

Pro Val Tyr Gln Glu Trp Gly Phe Trp Lys Arg Leu Thr Tyr Gln Tyr
                20                  25                  30

Met Ser Gly Leu Thr Ala Arg Trp Lys Tyr Tyr Phe Ile Trp Ser Ile
            35                  40                  45

Ser Glu Ala Ser Ile Ile Ile Ser Gly Leu Gly Phe Ser Gly Trp Thr
    50                  55                  60

Asp Thr Ser Pro Pro Lys Pro Gln Trp Asp Arg Ala Arg Asn Val Asp
65                  70                  75                  80

Ile Leu Gly Val Glu Phe Ala Lys Ser Ala Ala Glu Leu Pro Leu Val
                85                  90                  95

Trp Asn Ile Gln Val Ser Thr Trp Leu Arg His Tyr Val Tyr Asp Arg

```
                    100                 105                 110
Leu Val Pro Lys Gly Lys Lys Ala Gly Phe Leu Gln Leu Leu Ala Thr
            115                 120                 125

Gln Thr Thr Ser Ala Val Trp His Gly Leu Tyr Pro Gly Tyr Ile Ile
    130                 135                 140

Phe Phe Val Gln Ser Ala Leu Met Ile Ala Gly Ser Lys Val Ile Tyr
145                 150                 155                 160

Arg Trp Gln Gln Ala Ile Pro Ser Asn Lys Ala Leu Glu Lys Lys Ile
                165                 170                 175

Leu Val Phe Met Asn Phe Ala Tyr Thr Val Leu Val Leu Asn Tyr Ser
            180                 185                 190

Cys Val Gly Phe Met Val Leu Ser Leu His Glu Thr Ile Ala Ala Tyr
        195                 200                 205

Gly Ser Val Tyr Phe Ile Gly Thr Ile Val Pro Val Phe Phe Leu
    210                 215                 220

Leu Gly Phe Ile Ile Lys Pro Ala Arg Pro Ser Arg Ser Lys His Gly
225                 230                 235                 240

Thr Met Ser Glu Val Glu Thr Val Phe Leu Leu Leu
                245                 250

<210> SEQ ID NO 16
<211> LENGTH: 937
<212> TYPE: DNA
<213> ORGANISM: Grapevine

<400> SEQUENCE: 16
ctcgtccaat ctccacttcc tcgttcccat gcttcttggc tacgcggcta tgcttctctg      60
tcgccgtcga tgcggtgtga tcacctttt cttgggattc ggctacctca ttggctgcca     120
tgtatactac atgagtgggg atgcatggaa ggaaggggt attgatgcta ctggagctct     180
aatggtttta acattgaaag tcatttcatg tgcaatgaat tataatgatg gattgttaaa     240
agaagacggt ttgcgtgagg cacagaagaa aaaccgattg cttaagttac catcattgat     300
cgagtacttt ggttattgtc tctgctgtgg aagtcacttt gctggaccag tttatgaaat     360
aaaggattat cttgaatgga cagaaagaaa agggatttgg gccaaatcag agaaagggcc     420
accaccatca ccttatgggg caacgattcg agctcttatc caagctgcct tttgcatggg     480
cttgtatgtg tatctagtac cccatttcc cttgaccata tttactgatc ctgtatatca     540
agaatggggc ttctggaaac ggttgggata ccaatatatg tgtggcttta cagcacgctg     600
gaaatactat ttcatctggt caatctctga ggcagctgtc attatttctg gcctgggatt     660
cagtgggtgg acagaatctt ccccaccaaa accaaaatgg gaccgtgcaa agaatgttga     720
cattttaggt gttgagttgg caaagagtgc agtaacactg ccacttgttt ggaacataca     780
agtcagcacc tggctacgtt attatgttta tgagaggctc attcaaaatg gaagaaaacc     840
tggtttcttc cagttgctgg ctacacaaac tgtcagtgct gtttggcatg gattatatcc     900
tggatacatc atattctttg ttcagtctgc actgatg                             937

<210> SEQ ID NO 17
<211> LENGTH: 312
<212> TYPE: PRT
<213> ORGANISM: Grapevine

<400> SEQUENCE: 17

Ser Ser Asn Leu His Phe Leu Val Pro Met Leu Leu Gly Tyr Ala Ala
1               5                   10                  15
```

```
Met Leu Leu Cys Arg Arg Cys Gly Val Ile Thr Phe Phe Leu Gly
            20                  25                  30

Phe Gly Tyr Leu Ile Gly Cys His Val Tyr Tyr Met Ser Gly Asp Ala
        35                  40                  45

Trp Lys Glu Gly Gly Ile Asp Ala Thr Gly Ala Leu Met Val Leu Thr
50                  55                      60

Leu Lys Val Ile Ser Cys Ala Met Asn Tyr Asn Asp Gly Leu Leu Lys
65                  70                  75                  80

Glu Asp Gly Leu Arg Glu Ala Gln Lys Lys Asn Arg Leu Leu Lys Leu
                85                  90                  95

Pro Ser Leu Ile Glu Tyr Phe Gly Tyr Cys Leu Cys Cys Gly Ser His
            100                 105                 110

Phe Ala Gly Pro Val Tyr Glu Ile Lys Asp Tyr Leu Glu Trp Thr Glu
        115                 120                 125

Arg Lys Gly Ile Trp Ala Lys Ser Glu Lys Gly Pro Pro Ser Pro
130                 135                 140

Tyr Gly Ala Thr Ile Arg Ala Leu Ile Gln Ala Ala Phe Cys Met Gly
145                 150                 155                 160

Leu Tyr Val Tyr Leu Val Pro His Phe Pro Leu Thr Ile Phe Thr Asp
                165                 170                 175

Pro Val Tyr Gln Glu Trp Gly Phe Trp Lys Arg Leu Gly Tyr Gln Tyr
            180                 185                 190

Met Cys Gly Phe Thr Ala Arg Trp Lys Tyr Tyr Phe Ile Trp Ser Ile
        195                 200                 205

Ser Glu Ala Ala Val Ile Ile Ser Gly Leu Gly Phe Ser Gly Trp Thr
210                 215                 220

Glu Ser Ser Pro Pro Lys Pro Lys Trp Asp Arg Ala Lys Asn Val Asp
225                 230                 235                 240

Ile Leu Gly Val Glu Leu Ala Lys Ser Ala Val Thr Leu Pro Leu Val
                245                 250                 255

Trp Asn Ile Gln Val Ser Thr Trp Leu Arg Tyr Tyr Val Tyr Glu Arg
            260                 265                 270

Leu Ile Gln Asn Gly Lys Lys Pro Gly Phe Phe Gln Leu Leu Ala Thr
        275                 280                 285

Gln Thr Val Ser Ala Val Trp His Gly Leu Tyr Pro Gly Tyr Ile Ile
290                 295                 300

Phe Phe Val Gln Ser Ala Leu Met
305                 310

<210> SEQ ID NO 18
<211> LENGTH: 864
<212> TYPE: DNA
<213> ORGANISM: Maize
<220> FEATURE:
<221> NAME/KEY: misc_feature
<222> LOCATION: (727)..(727)
<223> OTHER INFORMATION: n can be A,T,G,C

<400> SEQUENCE: 18
catttcgtgt ctcataaact acagtgatgg tatcttgaag gaagagggtt tacgcgatgc      60
tcagattaaa caccgattga ctaagcttcc ttctctaatt gaatattttg ggtactgtct     120
ctgttgtggg agccactttg ctggaccggt atatgagatg aaagattatc ttgaatggac     180
tgaaaggaaa ggaatatggg ctagcccaac tccttcgcca ttgttaccta ctttgcgtgc     240
tctagttcag gctggtatat gcatgggggtt atatttatac ctgtcaccta aatttccact     300
ctcacggttt agtgagcccc tatattatga atggggtttt tggcaccgac tcttctatca     360
```

```
gtacatgtca ggctttaccg ctcgttggaa atattacttt atatggtcaa tttcagaagc    420
ctcaattatc atatctggtc taggctttac tggttggtcg gaatcttctc ccccaaaagc    480
caaatgggat cgtgcaaaaa atgttgatgt attaggtgtt gaattagctg gaagttcagt    540
tcaattgccc cttgtgtgga atattcaagt gagcacatgg ctacgatact atgtctatga    600
gaggttaatt cagaaaggaa agaaaccagg tttccttcaa ttgttgggta cacagacagt    660
cagtgccatc tggcatggac tatatcctgg atatatcata ttcttttttt catcagcatt    720
gatgatnaat ggttcacgag ttatatacag atggcagcaa gcagcgagca gttcattcct    780
gagcggtatc ctggcccttc taattttgct atacattgct ggggcttact actcctgcat    840
cggggtccag gtactgagct tcaa                                            864
```

<210> SEQ ID NO 19
<211> LENGTH: 287
<212> TYPE: PRT
<213> ORGANISM: Maize
<220> FEATURE:
<221> NAME/KEY: MISC_FEATURE
<222> LOCATION: (242)..(242)
<223> OTHER INFORMATION: X can be Met or Ile

<400> SEQUENCE: 19

```
Ile Ser Cys Leu Ile Asn Tyr Ser Asp Gly Ile Leu Lys Glu Glu Gly
1               5                   10                  15

Leu Arg Asp Ala Gln Ile Lys His Arg Leu Thr Lys Leu Pro Ser Leu
            20                  25                  30

Ile Glu Tyr Phe Gly Tyr Cys Leu Cys Cys Gly Ser His Phe Ala Gly
        35                  40                  45

Pro Val Tyr Glu Met Lys Asp Tyr Leu Glu Trp Thr Glu Arg Lys Gly
    50                  55                  60

Ile Trp Ala Ser Pro Thr Pro Ser Pro Leu Leu Pro Thr Leu Arg Ala
65                  70                  75                  80

Leu Val Gln Ala Gly Ile Cys Met Gly Leu Tyr Leu Tyr Leu Ser Pro
                85                  90                  95

Lys Phe Pro Leu Ser Arg Phe Ser Glu Pro Leu Tyr Tyr Glu Trp Gly
            100                 105                 110

Phe Trp His Arg Leu Phe Tyr Gln Tyr Met Ser Gly Phe Thr Ala Arg
        115                 120                 125

Trp Lys Tyr Tyr Phe Ile Trp Ser Ile Ser Glu Ala Ser Ile Ile Ile
    130                 135                 140

Ser Gly Leu Gly Phe Thr Gly Trp Ser Glu Ser Pro Pro Lys Ala
145                 150                 155                 160

Lys Trp Asp Arg Ala Lys Asn Val Asp Val Leu Gly Val Glu Leu Ala
                165                 170                 175

Gly Ser Ser Val Gln Leu Pro Leu Val Trp Asn Ile Gln Val Ser Thr
            180                 185                 190

Trp Leu Arg Tyr Tyr Val Tyr Glu Arg Leu Ile Gln Lys Gly Lys Lys
        195                 200                 205

Pro Gly Phe Leu Gln Leu Leu Gly Thr Gln Thr Val Ser Ala Ile Trp
    210                 215                 220

His Gly Leu Tyr Pro Gly Tyr Ile Ile Phe Phe Phe Ser Ala Leu
225                 230                 235                 240

Met Xaa Asn Gly Ser Arg Val Ile Tyr Arg Trp Gln Gln Ala Ala Ser
                245                 250                 255

Ser Ser Phe Leu Ser Gly Ile Leu Ala Leu Leu Ile Leu Leu Tyr Ile
```

```
                    260             265             270
Ala Gly Ala Tyr Tyr Ser Cys Ile Gly Val Gln Val Leu Ser Phe
            275                 280             285

<210> SEQ ID NO 20
<211> LENGTH: 641
<212> TYPE: DNA
<213> ORGANISM: Peach
<220> FEATURE:
<221> NAME/KEY: misc_feature
<222> LOCATION: (621)..(621)
<223> OTHER INFORMATION: n can be A T C G

<400> SEQUENCE: 20
aaatattatt tcatctggtc aatttcagag gcttctatca ttctttctgg tttgggtttc      60
actggctgga cagaatcttc accaccaaag ccgcgatggg atcgtgcaaa aaatgttgat     120
attctaggcg ttgagtttgc aaagagttca gttcagttac cacttgtttg aacatacaa     180 gtcagcacct ggctacgtca ttatgtttat gaaaggcttg ttaaacctgg caagaaggct     240
ggtttcttcc agttgctgac tacacagacc gtcagtgcgg tttggcatgg actctatcct     300
gggtacatca tattctttgt tcagtcagca ttgatgattc tggttcaag agtgatttac      360 agatggcaac aagctgtacc tcaaaacatg gatgctgtta agaacatact ggtgttcata     420
aactttgctt acactctctt ggttctgaac tactcctgcg ttggtttcat tgtattaagc     480
cttcgtgaaa cacttgcctc atatgggagc gtgcatttca tcggaaccat tcttccgata     540
gcattgatac tactgagtta cgtaataaaa cctccaaggc ctgcaagatc aaaggctcgg     600
aaggaagagt gaggttgtca nccgcaacag catttttaac g                        641

<210> SEQ ID NO 21
<211> LENGTH: 203
<212> TYPE: PRT
<213> ORGANISM: Peach

<400> SEQUENCE: 21

Lys Tyr Tyr Phe Ile Trp Ser Ile Ser Glu Ala Ser Ile Ile Leu Ser
1               5                   10                  15

Gly Leu Gly Phe Thr Gly Trp Thr Glu Ser Ser Pro Pro Lys Pro Arg
            20                  25                  30

Trp Asp Arg Ala Lys Asn Val Asp Ile Leu Gly Val Glu Phe Ala Lys
        35                  40                  45

Ser Ser Val Gln Leu Pro Leu Val Trp Asn Ile Gln Val Ser Thr Trp
    50                  55                  60

Leu Arg His Tyr Val Tyr Glu Arg Leu Val Lys Pro Gly Lys Lys Ala
65                  70                  75                  80

Gly Phe Phe Gln Leu Leu Thr Thr Gln Thr Val Ser Ala Val Trp His
                85                  90                  95

Gly Leu Tyr Pro Gly Tyr Ile Ile Phe Phe Val Gln Ser Ala Leu Met
            100                 105                 110

Ile Ala Gly Ser Arg Val Ile Tyr Arg Trp Gln Gln Ala Val Pro Gln
        115                 120                 125

Asn Met Asp Ala Val Lys Asn Ile Leu Val Phe Ile Asn Phe Ala Tyr
    130                 135                 140

Thr Leu Leu Val Leu Asn Tyr Ser Cys Val Gly Phe Ile Val Leu Ser
145                 150                 155                 160

Leu Arg Glu Thr Leu Ala Ser Tyr Gly Ser Val His Phe Ile Gly Thr
                165                 170                 175
```

```
Ile Leu Pro Ile Ala Leu Ile Leu Leu Ser Tyr Val Ile Lys Pro Pro
            180                 185                 190

Arg Pro Ala Arg Ser Lys Ala Arg Lys Glu Glu
            195                 200
```

<210> SEQ ID NO 22
<211> LENGTH: 459
<212> TYPE: PRT
<213> ORGANISM: Oryza sativa

<400> SEQUENCE: 22

```
Met Gly Leu Glu Met Glu Gly Met Ala Ala Ile Gly Val Ser Val
1               5                   10                  15

Pro Val Leu Arg Phe Leu Leu Cys Phe Ala Ala Thr Ile Pro Thr Gly
                20                  25                  30

Leu Met Trp Arg Ala Val Pro Gly Ala Ala Gly Arg His Leu Tyr Ala
            35                  40                  45

Gly Leu Thr Gly Ala Ala Leu Ser Tyr Leu Ser Phe Gly Ala Thr Ser
        50                  55                  60

Asn Leu Leu Phe Val Val Pro Met Ala Phe Gly Tyr Leu Ala Met Leu
65                  70                  75                  80

Leu Cys Arg Arg Leu Ala Gly Leu Val Thr Phe Leu Gly Ala Phe Gly
                85                  90                  95

Phe Leu Ile Ala Cys His Met Tyr Tyr Met Ser Gly Asp Ala Trp Lys
            100                 105                 110

Glu Gly Gly Ile Asp Ala Thr Gly Ala Leu Met Val Leu Thr Leu Lys
        115                 120                 125

Ile Ile Ser Cys Ala Ile Asn Tyr Ser Asp Gly Met Leu Lys Glu Glu
130                 135                 140

Gly Leu Arg Asp Ala Gln Lys Lys Tyr Arg Leu Ala Lys Leu Pro Ser
145                 150                 155                 160

Leu Ile Glu Tyr Phe Gly Tyr Cys Leu Cys Cys Gly Ser His Phe Ala
                165                 170                 175

Gly Pro Val Tyr Glu Met Lys Asp Tyr Leu Glu Tyr Thr Glu Arg Lys
            180                 185                 190

Gly Leu Trp Ala Ser Pro Thr Pro Ser Pro Leu Leu Pro Thr Leu Arg
        195                 200                 205

Ala Leu Val Gln Ala Gly Ala Cys Met Gly Leu Tyr Leu Tyr Leu Ser
210                 215                 220

Pro Gln Phe Pro Leu Ser Arg Phe Ser Glu Pro Leu Tyr Tyr Glu Trp
225                 230                 235                 240

Gly Phe Trp His Arg Leu Phe Tyr Gln Tyr Met Ser Gly Phe Thr Ala
                245                 250                 255

Arg Trp Lys Tyr Tyr Phe Ile Trp Ser Leu Ser Glu Ala Ala Ile Ile
            260                 265                 270

Ile Ser Gly Leu Gly Phe Ser Gly Trp Ser Asp Ser Pro Pro Lys
        275                 280                 285

Ala Lys Trp Asp Arg Ala Lys Asn Val Asp Val Leu Gly Val Glu Leu
290                 295                 300

Ala Thr Ser Ala Val Gln Leu Pro Leu Met Trp Asn Ile Gln Val Ser
305                 310                 315                 320

Thr Trp Leu Arg Tyr Tyr Val Tyr Glu Arg Leu Val Gln Lys Gly Lys
                325                 330                 335

Lys Pro Gly Phe Leu Gln Leu Leu Gly Thr Gln Thr Val Ser Ala Val
            340                 345                 350
```

```
Trp His Gly Leu Tyr Pro Gly Tyr Ile Phe Phe Val Gln Ser Ala
            355                 360                 365

Leu Met Ile Asn Gly Ser Lys Val Ile Tyr Arg Trp Gln Gln Ala Val
    370                 375                 380

Ser Asn Pro Val Phe His Ala Ile Leu Val Phe Val Asn Phe Ser Tyr
385                 390                 395                 400

Thr Leu Met Val Leu Asn Tyr Ser Cys Ile Gly Phe Gln Val Leu Ser
                405                 410                 415

Phe Lys Glu Thr Leu Ala Ser Tyr Gln Ser Val Tyr Tyr Ile Gly Thr
            420                 425                 430

Ile Val Pro Ile Val Val Leu Leu Gly Tyr Val Ile Lys Pro Ala
            435                 440                 445

Arg Pro Val Lys Pro Lys Ala Arg Lys Ala Glu
        450                 455

<210> SEQ ID NO 23
<211> LENGTH: 370
<212> TYPE: PRT
<213> ORGANISM: Rice

<400> SEQUENCE: 23

Met Tyr Tyr Met Ser Gly Asp Ala Trp Lys Glu Gly Gly Ile Asp Ala
1               5                   10                  15

Thr Gly Ala Leu Met Val Leu Thr Leu Lys Ile Ile Ser Cys Ala Ile
            20                  25                  30

Asn Tyr Ser Asp Gly Met Leu Lys Glu Glu Gly Leu Arg Asp Ala Gln
        35                  40                  45

Lys Lys Tyr Arg Leu Ala Lys Leu Pro Ser Leu Ile Glu Tyr Phe Gly
    50                  55                  60

Tyr Cys Leu Cys Cys Gly Ser His Phe Ala Gly Pro Val Tyr Glu Met
65                  70                  75                  80

Lys Asp Tyr Leu Glu Tyr Thr Glu Arg Lys Gly Leu Trp Ala Ser Pro
                85                  90                  95

Thr Pro Ser Pro Leu Leu Pro Thr Leu Arg Ala Leu Val Gln Ala Gly
            100                 105                 110

Ala Cys Met Gly Leu Tyr Leu Tyr Leu Ser Pro Gln Phe Pro Leu Ser
        115                 120                 125

Arg Phe Ser Glu Pro Leu Tyr Tyr Glu Trp Gly Phe Trp His Arg Leu
    130                 135                 140

Phe Tyr Gln Tyr Met Ser Gly Phe Thr Ala Arg Trp Lys Tyr Tyr Phe
145                 150                 155                 160

Ile Trp Ser Leu Ser Glu Ala Ala Ile Ile Ser Gly Leu Gly Phe
                165                 170                 175

Ser Gly Trp Ser Asp Ser Ser Pro Pro Lys Ala Lys Trp Asp Arg Ala
        180                 185                 190

Lys Asn Val Asp Val Leu Gly Val Glu Leu Ala Thr Ser Ala Val Gln
    195                 200                 205

Leu Pro Leu Met Trp Asn Ile Gln Val Ser Thr Trp Leu Arg Tyr Tyr
210                 215                 220

Val Tyr Glu Arg Leu Val Gln Lys Gly Lys Lys Pro Gly Phe Leu Gln
225                 230                 235                 240

Leu Leu Gly Thr Gln Thr Val Ser Ala Val Trp His Gly Leu Tyr Pro
                245                 250                 255

Gly Tyr Ile Ile Phe Phe Val Gln Ser Ala Leu Met Ile Asn Gly Ser
            260                 265                 270
```

```
Lys Val Ile Tyr Arg Trp Gln Gln Ala Val Ser Asn Pro Val Phe His
        275                 280                 285
Ala Ile Leu Val Phe Val Asn Phe Ser Tyr Thr Leu Met Val Leu Asn
    290                 295                 300
Tyr Ser Cys Ile Gly Phe Gln Phe Val Phe Thr Met Leu Tyr Thr Leu
305                 310                 315                 320
Arg Phe Leu Gln Val Leu Ser Phe Lys Glu Thr Leu Ala Ser Tyr Gln
                325                 330                 335
Ser Val Tyr Tyr Ile Gly Thr Ile Val Pro Ile Val Val Leu Leu
            340                 345                 350
Gly Tyr Val Ile Lys Pro Ala Arg Pro Val Lys Pro Lys Ala Arg Lys
        355                 360                 365
Ala Glu
   370

<210> SEQ ID NO 24
<211> LENGTH: 707
<212> TYPE: DNA
<213> ORGANISM: Snapdragon

<400> SEQUENCE: 24
gcattaatta caacgatgga ttacttaaaa aggaagatct acgtgagcca caaagaaaa      60
accgcttgct caagatgcca tcattacttg agtacattgg ttactgtttg tgttgtggaa    120
gtcactttgc tggtcctgtg tatgaaatga agattatct tgaatggact gagaggaaag     180
ggatctggca acatacaacc aagggaccga aaccttctcc gtattgggcg actctcaggg    240
ctattttgca agctgccatc tgtatgggct tgtatctata tcttgtacca cattacccac    300
tttccagatt cacggagcca gaataccaag agtatgggtt ctggaaacgg ttaagttacc    360
agtacatgtc aggcttcacc gctcgttgga agtactattt catttggtct atctcagaag    420
cttccataat tatttctggc ctggggttca gtggctggac agattctgat ccacccaaag    480
cactgtggga tcgtgcaaaa aatgttgatg tattaggtgt tgagttggca aagagttctg    540
tgcagttacc acttgtatgg aatattcaag ttagcacctg gcttaaacac tatgtctatg    600
agaggctggt tcagaaaggt aagaaaccag gcttcttcca gttgctggct acccagaccg    660
tgagtgcagt gtggcatgga ttgtaccctg ggtacatcat attcttt                  707

<210> SEQ ID NO 25
<211> LENGTH: 235
<212> TYPE: PRT
<213> ORGANISM: Snapdragon

<400> SEQUENCE: 25

Ile Asn Tyr Asn Asp Gly Leu Leu Lys Lys Glu Asp Leu Arg Glu Pro
1               5                   10                  15
Gln Lys Lys Asn Arg Leu Leu Lys Met Pro Ser Leu Leu Glu Tyr Ile
            20                  25                  30
Gly Tyr Cys Leu Cys Cys Gly Ser His Phe Ala Gly Pro Val Tyr Glu
        35                  40                  45
Met Lys Asp Tyr Leu Glu Trp Thr Glu Arg Lys Gly Ile Trp Gln His
    50                  55                  60
Thr Thr Lys Gly Pro Lys Pro Ser Pro Tyr Trp Ala Thr Leu Arg Ala
65                  70                  75                  80
Ile Leu Gln Ala Ala Ile Cys Met Gly Leu Tyr Leu Tyr Leu Val Pro
                85                  90                  95
His Tyr Pro Leu Ser Arg Phe Thr Glu Pro Glu Tyr Gln Glu Tyr Gly
```

```
              100                 105                 110
Phe Trp Lys Arg Leu Ser Tyr Gln Tyr Met Ser Gly Phe Thr Ala Arg
            115                 120                 125

Trp Lys Tyr Tyr Phe Ile Trp Ser Ile Ser Glu Ala Ser Ile Ile Ile
        130                 135                 140

Ser Gly Leu Gly Phe Ser Gly Trp Thr Asp Ser Asp Pro Pro Lys Ala
145                 150                 155                 160

Leu Trp Asp Arg Ala Lys Asn Val Asp Val Leu Gly Val Glu Leu Ala
                165                 170                 175

Lys Ser Ser Val Gln Leu Pro Leu Val Trp Asn Ile Gln Val Ser Thr
            180                 185                 190

Trp Leu Lys His Tyr Val Tyr Glu Arg Leu Val Gln Lys Gly Lys Lys
        195                 200                 205

Pro Gly Phe Phe Gln Leu Leu Ala Thr Gln Thr Val Ser Ala Val Trp
    210                 215                 220

His Gly Leu Tyr Pro Gly Tyr Ile Ile Phe Phe
225                 230                 235

<210> SEQ ID NO 26
<211> LENGTH: 653
<212> TYPE: DNA
<213> ORGANISM: Sorghum

<400> SEQUENCE: 26
gcacgaggct ctcacggttt agtgagccct tatattatga atggggtttc tggcaccgac    60
tcttctatca gtacatgtca ggcttcactg ctcgttggaa atattacttt atatggtcaa   120
tttcagaagc ctcaattatc atatctggtc tgggctttac tggttggtca gaatcttctc   180
ccccgaaagc caaatgggat cgtgcgaaaa atgttgatgt attaggtgtt gaattagctg   240
gaagtgcagt tcaaattccc cttgtgtgga atattcaagt gagcacatgg ttacgatact   300
atgtctatga gaggctaatt cagaaaggaa agaaaccagg tttccttcag ttgttgggta   360
cacagacagt cagcgccatc tggcatggac tgtatcctgg atatatcata ttctttgttc   420
agtcagcatt gatgataaat ggttcacgag ttatatacag atggcagcaa gcagtgagca   480
gttcattcct ccgcggtatc ctggctttc taaattttgc ttatacattg ctggtgctta   540
actactcctg catcgggttc ctggtactga gcttcaaaga aaccttggcg tcctaccaga   600
gcgtatatta tgttggcaca attgttccca ttgtgtttct cctgctgggc aat          653

<210> SEQ ID NO 27
<211> LENGTH: 217
<212> TYPE: PRT
<213> ORGANISM: Sorghum

<400> SEQUENCE: 27

Thr Arg Leu Ser Arg Phe Ser Glu Pro Leu Tyr Tyr Glu Trp Gly Phe
1               5                   10                  15

Trp His Arg Leu Phe Tyr Gln Tyr Met Ser Gly Phe Thr Ala Arg Trp
            20                  25                  30

Lys Tyr Tyr Phe Ile Trp Ser Ile Ser Glu Ala Ser Ile Ile Ile Ser
        35                  40                  45

Gly Leu Gly Phe Thr Gly Trp Ser Glu Ser Pro Pro Lys Ala Lys
    50                  55                  60

Trp Asp Arg Ala Lys Asn Val Asp Val Leu Gly Val Glu Leu Ala Gly
65                  70                  75                  80

Ser Ala Val Gln Ile Pro Leu Val Trp Asn Ile Gln Val Ser Thr Trp
```

```
                    85                  90                  95
Leu Arg Tyr Tyr Val Tyr Glu Arg Leu Ile Gln Lys Gly Lys Pro
            100                 105                 110

Gly Phe Leu Gln Leu Leu Gly Thr Gln Thr Val Ser Ala Ile Trp His
            115                 120                 125

Gly Leu Tyr Pro Gly Tyr Ile Ile Phe Phe Val Gln Ser Ala Leu Met
            130                 135                 140

Ile Asn Gly Ser Arg Val Ile Tyr Arg Trp Gln Gln Ala Val Ser Ser
145                 150                 155                 160

Ser Phe Leu Arg Gly Ile Leu Ala Phe Leu Asn Phe Ala Tyr Thr Leu
            165                 170                 175

Leu Val Leu Asn Tyr Ser Cys Ile Gly Phe Leu Val Leu Ser Phe Lys
            180                 185                 190

Glu Thr Leu Ala Ser Tyr Gln Ser Val Tyr Val Gly Thr Ile Val
            195                 200                 205

Pro Ile Val Phe Leu Leu Gly Asn
    210                 215

<210> SEQ ID NO 28
<211> LENGTH: 865
<212> TYPE: DNA
<213> ORGANISM: Sunflower

<400> SEQUENCE: 28
gaaaaccgca tacttaagtt gccatcttta atcgagtatg tgggatattg cttatgctgc      60
ggaagtcact ttgctggtcc ggtttacgaa atcaaagatt atttggattg gaccgaaaga     120
aaggggattt ggacaaagtc cgagaaaggc acaccatcac cattttttgcc aacactacga    180 gcgattctcc aagcgggttt ctgtatgggt ttgtatttat atctatcgcc ttcgtatccg     240 cttttcaagat tcagtgagcc gatatatcaa gaatggggat tgtgaaacg tctgaccgtc     300 caatacatgt cgggcttcac cgcgcgttgg aaatactatt tcatttggtc tatctcagaa     360
gcttctatca ttatttcggg cttcggtttc agtggctgga ctgattcttc tccaccaaaa     420
gcccgatggg accgtgcgaa aaacgttgac gttttgggtg ttgagtttgc aaagagttca     480
gttgagttac cactcgtgtg aatatccaa gtcagcacat ggcttcgtca ctatgtttat      540
gacagacttg ttcaaaaggg aaagaagcct ggcttttcc aattgttagc aacacagact     600
gttagcgctg tctggcatgg attatatcct gggtacttga tattctttgt tcaatctgct     660
ttgatgattt ccgggtcaag agccatttac agatggcagc aggcggttcc gccaaccgtt    720
aagaagtttt tgatgctcat gaactttgct tacacgcttc ttgttcttaa ctactcctgc    780
ataggtttta tggtattaag cctacacgaa acactggctg catacggaag tgtatactac    840
gttggaaaca tcattccagt ggcgt                                          865

<210> SEQ ID NO 29
<211> LENGTH: 288
<212> TYPE: PRT
<213> ORGANISM: Sunflower

<400> SEQUENCE: 29

Glu Asn Arg Ile Leu Lys Leu Pro Ser Leu Ile Glu Tyr Val Gly Tyr
1               5                   10                  15

Cys Leu Cys Cys Gly Ser His Phe Ala Gly Pro Val Tyr Glu Ile Lys
            20                  25                  30

Asp Tyr Leu Asp Trp Thr Glu Arg Lys Gly Ile Trp Lys Ser Glu
        35                  40                  45
```

```
Lys Gly Thr Pro Ser Pro Phe Leu Pro Thr Leu Arg Ala Ile Leu Gln
 50                  55                  60
Ala Gly Phe Cys Met Gly Leu Tyr Leu Tyr Leu Ser Pro Ser Tyr Pro
 65                  70                  75                  80
Leu Ser Arg Phe Ser Glu Pro Ile Tyr Gln Glu Trp Gly Phe Val Lys
                 85                  90                  95
Arg Leu Thr Val Gln Tyr Met Ser Gly Phe Thr Ala Arg Trp Lys Tyr
            100                 105                 110
Tyr Phe Ile Trp Ser Ile Ser Glu Ala Ser Ile Ile Ser Gly Phe
        115                 120                 125
Gly Phe Ser Gly Trp Thr Asp Ser Ser Pro Pro Lys Ala Arg Trp Asp
130                 135                 140
Arg Ala Lys Asn Val Asp Val Leu Gly Val Glu Phe Ala Lys Ser Ser
145                 150                 155                 160
Val Glu Leu Pro Leu Val Trp Asn Ile Gln Val Ser Thr Trp Leu Arg
                165                 170                 175
His Tyr Val Tyr Asp Arg Leu Val Gln Lys Gly Lys Lys Pro Gly Phe
            180                 185                 190
Phe Gln Leu Leu Ala Thr Gln Thr Val Ser Ala Val Trp His Gly Leu
        195                 200                 205
Tyr Pro Gly Tyr Leu Ile Phe Phe Val Gln Ser Ala Leu Met Ile Ser
210                 215                 220
Gly Ser Arg Ala Ile Tyr Arg Trp Gln Gln Ala Val Pro Pro Thr Val
225                 230                 235                 240
Lys Lys Phe Leu Met Leu Met Asn Phe Ala Tyr Thr Leu Leu Val Leu
                245                 250                 255
Asn Tyr Ser Cys Ile Gly Phe Met Val Leu Ser Leu His Glu Thr Leu
            260                 265                 270
Ala Ala Tyr Gly Ser Val Tyr Tyr Val Gly Asn Ile Ile Pro Val Ala
        275                 280                 285

<210> SEQ ID NO 30
<211> LENGTH: 748
<212> TYPE: DNA
<213> ORGANISM: Tomato

<400> SEQUENCE: 30
ggtatggggt tgtatctcta tctggtgcct cagttcccac tttccaggtt cactgagtca      60
gtataccacg aatggggttt cttcaaacga ctgggttacc aatatatggc tggctttact     120
gcccggtgga atattatttt tatttggtca atctctgaag cttctataat catatctgga     180
ctgggtttca gtggttggac aaactcttct ccgccaaaac cacgttggga ccgagcaaaa     240
aatgttgatg tattgggtgt tgagttagca aagagctcgg ttcagttacc actagtatgg     300
aacattcaag tcagcacatg gctgcggcat tatgtgtatg aaaggctcgt acagaaggga     360
aggaagcctg gtttcttcca gttgctggct acccaaactg tcagtgccgt ttggcatgga     420
ttatatcctg gatacatcat attctttgtt cagtccgctt tgatgattgc tggatcaaga     480
gtcatttaca gatggcagca agctacaaaa ggtactatgt ttgagaagat actgatagca     540
atgaattttg catacacact gctggttcta aactactccg ctgttggatt catggtatta     600
agtctgcatg aaactcttac tgcttatgga agtgtatact atattggaac aattgtacca     660
attcttctca tcctgcttag taaagtgatt aagcctccaa gacctgcgac gtctaaagct     720
aggaaagcag agtaaatcca agtcagtt                                         748
```

<210> SEQ ID NO 31
<211> LENGTH: 244
<212> TYPE: PRT
<213> ORGANISM: Tomato

<400> SEQUENCE: 31

```
Gly Met Gly Leu Tyr Leu Tyr Leu Val Pro Gln Phe Pro Leu Ser Arg
1               5                   10                  15
Phe Thr Glu Ser Val Tyr His Glu Trp Gly Phe Lys Arg Leu Gly
            20                  25                  30
Tyr Gln Tyr Met Ala Gly Phe Thr Ala Arg Trp Lys Tyr Tyr Phe Ile
            35                  40                  45
Trp Ser Ile Ser Glu Ala Ser Ile Ile Ser Gly Leu Gly Phe Ser
50                  55                  60
Gly Trp Thr Asn Ser Ser Pro Pro Lys Pro Arg Trp Asp Arg Ala Lys
65                  70                  75                  80
Asn Val Asp Val Leu Gly Val Glu Leu Ala Lys Ser Ser Val Gln Leu
                85                  90                  95
Pro Leu Val Trp Asn Ile Gln Val Ser Thr Trp Leu Arg His Tyr Val
            100                 105                 110
Tyr Glu Arg Leu Val Gln Lys Gly Arg Lys Pro Gly Phe Phe Gln Leu
            115                 120                 125
Leu Ala Thr Gln Thr Val Ser Ala Val Trp His Gly Leu Tyr Pro Gly
130                 135                 140
Tyr Ile Ile Phe Phe Val Gln Ser Ala Leu Met Ile Ala Gly Ser Arg
145                 150                 155                 160
Val Ile Tyr Arg Trp Gln Gln Ala Thr Lys Gly Thr Met Phe Glu Lys
                165                 170                 175
Ile Leu Ile Ala Met Asn Phe Ala Tyr Thr Leu Leu Val Leu Asn Tyr
            180                 185                 190
Ser Ala Val Gly Phe Met Val Leu Ser Leu His Glu Thr Leu Thr Ala
            195                 200                 205
Tyr Gly Ser Val Tyr Tyr Ile Gly Thr Ile Val Pro Ile Leu Leu Ile
210                 215                 220
Leu Leu Ser Lys Val Ile Lys Pro Pro Arg Pro Ala Thr Ser Lys Ala
225                 230                 235                 240
Arg Lys Ala Glu
```

<210> SEQ ID NO 32
<211> LENGTH: 609
<212> TYPE: DNA
<213> ORGANISM: Vaccinium corymbosum

<400> SEQUENCE: 32

```
ggggttgggt taccagtaca tggctggctt tacagcacgg tggaagtatt atttcatttg    60
gtcaatctca gaagcttcca tcatcatttc tggcctgggg ttcagtggtt ggacagattc   120
ttctccacca aaaccaaaat gggaccgtgc aaagaatgta gatattttgc gggttgagtt   180
tgcaaagact gcagctcaga ttccacttgc atggaacatt caagtcagca cctggctacg   240
ccattatgtt tatgagaggc tcgtgcagaa gggaagaaaa cctggtttct tcagttgtt    300
ggctacccag actgtcagtg ctgtttggca tggtttatat cctggataca tcatattctt   360
tgtgcagtca gcattgatga ttgctggttc aagagttatt tatagatggc agcaagctgt   420
tcctcctaaa atggatctgg tgaagaaagt attcgtactt ttaaactttg cttacacagt   480
tctggtgttg aactactcct ctgtcggttt catggtacta agcctacatg aaacaattgt   540
```

```
tgcatacggg agcgtgtatt cgttggaacc attgttccca tacttgtaat cctccttggt    600
tacgtaatt                                                             609
```

<210> SEQ ID NO 33
<211> LENGTH: 195
<212> TYPE: PRT
<213> ORGANISM: Vaccinium corymbosum

<400> SEQUENCE: 33

```
Gly Leu Gly Tyr Gln Tyr Met Ala Gly Phe Thr Ala Arg Trp Lys Tyr
1               5                   10                  15

Tyr Phe Ile Trp Ser Ile Ser Glu Ala Ser Ile Ile Ser Gly Leu
            20                  25                  30

Gly Phe Ser Gly Trp Thr Asp Ser Ser Pro Lys Pro Lys Trp Asp
        35                  40                  45

Arg Ala Lys Asn Val Asp Ile Leu Arg Val Glu Phe Ala Lys Thr Ala
    50                  55                  60

Ala Gln Ile Pro Leu Ala Trp Asn Ile Gln Val Ser Thr Trp Leu Arg
65                  70                  75                  80

His Tyr Val Tyr Glu Arg Leu Val Gln Lys Gly Lys Lys Pro Gly Phe
                85                  90                  95

Phe Gln Leu Leu Ala Thr Gln Thr Val Ser Ala Val Trp His Gly Leu
            100                 105                 110

Tyr Pro Gly Tyr Ile Ile Phe Phe Val Gln Ser Ala Leu Met Ile Ala
        115                 120                 125

Gly Ser Arg Val Ile Tyr Arg Trp Gln Gln Ala Val Pro Pro Lys Met
    130                 135                 140

Asp Leu Val Lys Lys Val Phe Val Leu Leu Asn Phe Ala Tyr Thr Val
145                 150                 155                 160

Leu Val Leu Asn Tyr Ser Ser Val Gly Phe Met Val Leu Ser Leu His
                165                 170                 175

Glu Thr Ile Val Ala Tyr Gly Ser Val Tyr Ser Leu Glu Pro Leu Phe
            180                 185                 190

Pro Tyr Leu
        195
```

<210> SEQ ID NO 34
<211> LENGTH: 841
<212> TYPE: DNA
<213> ORGANISM: Wheat

<400> SEQUENCE: 34

```
cactttgctg gaccagtata tgagatgaaa gattatcttg aatggactga aaggaaagga    60
atatgggccg gctcaactcc ttcaccatta ttacctactc tgcgtgctct agttcaggct    120
ggaatatgca tggggttata tttgtatctg tcacctatgt ttccccattc ataatataga    180
ggttcactaa atcgtgaaag gggtttctgg caccggctct tctttcaata catgtcagga    240
tttactgctc gatggaaata ctactttata tggtcagtct cagaagctgc aattattata    300
tctggcctgg gtttcactgg ttggtctgat cttctcccc caaaagccaa atgggaccgt    360
gctataaatg ttgatattct gggcgtcgag ctagctggaa gtgcagctca attgccactt    420
aagtggaata ttcaagtgag cacatggcta agatactatg tgtatgagag gttaattcag    480
aaagggaaga agcctggttt ccttcagttg ttgggtacac agacagtcag tgctatctgg    540
catggactgt atccaggata tatgtttttc tttgttcagt cagcgttgat gataaatggt    600
```

```
tcaaaagtta tatacagatg caacaagct gtgagcaatc caggcctccg cactatcctg      660
tctttactaa attgtgcata caccatgatg gtgcttaact actcatgcat tggcttccag      720
gtactgagct tccaggagac cttagcatcc tacaagagcg tgtattatgt cggcacaatc      780
gttcctattc tatgtgtctt gctgggctat gtcgtcaagc ccacgagacc tgtgaagccg      840
a                                                                       841
```

<210> SEQ ID NO 35
<211> LENGTH: 279
<212> TYPE: PRT
<213> ORGANISM: Wheat

<400> SEQUENCE: 35

```
His Phe Ala Gly Pro Val Tyr Glu Met Lys Asp Tyr Leu Glu Trp Thr
1               5                   10                  15

Glu Arg Lys Gly Ile Trp Ala Gly Ser Thr Pro Ser Pro Leu Leu Pro
            20                  25                  30

Thr Leu Arg Ala Leu Val Gln Ala Gly Ile Cys Met Gly Leu Tyr Leu
        35                  40                  45

Tyr Leu Ser Pro Met Phe Pro His Ser Tyr Arg Gly Ser Leu Asn Arg
    50                  55                  60

Glu Arg Gly Phe Trp His Arg Leu Phe Phe Gln Tyr Met Ser Gly Phe
65                  70                  75                  80

Thr Ala Arg Trp Lys Tyr Tyr Phe Ile Trp Ser Val Ser Glu Ala Ala
                85                  90                  95

Ile Ile Ile Ser Gly Leu Gly Phe Thr Gly Trp Ser Asp Ser Ser Pro
            100                 105                 110

Pro Lys Ala Lys Trp Asp Arg Ala Ile Asn Val Asp Ile Leu Gly Val
        115                 120                 125

Glu Leu Ala Gly Ser Ala Ala Gln Leu Pro Leu Lys Trp Asn Ile Gln
    130                 135                 140

Val Ser Thr Trp Leu Arg Tyr Tyr Val Tyr Glu Arg Leu Ile Gln Lys
145                 150                 155                 160

Gly Lys Lys Pro Gly Phe Leu Gln Leu Leu Gly Thr Gln Thr Val Ser
                165                 170                 175

Ala Ile Trp His Gly Leu Tyr Pro Gly Tyr Met Phe Phe Val Gln
            180                 185                 190

Ser Ala Leu Met Ile Asn Gly Ser Lys Val Ile Tyr Arg Trp Gln Gln
        195                 200                 205

Ala Val Ser Asn Pro Gly Leu Arg Thr Ile Leu Ser Leu Leu Asn Cys
    210                 215                 220

Ala Tyr Thr Met Met Val Leu Asn Tyr Ser Cys Ile Gly Phe Gln Val
225                 230                 235                 240

Leu Ser Phe Gln Glu Thr Leu Ala Ser Tyr Lys Ser Val Tyr Val
                245                 250                 255

Gly Thr Ile Val Pro Ile Leu Cys Val Leu Gly Tyr Val Val Lys
            260                 265                 270

Pro Thr Arg Pro Val Lys Pro
        275
```

<210> SEQ ID NO 36
<211> LENGTH: 462
<212> TYPE: PRT
<213> ORGANISM: Arabidopsis thaliana

<400> SEQUENCE: 36

```
Met Asp Met Ser Ser Met Ala Gly Ser Ile Gly Val Ser Val Ala Val
1               5                   10                  15
Leu Arg Phe Leu Leu Cys Phe Val Ala Thr Ile Pro Val Ser Phe Ala
            20                  25                  30
Cys Arg Ile Val Pro Ser Arg Leu Gly Lys His Leu Tyr Ala Ala Ala
            35                  40                  45
Ser Gly Ala Phe Leu Ser Tyr Leu Ser Phe Gly Phe Ser Ser Asn Leu
    50                  55                  60
His Phe Leu Val Pro Met Thr Ile Gly Tyr Ala Ser Met Ala Ile Tyr
65                  70                  75                  80
Arg Pro Lys Cys Gly Ile Ile Thr Phe Phe Leu Gly Phe Ala Tyr Leu
                85                  90                  95
Ile Gly Cys His Val Phe Tyr Met Ser Gly Asp Ala Trp Lys Glu Gly
            100                 105                 110
Gly Ile Asp Ser Thr Gly Ala Leu Met Val Leu Thr Leu Lys Val Ile
            115                 120                 125
Ser Cys Ser Met Asn Tyr Asn Asp Gly Met Leu Lys Glu Glu Gly Leu
    130                 135                 140
Arg Glu Ala Gln Lys Lys Asn Arg Leu Ile Gln Met Pro Ser Leu Ile
145                 150                 155                 160
Glu Tyr Phe Gly Tyr Cys Leu Cys Gly Ser His Phe Ala Gly Pro
            165                 170                 175
Val Tyr Glu Met Lys Asp Tyr Leu Glu Trp Thr Gly Lys Gly Ile
            180                 185                 190
Trp Asp Thr Thr Glu Lys Arg Lys Lys Pro Ser Pro Tyr Gly Ala Thr
            195                 200                 205
Ile Arg Ala Ile Leu Gln Ala Ala Ile Cys Met Ala Leu Tyr Leu Tyr
    210                 215                 220
Leu Val Pro Gln Tyr Pro Leu Thr Arg Phe Thr Glu Pro Val Tyr Gln
225                 230                 235                 240
Glu Trp Gly Phe Leu Arg Lys Phe Ser Tyr Gln Tyr Met Ala Gly Phe
            245                 250                 255
Thr Ala Arg Trp Lys Tyr Tyr Phe Ile Trp Ser Ile Ser Glu Ala Ser
            260                 265                 270
Ile Ile Ile Ser Gly Leu Gly Phe Ser Gly Trp Thr Asp Asp Ala Ser
    275                 280                 285
Pro Lys Pro Lys Trp Asp Arg Ala Lys Asn Val Asp Ile Leu Gly Val
    290                 295                 300
Glu Leu Ala Lys Ser Ala Val Gln Ile Pro Leu Val Trp Asn Ile Gln
305                 310                 315                 320
Val Ser Thr Trp Leu Arg His Tyr Val Tyr Glu Arg Leu Val Gln Asn
            325                 330                 335
Gly Lys Lys Ala Gly Phe Phe Gln Leu Leu Ala Thr Gln Thr Val Ser
            340                 345                 350
Ala Val Trp His Gly Leu Tyr Pro Gly Tyr Met Met Phe Phe Val Gln
            355                 360                 365
Ser Ala Leu Met Ile Ala Gly Ser Arg Val Ile Tyr Arg Trp Gln Gln
    370                 375                 380
Ala Ile Ser Pro Lys Met Ala Met Leu Arg Asn Ile Met Val Phe Ile
385                 390                 395                 400
Asn Phe Leu Tyr Thr Val Leu Val Leu Asn Tyr Ser Ala Val Gly Phe
            405                 410                 415
Met Val Leu Ser Leu His Glu Thr Leu Thr Ala Tyr Gly Ser Val Tyr
            420                 425                 430
```

Tyr Ile Gly Thr Ile Ile Pro Val Gly Leu Ile Leu Ser Tyr Val
                435                 440                 445

Val Pro Ala Lys Pro Ser Arg Pro Lys Pro Arg Lys Glu Glu
        450                 455                 460

<210> SEQ ID NO 37
<211> LENGTH: 465
<212> TYPE: PRT
<213> ORGANISM: Arabidopsis thaliana

<400> SEQUENCE: 37

Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
                20                  25                  30

Ser Phe Leu Trp Arg Phe Ile Pro Ser Arg Leu Gly Lys His Ile Tyr
            35                  40                  45

Ser Ala Ala Ser Gly Ala Phe Leu Ser Tyr Leu Ser Phe Gly Phe Ser
        50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Ser Glu Lys Gly Lys Arg Pro Ser Pro Tyr
        195                 200                 205

Gly Ala Met Ile Arg Ala Val Phe Gln Ala Ala Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                245                 250                 255

Ala Gly Phe Thr Ala Arg Trp Lys Tyr Tyr Phe Ile Trp Ser Ile Ser
            260                 265                 270

Glu Ala Ser Ile Ile Ser Gly Leu Gly Phe Ser Gly Trp Thr Asp
        275                 280                 285

Glu Thr Gln Thr Lys Ala Lys Trp Asp Arg Ala Lys Asn Val Asp Ile
    290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
                325                 330                 335

Val Lys Pro Gly Lys Lys Ala Gly Phe Phe Gln Leu Leu Ala Thr Gln
            340                 345                 350

```
Thr Val Ser Ala Val Trp His Gly Leu Tyr Pro Gly Tyr Ile Ile Phe
            355                 360                 365

Phe Val Gln Ser Ala Leu Met Ile Asp Gly Ser Lys Ala Ile Tyr Arg
    370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
                405                 410                 415

Val Gly Phe Met Val Leu Ser Leu His Glu Thr Leu Val Ala Phe Lys
            420                 425                 430

Ser Val Tyr Tyr Ile Gly Thr Val Ile Pro Ile Ala Val Leu Leu Leu
            435                 440                 445

Ser Tyr Leu Val Pro Val Lys Pro Val Arg Pro Lys Thr Arg Lys Glu
            450                 455                 460

Glu
465

<210> SEQ ID NO 38
<211> LENGTH: 722
<212> TYPE: PRT
<213> ORGANISM: Drosophila melanogaster

<400> SEQUENCE: 38

Met Leu Glu Pro Pro Lys Phe Ile Glu Asn Asp Cys Tyr Asn Gly Ser
1               5                   10                  15

Arg Thr Phe Thr Trp Leu Ala Asp Met Val Gly Leu Ser Val Asp Leu
            20                  25                  30

Val Asn Phe Leu Ile Cys Gln Ile Ser Ala Leu Phe Leu Ala Ser Leu
            35                  40                  45

Phe Arg Ser Met Leu His Pro Ser Lys Val Ser Lys Leu Arg His
    50                  55                  60

Thr Phe Ala Leu Ser Ile Gly Leu Ala Phe Gly Tyr Phe Cys Phe Gly
65                  70                  75                  80

Gln Gln Ala Ile His Ile Ala Gly Leu Pro Ala Ile Cys Tyr Ile Val
            85                  90                  95

Ile Arg Thr Gln Asp Pro Arg Ile Val Gln Arg Ala Val Leu Leu Val
            100                 105                 110

Ala Met Ser Tyr Leu Leu Cys Val His Leu Met Arg Gln Leu Tyr Asp
            115                 120                 125

Tyr Gly Ser Tyr Ala Leu Asp Ile Thr Gly Pro Leu Met Ile Ile Thr
            130                 135                 140

Gln Lys Val Thr Ser Leu Ala Phe Ser Ile His Asp Gly Phe Val Arg
145                 150                 155                 160

Gly Asp Glu Glu Leu Thr Lys Ala Gln Gln Tyr His Ala Ile Arg Lys
            165                 170                 175

Met Pro Ser Ala Leu Glu Tyr Phe Ser Tyr Val Trp His Phe Gln Ser
            180                 185                 190

Ile Leu Ala Gly Pro Leu Val Phe Tyr Lys Asp Tyr Ile Glu Phe Val
            195                 200                 205

Glu Gly Tyr Asn Leu Leu Ser Thr Pro Pro Gly Asn Gly Asn Leu Asp
            210                 215                 220

Ser Ser Lys Arg Glu Val Val Leu Glu Pro Ser Pro Thr Lys Ala Val
225                 230                 235                 240

Ile Arg Lys Val Val Gly Ser Leu Val Cys Ala Phe Ile Phe Met Lys
            245                 250                 255
```

```
Phe Val Lys Ile Tyr Pro Val Lys Asp Met Lys Glu Asp Asp Phe Met
            260                 265                 270

Asn Asn Thr Ser Met Val Tyr Lys Tyr Trp Tyr Ala Met Met Ala Thr
            275                 280                 285

Thr Cys Ile Arg Phe Lys Tyr Tyr His Ala Trp Leu Leu Ala Asp Ala
            290                 295                 300

Ile Cys Asn Asn Ser Gly Leu Gly Phe Thr Gly Tyr Asp Lys Asp Gly
305                 310                 315                 320

Asn Ser Lys Trp Asp Leu Ile Ser Asn Ile Asn Val Leu Ser Phe Glu
                325                 330                 335

Phe Ser Thr Asn Met Arg Asp Ala Ile Asn Asn Trp Asn Cys Gly Thr
                340                 345                 350

Asn Arg Trp Leu Arg Thr Leu Val Tyr Glu Arg Val Pro Gln Gln Tyr
            355                 360                 365

Gly Thr Leu Leu Thr Phe Ala Leu Ser Ala Val Trp His Gly Phe Tyr
            370                 375                 380

Pro Gly Tyr Tyr Leu Thr Phe Ala Thr Gly Ala Val Val Thr Ala
385                 390                 395                 400

Ala Arg Thr Gly Arg Arg Leu Phe Arg His Arg Phe Gln Ser Thr Gln
                405                 410                 415

Val Thr Arg Met Phe Tyr Asp Ile Leu Thr Cys Leu Ile Thr Arg Val
            420                 425                 430

Val Leu Gly Tyr Ala Thr Phe Pro Phe Val Leu Leu Glu Phe Met Gly
            435                 440                 445

Ser Ile Lys Leu Tyr Leu Arg Phe Tyr Leu Cys Leu His Ile Ile Ser
450                 455                 460

Leu Val Thr Ile Phe Ile Leu Pro Lys Phe Ile Arg Gly Glu Arg Arg
465                 470                 475                 480

Leu Arg Thr Ser Asn Gly Asn Gly Asn Val Arg Leu Ser Gly Ser Gly
                485                 490                 495

Asn Thr Lys Asp Ala Val Thr Thr Ser Val Glu Ser Thr Ala Ala Leu
            500                 505                 510

Thr Ala Gly Asn Asp Leu Asn Glu Asp Lys Glu Glu Asp Lys His Ala
            515                 520                 525

Gln Cys Lys Val His Thr Pro Thr Gln Gln Pro Ala Ala Gly Pro
530                 535                 540

His Lys Thr Thr Val Glu Gln Pro Thr Glu Gln Pro Asn Asn Val Asn
545                 550                 555                 560

Leu Arg Ser Arg Pro Gln Gln Gln Pro His Leu Glu Lys Lys Ala
                565                 570                 575

Met Pro Pro Thr Cys Ala Arg Asp Ala Val Ser Val Pro His Asp Gln
                580                 585                 590

Cys Glu Met Asp Gln Leu Ser Ser Lys Leu Lys Glu Lys Ile Glu Ala
                595                 600                 605

Glu Thr Lys Asn Ile Glu Glu Phe Ile Asp Lys Thr Val Thr Glu Thr
            610                 615                 620

Val Ser Gly Ile Val Glu Phe Lys Asn Asp Leu Met Arg Asp Ile Glu
625                 630                 635                 640

Phe Pro Lys Leu Lys Leu Pro Gly Ser Asn Gly Ala Ile Ser Leu Asp
                645                 650                 655

Ser Ser Asn Gly Gly Gly Leu Arg Lys Arg Asn Ile Ser Ser Val His
                660                 665                 670

Asp Asn Gly Thr Asp Pro Gly His Ala Thr Ala Asp Leu His Pro Pro
```

```
                     675                 680                 685
Leu Glu Glu Asn Gly Ala Ala Phe Leu Lys Lys Glu Ile Glu Val Ile
            690                 695                 700

Asn Ala Val Val Gln Gln Ala Val Pro Ala Val Leu Ser Asn Gly His
705                 710                 715                 720

Ala Lys

<210> SEQ ID NO 39
<211> LENGTH: 497
<212> TYPE: PRT
<213> ORGANISM: Drosophila melanogaster

<400> SEQUENCE: 39

Met Ala Glu Phe Glu Glu Asp Leu Pro His Asn Gly Leu Met Asp Gly
1               5                   10                  15

Ile Ala Ser Gly Val Gly Val Pro Val Glu Ala Leu Arg Leu Leu Leu
            20                  25                  30

Thr Ile Leu Ala Gly Tyr Pro Val Ala Leu Tyr Gln Lys Phe Ile
        35                  40                  45

Ser Val Ile Ala Asp Lys Thr Val His His Met Phe Phe Ala Gly Cys
50                  55                  60

Gly Ala Gly Leu Cys Tyr Phe Asn Tyr Gly Leu Asp Thr Tyr His Ser
65                  70                  75                  80

Leu Ile Ala Ile Leu Thr Thr Tyr Phe Leu Val Leu Leu Arg Lys
            85                  90                  95

Lys Thr Gln Ile Phe Leu Ala Ile Asn Phe Val Phe His Met Ser Tyr
            100                 105                 110

Leu Leu Leu Gly Tyr Phe Tyr Thr Ser Ser Asn Asp Tyr Asp Ile Leu
            115                 120                 125

Trp Thr Met Pro His Cys Ile Leu Val Leu Arg Met Ile Gly Tyr Gly
        130                 135                 140

Phe Asp Ile Thr Asp Gly Leu Lys Glu Glu Ser Glu Leu Ser Lys Asp
145                 150                 155                 160

Gln Lys Glu Thr Ala Leu Lys Lys Pro Ser Leu Leu Glu Leu Leu
            165                 170                 175

Ala Phe Ser Tyr Phe Pro Ser Gly Phe Leu Val Gly Pro Gln Phe Pro
            180                 185                 190

Phe Arg Arg Tyr Lys Ala Phe Val Asp Gly Glu Phe Arg Gln His Glu
            195                 200                 205

Gly Asn Val Glu Ala Gly Val Arg Arg Phe Gly Ala Gly Ala Phe Tyr
        210                 215                 220

Leu Ile Val Cys Gln Val Gly Leu Arg Tyr Leu Pro Asp Ser Tyr Phe
225                 230                 235                 240

Leu Thr Pro Glu Phe Ala Gln Val Ser Phe Val Lys Arg Ile Tyr Leu
            245                 250                 255

Leu Gly Phe Trp Ala Lys Phe Ser Leu Tyr Lys Tyr Ile Ser Cys Trp
            260                 265                 270

Leu Leu Thr Glu Gly Ala Leu Ile Cys Ile Gly Leu Thr Tyr Lys Gly
            275                 280                 285

Glu Asp Lys Asn Gly Gln Pro Asp Trp Ser Gly Cys Ser Asn Val Lys
            290                 295                 300

Leu Lys Leu Leu Glu Thr Gly Asn Thr Met Glu His Tyr Val Gln Ser
305                 310                 315                 320

Phe Asn Val Asn Thr Asn Gln Trp Val Gly Gln Tyr Ile Tyr Lys Arg
            325                 330                 335
```

-continued

```
Leu Lys Phe Leu Asn Asn Arg Thr Ile Ser Tyr Gly Ala Ala Leu Gly
            340                 345                 350

Phe Leu Ala Val Trp His Gly Tyr His Ser Gly Tyr Tyr Met Thr Phe
            355                 360                 365

Leu Met Glu Tyr Met Val Val Ser Thr Glu Lys Gln Ile Thr Arg Phe
            370                 375                 380

Tyr Thr Lys Val Val Leu Pro Gln Trp Gly His Ile Leu Asn Asn Ser
385                 390                 395                 400

Asp Ile Tyr Lys Leu Leu Tyr Phe Ile Thr Leu Lys Ser Tyr Asn Val
            405                 410                 415

Val Tyr Met Gly Trp Cys Leu Thr Ala Phe Val Phe Leu Lys Tyr Glu
            420                 425                 430

Arg Trp Ile Val Val Tyr Gly Ala Val Ser Tyr Gly Phe Thr Phe Phe
            435                 440                 445

Leu Val Leu Trp Ala Ala Phe Tyr His Thr Phe Asn His Phe Phe Arg
            450                 455                 460

Ser Ser Ser Arg Lys Leu Ala Gly Glu Asp Gln Lys Leu Gln Asp Ser
465                 470                 475                 480

Asn Thr Asp Lys Leu Val Glu Glu Lys Lys Pro Glu Asp Lys Lys Ser
            485                 490                 495

Glu

<210> SEQ ID NO 40
<211> LENGTH: 506
<212> TYPE: PRT
<213> ORGANISM: Homo sapiens

<400> SEQUENCE: 40

Met Lys Cys Cys Phe His His Ile Ile Pro Arg Val Asn Phe Val Val
1               5                   10                  15

Cys Gln Leu Phe Ala Leu Leu Ala Ala Ile Trp Phe Arg Thr Tyr Leu
            20                  25                  30

His Ser Ser Lys Thr Ser Ser Phe Ile Arg His Val Val Ala Thr Leu
            35                  40                  45

Leu Gly Leu Tyr Leu Ala Leu Phe Cys Phe Gly Trp Tyr Ala Leu His
        50                  55                  60

Phe Leu Val Gln Ser Gly Ile Ser Tyr Cys Ile Met Ile Ile Ile Gly
65                  70                  75                  80

Val Glu Asn Met His Asn Tyr Cys Phe Val Phe Ala Leu Gly Tyr Leu
            85                  90                  95

Thr Val Cys Gln Val Thr Arg Val Tyr Ile Phe Asp Tyr Gly Gln Tyr
            100                 105                 110

Ser Ala Asp Phe Ser Gly Pro Met Met Ile Ile Thr Gln Lys Ile Thr
            115                 120                 125

Ser Leu Ala Cys Glu Ile His Asp Gly Met Phe Arg Lys Asp Glu Glu
            130                 135                 140

Leu Thr Ser Ser Gln Arg Asp Leu Ala Val Arg Arg Met Pro Ser Leu
145                 150                 155                 160

Leu Glu Tyr Leu Ser Tyr Asn Cys Asn Phe Met Gly Ile Leu Ala Gly
            165                 170                 175

Pro Leu Cys Ser Tyr Lys Asp Tyr Ile Thr Phe Ile Glu Gly Arg Ser
            180                 185                 190

Tyr His Ile Thr Gln Ser Gly Glu Asn Gly Lys Glu Gly Thr Gln Tyr
            195                 200                 205
```

Glu Arg Thr Glu Pro Ser Pro Asn Thr Ala Val Val Gln Lys Leu Leu
    210                 215                 220

Val Cys Gly Leu Ser Leu Leu Phe His Leu Thr Ile Cys Thr Thr Leu
225                 230                 235                 240

Pro Val Glu Tyr Asn Ile Asp Glu His Phe Gln Ala Thr Ala Ser Trp
                245                 250                 255

Pro Thr Lys Ile Ile Tyr Leu Tyr Ile Ser Leu Leu Ala Ala Arg Pro
            260                 265                 270

Lys Tyr Tyr Phe Ala Trp Thr Leu Ala Asp Ala Ile Asn Asn Ala Ala
        275                 280                 285

Gly Phe Gly Phe Arg Gly Tyr Asp Glu Asn Gly Ala Ala Arg Trp Asp
290                 295                 300

Leu Ile Ser Asn Leu Arg Ile Gln Gln Ile Glu Met Ser Thr Ser Phe
305                 310                 315                 320

Lys Met Phe Leu Asp Asn Trp Asn Ile Gln Thr Ala Leu Trp Leu Lys
                325                 330                 335

Arg Val Cys Tyr Glu Arg Thr Ser Phe Ser Pro Thr Ile Gln Thr Phe
                340                 345                 350

Ile Leu Ser Ala Ile Trp His Gly Val Tyr Pro Gly Tyr Tyr Leu Thr
            355                 360                 365

Phe Leu Thr Gly Val Leu Met Thr Leu Ala Ala Arg Ala Met Arg Asn
370                 375                 380

Asn Phe Arg His Tyr Phe Ile Glu Pro Ser Gln Leu Lys Leu Phe Tyr
385                 390                 395                 400

Asp Val Ile Thr Trp Ile Val Thr Gln Val Ala Ile Ser Tyr Thr Val
                405                 410                 415

Val Pro Phe Val Leu Leu Ser Ile Lys Pro Ser Leu Thr Phe Tyr Ser
            420                 425                 430

Ser Trp Tyr Tyr Cys Leu His Ile Leu Gly Ile Leu Val Leu Leu Leu
        435                 440                 445

Leu Pro Val Lys Lys Thr Gln Arg Arg Lys Asn Thr His Glu Asn Ile
    450                 455                 460

Gln Leu Ser Gln Ser Lys Lys Phe Asp Glu Gly Glu Asn Ser Leu Gly
465                 470                 475                 480

Gln Asn Ser Phe Ser Thr Thr Asn Asn Val Cys Asn Gln Asn Gln Glu
                485                 490                 495

Ile Ala Ser Arg His Ser Ser Leu Lys Gln
            500                 505

<210> SEQ ID NO 41
<211> LENGTH: 520
<212> TYPE: PRT
<213> ORGANISM: Homo sapiens

<400> SEQUENCE: 41

Met Ala Thr Thr Ser Thr Thr Gly Ser Thr Leu Leu Gln Pro Leu Ser
1               5                   10                  15

Asn Ala Val Gln Leu Pro Ile Asp Gln Val Asn Phe Val Val Cys Gln
                20                  25                  30

Leu Phe Ala Leu Leu Ala Ala Ile Trp Phe Arg Thr Tyr Leu His Ser
            35                  40                  45

Ser Lys Thr Ser Ser Phe Ile Arg His Val Val Ala Thr Leu Leu Gly
        50                  55                  60

Leu Tyr Leu Ala Leu Phe Cys Phe Gly Trp Tyr Ala Leu His Phe Leu
65                  70                  75                  80

```
Val Gln Ser Gly Ile Ser Tyr Cys Ile Met Ile Ile Gly Val Glu
                 85                  90                  95

Asn Met His Asn Tyr Cys Phe Val Phe Ala Leu Gly Tyr Leu Thr Val
            100                 105                 110

Cys Gln Val Thr Arg Val Tyr Ile Phe Asp Tyr Gly Gln Tyr Ser Ala
        115                 120                 125

Asp Phe Ser Gly Pro Met Met Ile Ile Thr Gln Lys Ile Thr Ser Leu
    130                 135                 140

Ala Cys Glu Ile His Asp Gly Met Phe Arg Lys Asp Glu Glu Leu Thr
145                 150                 155                 160

Ser Ser Gln Arg Asp Leu Ala Val Arg Arg Met Pro Ser Leu Leu Glu
                165                 170                 175

Tyr Leu Ser Tyr Asn Cys Asn Phe Met Gly Ile Leu Ala Gly Pro Leu
            180                 185                 190

Cys Ser Tyr Lys Asp Tyr Ile Thr Phe Ile Glu Gly Arg Ser Tyr His
        195                 200                 205

Ile Thr Gln Ser Gly Glu Asn Gly Lys Glu Glu Thr Gln Tyr Glu Arg
    210                 215                 220

Thr Glu Pro Ser Pro Asn Thr Ala Val Val Gln Lys Leu Leu Val Cys
225                 230                 235                 240

Gly Leu Ser Leu Leu Phe His Leu Thr Ile Cys Thr Thr Leu Pro Val
                245                 250                 255

Glu Tyr Asn Ile Asp Glu His Phe Gln Ala Thr Ala Ser Trp Pro Thr
            260                 265                 270

Lys Ile Ile Tyr Leu Tyr Ile Ser Leu Leu Ala Ala Arg Pro Lys Tyr
        275                 280                 285

Tyr Phe Ala Trp Thr Leu Ala Asp Ala Ile Asn Asn Ala Ala Gly Phe
    290                 295                 300

Gly Phe Arg Gly Tyr Asp Glu Asn Gly Ala Ala Arg Trp Asp Leu Ile
305                 310                 315                 320

Ser Asn Leu Arg Ile Gln Gln Ile Glu Met Ser Thr Ser Phe Lys Met
                325                 330                 335

Phe Leu Asp Asn Trp Asn Ile Gln Thr Ala Leu Trp Leu Lys Arg Val
            340                 345                 350

Cys Tyr Glu Arg Thr Ser Phe Ser Pro Thr Ile Gln Thr Phe Ile Leu
        355                 360                 365

Ser Ala Ile Trp His Gly Val Tyr Pro Gly Tyr Tyr Leu Thr Phe Leu
    370                 375                 380

Thr Gly Val Leu Met Thr Leu Ala Ala Arg Ala Met Arg Asn Asn Phe
385                 390                 395                 400

Arg His Tyr Phe Ile Glu Pro Ser Gln Leu Lys Leu Phe Tyr Asp Val
                405                 410                 415

Ile Thr Trp Ile Val Thr Gln Val Ala Ile Ser Tyr Thr Val Val Pro
            420                 425                 430

Phe Val Leu Leu Ser Ile Lys Pro Ser Leu Thr Phe Tyr Ser Ser Trp
        435                 440                 445

Tyr Tyr Cys Leu His Ile Leu Gly Ile Leu Val Leu Leu Leu Leu Pro
    450                 455                 460

Val Lys Lys Thr Gln Arg Arg Lys Asn Thr His Glu Asn Ile Gln Leu
465                 470                 475                 480

Ser Gln Ser Arg Lys Phe Asp Glu Gly Glu Asn Ser Leu Gly Gln Asn
                485                 490                 495

Ser Phe Ser Thr Thr Asn Asn Val Cys Asn Gln Asn Gln Glu Ile Ala
            500                 505                 510
```

Ser Arg His Ser Ser Leu Lys Gln
        515                 520

<210> SEQ ID NO 42
<211> LENGTH: 492
<212> TYPE: PRT
<213> ORGANISM: Mus musculus

<400> SEQUENCE: 42

Met Ala Ala Arg Pro Ala Ser Leu Ser Tyr Arg Thr Thr Gly Ser
1               5                   10                  15

Thr Cys Leu His Pro Leu Ser Gln Leu Leu Gly Ile Pro Leu Asp Gln
                20                  25                  30

Val Asn Phe Val Ala Cys Gln Leu Phe Ala Leu Ser Ala Ala Phe Trp
            35                  40                  45

Phe Arg Ile Tyr Leu His Pro Gly Lys Ala Ser Pro Glu Val Arg His
    50                  55                  60

Thr Leu Ala Thr Ile Leu Gly Ile Tyr Phe Val Phe Cys Phe Gly
65                  70                  75                  80

Trp Tyr Ala Val His Leu Phe Val Leu Val Leu Met Cys Tyr Gly Val
                85                  90                  95

Met Val Ser Ala Ser Val Ser Asn Ile His Arg Tyr Ser Phe Phe Val
                100                 105                 110

Ala Met Gly Tyr Leu Thr Ile Cys His Ile Ser Arg Ile Tyr Ile Phe
            115                 120                 125

His Tyr Gly Ile Leu Thr Thr Asp Phe Ser Gly Pro Leu Met Ile Val
    130                 135                 140

Thr Gln Lys Ile Thr Thr Leu Ala Phe Gln Val His Asp Gly Leu Gly
145                 150                 155                 160

Arg Lys Ala Glu Asp Leu Ser Ala Glu Gln His Arg Leu Ala Val Lys
                165                 170                 175

Ala Lys Pro Ser Leu Leu Glu Tyr Leu Ser Tyr His Leu Asn Phe Met
            180                 185                 190

Ser Val Ile Ala Gly Pro Cys Asn Asn Phe Lys Asp Tyr Val Ala Phe
    195                 200                 205

Ile Glu Gly Arg His Ile His Met Lys Leu Leu Glu Val Asn Trp Thr
210                 215                 220

Gln Arg Gly Phe Gln Ser Leu Pro Glu Pro Ser Pro Thr Gly Ala Val
225                 230                 235                 240

Ile Gln Lys Leu Cys Val Thr Leu Met Ser Leu Leu Leu Phe Leu Thr
                245                 250                 255

Leu Ser Lys Ser Phe Pro Val Thr Phe Leu Ile Asp Asp Trp Phe Val
            260                 265                 270

His Lys Ala Asn Phe Leu Ser Arg Leu Trp Tyr Leu Tyr Val Val Met
    275                 280                 285

Gln Ala Ala Lys Pro Lys Tyr Tyr Phe Ala Trp Thr Leu Ala Asp Ala
290                 295                 300

Val His Asn Ala Ala Gly Phe Gly Phe Asn Gly Met Asp Thr Asp Gly
305                 310                 315                 320

Lys Ser Arg Trp Asp Leu Leu Ser Asn Leu Asn Ile Trp Lys Ile Glu
                325                 330                 335

Thr Ala Thr Ser Phe Lys Met Tyr Leu Glu Asn Trp Asn Ile Gln Thr
            340                 345                 350

Ser Thr Trp Leu Lys Cys Val Cys Tyr Glu Arg Val Ser Trp Tyr Pro
    355                 360                 365

```
Thr Val Leu Thr Phe Leu Leu Ser Ala Leu Trp His Gly Val Tyr Pro
    370                 375                 380

Gly Tyr Tyr Phe Thr Phe Leu Thr Gly Val Pro Val Thr Leu Ala Ala
385                 390                 395                 400

Arg Ala Val Arg Asn Asn Tyr Arg His His Phe Leu Ser Ser Lys Ala
                405                 410                 415

Arg Lys Ile Ala Tyr Asp Val Val Thr Trp Ala Val Thr Gln Leu Ala
                420                 425                 430

Val Ser Tyr Thr Ala Ala Pro Phe Val Met Leu Ala Val Glu Pro Thr
                435                 440                 445

Ile Ser Leu Tyr Lys Ser Val Phe Phe Leu His Ile Ile Cys Leu
    450                 455                 460

Leu Ile Ile Leu Phe Leu Pro Ile Lys Pro His Gln Pro Gln Arg Gln
465                 470                 475                 480

Ser Arg Ser Pro Asn Ser Val Lys Lys Ala Asp
                485                 490

<210> SEQ ID NO 43
<211> LENGTH: 519
<212> TYPE: PRT
<213> ORGANISM: Mus musculus

<400> SEQUENCE: 43

Met Ala Thr Thr Ser Thr Thr Gly Ser Thr Leu Leu Gln Pro Leu Ser
1               5                   10                  15

Asn Ala Val Gln Leu Pro Ile Asp Gln Val Asn Phe Val Val Cys Gln
                20                  25                  30

Leu Phe Ala Leu Leu Ala Ala Val Trp Phe Arg Thr Tyr Leu His Ser
            35                  40                  45

Ser Lys Thr Ser Ser Phe Ile Arg His Val Val Ala Thr Leu Leu Gly
    50                  55                  60

Leu Tyr Leu Ala Phe Phe Cys Phe Gly Trp Tyr Ala Leu His Phe Leu
65                  70                  75                  80

Val Gln Ser Gly Ile Ser Tyr Cys Ile Met Ile Ile Ala Gly Val Glu
                85                  90                  95

Ser Met Gln Gln Cys Cys Phe Val Phe Ala Leu Gly Tyr Leu Ser Val
                100                 105                 110

Cys Gln Ile Thr Arg Val Tyr Ile Phe Asp Tyr Gly Gln Tyr Ser Ala
                115                 120                 125

Asp Phe Ser Gly Pro Met Met Ile Ile Thr Gln Lys Ile Thr Ser Leu
130                 135                 140

Ala Tyr Glu Ile His Asp Gly Met Phe Arg Lys Asp Glu Glu Leu Thr
145                 150                 155                 160

Pro Ser Gln Arg Gly Leu Ala Val Arg Arg Met Pro Ser Leu Leu Glu
                165                 170                 175

Tyr Val Ser Tyr Thr Cys Asn Phe Met Gly Ile Leu Ala Gly Pro Leu
                180                 185                 190

Cys Ser Tyr Lys Asp Tyr Ile Ala Phe Ile Glu Gly Arg Ala Ser His
                195                 200                 205

Val Ala Gln Pro Ser Glu Asn Gly Lys Asp Glu Gln His Gly Lys Ala
            210                 215                 220

Asp Pro Ser Pro Asn Ala Ala Val Thr Glu Lys Leu Leu Val Cys Gly
225                 230                 235                 240

Leu Ser Leu Leu Phe His Leu Thr Ile Ser Asn Met Leu Pro Val Glu
                245                 250                 255
```

```
Tyr Asn Ile Asp Glu His Phe Gln Ala Thr Ala Ser Trp Pro Thr Lys
            260                 265                 270

Ala Thr Tyr Leu Tyr Val Ser Leu Leu Ala Ala Arg Pro Lys Tyr Tyr
        275                 280                 285

Phe Ala Trp Thr Leu Ala Asp Ala Ile Asn Asn Ala Gly Phe Gly
    290                 295                 300

Phe Arg Gly Tyr Asp Lys Asn Gly Val Ala Arg Trp Asp Leu Ile Ser
305                 310                 315                 320

Asn Leu Arg Ile Gln Gln Ile Glu Met Ser Thr Ser Phe Lys Met Phe
                325                 330                 335

Leu Asp Asn Trp Asn Ile Gln Thr Ala Leu Trp Leu Lys Arg Val Cys
            340                 345                 350

Tyr Glu Arg Ala Thr Phe Ser Pro Thr Ile Gln Thr Phe Phe Leu Ser
                355                 360                 365

Ala Ile Trp His Gly Val Tyr Pro Gly Tyr Tyr Leu Thr Phe Leu Thr
        370                 375                 380

Gly Val Leu Met Thr Leu Ala Ala Arg Ala Val Arg Asn Asn Phe Arg
385                 390                 395                 400

His Tyr Phe Leu Glu Pro Pro Gln Leu Lys Leu Phe Tyr Asp Leu Ile
                405                 410                 415

Thr Trp Val Ala Thr Gln Ile Thr Ile Ser Tyr Thr Val Pro Phe
            420                 425                 430

Val Leu Leu Ser Ile Lys Pro Ser Phe Thr Phe Tyr Ser Ser Trp Tyr
                435                 440                 445

Tyr Cys Leu His Val Cys Ser Ile Leu Val Leu Leu Leu Pro Val
        450                 455                 460

Lys Lys Ser Gln Arg Arg Thr Ser Thr Gln Glu Asn Val His Leu Ser
465                 470                 475                 480

Gln Ala Lys Lys Phe Asp Glu Arg Asp Asn Pro Leu Gly Gln Asn Ser
                485                 490                 495

Phe Ser Thr Met Asn Asn Val Cys Ser Gln Asn Arg Asp Thr Gly Ser
                500                 505                 510

Arg His Ser Ser Leu Thr Gln
            515

<210> SEQ ID NO 44
<211> LENGTH: 509
<212> TYPE: PRT
<213> ORGANISM: Schizosaccharomyces pombe

<400> SEQUENCE: 44

Met Ala Tyr Leu Ile Asp Ile Pro Phe Glu Tyr Phe Ser Ser Phe Leu
1               5                   10                  15

Gly Val His Pro Asp Gln Leu Lys Leu Leu Phe Cys Phe Leu Ser Ala
            20                  25                  30

Tyr Pro Phe Ala Gly Ile Leu Lys Arg Leu Pro Ser Ala Pro Trp Ile
        35                  40                  45

Arg Asn Leu Phe Ser Ile Ser Ile Gly Leu Phe Tyr Leu Ile Gly Val
    50                  55                  60

His His Leu Tyr Asp Gly Val Leu Val Leu Phe Asp Ala Leu Phe
65                  70                  75                  80

Thr Tyr Phe Val Ala Ala Phe Tyr Arg Ser Ser Arg Met Pro Trp Ile
                85                  90                  95

Ile Phe Ile Val Ile Leu Gly His Thr Phe Ser Ser His Val Ile Arg
            100                 105                 110
```

Tyr Ile Tyr Pro Ser Glu Asn Thr Asp Ile Thr Ala Ser Gln Met Val
            115                 120                 125

Leu Cys Met Lys Leu Thr Ala Phe Ala Trp Ser Val Tyr Asp Gly Arg
130                 135                 140

Leu Pro Ser Ser Glu Leu Ser Ser Tyr Gln Lys Asp Arg Ala Leu Arg
145                 150                 155                 160

Lys Ile Pro Asn Ile Leu Tyr Phe Leu Gly Tyr Val Phe Phe Phe Pro
                165                 170                 175

Ser Leu Leu Val Gly Pro Ala Phe Asp Tyr Val Asp Tyr Glu Arg Phe
            180                 185                 190

Ile Thr Leu Ser Met Phe Lys Pro Leu Ala Asp Pro Tyr Glu Lys Gln
        195                 200                 205

Ile Thr Pro His Ser Leu Glu Pro Ala Leu Gly Arg Cys Trp Arg Gly
    210                 215                 220

Leu Leu Trp Leu Ile Leu Phe Ile Thr Gly Ser Ser Ile Tyr Pro Leu
225                 230                 235                 240

Lys Phe Leu Leu Thr Pro Lys Phe Ala Ser Ser Pro Ile Leu Leu Lys
                245                 250                 255

Tyr Gly Tyr Val Cys Ile Thr Ala Phe Val Ala Arg Met Lys Tyr Tyr
            260                 265                 270

Gly Ala Trp Glu Leu Ser Asp Gly Ala Cys Ile Leu Ser Gly Ile Gly
        275                 280                 285

Tyr Asn Gly Leu Asp Ser Ser Lys His Pro Arg Trp Asp Arg Val Lys
    290                 295                 300

Asn Ile Asp Pro Ile Lys Phe Glu Phe Ala Asp Asn Ile Lys Cys Ala
305                 310                 315                 320

Leu Glu Ala Trp Asn Met Asn Thr Asn Lys Trp Leu Arg Asn Tyr Val
                325                 330                 335

Tyr Leu Arg Val Ala Lys Lys Gly Lys Arg Pro Gly Phe Lys Ser Thr
            340                 345                 350

Leu Ser Thr Phe Thr Val Ser Ala Met Trp His Gly Val Ser Ala Gly
        355                 360                 365

Tyr Tyr Leu Thr Phe Val Ser Ala Ala Phe Ile Gln Thr Val Ala Lys
    370                 375                 380

Tyr Thr Arg Arg His Val Arg Pro Phe Leu Lys Pro Asp Met Glu
385                 390                 395                 400

Thr Pro Gly Pro Phe Lys Arg Val Tyr Asp Val Ile Gly Met Val Ala
                405                 410                 415

Thr Asn Leu Ser Leu Ser Tyr Leu Ile Ile Ser Phe Leu Leu Leu Asn
            420                 425                 430

Leu Lys Glu Ser Ile His Val Trp Lys Glu Leu Tyr Phe Ile Val His
        435                 440                 445

Ile Tyr Ile Leu Ile Ala Leu Ala Val Phe Asn Ser Pro Ile Arg Ser
    450                 455                 460

Lys Leu Asp Asn Lys Ile Arg Ser Arg Val Asn Ser Tyr Lys Leu Lys
465                 470                 475                 480

Ser Tyr Glu Gln Ser Met Lys Ser Thr Ser Asp Thr Asp Met Leu Asn
                485                 490                 495

Met Ser Val Pro Lys Arg Glu Asp Phe Glu Asn Asp Glu
            500                 505

<210> SEQ ID NO 45
<211> LENGTH: 539
<212> TYPE: PRT

<213> ORGANISM: Aspergillus oryzae

<400> SEQUENCE: 45

```
Met Leu Pro Tyr Val Asp Leu Lys Leu Ile Ala Ser Phe Leu Leu
1               5                   10                  15

Ser Tyr Pro Leu Ala Ala Leu Leu Lys Arg Ile Pro Asp Ala Gln Pro
                20                  25                  30

Trp Lys Lys Asn Ala Phe Ile Ile Ala Val Ser Leu Phe Tyr Leu Val
            35                  40                  45

Gly Leu Phe Asp Leu Trp Asp Gly Leu Arg Thr Leu Ala Tyr Ser Ala
        50                  55                  60

Ala Gly Ile Tyr Ala Ile Ala Tyr Tyr Ile Asp Gly Ser Leu Met Pro
65                  70                  75                  80

Trp Ile Gly Phe Ile Phe Leu Met Gly His Met Ser Ile Ser His Ile
                85                  90                  95

Tyr Arg Gln Ile Ile Asp Asp Ala His Val Thr Asp Ile Thr Gly Ala
            100                 105                 110

Gln Met Val Leu Val Met Lys Leu Ser Ser Phe Cys Trp Asn Val His
        115                 120                 125

Asp Gly Arg Leu Ser Gln Glu Gln Leu Ser Asp Pro Gln Lys Tyr Ala
130                 135                 140

Ala Ile Lys Asp Phe Pro Gly Ile Leu Asp Tyr Leu Gly Tyr Val Leu
145                 150                 155                 160

Phe Phe Pro Ser Leu Phe Ala Gly Pro Ser Phe Glu Tyr Val Asp Tyr
                165                 170                 175

Arg Arg Trp Ile Asp Thr Thr Leu Phe Asp Val Pro Pro Gly Thr Asp
            180                 185                 190

Pro Ser Lys Val Pro Pro Thr Arg Lys Arg Lys Ile Pro Arg Ser
        195                 200                 205

Gly Thr Pro Ala Ala Lys Lys Ala Leu Ala Gly Leu Gly Trp Ile Leu
210                 215                 220

Ala Phe Leu Gln Leu Gly Ser Leu Tyr Asn Gln Glu Leu Val Leu Asp
225                 230                 235                 240

Glu Thr Phe Met Gln Tyr Ser Phe Val Gln Arg Val Trp Ile Leu His
                245                 250                 255

Met Leu Gly Phe Thr Ala Arg Leu Lys Tyr Tyr Gly Val Trp Tyr Leu
            260                 265                 270

Thr Glu Gly Ala Cys Val Leu Ser Gly Met Gly Tyr Asn Gly Phe Asp
        275                 280                 285

Pro Lys Ser Gly Lys Val Phe Trp Asn Arg Leu Glu Asn Val Asp Pro
        290                 295                 300

Trp Ser Leu Glu Thr Ala Gln Asn Ser His Gly Tyr Leu Gly Ser Trp
305                 310                 315                 320

Asn Lys Asn Thr Asn His Trp Leu Arg Asn Tyr Val Tyr Leu Arg Val
                325                 330                 335

Thr Pro Lys Gly Lys Pro Gly Phe Arg Ala Ser Leu Ala Thr Phe
            340                 345                 350

Val Thr Ser Ala Phe Trp His Gly Phe Tyr Pro Gly Tyr Tyr Leu Thr
        355                 360                 365

Phe Val Leu Gly Ser Phe Ile Gln Thr Val Ala Lys Asn Phe Arg Arg
        370                 375                 380

His Val Arg Pro Phe Phe Leu Thr Pro Asp Gly Ser Arg Pro Thr Ala
385                 390                 395                 400

Tyr Lys Lys Tyr Tyr Asp Ile Ala Ser Tyr Val Val Thr Gln Leu Thr
```

-continued

```
                        405                 410                 415
Leu Ser Phe Ala Val Met Pro Phe Ile Phe Leu Ser Phe Gly Asp Ser
            420                 425                 430

Ile Lys Val Trp His Ser Val Tyr Phe Tyr Gly Ile Val Gly Asn Ile
            435                 440                 445

Val Ser Leu Ala Phe Phe Val Ser Pro Ala Arg Gly Leu Leu Lys
            450                 455                 460

Lys Leu Lys Ala Arg Asn Lys Pro His Val Pro Arg Ala Val Ser Ser
465                 470                 475                 480

Glu Asn Ile Arg Gln Pro Thr Leu Gly Leu Pro Asn Asp Ala Ile Gln
                485                 490                 495

Glu Phe Asp Asp Ala Val Gln Glu Ile Arg Ala Glu Ile Glu Ser Arg
                500                 505                 510

Gln Arg Arg Gly Ser Leu Ala His Met Pro Ile Gly Asp Glu Leu Lys
            515                 520                 525

Ala Ala Val Glu Asp Lys Ile Gly Arg Gly His
            530                 535

<210> SEQ ID NO 46
<211> LENGTH: 17
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X can be Val or Ile
<220> FEATURE:
<221> NAME/KEY: MISC_FEATURE
<222> LOCATION: (3)..(3)
<223> OTHER INFORMATION: X can be Leu or Ile
<220> FEATURE:
<221> NAME/KEY: MISC_FEATURE
<222> LOCATION: (4)..(5)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be Leu, Ile or Val
<220> FEATURE:
<221> NAME/KEY: MISC_FEATURE
<222> LOCATION: (8)..(15)
<223> OTHER INFORMATION: X can be any amino acid

<400> SEQUENCE: 46

Met Xaa Xaa Xaa Xaa Lys Xaa Xaa Xaa Xaa Xaa Xaa Xaa Xaa Xaa Asp
1               5                   10                  15

Gly

<210> SEQ ID NO 47
<211> LENGTH: 24
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (6)..(7)
<223> OTHER INFORMATION: X can be any amino acid
<220> FEATURE:
<221> NAME/KEY: MISC_FEATURE
<222> LOCATION: (9)..(11)
<223> OTHER INFORMATION: X can be any amino acid
```

```
<220> FEATURE:
<221> NAME/KEY: MISC_FEATURE
<222> LOCATION: (12)..(12)
<223> OTHER INFORMATION: X can be Glu or Asp
<220> FEATURE:
<221> NAME/KEY: MISC_FEATURE
<222> LOCATION: (13)..(13)
<223> OTHER INFORMATION: X can be Ala or Gly
<220> FEATURE:
<221> NAME/KEY: MISC_FEATURE
<222> LOCATION: (14)..(18)
<223> OTHER INFORMATION: X can be any amino acid
<220> FEATURE:
<221> NAME/KEY: MISC_FEATURE
<222> LOCATION: (20)..(20)
<223> OTHER INFORMATION: X can be any amino acid
<220> FEATURE:
<221> NAME/KEY: MISC_FEATURE
<222> LOCATION: (22)..(22)
<223> OTHER INFORMATION: X can be Phe or Tyr
<220> FEATURE:
<221> NAME/KEY: MISC_FEATURE
<222> LOCATION: (23)..(23)
<223> OTHER INFORMATION: X can be any amino acid

<400> SEQUENCE: 47

Arg Xaa Lys Tyr Tyr Xaa Xaa Trp Xaa Xaa Xaa Xaa Xaa Xaa Xaa
1               5                   10                  15

Xaa Xaa Gly Xaa Gly Xaa Xaa Gly
            20

<210> SEQ ID NO 48
<211> LENGTH: 20
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(12)
<223> OTHER INFORMATION: X can be any amino acid
<220> FEATURE:
<221> NAME/KEY: MISC_FEATURE
<222> LOCATION: (15)..(16)
<223> OTHER INFORMATION: X can be any amino acid
<220> FEATURE:
<221> NAME/KEY: MISC_FEATURE
<222> LOCATION: (17)..(17)
<223> OTHER INFORMATION: X can be Thr or Val
<220> FEATURE:
<221> NAME/KEY: MISC_FEATURE
<222> LOCATION: (18)..(19)
<223> OTHER INFORMATION: X can be any amino acid

<400> SEQUENCE: 48

Glu Xaa Xaa Xaa Xaa Xaa Xaa Xaa Xaa Xaa Xaa Xaa Trp Asn Xaa Xaa
1               5                   10                  15

Xaa Xaa Xaa Trp
            20

<210> SEQ ID NO 49
<211> LENGTH: 15
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (7)..(8)
<223> OTHER INFORMATION: X can be any amino acid
```

```
<220> FEATURE:
<221> NAME/KEY: MISC_FEATURE
<222> LOCATION: (12)..(13)
<223> OTHER INFORMATION: X can be any amino acid
<220> FEATURE:
<221> NAME/KEY: MISC_FEATURE
<222> LOCATION: (14)..(14)
<223> OTHER INFORMATION: X can be Thr or Phe

<400> SEQUENCE: 49

Ser Ala Xaa Trp His Gly Xaa Xaa Pro Gly Tyr Xaa Xaa Xaa Phe
1               5                   10                  15

<210> SEQ ID NO 50
<211> LENGTH: 539
<212> TYPE: PRT
<213> ORGANISM: Aspergillus oryzae

<400> SEQUENCE: 50

Met Leu Pro Tyr Val Asp Leu Leu Lys Leu Ile Ala Ser Phe Leu Leu
1               5                   10                  15

Ser Tyr Pro Leu Ala Ala Leu Leu Lys Arg Ile Pro Asp Ala Gln Pro
            20                  25                  30

Trp Lys Lys Asn Ala Phe Ile Ile Ala Val Ser Leu Phe Tyr Leu Val
        35                  40                  45

Gly Leu Phe Asp Leu Trp Asp Gly Leu Arg Thr Leu Ala Tyr Ser Ala
    50                  55                  60

Ala Gly Ile Tyr Ala Ile Ala Tyr Tyr Ile Asp Gly Ser Leu Met Pro
65                  70                  75                  80

Trp Ile Gly Phe Ile Phe Leu Met Gly His Met Ser Ile Ser His Ile
                85                  90                  95

Tyr Arg Gln Ile Ile Asp Asp Ala His Val Thr Asp Ile Thr Gly Ala
            100                 105                 110

Gln Met Val Leu Val Met Lys Leu Ser Ser Phe Cys Trp Asn Val His
        115                 120                 125

Asp Gly Arg Leu Ser Gln Glu Gln Leu Ser Asp Pro Gln Lys Tyr Ala
    130                 135                 140

Ala Ile Lys Asp Phe Pro Gly Ile Leu Asp Tyr Leu Gly Tyr Val Leu
145                 150                 155                 160

Phe Phe Pro Ser Leu Phe Ala Gly Pro Ser Phe Glu Tyr Val Asp Tyr
                165                 170                 175

Arg Arg Trp Ile Asp Thr Thr Leu Phe Asp Val Pro Pro Gly Thr Asp
            180                 185                 190

Pro Ser Lys Val Pro Pro Thr Arg Lys Lys Arg Lys Ile Pro Arg Ser
        195                 200                 205

Gly Thr Pro Ala Ala Lys Lys Ala Leu Ala Gly Leu Gly Trp Ile Leu
    210                 215                 220

Ala Phe Leu Gln Leu Gly Ser Leu Tyr Asn Gln Glu Leu Val Leu Asp
225                 230                 235                 240

Glu Thr Phe Met Gln Tyr Ser Phe Val Gln Arg Val Trp Ile Leu His
                245                 250                 255

Met Leu Gly Phe Thr Ala Arg Leu Lys Tyr Tyr Gly Val Trp Tyr Leu
            260                 265                 270

Thr Glu Gly Ala Cys Val Leu Ser Gly Met Gly Tyr Asn Gly Phe Asp
        275                 280                 285

Pro Lys Ser Gly Lys Val Phe Trp Asn Arg Leu Glu Asn Val Asp Pro
    290                 295                 300

Trp Ser Leu Glu Thr Ala Gln Asn Ser His Gly Tyr Leu Gly Ser Trp
```

```
                305                 310                 315                 320
Asn Lys Asn Thr Asn His Trp Leu Arg Asn Tyr Val Tyr Leu Arg Val
                    325                 330                 335

Thr Pro Lys Gly Lys Pro Gly Phe Arg Ala Ser Leu Ala Thr Phe
                340                 345                 350

Val Thr Ser Ala Phe Trp His Gly Phe Tyr Pro Gly Tyr Tyr Leu Thr
                    355                 360                 365

Phe Val Leu Gly Ser Phe Ile Gln Thr Val Ala Lys Asn Phe Arg Arg
                370                 375                 380

His Val Arg Pro Phe Phe Leu Thr Pro Asp Gly Ser Arg Pro Thr Ala
385                 390                 395                 400

Tyr Lys Lys Tyr Tyr Asp Ile Ala Ser Tyr Val Val Thr Gln Leu Thr
                    405                 410                 415

Leu Ser Phe Ala Val Met Pro Phe Ile Phe Leu Ser Phe Gly Asp Ser
                420                 425                 430

Ile Lys Val Trp His Ser Val Tyr Phe Tyr Gly Ile Val Gly Asn Ile
                    435                 440                 445

Val Ser Leu Ala Phe Phe Val Ser Pro Ala Arg Gly Leu Leu Leu Lys
                450                 455                 460

Lys Leu Lys Ala Arg Asn Lys Pro His Val Pro Arg Ala Val Ser Ser
465                 470                 475                 480

Glu Asn Ile Arg Gln Pro Thr Leu Gly Leu Pro Asn Asp Ala Ile Gln
                    485                 490                 495

Glu Phe Asp Asp Ala Val Gln Glu Ile Arg Ala Glu Ile Glu Ser Arg
                500                 505                 510

Gln Arg Arg Gly Ser Leu Ala His Met Pro Ile Gly Asp Glu Leu Lys
                515                 520                 525

Ala Ala Val Glu Asp Lys Ile Gly Arg Gly His
                530                 535

<210> SEQ ID NO 51
<211> LENGTH: 539
<212> TYPE: PRT
<213> ORGANISM: Schizosaccharomyces pombe

<400> SEQUENCE: 51

Met Leu Pro Tyr Val Asp Leu Leu Lys Leu Ile Ala Ser Phe Leu Leu
1               5                   10                  15

Ser Tyr Pro Leu Ala Ala Leu Leu Lys Arg Ile Pro Asp Ala Gln Pro
                20                  25                  30

Trp Lys Lys Asn Ala Phe Ile Ile Ala Val Ser Leu Phe Tyr Leu Val
                35                  40                  45

Gly Leu Phe Asp Leu Trp Asp Gly Leu Arg Thr Leu Ala Tyr Ser Ala
                50                  55                  60

Ala Gly Ile Tyr Ala Ile Ala Tyr Tyr Ile Asp Gly Ser Leu Met Pro
65                  70                  75                  80

Trp Ile Gly Phe Ile Phe Leu Met Gly His Met Ser Ile Ser His Ile
                85                  90                  95

Tyr Arg Gln Ile Ile Asp Asp Ala His Val Thr Asp Ile Thr Gly Ala
                100                 105                 110

Gln Met Val Leu Val Met Lys Leu Ser Ser Phe Cys Trp Asn Val His
                115                 120                 125

Asp Gly Arg Leu Ser Gln Glu Gln Leu Ser Asp Pro Gln Lys Tyr Ala
                130                 135                 140

Ala Ile Lys Asp Phe Pro Gly Ile Leu Asp Tyr Leu Gly Tyr Val Leu
```

```
                145                 150                 155                 160
Phe Phe Pro Ser Leu Phe Ala Gly Pro Ser Phe Glu Tyr Val Asp Tyr
                    165                 170                 175

Arg Arg Trp Ile Asp Thr Thr Leu Phe Asp Val Pro Pro Gly Thr Asp
            180                 185                 190

Pro Ser Lys Val Pro Pro Thr Arg Lys Arg Lys Ile Pro Arg Ser
        195                 200                 205

Gly Thr Pro Ala Ala Lys Lys Ala Leu Ala Gly Leu Gly Trp Ile Leu
    210                 215                 220

Ala Phe Leu Gln Leu Gly Ser Leu Tyr Asn Gln Glu Leu Val Leu Asp
225                 230                 235                 240

Glu Thr Phe Met Gln Tyr Ser Phe Val Gln Arg Val Trp Ile Leu His
                245                 250                 255

Met Leu Gly Phe Thr Ala Arg Leu Lys Tyr Tyr Gly Val Trp Tyr Leu
                260                 265                 270

Thr Glu Gly Ala Cys Val Leu Ser Gly Met Gly Tyr Asn Gly Phe Asp
            275                 280                 285

Pro Lys Ser Gly Lys Val Phe Trp Asn Arg Leu Glu Asn Val Asp Pro
        290                 295                 300

Trp Ser Leu Glu Thr Ala Gln Asn Ser His Gly Tyr Leu Gly Ser Trp
305                 310                 315                 320

Asn Lys Asn Thr Asn His Trp Leu Arg Asn Tyr Val Tyr Leu Arg Val
                325                 330                 335

Thr Pro Lys Gly Lys Pro Gly Phe Arg Ala Ser Leu Ala Thr Phe
                340                 345                 350

Val Thr Ser Ala Phe Trp His Gly Phe Tyr Pro Gly Tyr Tyr Leu Thr
            355                 360                 365

Phe Val Leu Gly Ser Phe Ile Gln Thr Val Ala Lys Asn Phe Arg Arg
370                 375                 380

His Val Arg Pro Phe Phe Leu Thr Pro Asp Gly Ser Arg Pro Thr Ala
385                 390                 395                 400

Tyr Lys Lys Tyr Tyr Asp Ile Ala Ser Tyr Val Val Thr Gln Leu Thr
                405                 410                 415

Leu Ser Phe Ala Val Met Pro Phe Ile Phe Leu Ser Phe Gly Asp Ser
                420                 425                 430

Ile Lys Val Trp His Ser Val Tyr Phe Tyr Gly Ile Val Gly Asn Ile
            435                 440                 445

Val Ser Leu Ala Phe Val Ser Pro Ala Arg Gly Leu Leu Leu Lys
    450                 455                 460

Lys Leu Lys Ala Arg Asn Lys Pro His Val Pro Arg Ala Val Ser Ser
465                 470                 475                 480

Glu Asn Ile Arg Gln Pro Thr Leu Gly Leu Pro Asn Asp Ala Ile Gln
                485                 490                 495

Glu Phe Asp Asp Ala Val Gln Glu Ile Arg Ala Glu Ile Glu Ser Arg
            500                 505                 510

Gln Arg Arg Gly Ser Leu Ala His Met Pro Ile Gly Asp Glu Leu Lys
        515                 520                 525

Ala Ala Val Glu Asp Lys Ile Gly Arg Gly His
    530                 535

<210> SEQ ID NO 52
<211> LENGTH: 619
<212> TYPE: PRT
<213> ORGANISM: Saccharomyces cerevisiae
```

```
<400> SEQUENCE: 52

Met Tyr Asn Pro Val Asp Ala Val Leu Thr Lys Ile Ile Thr Asn Tyr
1               5                   10                  15

Gly Ile Asp Ser Phe Thr Leu Arg Tyr Ala Ile Cys Leu Leu Gly Ser
            20                  25                  30

Phe Pro Leu Asn Ala Ile Leu Lys Arg Ile Pro Glu Lys Arg Ile Gly
                35                  40                  45

Leu Lys Cys Cys Phe Ile Ile Ser Met Ser Met Phe Tyr Leu Phe Gly
    50                  55                  60

Val Leu Asn Leu Val Ser Gly Phe Arg Thr Leu Phe Ile Ser Thr Met
65                  70                  75                  80

Phe Thr Tyr Leu Ile Ser Arg Phe Tyr Arg Ser Lys Phe Met Pro His
                85                  90                  95

Leu Asn Phe Met Phe Val Met Gly His Leu Ala Ile Asn His Ile His
                100                 105                 110

Ala Gln Phe Leu Asn Glu Gln Thr Gln Thr Thr Val Asp Ile Thr Ser
            115                 120                 125

Ser Gln Met Val Leu Ala Met Lys Leu Thr Ser Phe Ala Trp Ser Tyr
130                 135                 140

Tyr Asp Gly Ser Cys Thr Ser Glu Ser Asp Phe Lys Asp Leu Thr Glu
145                 150                 155                 160

His Gln Lys Ser Arg Ala Val Arg Gly His Pro Pro Leu Leu Lys Phe
                165                 170                 175

Leu Ala Tyr Ala Phe Phe Tyr Ser Thr Leu Leu Thr Gly Pro Ser Phe
            180                 185                 190

Asp Tyr Ala Asp Phe Asp Ser Trp Leu Asn Cys Glu Met Phe Arg Asp
        195                 200                 205

Leu Pro Glu Ser Lys Lys Pro Met Arg Arg His His Pro Gly Glu Arg
210                 215                 220

Arg Gln Ile Pro Lys Asn Gly Lys Leu Ala Leu Trp Lys Val Val Gln
225                 230                 235                 240

Gly Leu Ala Trp Met Ile Leu Ser Thr Leu Gly Met Lys His Phe Pro
                245                 250                 255

Val Lys Tyr Val Leu Asp Lys Asp Gly Phe Pro Thr Arg Ser Phe Ile
            260                 265                 270

Phe Arg Ile His Tyr Leu Phe Leu Leu Gly Phe Ile His Arg Phe Lys
        275                 280                 285

Tyr Tyr Ala Ala Trp Thr Ile Ser Glu Gly Ser Cys Ile Leu Cys Gly
290                 295                 300

Leu Gly Tyr Asn Gly Tyr Asp Ser Lys Thr Gln Lys Ile Arg Trp Asp
305                 310                 315                 320

Arg Val Arg Asn Ile Asp Ile Trp Thr Val Glu Thr Ala Gln Asn Thr
                325                 330                 335

Arg Glu Met Leu Glu Ala Trp Asn Met Asn Thr Asn Lys Trp Leu Lys
            340                 345                 350

Tyr Ser Val Tyr Leu Arg Val Thr Lys Lys Gly Lys Lys Pro Gly Phe
        355                 360                 365

Arg Ser Thr Leu Phe Thr Phe Leu Thr Ser Ala Phe Trp His Gly Thr
370                 375                 380

Arg Pro Gly Tyr Tyr Leu Thr Phe Ala Thr Gly Ala Leu Tyr Gln Thr
385                 390                 395                 400

Cys Gly Lys Ile Tyr Arg Arg Asn Phe Arg Pro Ile Phe Leu Arg Glu
            405                 410                 415
```

```
Asp Gly Val Thr Pro Leu Pro Ser Lys Lys Ile Tyr Asp Leu Val Gly
            420                 425                 430

Ile Tyr Ala Ile Lys Leu Ala Phe Gly Tyr Met Val Gln Pro Phe Ile
            435                 440                 445

Ile Leu Asp Leu Lys Pro Ser Leu Met Val Trp Gly Ser Val Tyr Phe
        450                 455                 460

Tyr Val His Ile Ile Val Ala Phe Ser Phe Leu Phe Arg Gly Pro
465                 470                 475                 480

Tyr Ala Lys Gln Val Thr Glu Phe Phe Lys Ser Lys Gln Pro Lys Glu
                485                 490                 495

Ile Phe Ile Arg Lys Gln Lys Lys Leu Glu Lys Asp Ile Ser Ala Ser
            500                 505                 510

Ser Pro Asn Leu Gly Gly Ile Leu Lys Ala Lys Ile Glu His Glu Lys
            515                 520                 525

Gly Lys Thr Ala Glu Glu Glu Met Asn Leu Gly Ile Pro Pro Ile
        530                 535                 540

Glu Leu Glu Lys Trp Asp Asn Ala Lys Glu Asp Trp Glu Asp Phe Cys
545                 550                 555                 560

Lys Asp Tyr Lys Glu Trp Arg Asn Lys Asn Gly Leu Glu Ile Glu Glu
                565                 570                 575

Glu Asn Leu Ser Lys Ala Phe Glu Arg Phe Lys Gln Glu Phe Ser Asn
            580                 585                 590

Ala Ala Ser Gly Ser Gly Glu Arg Val Arg Lys Met Ser Phe Ser Gly
            595                 600                 605

Tyr Ser Pro Lys Pro Ile Ser Lys Lys Glu Glu
        610                 615

<210> SEQ ID NO 53
<211> LENGTH: 487
<212> TYPE: PRT
<213> ORGANISM: Thalassiosira pseudonana

<400> SEQUENCE: 53

Met Arg Leu Tyr Leu Gln Phe Asn Leu Ser Ile Asn Asp Tyr Cys His
1               5                   10                  15

Phe Phe Thr Val Pro Ser Phe Val Lys Glu Gly Val Glu Ser Leu Ser
            20                  25                  30

Ala Ser Thr Gly Gln Asp Val Glu Thr Leu Glu Tyr Leu Leu Gly Met
        35                  40                  45

Leu Ile Cys Tyr Pro Leu Gly Met Ile Met Leu Ala Leu Pro Tyr Gly
    50                  55                  60

Lys Val Lys His Leu Phe Ser Phe Ile Leu Gly Ala Phe Leu Leu Gln
65                  70                  75                  80

Phe Thr Ile Gly Ile Gln Trp Ile His His Leu Ile Ser Ser Met Ile
                85                  90                  95

Ala Tyr Val Met Phe Leu Val Leu Pro Ala Lys Phe Ala Lys Thr Ala
            100                 105                 110

Val Pro Val Phe Ala Met Ile Tyr Ile Thr Ala Gly His Leu His Arg
        115                 120                 125

Gln Tyr Ile Asn Tyr Leu Gly Trp Asp Met Asp Phe Thr Gly Pro Gln
    130                 135                 140

Met Val Leu Thr Met Lys Leu Tyr Met Leu Ala Tyr Asn Leu Ala Asp
145                 150                 155                 160

Gly Asp Leu Leu Lys Lys Gly Lys Glu Asp Arg Ala Ala Lys Lys Cys
                165                 170                 175
```

-continued

```
Ala Asp Val Ala Ile Ser Ser Val Pro Gly Ile Ile Glu Tyr Leu Gly
            180                 185                 190

Tyr Thr Phe Cys Phe Ala Ser Val Leu Ala Gly Pro Ala Phe Glu Tyr
            195                 200                 205

Lys Phe Tyr Ala Asp Ala Cys Asp Gly Ser Leu Leu Tyr Asp Lys Ser
            210                 215                 220

Gly Lys Pro Lys Gly Lys Ile Pro Ser Gln Val Trp Pro Thr Leu Arg
225                 230                 235                 240

Pro Leu Phe Gly Ser Leu Leu Cys Leu Gly Ile Phe Val Val Gly Thr
                245                 250                 255

Gly Met Tyr Pro Leu Leu Asp Pro Asn Asp Pro Gln Asn Ala Thr Pro
            260                 265                 270

Ile Pro Leu Thr Pro Glu Met Leu Ala Lys Pro Ala Tyr Ala Arg Tyr
            275                 280                 285

Ala Tyr Ser Trp Leu Ala Leu Phe Phe Ile Arg Phe Lys Tyr Tyr Phe
            290                 295                 300

Ala Trp Met Asn Ala Glu Gly Ala Ser Asn Ile Trp Tyr Ala Gly Phe
305                 310                 315                 320

Glu Gly Phe Asp Ala Ser Gly Asn Pro Lys Gly Trp Glu Val Ser Asn
                325                 330                 335

Asn Ile Asp Val Ile Gln Phe Glu Thr Ala Pro Asn Leu Lys Thr Leu
            340                 345                 350

Ser Ala Ala Trp Asn Lys Lys Thr Ala Asn Trp Leu Ala Lys Tyr Val
            355                 360                 365

Tyr Ile Arg Thr Gly Gly Ser Leu Phe Ala Thr Tyr Gly Met Ser Ala
            370                 375                 380

Phe Trp His Gly Phe Tyr Pro Gly Tyr Tyr Leu Phe Phe Met Ser Val
385                 390                 395                 400

Pro Met Met Ala Phe Cys Glu Arg Ile Gly Arg Lys Lys Leu Thr Pro
                405                 410                 415

Arg Phe Gly Asn Gly Lys Lys Trp Ser Pro Tyr Gly Ile Val Cys Ile
            420                 425                 430

Ile Ala Thr Ser Leu Met Thr Glu Tyr Met Ile Gln Pro Phe Gln Leu
            435                 440                 445

Leu Ala Phe Asp Trp Ala Trp Glu Asn Trp Ser Ser Tyr Tyr Phe Ala
            450                 455                 460

Gly His Ile Val Cys Val Phe Tyr Leu Val Val Ser Asn Met Pro
465                 470                 475                 480

Thr Pro Lys Thr Lys Glu Thr
            485

<210> SEQ ID NO 54
<211> LENGTH: 462
<212> TYPE: PRT
<213> ORGANISM: Arabidopsis thaliana

<400> SEQUENCE: 54

Met Asp Met Ser Ser Met Ala Gly Ser Ile Gly Val Ser Val Ala Val
1               5                   10                  15

Leu Arg Phe Leu Leu Cys Phe Val Ala Thr Ile Pro Val Ser Phe Ala
            20                  25                  30

Cys Arg Ile Val Pro Ser Arg Leu Gly Lys His Leu Tyr Ala Ala Ala
            35                  40                  45

Ser Gly Ala Phe Leu Ser Tyr Leu Ser Phe Gly Phe Ser Ser Asn Leu
        50                  55                  60
```

```
His Phe Leu Val Pro Met Thr Ile Gly Tyr Ala Ser Met Ala Ile Tyr
 65                  70                  75                  80

Arg Pro Lys Cys Gly Ile Ile Thr Phe Phe Leu Gly Phe Ala Tyr Leu
                 85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
            115                 120                 125

Ser Cys Ser Met Asn Tyr Asn Asp Gly Met Leu Lys Glu Glu Gly Leu
130                 135                 140

Arg Glu Ala Gln Lys Lys Asn Arg Leu Ile Gln Met Pro Ser Leu Ile
145                 150                 155                 160

Glu Tyr Phe Gly Tyr Cys Leu Cys Cys Gly Ser His Phe Ala Gly Pro
                165                 170                 175

Val Tyr Glu Met Lys Asp Tyr Leu Glu Trp Thr Glu Gly Lys Gly Ile
            180                 185                 190

Trp Asp Thr Thr Glu Lys Arg Lys Pro Ser Pro Tyr Gly Ala Thr
            195                 200                 205

Ile Arg Ala Ile Leu Gln Ala Ala Ile Cys Met Ala Leu Tyr Leu Tyr
210                 215                 220

Leu Val Pro Gln Tyr Pro Leu Thr Arg Phe Thr Glu Pro Val Tyr Gln
225                 230                 235                 240

Glu Trp Gly Phe Leu Arg Lys Phe Ser Tyr Gln Tyr Met Ala Gly Phe
                245                 250                 255

Thr Ala Arg Trp Lys Tyr Tyr Phe Ile Trp Ser Ile Ser Glu Ala Ser
            260                 265                 270

Ile Ile Ile Ser Gly Leu Gly Phe Ser Gly Trp Thr Asp Asp Ala Ser
            275                 280                 285

Pro Lys Pro Lys Trp Asp Arg Ala Lys Asn Val Asp Ile Leu Gly Val
290                 295                 300

Glu Leu Ala Lys Ser Ala Val Gln Ile Pro Leu Val Trp Asn Ile Gln
305                 310                 315                 320

Val Ser Thr Trp Leu Arg His Tyr Val Tyr Glu Arg Leu Val Gln Asn
                325                 330                 335

Gly Lys Lys Ala Gly Phe Phe Gln Leu Leu Ala Thr Gln Thr Val Ser
            340                 345                 350

Ala Val Trp His Gly Leu Tyr Pro Gly Tyr Met Met Phe Phe Val Gln
            355                 360                 365

Ser Ala Leu Met Ile Ala Gly Ser Arg Val Ile Tyr Arg Trp Gln Gln
370                 375                 380

Ala Ile Ser Pro Lys Met Ala Met Leu Arg Asn Ile Met Val Phe Ile
385                 390                 395                 400

Asn Phe Leu Tyr Thr Val Leu Val Leu Asn Tyr Ser Ala Val Gly Phe
                405                 410                 415

Met Val Leu Ser Leu His Glu Thr Leu Thr Ala Tyr Gly Ser Val Tyr
            420                 425                 430

Tyr Ile Gly Thr Ile Ile Pro Val Gly Leu Ile Leu Ser Tyr Val
            435                 440                 445

Val Pro Ala Lys Pro Ser Arg Pro Lys Pro Arg Lys Glu Glu
450                 455                 460

<210> SEQ ID NO 55
<211> LENGTH: 465
<212> TYPE: PRT
<213> ORGANISM: Arabidopsis thaliana
```

<400> SEQUENCE: 55

```
Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
            20                  25                  30

Ser Phe Leu Trp Arg Phe Ile Pro Ser Arg Leu Gly Lys His Ile Tyr
        35                  40                  45

Ser Ala Ala Ser Gly Ala Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
            85                  90                  95

Ala Tyr Leu Ile Gly Cys His Val Phe Tyr Met Ser Gly Asp Ala Trp
        100                 105                 110

Lys Glu Gly Gly Ile Asp Ser Thr Gly Ala Leu Met Val Leu Thr Leu
    115                 120                 125

Lys Val Ile Ser Cys Ser Ile Asn Tyr Asn Asp Gly Met Leu Lys Glu
130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Gly Ser His Phe
            165                 170                 175

Ala Gly Pro Val Phe Glu Met Lys Asp Tyr Leu Glu Trp Thr Glu Glu
        180                 185                 190

Lys Gly Ile Trp Ala Val Ser Glu Lys Gly Lys Arg Pro Ser Pro Tyr
    195                 200                 205

Gly Ala Met Ile Arg Ala Val Phe Gln Ala Ala Ile Cys Met Ala Leu
210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
            245                 250                 255

Ala Gly Phe Thr Ala Arg Trp Lys Tyr Tyr Phe Ile Trp Ser Ile Ser
        260                 265                 270

Glu Ala Ser Ile Ile Ile Ser Gly Leu Gly Phe Ser Gly Trp Thr Asp
    275                 280                 285

Glu Thr Gln Thr Lys Ala Lys Trp Asp Arg Ala Lys Asn Val Asp Ile
290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
            325                 330                 335

Val Lys Pro Gly Lys Lys Ala Gly Phe Phe Gln Leu Leu Ala Thr Gln
        340                 345                 350

Thr Val Ser Ala Val Trp His Gly Leu Tyr Pro Gly Tyr Ile Ile Phe
    355                 360                 365

Phe Val Gln Ser Ala Leu Met Ile Asp Gly Ser Lys Ala Ile Tyr Arg
370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
            405                 410                 415
```

-continued

```
Val Gly Phe Met Val Leu Ser Leu His Glu Thr Leu Ala Phe Lys
            420                 425                 430

Ser Val Tyr Tyr Ile Gly Thr Val Pro Ile Ala Val Leu Leu Leu
            435                 440                 445

Ser Tyr Leu Val Pro Val Lys Pro Val Arg Pro Lys Thr Arg Lys Glu
450                 455                 460

Glu
465

<210> SEQ ID NO 56
<211> LENGTH: 459
<212> TYPE: PRT
<213> ORGANISM: Oryza sativa

<400> SEQUENCE: 56

Met Gly Leu Glu Met Glu Gly Met Ala Ala Ile Gly Val Ser Val
1               5                   10                  15

Pro Val Leu Arg Phe Leu Leu Cys Phe Ala Ala Thr Ile Pro Thr Gly
            20                  25                  30

Leu Met Trp Arg Ala Val Pro Gly Ala Ala Gly Arg His Leu Tyr Ala
            35                  40                  45

Gly Leu Thr Gly Ala Ala Leu Ser Tyr Leu Ser Phe Gly Ala Thr Ser
        50                  55                  60

Asn Leu Leu Phe Val Val Pro Met Ala Phe Gly Tyr Leu Ala Met Leu
65                  70                  75                  80

Leu Cys Arg Arg Leu Ala Gly Leu Val Thr Phe Leu Gly Ala Phe Gly
                85                  90                  95

Phe Leu Ile Ala Cys His Met Tyr Tyr Met Ser Gly Asp Ala Trp Lys
            100                 105                 110

Glu Gly Gly Ile Asp Ala Thr Gly Ala Leu Met Val Leu Thr Leu Lys
        115                 120                 125

Ile Ile Ser Cys Ala Ile Asn Tyr Ser Asp Gly Met Leu Lys Glu Glu
130                 135                 140

Gly Leu Arg Asp Ala Gln Lys Lys Tyr Arg Leu Ala Lys Leu Pro Ser
145                 150                 155                 160

Leu Ile Glu Tyr Phe Gly Tyr Cys Leu Cys Cys Gly Ser His Phe Ala
                165                 170                 175

Gly Pro Val Tyr Glu Met Lys Asp Tyr Leu Glu Tyr Thr Glu Arg Lys
            180                 185                 190

Gly Leu Trp Ala Ser Pro Thr Pro Ser Pro Leu Leu Pro Thr Leu Arg
        195                 200                 205

Ala Leu Val Gln Ala Gly Ala Cys Met Gly Leu Tyr Leu Tyr Leu Ser
210                 215                 220

Pro Gln Phe Pro Leu Ser Arg Phe Ser Glu Pro Leu Tyr Tyr Glu Trp
225                 230                 235                 240

Gly Phe Trp His Arg Leu Phe Tyr Gln Tyr Met Ser Gly Phe Thr Ala
                245                 250                 255

Arg Trp Lys Tyr Tyr Phe Ile Trp Ser Leu Ser Glu Ala Ala Ile Ile
            260                 265                 270

Ile Ser Gly Leu Gly Phe Ser Gly Trp Ser Asp Ser Pro Pro Lys
        275                 280                 285

Ala Lys Trp Asp Arg Ala Lys Asn Val Asp Val Leu Gly Val Glu Leu
290                 295                 300

Ala Thr Ser Ala Val Gln Leu Pro Leu Met Trp Asn Ile Gln Val Ser
305                 310                 315                 320
```

```
Thr Trp Leu Arg Tyr Tyr Val Tyr Glu Arg Leu Val Gln Lys Gly Lys
                325                 330                 335

Lys Pro Gly Phe Leu Gln Leu Leu Gly Thr Gln Thr Val Ser Ala Val
            340                 345                 350

Trp His Gly Leu Tyr Pro Gly Tyr Ile Ile Phe Phe Val Gln Ser Ala
        355                 360                 365

Leu Met Ile Asn Gly Ser Lys Val Ile Tyr Arg Trp Gln Gln Ala Val
    370                 375                 380

Ser Asn Pro Val Phe His Ala Ile Leu Val Phe Val Asn Phe Ser Tyr
385                 390                 395                 400

Thr Leu Met Val Leu Asn Tyr Ser Cys Ile Gly Phe Gln Val Leu Ser
                405                 410                 415

Phe Lys Glu Thr Leu Ala Ser Tyr Gln Ser Val Tyr Tyr Ile Gly Thr
            420                 425                 430

Ile Val Pro Ile Val Val Leu Leu Gly Tyr Val Ile Lys Pro Ala
        435                 440                 445

Arg Pro Val Lys Pro Lys Ala Arg Lys Ala Glu
    450                 455

<210> SEQ ID NO 57
<211> LENGTH: 370
<212> TYPE: PRT
<213> ORGANISM: Rice

<400> SEQUENCE: 57

Met Tyr Tyr Met Ser Gly Asp Ala Trp Lys Glu Gly Gly Ile Asp Ala
1               5                   10                  15

Thr Gly Ala Leu Met Val Leu Thr Leu Lys Ile Ile Ser Cys Ala Ile
            20                  25                  30

Asn Tyr Ser Asp Gly Met Leu Lys Glu Glu Gly Leu Arg Asp Ala Gln
        35                  40                  45

Lys Lys Tyr Arg Leu Ala Lys Leu Pro Ser Leu Ile Glu Tyr Phe Gly
    50                  55                  60

Tyr Cys Leu Cys Cys Gly Ser His Phe Ala Gly Pro Val Tyr Glu Met
65                  70                  75                  80

Lys Asp Tyr Leu Glu Tyr Thr Glu Arg Lys Gly Leu Trp Ala Ser Pro
                85                  90                  95

Thr Pro Ser Pro Leu Leu Pro Thr Leu Arg Ala Leu Val Gln Ala Gly
            100                 105                 110

Ala Cys Met Gly Leu Tyr Leu Tyr Leu Ser Pro Gln Phe Pro Leu Ser
        115                 120                 125

Arg Phe Ser Glu Pro Leu Tyr Tyr Glu Trp Gly Phe Trp His Arg Leu
    130                 135                 140

Phe Tyr Gln Tyr Met Ser Gly Phe Thr Ala Arg Trp Lys Tyr Tyr Phe
145                 150                 155                 160

Ile Trp Ser Leu Ser Glu Ala Ala Ile Ile Ile Ser Gly Leu Gly Phe
                165                 170                 175

Ser Gly Trp Ser Asp Ser Ser Pro Pro Lys Ala Lys Trp Asp Arg Ala
            180                 185                 190

Lys Asn Val Asp Val Leu Gly Val Glu Leu Ala Thr Ser Ala Val Gln
        195                 200                 205

Leu Pro Leu Met Trp Asn Ile Gln Val Ser Thr Trp Leu Arg Tyr Tyr
    210                 215                 220

Val Tyr Glu Arg Leu Val Gln Lys Gly Lys Lys Pro Gly Phe Leu Gln
225                 230                 235                 240
```

Leu Leu Gly Thr Gln Thr Val Ser Ala Val Trp His Gly Leu Tyr Pro
            245                 250                 255

Gly Tyr Ile Ile Phe Phe Val Gln Ser Ala Leu Met Ile Asn Gly Ser
            260                 265                 270

Lys Val Ile Tyr Arg Trp Gln Gln Ala Val Ser Asn Pro Val Phe His
            275                 280                 285

Ala Ile Leu Val Phe Val Asn Phe Ser Tyr Thr Leu Met Val Leu Asn
            290                 295                 300

Tyr Ser Cys Ile Gly Phe Gln Phe Val Phe Thr Met Leu Tyr Thr Leu
305                 310                 315                 320

Arg Phe Leu Gln Val Leu Ser Phe Lys Glu Thr Leu Ala Ser Tyr Gln
            325                 330                 335

Ser Val Tyr Tyr Ile Gly Thr Ile Val Pro Ile Val Val Leu Leu
            340                 345                 350

Gly Tyr Val Ile Lys Pro Ala Arg Pro Val Lys Pro Lys Ala Arg Lys
            355                 360                 365

Ala Glu
    370

<210> SEQ ID NO 58
<211> LENGTH: 722
<212> TYPE: PRT
<213> ORGANISM: Drosophila melanogaster

<400> SEQUENCE: 58

Met Leu Glu Pro Pro Lys Phe Ile Glu Asn Asp Cys Tyr Asn Gly Ser
1               5                   10                  15

Arg Thr Phe Thr Trp Leu Ala Asp Met Val Gly Leu Ser Val Asp Leu
            20                  25                  30

Val Asn Phe Leu Ile Cys Gln Ile Ser Ala Leu Phe Leu Ala Ser Leu
            35                  40                  45

Phe Arg Ser Met Leu His Pro Ser Lys Val Ser Ser Lys Leu Arg His
    50                  55                  60

Thr Phe Ala Leu Ser Ile Gly Leu Ala Phe Gly Tyr Phe Cys Phe Gly
65                  70                  75                  80

Gln Gln Ala Ile His Ile Ala Gly Leu Pro Ala Ile Cys Tyr Ile Val
                85                  90                  95

Ile Arg Thr Gln Asp Pro Arg Ile Val Gln Arg Ala Val Leu Leu Val
            100                 105                 110

Ala Met Ser Tyr Leu Leu Cys Val His Leu Met Arg Gln Leu Tyr Asp
            115                 120                 125

Tyr Gly Ser Tyr Ala Leu Asp Ile Thr Gly Pro Leu Met Ile Ile Thr
        130                 135                 140

Gln Lys Val Thr Ser Leu Ala Phe Ser Ile His Asp Gly Phe Val Arg
145                 150                 155                 160

Gly Asp Glu Glu Leu Thr Lys Ala Gln Gln Tyr His Ala Ile Arg Lys
            165                 170                 175

Met Pro Ser Ala Leu Glu Tyr Phe Ser Tyr Val Trp His Phe Gln Ser
            180                 185                 190

Ile Leu Ala Gly Pro Leu Val Phe Tyr Lys Asp Tyr Ile Glu Phe Val
            195                 200                 205

Glu Gly Tyr Asn Leu Leu Ser Thr Pro Pro Gly Asn Gly Asn Leu Asp
        210                 215                 220

Ser Ser Lys Arg Glu Val Val Leu Glu Pro Ser Pro Thr Lys Ala Val
225                 230                 235                 240

```
Ile Arg Lys Val Val Gly Ser Leu Val Cys Ala Phe Ile Phe Met Lys
            245                 250                 255

Phe Val Lys Ile Tyr Pro Val Lys Asp Met Lys Glu Asp Asp Phe Met
            260                 265                 270

Asn Asn Thr Ser Met Val Tyr Lys Tyr Trp Tyr Ala Met Met Ala Thr
            275                 280                 285

Thr Cys Ile Arg Phe Lys Tyr Tyr His Ala Trp Leu Leu Ala Asp Ala
            290                 295                 300

Ile Cys Asn Asn Ser Gly Leu Gly Phe Thr Gly Tyr Asp Lys Asp Gly
305                 310                 315                 320

Asn Ser Lys Trp Asp Leu Ile Ser Asn Ile Asn Val Leu Ser Phe Glu
            325                 330                 335

Phe Ser Thr Asn Met Arg Asp Ala Ile Asn Asn Trp Asn Cys Gly Thr
            340                 345                 350

Asn Arg Trp Leu Arg Thr Leu Val Tyr Glu Arg Val Pro Gln Gln Tyr
            355                 360                 365

Gly Thr Leu Leu Thr Phe Ala Leu Ser Ala Val Trp His Gly Phe Tyr
            370                 375                 380

Pro Gly Tyr Tyr Leu Thr Phe Ala Thr Gly Ala Val Val Val Thr Ala
385                 390                 395                 400

Ala Arg Thr Gly Arg Arg Leu Phe Arg His Arg Phe Gln Ser Thr Gln
            405                 410                 415

Val Thr Arg Met Phe Tyr Asp Ile Leu Thr Cys Leu Ile Thr Arg Val
            420                 425                 430

Val Leu Gly Tyr Ala Thr Phe Pro Phe Val Leu Leu Glu Phe Met Gly
            435                 440                 445

Ser Ile Lys Leu Tyr Leu Arg Phe Tyr Leu Cys Leu His Ile Ile Ser
            450                 455                 460

Leu Val Thr Ile Phe Ile Leu Pro Lys Phe Ile Arg Gly Glu Arg Arg
465                 470                 475                 480

Leu Arg Thr Ser Asn Gly Asn Gly Asn Val Arg Leu Ser Gly Ser Gly
            485                 490                 495

Asn Thr Lys Asp Ala Val Thr Thr Ser Val Glu Ser Thr Ala Ala Leu
            500                 505                 510

Thr Ala Gly Asn Asp Leu Asn Glu Asp Lys Glu Glu Asp Lys His Ala
            515                 520                 525

Gln Cys Lys Val His Thr Pro Thr Gln Gln Pro Ala Ala Gly Pro
            530                 535                 540

His Lys Thr Thr Val Glu Gln Pro Thr Glu Gln Pro Asn Asn Val Asn
545                 550                 555                 560

Leu Arg Ser Arg Pro Gln Gln Gln Gln Pro His Leu Glu Lys Lys Ala
            565                 570                 575

Met Pro Pro Thr Cys Ala Arg Asp Ala Val Ser Val Pro His Asp Gln
            580                 585                 590

Cys Glu Met Asp Gln Leu Ser Ser Lys Leu Lys Glu Lys Ile Glu Ala
            595                 600                 605

Glu Thr Lys Asn Ile Glu Glu Phe Ile Asp Lys Thr Val Thr Glu Thr
            610                 615                 620

Val Ser Gly Ile Val Glu Phe Lys Asn Asp Leu Met Arg Asp Ile Glu
625                 630                 635                 640

Phe Pro Lys Leu Lys Leu Pro Gly Ser Asn Gly Ala Ile Ser Leu Asp
            645                 650                 655

Ser Ser Asn Gly Gly Gly Leu Arg Lys Arg Asn Ile Ser Ser Val His
```

-continued

```
                        660                 665                 670
Asp Asn Gly Thr Asp Pro Gly His Ala Thr Ala Asp Leu His Pro Pro
                675                 680                 685

Leu Glu Glu Asn Gly Ala Ala Phe Leu Lys Lys Glu Ile Glu Val Ile
            690                 695                 700

Asn Ala Val Val Gln Gln Ala Val Pro Ala Val Leu Ser Asn Gly His
705                 710                 715                 720

Ala Lys

<210> SEQ ID NO 59
<211> LENGTH: 471
<212> TYPE: PRT
<213> ORGANISM: Homo Sapiens

<400> SEQUENCE: 59

Lys Thr Ser Ser Phe Ile Arg His Val Val Ala Thr Leu Leu Gly Leu
1               5                   10                  15

Tyr Leu Ala Leu Phe Cys Phe Gly Trp Tyr Ala Leu His Phe Leu Val
                20                  25                  30

Gln Ser Gly Ile Ser Tyr Cys Ile Met Ile Ile Gly Val Glu Asn
            35                  40                  45

Met His Asn Tyr Cys Phe Val Phe Ala Leu Gly Tyr Leu Thr Val Cys
    50                  55                  60

Gln Val Thr Arg Val Tyr Ile Phe Asp Tyr Gly Gln Tyr Ser Ala Asp
65                  70                  75                  80

Phe Ser Gly Pro Met Met Ile Ile Thr Gln Lys Ile Thr Ser Leu Ala
                85                  90                  95

Cys Glu Ile His Asp Gly Met Phe Arg Lys Asp Glu Glu Leu Thr Ser
            100                 105                 110

Ser Gln Arg Asp Leu Ala Val Arg Arg Met Pro Ser Leu Leu Glu Tyr
        115                 120                 125

Leu Ser Tyr Asn Cys Asn Phe Met Gly Ile Leu Ala Gly Pro Leu Cys
    130                 135                 140

Ser Tyr Lys Asp Tyr Ile Thr Phe Ile Glu Gly Arg Ser Tyr His Ile
145                 150                 155                 160

Thr Gln Ser Gly Glu Asn Gly Lys Glu Thr Gln Tyr Glu Arg Thr
                165                 170                 175

Glu Pro Ser Pro Asn Thr Ala Val Val Gln Lys Leu Leu Val Cys Gly
            180                 185                 190

Leu Ser Leu Leu Phe His Leu Thr Ile Cys Thr Thr Leu Pro Val Glu
        195                 200                 205

Tyr Asn Ile Asp Glu His Phe Gln Ala Thr Ala Ser Trp Pro Thr Lys
    210                 215                 220

Ile Ile Tyr Leu Tyr Ile Ser Leu Leu Ala Ala Arg Pro Lys Tyr Tyr
225                 230                 235                 240

Phe Ala Trp Thr Leu Ala Asp Ala Ile Asn Asn Ala Ala Gly Phe Gly
                245                 250                 255

Phe Arg Gly Tyr Asp Glu Asn Gly Ala Ala Arg Trp Asp Leu Ile Ser
            260                 265                 270

Asn Leu Arg Ile Gln Gln Ile Glu Met Ser Thr Ser Phe Lys Met Phe
        275                 280                 285

Leu Asp Asn Trp Asn Ile Gln Thr Ala Leu Trp Leu Lys Arg Val Cys
    290                 295                 300

Tyr Glu Arg Thr Ser Phe Ser Pro Thr Ile Gln Thr Phe Ile Leu Ser
305                 310                 315                 320
```

```
Ala Ile Trp His Gly Val Tyr Pro Gly Tyr Tyr Leu Thr Phe Leu Thr
            325                 330                 335

Gly Val Leu Met Thr Leu Ala Ala Arg Ala Met Arg Asn Asn Phe Arg
            340                 345                 350

His Tyr Phe Ile Glu Pro Ser Gln Leu Lys Leu Phe Tyr Asp Val Ile
            355                 360                 365

Thr Trp Ile Val Thr Gln Val Ala Ile Ser Tyr Thr Val Val Pro Phe
370                 375                 380

Val Leu Leu Ser Ile Lys Pro Ser Leu Thr Phe Tyr Ser Ser Trp Tyr
385                 390                 395                 400

Tyr Cys Leu His Ile Leu Gly Ile Leu Val Leu Leu Leu Leu Pro Val
                405                 410                 415

Lys Lys Thr Gln Arg Arg Lys Asn Thr His Glu Asn Ile Gln Leu Ser
            420                 425                 430

Gln Ser Lys Lys Phe Asp Glu Gly Glu Asn Ser Leu Gly Gln Asn Ser
            435                 440                 445

Phe Ser Thr Thr Asn Asn Val Cys Asn Gln Gln Glu Ile Ala Ser
            450                 455                 460

Arg His Ser Ser Leu Lys Gln
465                 470

<210> SEQ ID NO 60
<211> LENGTH: 471
<212> TYPE: PRT
<213> ORGANISM: Homo Sapiens

<400> SEQUENCE: 60

Lys Thr Ser Ser Phe Ile Arg His Val Val Ala Thr Leu Leu Gly Leu
1               5                   10                  15

Tyr Leu Ala Leu Phe Cys Phe Gly Trp Tyr Ala Leu His Phe Leu Val
                20                  25                  30

Gln Ser Gly Ile Ser Tyr Cys Ile Met Ile Ile Ile Gly Val Glu Asn
            35                  40                  45

Met His Asn Tyr Cys Phe Val Phe Ala Leu Gly Tyr Leu Thr Val Cys
        50                  55                  60

Gln Val Thr Arg Val Tyr Ile Phe Asp Tyr Gly Gln Tyr Ser Ala Asp
65                  70                  75                  80

Phe Ser Gly Pro Met Met Ile Ile Thr Gln Lys Ile Thr Ser Leu Ala
                85                  90                  95

Cys Glu Ile His Asp Gly Met Phe Arg Lys Asp Glu Glu Leu Thr Ser
            100                 105                 110

Ser Gln Arg Asp Leu Ala Val Arg Arg Met Pro Ser Leu Leu Glu Tyr
            115                 120                 125

Leu Ser Tyr Asn Cys Asn Phe Met Gly Ile Leu Ala Gly Pro Leu Cys
130                 135                 140

Ser Tyr Lys Asp Tyr Ile Thr Phe Ile Glu Gly Arg Ser Tyr His Ile
145                 150                 155                 160

Thr Gln Ser Gly Glu Asn Gly Lys Glu Glu Thr Gln Tyr Glu Arg Thr
                165                 170                 175

Glu Pro Ser Pro Asn Thr Ala Val Val Gln Lys Leu Leu Val Cys Gly
            180                 185                 190

Leu Ser Leu Leu Phe His Leu Thr Ile Cys Thr Thr Leu Pro Val Glu
            195                 200                 205

Tyr Asn Ile Asp Glu His Phe Gln Ala Thr Ala Ser Trp Pro Thr Lys
210                 215                 220
```

```
Ile Ile Tyr Leu Tyr Ile Ser Leu Leu Ala Ala Arg Pro Lys Tyr Tyr
225                 230                 235                 240

Phe Ala Trp Thr Leu Ala Asp Ala Ile Asn Asn Ala Ala Gly Phe Gly
            245                 250                 255

Phe Arg Gly Tyr Asp Glu Asn Gly Ala Ala Arg Trp Asp Leu Ile Ser
        260                 265                 270

Asn Leu Arg Ile Gln Gln Ile Glu Met Ser Thr Ser Phe Lys Met Phe
    275                 280                 285

Leu Asp Asn Trp Asn Ile Gln Thr Ala Leu Trp Leu Lys Arg Val Cys
290                 295                 300

Tyr Glu Arg Thr Ser Phe Ser Pro Thr Ile Gln Thr Phe Ile Leu Ser
305                 310                 315                 320

Ala Ile Trp His Gly Val Tyr Pro Gly Tyr Leu Thr Phe Leu Thr
            325                 330                 335

Gly Val Leu Met Thr Leu Ala Ala Arg Ala Met Arg Asn Asn Phe Arg
            340                 345                 350

His Tyr Phe Ile Glu Pro Ser Gln Leu Lys Leu Phe Tyr Asp Val Ile
        355                 360                 365

Thr Trp Ile Val Thr Gln Val Ala Ile Ser Tyr Thr Val Val Pro Phe
    370                 375                 380

Val Leu Leu Ser Ile Lys Pro Ser Leu Thr Phe Tyr Ser Ser Trp Tyr
385                 390                 395                 400

Tyr Cys Leu His Ile Leu Gly Ile Leu Val Leu Leu Leu Pro Val
            405                 410                 415

Lys Lys Thr Gln Arg Arg Lys Asn Thr His Glu Asn Ile Gln Leu Ser
            420                 425                 430

Gln Ser Arg Lys Phe Asp Glu Gly Glu Asn Ser Leu Gly Gln Asn Ser
        435                 440                 445

Phe Ser Thr Thr Asn Asn Val Cys Asn Gln Asn Gln Glu Ile Ala Ser
450                 455                 460

Arg His Ser Ser Leu Lys Gln
465                 470

<210> SEQ ID NO 61
<211> LENGTH: 470
<212> TYPE: PRT
<213> ORGANISM: Mus musculus

<400> SEQUENCE: 61

Lys Thr Ser Ser Phe Ile Arg His Val Val Ala Thr Leu Leu Gly Leu
1               5                   10                  15

Tyr Leu Ala Phe Phe Cys Phe Gly Trp Tyr Ala Leu His Phe Leu Val
            20                  25                  30

Gln Ser Gly Ile Ser Tyr Cys Ile Met Ile Ala Gly Val Glu Ser
        35                  40                  45

Met Gln Gln Cys Cys Phe Val Phe Ala Leu Gly Tyr Leu Ser Val Cys
    50                  55                  60

Gln Ile Thr Arg Val Tyr Ile Asp Tyr Gly Gln Tyr Ser Ala Asp
65                  70                  75                  80

Phe Ser Gly Pro Met Met Ile Ile Thr Gln Lys Ile Thr Ser Leu Ala
            85                  90                  95

Tyr Glu Ile His Asp Gly Met Phe Arg Lys Asp Glu Glu Leu Thr Pro
        100                 105                 110

Ser Gln Arg Gly Leu Ala Val Arg Met Pro Ser Leu Leu Glu Tyr
    115                 120                 125
```

```
Val Ser Tyr Thr Cys Asn Phe Met Gly Ile Leu Ala Gly Pro Leu Cys
    130                 135                 140

Ser Tyr Lys Asp Tyr Ile Ala Phe Ile Glu Gly Arg Ala Ser His Val
145                 150                 155                 160

Ala Gln Pro Ser Glu Asn Gly Lys Asp Glu Gln His Gly Lys Ala Asp
                165                 170                 175

Pro Ser Pro Asn Ala Ala Val Thr Glu Lys Leu Leu Val Cys Gly Leu
                180                 185                 190

Ser Leu Leu Phe His Leu Thr Ile Ser Asn Met Leu Pro Val Glu Tyr
                195                 200                 205

Asn Ile Asp Glu His Phe Gln Ala Thr Ala Ser Trp Pro Thr Lys Ala
                210                 215                 220

Thr Tyr Leu Tyr Val Ser Leu Leu Ala Ala Arg Pro Lys Tyr Tyr Phe
225                 230                 235                 240

Ala Trp Thr Leu Ala Asp Ala Ile Asn Asn Ala Ala Gly Phe Gly Phe
                245                 250                 255

Arg Gly Tyr Asp Lys Asn Gly Val Ala Arg Trp Asp Leu Ile Ser Asn
                260                 265                 270

Leu Arg Ile Gln Gln Ile Glu Met Ser Thr Ser Phe Lys Met Phe Leu
                275                 280                 285

Asp Asn Trp Asn Ile Gln Thr Ala Leu Trp Leu Lys Arg Val Cys Tyr
                290                 295                 300

Glu Arg Ala Thr Phe Ser Pro Thr Ile Gln Thr Phe Phe Leu Ser Ala
305                 310                 315                 320

Ile Trp His Gly Val Tyr Pro Gly Tyr Tyr Leu Thr Phe Leu Thr Gly
                325                 330                 335

Val Leu Met Thr Leu Ala Ala Arg Ala Val Arg Asn Asn Phe Arg His
                340                 345                 350

Tyr Phe Leu Glu Pro Pro Gln Leu Lys Leu Phe Tyr Asp Leu Ile Thr
                355                 360                 365

Trp Val Ala Thr Gln Ile Thr Ile Ser Tyr Thr Val Val Pro Phe Val
                370                 375                 380

Leu Leu Ser Ile Lys Pro Ser Phe Thr Phe Tyr Ser Ser Trp Tyr Tyr
385                 390                 395                 400

Cys Leu His Val Cys Ser Ile Leu Val Leu Leu Leu Pro Val Lys
                405                 410                 415

Lys Ser Gln Arg Arg Thr Ser Thr Gln Glu Asn Val His Leu Ser Gln
                420                 425                 430

Ala Lys Lys Phe Asp Glu Arg Asp Asn Pro Leu Gly Gln Asn Ser Phe
                435                 440                 445

Ser Thr Met Asn Asn Val Cys Asn Gln Asn Arg Asp Thr Gly Ser Arg
                450                 455                 460

His Ser Ser Leu Thr Gln
465                 470

<210> SEQ ID NO 62
<211> LENGTH: 492
<212> TYPE: PRT
<213> ORGANISM: Mus musculus

<400> SEQUENCE: 62

Met Ala Ala Arg Pro Pro Ala Ser Leu Ser Tyr Arg Thr Thr Gly Ser
1               5                   10                  15

Thr Cys Leu His Pro Leu Ser Gln Leu Leu Gly Ile Pro Leu Asp Gln
                20                  25                  30
```

```
Val Asn Phe Val Ala Cys Gln Leu Phe Ala Leu Ser Ala Ala Phe Trp
         35                  40                  45

Phe Arg Ile Tyr Leu His Pro Gly Lys Ala Ser Pro Glu Val Arg His
 50                  55                  60

Thr Leu Ala Thr Ile Leu Gly Ile Tyr Phe Val Phe Cys Phe Gly
 65                  70                  75                  80

Trp Tyr Ala Val His Leu Phe Val Leu Met Cys Tyr Gly Val
                 85                  90                  95

Met Val Ser Ala Ser Val Ser Asn Ile His Arg Tyr Ser Phe Phe Val
            100                 105                 110

Ala Met Gly Tyr Leu Thr Ile Cys His Ile Ser Arg Ile Tyr Ile Phe
            115                 120                 125

His Tyr Gly Ile Leu Thr Thr Asp Phe Ser Gly Pro Leu Met Ile Val
            130                 135                 140

Thr Gln Lys Ile Thr Thr Leu Ala Phe Gln Val His Asp Gly Leu Gly
145                 150                 155                 160

Arg Lys Ala Glu Asp Leu Ser Ala Glu Gln His Arg Leu Ala Val Lys
                165                 170                 175

Ala Lys Pro Ser Leu Leu Glu Tyr Leu Ser Tyr His Leu Asn Phe Met
            180                 185                 190

Ser Val Ile Ala Gly Pro Cys Asn Asn Phe Lys Asp Tyr Val Ala Phe
            195                 200                 205

Ile Glu Gly Arg His Ile His Met Lys Leu Leu Glu Val Asn Trp Thr
            210                 215                 220

Gln Arg Gly Phe Gln Ser Leu Pro Glu Pro Ser Pro Thr Gly Ala Val
225                 230                 235                 240

Ile Gln Lys Leu Cys Val Thr Leu Met Ser Leu Leu Leu Phe Leu Thr
                245                 250                 255

Leu Ser Lys Ser Phe Pro Val Thr Phe Leu Ile Asp Asp Trp Phe Val
            260                 265                 270

His Lys Ala Asn Phe Leu Ser Arg Leu Trp Tyr Leu Tyr Val Val Met
            275                 280                 285

Gln Ala Ala Lys Pro Lys Tyr Tyr Phe Ala Trp Thr Leu Ala Asp Ala
            290                 295                 300

Val His Asn Ala Ala Gly Phe Gly Phe Asn Gly Met Asp Thr Asp Gly
305                 310                 315                 320

Lys Ser Arg Trp Asp Leu Leu Ser Asn Leu Asn Ile Trp Lys Ile Glu
                325                 330                 335

Thr Ala Thr Ser Phe Lys Met Tyr Leu Glu Asn Trp Asn Ile Gln Thr
            340                 345                 350

Ser Thr Trp Leu Lys Cys Val Cys Tyr Glu Arg Val Ser Trp Tyr Pro
            355                 360                 365

Thr Val Leu Thr Phe Leu Leu Ser Ala Leu Trp His Gly Val Tyr Pro
370                 375                 380

Gly Tyr Tyr Phe Thr Phe Leu Thr Gly Val Pro Val Thr Leu Ala Ala
385                 390                 395                 400

Arg Ala Val Arg Asn Asn Tyr Arg His His Phe Leu Ser Ser Lys Ala
                405                 410                 415

Arg Lys Ile Ala Tyr Asp Val Val Thr Trp Ala Val Thr Gln Leu Ala
            420                 425                 430

Val Ser Tyr Thr Ala Ala Pro Phe Val Met Leu Ala Val Glu Pro Thr
            435                 440                 445

Ile Ser Leu Tyr Lys Ser Val Phe Phe Phe Leu His Ile Ile Cys Leu
```

-continued

```
                450                 455                 460
Leu Ile Ile Leu Phe Leu Pro Ile Lys Pro His Gln Pro Gln Arg Gln
465                 470                 475                 480

Ser Arg Ser Pro Asn Ser Val Lys Lys Ala Asp
                485                 490

<210> SEQ ID NO 63
<211> LENGTH: 497
<212> TYPE: PRT
<213> ORGANISM: Drosophila melanogaster

<400> SEQUENCE: 63

Met Ala Glu Phe Glu Glu Asp Leu Pro His Asn Gly Leu Met Asp Gly
1               5                   10                  15

Ile Ala Ser Gly Val Gly Val Pro Val Glu Ala Leu Arg Leu Leu Leu
                20                  25                  30

Thr Ile Leu Ala Gly Tyr Pro Val Ala Leu Tyr Gln Lys Phe Ile
            35                  40                  45

Ser Val Ile Ala Asp Lys Thr Val His His Met Phe Phe Ala Gly Cys
50                  55                  60

Gly Ala Gly Leu Cys Tyr Phe Asn Tyr Gly Leu Asp Thr Tyr His Ser
65                  70                  75                  80

Leu Ile Ala Ile Leu Thr Thr Tyr Phe Leu Val Leu Leu Arg Lys
                85                  90                  95

Lys Thr Gln Ile Phe Leu Ala Ile Asn Phe Val Phe His Met Ser Tyr
            100                 105                 110

Leu Leu Leu Gly Tyr Phe Tyr Thr Ser Ser Asn Asp Tyr Asp Ile Leu
            115                 120                 125

Trp Thr Met Pro His Cys Ile Leu Val Leu Arg Met Ile Gly Tyr Gly
            130                 135                 140

Phe Asp Ile Thr Asp Gly Leu Lys Glu Glu Ser Glu Leu Ser Lys Asp
145                 150                 155                 160

Gln Lys Glu Thr Ala Leu Lys Lys Pro Pro Ser Leu Leu Glu Leu Leu
                165                 170                 175

Ala Phe Ser Tyr Phe Pro Ser Gly Phe Leu Val Gly Pro Gln Phe Pro
            180                 185                 190

Phe Arg Arg Tyr Lys Ala Phe Val Asp Gly Glu Phe Arg Gln His Glu
            195                 200                 205

Gly Asn Val Glu Ala Gly Val Arg Arg Phe Gly Ala Gly Ala Phe Tyr
            210                 215                 220

Leu Ile Val Cys Gln Val Gly Leu Arg Tyr Leu Pro Asp Ser Tyr Phe
225                 230                 235                 240

Leu Thr Pro Glu Phe Ala Gln Val Ser Phe Val Lys Arg Ile Tyr Leu
                245                 250                 255

Leu Gly Phe Trp Ala Lys Phe Ser Leu Tyr Lys Tyr Ile Ser Cys Trp
            260                 265                 270

Leu Leu Thr Glu Gly Ala Leu Ile Cys Ile Gly Leu Thr Tyr Lys Gly
            275                 280                 285

Glu Asp Lys Asn Gly Gln Pro Asp Trp Ser Gly Cys Ser Asn Val Lys
            290                 295                 300

Leu Lys Leu Leu Glu Thr Gly Asn Thr Met Glu His Tyr Val Gln Ser
305                 310                 315                 320

Phe Asn Val Asn Thr Asn Gln Trp Val Gly Gln Tyr Ile Tyr Lys Arg
                325                 330                 335

Leu Lys Phe Leu Asn Asn Arg Thr Ile Ser Tyr Gly Ala Ala Leu Gly
```

```
            340             345             350
Phe Leu Ala Val Trp His Gly Tyr His Ser Gly Tyr Tyr Met Thr Phe
            355             360             365
Leu Met Glu Tyr Met Val Val Ser Thr Glu Lys Gln Ile Thr Arg Phe
370             375             380
Tyr Thr Lys Val Val Leu Pro Gln Trp Gly His Ile Leu Asn Asn Ser
385             390             395             400
Asp Ile Tyr Lys Leu Leu Tyr Phe Ile Thr Leu Lys Ser Tyr Asn Val
                405             410             415
Val Tyr Met Gly Trp Cys Leu Thr Ala Phe Val Phe Leu Lys Tyr Glu
            420             425             430
Arg Trp Ile Val Val Tyr Gly Ala Val Ser Tyr Tyr Gly Phe Thr Phe
            435             440             445
Leu Val Leu Trp Ala Ala Phe Tyr His Thr Phe Asn His Phe Phe Arg
            450             455             460
Ser Ser Ser Arg Lys Leu Ala Gly Glu Asp Gln Lys Leu Gln Asp Ser
465             470             475             480
Asn Thr Asp Lys Leu Val Glu Glu Lys Lys Pro Glu Asp Lys Lys Ser
            485             490             495
Glu

<210> SEQ ID NO 64
<211> LENGTH: 209
<212> TYPE: PRT
<213> ORGANISM: Apple

<400> SEQUENCE: 64

Arg Arg Pro Lys Phe Pro Leu Ser Arg Phe Thr Glu Pro Ile Tyr Gln
1               5                   10                  15
Glu Trp Gly Phe Trp Lys Arg Leu Phe Gln Tyr Met Ser Gly Phe
                20                  25                  30
Thr Ala Arg Trp Lys Tyr Tyr Phe Ile Trp Ser Ile Ser Glu Ala Ser
            35                  40                  45
Ile Ile Leu Ser Gly Leu Gly Phe Ser Gly Trp Thr Glu Ser Ser Pro
        50                  55                  60
Pro Lys Pro Arg Trp Asp Arg Ala Lys Asn Val Asp Ile Ile Gly Val
65                  70                  75                  80
Glu Phe Ala Lys Ser Ser Val Gln Leu Pro Leu Val Trp Asn Ile Gln
                85                  90                  95
Val Ser Thr Trp Leu Arg His Tyr Val Tyr Asp Arg Leu Val Lys Pro
                100                 105                 110
Gly Lys Lys Pro Gly Phe Phe Gln Leu Leu Ala Thr Gln Thr Val Ser
            115                 120                 125
Ala Val Trp His Gly Leu Tyr Pro Gly Tyr Ile Ile Phe Phe Val Gln
        130                 135                 140
Ser Ala Leu Met Ile Ala Gly Ser Arg Val Ile Tyr Arg Trp Gln Gln
145                 150                 155                 160
Ala Val Pro Pro Thr Met Asp Val Val Lys Lys Ile Leu Val Phe Ile
                165                 170                 175
Asn Phe Ala Tyr Thr Val Leu Val Leu Asn Tyr Ser Cys Val Gly Phe
                180                 185                 190
Ile Val Leu Ser Leu Arg Glu Thr Leu Ala Ser Tyr Gly Ser Val His
            195                 200                 205

Phe
```

```
<210> SEQ ID NO 65
<211> LENGTH: 203
<212> TYPE: PRT
<213> ORGANISM: Peach

<400> SEQUENCE: 65

Lys Tyr Tyr Phe Ile Trp Ser Ile Ser Glu Ala Ser Ile Ile Leu Ser
1               5                   10                  15

Gly Leu Gly Phe Thr Gly Trp Thr Glu Ser Ser Pro Pro Lys Pro Arg
            20                  25                  30

Trp Asp Arg Ala Lys Asn Val Asp Ile Leu Gly Val Glu Phe Ala Lys
        35                  40                  45

Ser Ser Val Gln Leu Pro Leu Val Trp Asn Ile Gln Val Ser Thr Trp
    50                  55                  60

Leu Arg His Tyr Val Tyr Glu Arg Leu Val Lys Pro Gly Lys Lys Ala
65                  70                  75                  80

Gly Phe Phe Gln Leu Leu Thr Thr Gln Thr Val Ser Ala Val Trp His
                85                  90                  95

Gly Leu Tyr Pro Gly Tyr Ile Ile Phe Phe Val Gln Ser Ala Leu Met
            100                 105                 110

Ile Ala Gly Ser Arg Val Ile Tyr Arg Trp Gln Gln Ala Val Pro Gln
        115                 120                 125

Asn Met Asp Ala Val Lys Asn Ile Leu Val Phe Ile Asn Phe Ala Tyr
    130                 135                 140

Thr Leu Leu Val Leu Asn Tyr Ser Cys Val Gly Phe Ile Val Leu Ser
145                 150                 155                 160

Leu Arg Glu Thr Leu Ala Ser Tyr Gly Ser Val His Phe Ile Gly Thr
                165                 170                 175

Ile Leu Pro Ile Ala Leu Ile Leu Ser Tyr Val Ile Lys Pro Pro
            180                 185                 190

Arg Pro Ala Arg Ser Lys Ala Arg Lys Glu Glu
        195                 200

<210> SEQ ID NO 66
<211> LENGTH: 135
<212> TYPE: PRT
<213> ORGANISM: Barley

<400> SEQUENCE: 66

Glu Ala Ala Ile Ile Ile Ser Gly Leu Gly Phe Thr Gly Trp Ser Asp
1               5                   10                  15

Ser Ser Pro Pro Lys Ala Lys Trp Asp Arg Ala Ile Asn Val Asp Ile
            20                  25                  30

Leu Gly Val Glu Leu Ala Gly Ser Ala Ala Gln Leu Pro Leu Lys Trp
        35                  40                  45

Asn Ile Gln Val Ser Thr Trp Leu Arg Tyr Tyr Val Tyr Glu Arg Leu
    50                  55                  60

Ile Gln Lys Gly Lys Lys Pro Gly Phe Leu Gln Leu Leu Gly Thr Gln
65                  70                  75                  80

Thr Val Ser Ala Ile Trp His Gly Leu Tyr Pro Gly Tyr Met Ile Phe
                85                  90                  95

Phe Val Gln Ser Ala Leu Met Ile Asn Gly Ser Lys Val Ile Tyr Arg
            100                 105                 110

Trp Gln Gln Ala Val Lys Gln Phe Arg Pro Pro His Tyr Pro Val Phe
        115                 120                 125

Thr Lys Leu Leu His Thr Pro
```

-continued 130            135

<210> SEQ ID NO 67
<211> LENGTH: 279
<212> TYPE: PRT
<213> ORGANISM: Wheat

<400> SEQUENCE: 67

His Phe Ala Gly Pro Val Tyr Glu Met Lys Asp Tyr Leu Glu Trp Thr
1               5                   10                  15

Glu Arg Lys Gly Ile Trp Ala Gly Ser Thr Pro Ser Pro Leu Leu Pro
            20                  25                  30

Thr Leu Arg Ala Leu Val Gln Ala Gly Ile Cys Met Gly Leu Tyr Leu
        35                  40                  45

Tyr Leu Ser Pro Met Phe Pro His Ser Tyr Arg Gly Ser Leu Asn Arg
    50                  55                  60

Glu Arg Gly Phe Trp His Arg Leu Phe Phe Gln Tyr Met Ser Gly Phe
65                  70                  75                  80

Thr Ala Arg Trp Lys Tyr Tyr Phe Ile Trp Ser Val Ser Glu Ala Ala
                85                  90                  95

Ile Ile Ile Ser Gly Leu Gly Phe Thr Gly Trp Ser Asp Ser Ser Pro
            100                 105                 110

Pro Lys Ala Lys Trp Asp Arg Ala Ile Asn Val Asp Ile Leu Gly Val
        115                 120                 125

Glu Leu Ala Gly Ser Ala Ala Gln Leu Pro Leu Lys Trp Asn Ile Gln
    130                 135                 140

Val Ser Thr Trp Leu Arg Tyr Tyr Val Tyr Glu Arg Leu Ile Gln Lys
145                 150                 155                 160

Gly Lys Lys Pro Gly Phe Leu Gln Leu Leu Gly Thr Gln Thr Val Ser
                165                 170                 175

Ala Ile Trp His Gly Leu Tyr Pro Gly Tyr Met Phe Phe Val Gln
            180                 185                 190

Ser Ala Leu Met Ile Asn Gly Ser Lys Val Ile Tyr Arg Trp Gln Gln
        195                 200                 205

Ala Val Ser Asn Pro Gly Leu Arg Thr Ile Leu Ser Leu Leu Asn Cys
    210                 215                 220

Ala Tyr Thr Met Met Val Leu Asn Tyr Ser Cys Ile Gly Phe Gln Val
225                 230                 235                 240

Leu Ser Phe Gln Glu Thr Leu Ala Ser Tyr Lys Ser Val Tyr Val
                245                 250                 255

Gly Thr Ile Val Pro Ile Leu Cys Val Leu Gly Tyr Val Val Lys
            260                 265                 270

Pro Thr Arg Pro Val Lys Pro
        275

<210> SEQ ID NO 68
<211> LENGTH: 287
<212> TYPE: PRT
<213> ORGANISM: Maize
<220> FEATURE:
<221> NAME/KEY: MISC_FEATURE
<222> LOCATION: (242)..(242)
<223> OTHER INFORMATION: X can be any amino acid

<400> SEQUENCE: 68

Ile Ser Cys Leu Ile Asn Tyr Ser Asp Gly Ile Leu Lys Glu Glu Gly
1               5                   10                  15

Leu Arg Asp Ala Gln Ile Lys His Arg Leu Thr Lys Leu Pro Ser Leu

-continued

```
                20                  25                  30
Ile Glu Tyr Phe Gly Tyr Cys Leu Cys Cys Gly Ser His Phe Ala Gly
        35                  40                  45

Pro Val Tyr Glu Met Lys Asp Tyr Leu Glu Trp Thr Glu Arg Lys Gly
    50                  55                  60

Ile Trp Ala Ser Pro Thr Pro Ser Pro Leu Leu Pro Thr Leu Arg Ala
 65                  70                  75                  80

Leu Val Gln Ala Gly Ile Cys Met Gly Leu Tyr Leu Tyr Leu Ser Pro
                85                  90                  95

Lys Phe Pro Leu Ser Arg Phe Ser Glu Pro Leu Tyr Tyr Glu Trp Gly
            100                 105                 110

Phe Trp His Arg Leu Phe Tyr Gln Tyr Met Ser Gly Phe Thr Ala Arg
        115                 120                 125

Trp Lys Tyr Tyr Phe Ile Trp Ser Ile Ser Glu Ala Ser Ile Ile Ile
    130                 135                 140

Ser Gly Leu Gly Phe Thr Gly Trp Ser Glu Ser Pro Pro Lys Ala
145                 150                 155                 160

Lys Trp Asp Arg Ala Lys Asn Val Asp Val Leu Gly Val Glu Leu Ala
                165                 170                 175

Gly Ser Ser Val Gln Leu Pro Leu Val Trp Asn Ile Gln Val Ser Thr
            180                 185                 190

Trp Leu Arg Tyr Tyr Val Tyr Glu Arg Leu Ile Gln Lys Gly Lys Lys
        195                 200                 205

Pro Gly Phe Leu Gln Leu Leu Gly Thr Gln Thr Val Ser Ala Ile Trp
    210                 215                 220

His Gly Leu Tyr Pro Gly Tyr Ile Ile Phe Phe Ser Ser Ala Leu
225                 230                 235                 240

Met Xaa Asn Gly Ser Arg Val Ile Tyr Arg Trp Gln Ala Ala Ser
                245                 250                 255

Ser Ser Phe Leu Ser Gly Ile Leu Ala Leu Leu Ile Leu Leu Tyr Ile
            260                 265                 270

Ala Gly Ala Tyr Tyr Ser Cys Ile Gly Val Gln Val Leu Ser Phe
        275                 280                 285

<210> SEQ ID NO 69
<211> LENGTH: 217
<212> TYPE: PRT
<213> ORGANISM: Sorghum

<400> SEQUENCE: 69

Thr Arg Leu Ser Arg Phe Ser Glu Pro Leu Tyr Tyr Glu Trp Gly Phe
 1               5                  10                  15

Trp His Arg Leu Phe Tyr Gln Tyr Met Ser Gly Phe Thr Ala Arg Trp
                20                  25                  30

Lys Tyr Tyr Phe Ile Trp Ser Ile Ser Glu Ala Ser Ile Ile Ile Ser
            35                  40                  45

Gly Leu Gly Phe Thr Gly Trp Ser Glu Ser Pro Pro Lys Ala Lys
        50                  55                  60

Trp Asp Arg Ala Lys Asn Val Asp Val Leu Gly Val Glu Leu Ala Gly
 65                  70                  75                  80

Ser Ala Val Gln Ile Pro Leu Val Trp Asn Ile Gln Val Ser Thr Trp
                85                  90                  95

Leu Arg Tyr Tyr Val Tyr Glu Arg Leu Ile Gln Lys Gly Lys Lys Pro
            100                 105                 110

Gly Phe Leu Gln Leu Leu Gly Thr Gln Thr Val Ser Ala Ile Trp His
```

```
                    115                 120                 125
Gly Leu Tyr Pro Gly Tyr Ile Ile Phe Phe Val Gln Ser Ala Leu Met
    130                 135                 140

Ile Asn Gly Ser Arg Val Ile Tyr Arg Trp Gln Gln Ala Val Ser Ser
145                 150                 155                 160

Ser Phe Leu Arg Gly Ile Leu Ala Phe Leu Asn Phe Ala Tyr Thr Leu
                165                 170                 175

Leu Val Leu Asn Tyr Ser Cys Ile Gly Phe Leu Val Leu Ser Phe Lys
            180                 185                 190

Glu Thr Leu Ala Ser Tyr Gln Ser Val Tyr Tyr Val Gly Thr Ile Val
        195                 200                 205

Pro Ile Val Phe Leu Leu Gly Asn
    210                 215

<210> SEQ ID NO 70
<211> LENGTH: 459
<212> TYPE: PRT
<213> ORGANISM: Oryza sativa

<400> SEQUENCE: 70

Met Gly Leu Glu Met Glu Gly Met Ala Ala Ile Gly Val Ser Val
1               5                   10                  15

Pro Val Leu Arg Phe Leu Leu Cys Phe Ala Ala Thr Ile Pro Thr Gly
                20                  25                  30

Leu Met Trp Arg Ala Val Pro Gly Ala Ala Gly Arg His Leu Tyr Ala
            35                  40                  45

Gly Leu Thr Gly Ala Ala Leu Ser Tyr Leu Ser Phe Gly Ala Thr Ser
    50                  55                  60

Asn Leu Leu Phe Val Val Pro Met Ala Phe Gly Tyr Leu Ala Met Leu
65                  70                  75                  80

Leu Cys Arg Arg Leu Ala Gly Leu Val Thr Phe Leu Gly Ala Phe Gly
                85                  90                  95

Phe Leu Ile Ala Cys His Met Tyr Tyr Met Ser Gly Asp Ala Trp Lys
            100                 105                 110

Glu Gly Gly Ile Asp Ala Thr Gly Ala Leu Met Val Leu Thr Leu Lys
        115                 120                 125

Ile Ile Ser Cys Ala Ile Asn Tyr Ser Asp Gly Met Leu Lys Glu Glu
    130                 135                 140

Gly Leu Arg Asp Ala Gln Lys Lys Tyr Arg Leu Ala Lys Leu Pro Ser
145                 150                 155                 160

Leu Ile Glu Tyr Phe Gly Tyr Cys Leu Cys Cys Gly Ser His Phe Ala
                165                 170                 175

Gly Pro Val Tyr Glu Met Lys Asp Tyr Leu Glu Tyr Thr Glu Arg Lys
            180                 185                 190

Gly Leu Trp Ala Ser Pro Thr Pro Ser Pro Leu Leu Pro Thr Leu Arg
        195                 200                 205

Ala Leu Val Gln Ala Gly Ala Cys Met Gly Leu Tyr Leu Tyr Leu Ser
    210                 215                 220

Pro Gln Phe Pro Leu Ser Arg Phe Ser Glu Pro Leu Tyr Tyr Glu Trp
225                 230                 235                 240

Gly Phe Trp His Arg Leu Phe Tyr Gln Tyr Met Ser Gly Phe Thr Ala
                245                 250                 255

Arg Trp Lys Tyr Tyr Phe Ile Trp Ser Leu Ser Glu Ala Ala Ile Ile
            260                 265                 270

Ile Ser Gly Leu Gly Phe Ser Gly Trp Ser Asp Ser Ser Pro Pro Lys
```

```
                    275                 280                 285
Ala Lys Trp Asp Arg Ala Lys Asn Val Asp Val Leu Gly Val Glu Leu
290                 295                 300

Ala Thr Ser Ala Val Gln Leu Pro Leu Met Trp Asn Ile Gln Val Ser
305                 310                 315                 320

Thr Trp Leu Arg Tyr Tyr Val Tyr Glu Arg Leu Val Gln Lys Gly Lys
                325                 330                 335

Lys Pro Gly Phe Leu Gln Leu Leu Gly Thr Gln Thr Val Ser Ala Val
            340                 345                 350

Trp His Gly Leu Tyr Pro Gly Tyr Ile Ile Phe Phe Val Gln Ser Ala
        355                 360                 365

Leu Met Ile Asn Gly Ser Lys Val Ile Tyr Arg Trp Gln Gln Ala Val
    370                 375                 380

Ser Asn Pro Val Phe His Ala Ile Leu Val Phe Val Asn Phe Ser Tyr
385                 390                 395                 400

Thr Leu Met Val Leu Asn Tyr Ser Cys Ile Gly Phe Gln Val Leu Ser
                405                 410                 415

Phe Lys Glu Thr Leu Ala Ser Tyr Gln Ser Val Tyr Tyr Ile Gly Thr
            420                 425                 430

Ile Val Pro Ile Val Val Leu Leu Gly Tyr Val Ile Lys Pro Ala
        435                 440                 445

Arg Pro Val Lys Pro Lys Ala Arg Lys Ala Glu
    450                 455

<210> SEQ ID NO 71
<211> LENGTH: 370
<212> TYPE: PRT
<213> ORGANISM: Rice

<400> SEQUENCE: 71

Met Tyr Tyr Met Ser Gly Asp Ala Trp Lys Glu Gly Gly Ile Asp Ala
1               5                   10                  15

Thr Gly Ala Leu Met Val Leu Thr Leu Lys Ile Ile Ser Cys Ala Ile
            20                  25                  30

Asn Tyr Ser Asp Gly Met Leu Lys Glu Glu Gly Leu Arg Asp Ala Gln
        35                  40                  45

Lys Lys Tyr Arg Leu Ala Lys Leu Pro Ser Leu Ile Glu Tyr Phe Gly
    50                  55                  60

Tyr Cys Leu Cys Cys Gly Ser His Phe Ala Gly Pro Val Tyr Glu Met
65                  70                  75                  80

Lys Asp Tyr Leu Glu Tyr Thr Glu Arg Lys Gly Leu Trp Ala Ser Pro
                85                  90                  95

Thr Pro Ser Pro Leu Leu Pro Thr Leu Arg Ala Leu Val Gln Ala Gly
            100                 105                 110

Ala Cys Met Gly Leu Tyr Leu Tyr Leu Ser Pro Gln Phe Pro Leu Ser
        115                 120                 125

Arg Phe Ser Glu Pro Leu Tyr Tyr Glu Trp Gly Phe Trp His Arg Leu
    130                 135                 140

Phe Tyr Gln Tyr Met Ser Gly Phe Thr Ala Arg Trp Lys Tyr Tyr Phe
145                 150                 155                 160

Ile Trp Ser Leu Ser Glu Ala Ile Ile Ser Gly Leu Gly Phe
                165                 170                 175

Ser Gly Trp Ser Asp Ser Ser Pro Pro Lys Ala Lys Trp Asp Arg Ala
            180                 185                 190

Lys Asn Val Asp Val Leu Gly Val Glu Leu Ala Thr Ser Ala Val Gln
```

```
                 195                 200                 205
Leu Pro Leu Met Trp Asn Ile Gln Val Ser Thr Trp Leu Arg Tyr Tyr
210                 215                 220

Val Tyr Glu Arg Leu Val Gln Lys Gly Lys Pro Gly Phe Leu Gln
225                 230                 235                 240

Leu Leu Gly Thr Gln Thr Val Ser Ala Val Trp His Gly Leu Tyr Pro
            245                 250                 255

Gly Tyr Ile Ile Phe Phe Val Gln Ser Ala Leu Met Ile Asn Gly Ser
                260                 265                 270

Lys Val Ile Tyr Arg Trp Gln Gln Ala Val Ser Asn Pro Val Phe His
            275                 280                 285

Ala Ile Leu Val Phe Val Asn Phe Ser Tyr Thr Leu Met Val Leu Asn
        290                 295                 300

Tyr Ser Cys Ile Gly Phe Gln Phe Val Phe Thr Met Leu Tyr Thr Leu
305                 310                 315                 320

Arg Phe Leu Gln Val Leu Ser Phe Lys Glu Thr Leu Ala Ser Tyr Gln
                325                 330                 335

Ser Val Tyr Tyr Ile Gly Thr Ile Val Pro Ile Val Val Leu Leu
            340                 345                 350

Gly Tyr Val Ile Lys Pro Ala Arg Pro Val Lys Pro Lys Ala Arg Lys
            355                 360                 365

Ala Glu
    370

<210> SEQ ID NO 72
<211> LENGTH: 312
<212> TYPE: PRT
<213> ORGANISM: Grapevine

<400> SEQUENCE: 72

Ser Ser Asn Leu His Phe Leu Val Pro Met Leu Leu Gly Tyr Ala Ala
1               5                   10                  15

Met Leu Leu Cys Arg Arg Cys Gly Val Ile Thr Phe Phe Leu Gly
            20                  25                  30

Phe Gly Tyr Leu Ile Gly Cys His Val Tyr Tyr Met Ser Gly Asp Ala
            35                  40                  45

Trp Lys Glu Gly Ile Asp Ala Thr Gly Ala Leu Met Val Leu Thr
    50                  55                  60

Leu Lys Val Ile Ser Cys Ala Met Asn Tyr Asn Asp Gly Leu Leu Lys
65                  70                  75                  80

Glu Asp Gly Leu Arg Glu Ala Gln Lys Lys Asn Arg Leu Leu Lys Leu
                85                  90                  95

Pro Ser Leu Ile Glu Tyr Phe Gly Tyr Cys Leu Cys Cys Gly Ser His
            100                 105                 110

Phe Ala Gly Pro Val Tyr Glu Ile Lys Asp Tyr Leu Glu Trp Thr Glu
        115                 120                 125

Arg Lys Gly Ile Trp Ala Lys Ser Glu Lys Gly Pro Pro Ser Pro
    130                 135                 140

Tyr Gly Ala Thr Ile Arg Ala Leu Ile Gln Ala Ala Phe Cys Met Gly
145                 150                 155                 160

Leu Tyr Val Tyr Leu Val Pro His Phe Pro Leu Thr Ile Phe Thr Asp
                165                 170                 175

Pro Val Tyr Gln Glu Trp Gly Phe Trp Lys Arg Leu Gly Tyr Gln Tyr
            180                 185                 190

Met Cys Gly Phe Thr Ala Arg Trp Lys Tyr Tyr Phe Ile Trp Ser Ile
```

```
              195                 200                 205
Ser Glu Ala Ala Val Ile Ile Ser Gly Leu Gly Phe Ser Gly Trp Thr
    210                 215                 220

Glu Ser Ser Pro Pro Lys Pro Lys Trp Asp Arg Ala Lys Asn Val Asp
225                 230                 235                 240

Ile Leu Gly Val Glu Leu Ala Lys Ser Ala Val Thr Leu Pro Leu Val
                245                 250                 255

Trp Asn Ile Gln Val Ser Thr Trp Leu Arg Tyr Tyr Val Tyr Glu Arg
            260                 265                 270

Leu Ile Gln Asn Gly Lys Lys Pro Gly Phe Phe Gln Leu Leu Ala Thr
        275                 280                 285

Gln Thr Val Ser Ala Val Trp His Gly Leu Tyr Pro Gly Tyr Ile Ile
    290                 295                 300

Phe Val Gln Ser Ala Leu Met
305                 310

<210> SEQ ID NO 73
<211> LENGTH: 195
<212> TYPE: PRT
<213> ORGANISM: Vaccinium corymbosum

<400> SEQUENCE: 73

Gly Leu Gly Tyr Gln Tyr Met Ala Gly Phe Thr Ala Arg Trp Lys Tyr
1               5                   10                  15

Tyr Phe Ile Trp Ser Ile Ser Glu Ala Ser Ile Ile Ser Gly Leu
            20                  25                  30

Gly Phe Ser Gly Trp Thr Asp Ser Ser Pro Lys Pro Lys Trp Asp
        35                  40                  45

Arg Ala Lys Asn Val Asp Ile Leu Arg Val Glu Phe Ala Lys Thr Ala
50                  55                  60

Ala Gln Ile Pro Leu Ala Trp Asn Ile Gln Val Ser Thr Trp Leu Arg
65                  70                  75                  80

His Tyr Val Tyr Glu Arg Leu Val Gln Lys Gly Lys Lys Pro Gly Phe
                85                  90                  95

Phe Gln Leu Leu Ala Thr Gln Thr Val Ser Ala Val Trp His Gly Leu
            100                 105                 110

Tyr Pro Gly Tyr Ile Ile Phe Phe Val Gln Ser Ala Leu Met Ile Ala
        115                 120                 125

Gly Ser Arg Val Ile Tyr Arg Trp Gln Gln Ala Val Pro Pro Lys Met
    130                 135                 140

Asp Leu Val Lys Lys Val Phe Val Leu Leu Asn Phe Ala Tyr Thr Val
145                 150                 155                 160

Leu Val Leu Asn Tyr Ser Ser Val Gly Phe Met Val Leu Ser Leu His
                165                 170                 175

Glu Thr Ile Val Ala Tyr Gly Ser Val Tyr Ser Leu Glu Pro Leu Phe
            180                 185                 190

Pro Tyr Leu
        195

<210> SEQ ID NO 74
<211> LENGTH: 462
<212> TYPE: PRT
<213> ORGANISM: Arabidopsis thaliana

<400> SEQUENCE: 74

Met Asp Met Ser Ser Met Ala Gly Ser Ile Gly Val Ser Val Ala Val
1               5                   10                  15
```

-continued

```
Leu Arg Phe Leu Leu Cys Phe Val Ala Thr Ile Pro Val Ser Phe Ala
            20                  25                  30
Cys Arg Ile Val Pro Ser Arg Leu Gly Lys His Leu Tyr Ala Ala Ala
        35                  40                  45
Ser Gly Ala Phe Leu Ser Tyr Leu Ser Phe Gly Phe Ser Asn Leu
    50                  55                  60
His Phe Leu Val Pro Met Thr Ile Gly Tyr Ala Ser Met Ala Ile Tyr
65                  70                  75                  80
Arg Pro Lys Cys Gly Ile Ile Thr Phe Phe Leu Gly Phe Ala Tyr Leu
                85                  90                  95
Ile Gly Cys His Val Phe Tyr Met Ser Gly Asp Ala Trp Lys Glu Gly
            100                 105                 110
Gly Ile Asp Ser Thr Gly Ala Leu Met Val Leu Thr Leu Lys Val Ile
            115                 120                 125
Ser Cys Ser Met Asn Tyr Asn Asp Gly Met Leu Lys Glu Glu Gly Leu
    130                 135                 140
Arg Glu Ala Gln Lys Lys Asn Arg Leu Ile Gln Met Pro Ser Leu Ile
145                 150                 155                 160
Glu Tyr Phe Gly Tyr Cys Leu Cys Cys Gly Ser His Phe Ala Gly Pro
                165                 170                 175
Val Tyr Glu Met Lys Asp Tyr Leu Glu Trp Thr Glu Gly Lys Gly Ile
            180                 185                 190
Trp Asp Thr Thr Glu Lys Arg Lys Pro Ser Pro Tyr Gly Ala Thr
        195                 200                 205
Ile Arg Ala Ile Leu Gln Ala Ala Ile Cys Met Ala Leu Tyr Leu Tyr
        210                 215                 220
Leu Val Pro Gln Tyr Pro Leu Thr Arg Phe Thr Glu Pro Val Tyr Gln
225                 230                 235                 240
Glu Trp Gly Phe Leu Arg Lys Phe Ser Tyr Gln Tyr Met Ala Gly Phe
                245                 250                 255
Thr Ala Arg Trp Lys Tyr Tyr Phe Ile Trp Ser Ile Ser Glu Ala Ser
            260                 265                 270
Ile Ile Ile Ser Gly Leu Gly Phe Ser Gly Trp Thr Asp Asp Ala Ser
        275                 280                 285
Pro Lys Pro Lys Trp Asp Arg Ala Lys Asn Val Asp Ile Leu Gly Val
        290                 295                 300
Glu Leu Ala Lys Ser Ala Val Gln Ile Pro Leu Val Trp Asn Ile Gln
305                 310                 315                 320
Val Ser Thr Trp Leu Arg His Tyr Val Tyr Glu Arg Leu Val Gln Asn
            325                 330                 335
Gly Lys Lys Ala Gly Phe Phe Gln Leu Leu Ala Thr Gln Thr Val Ser
        340                 345                 350
Ala Val Trp His Gly Leu Tyr Pro Gly Tyr Met Met Phe Phe Val Gln
        355                 360                 365
Ser Ala Leu Met Ile Ala Gly Ser Arg Val Ile Tyr Arg Trp Gln Gln
    370                 375                 380
Ala Ile Ser Pro Lys Met Ala Met Leu Arg Asn Ile Met Val Phe Ile
385                 390                 395                 400
Asn Phe Leu Tyr Thr Val Leu Val Leu Asn Tyr Ser Ala Val Gly Phe
                405                 410                 415
Met Val Leu Ser Leu His Glu Thr Leu Thr Ala Tyr Gly Ser Val Tyr
            420                 425                 430
Tyr Ile Gly Thr Ile Ile Pro Val Gly Leu Ile Leu Leu Ser Tyr Val
```

```
                435             440             445
Val Pro Ala Lys Pro Ser Arg Pro Lys Pro Arg Lys Glu Glu
    450                 455                 460

<210> SEQ ID NO 75
<211> LENGTH: 465
<212> TYPE: PRT
<213> ORGANISM: Arabidopsis thaliana

<400> SEQUENCE: 75

Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
                20                  25                  30

Ser Phe Leu Trp Arg Phe Ile Pro Ser Arg Leu Gly Lys His Ile Tyr
            35                  40                  45

Ser Ala Ala Ser Gly Ala Phe Leu Ser Tyr Leu Ser Phe Gly Phe Ser
        50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Ser Glu Lys Gly Lys Arg Pro Ser Pro Tyr
        195                 200                 205

Gly Ala Met Ile Arg Ala Val Phe Gln Ala Ala Ile Cys Met Ala Leu
210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                245                 250                 255

Ala Gly Phe Thr Ala Arg Trp Lys Tyr Tyr Phe Ile Trp Ser Ile Ser
            260                 265                 270

Glu Ala Ser Ile Ile Ile Ser Gly Leu Gly Phe Ser Gly Trp Thr Asp
        275                 280                 285

Glu Thr Gln Thr Lys Ala Lys Trp Asp Arg Ala Lys Asn Val Asp Ile
290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
                325                 330                 335

Val Lys Pro Gly Lys Lys Ala Gly Phe Phe Gln Leu Leu Ala Thr Gln
            340                 345                 350

Thr Val Ser Ala Val Trp His Gly Leu Tyr Pro Gly Tyr Ile Ile Phe
```

-continued

```
                355                 360                 365
Phe Val Gln Ser Ala Leu Met Ile Asp Gly Ser Lys Ala Ile Tyr Arg
370                 375                 380

Trp Gln Gln Ala Ile Pro Pro Lys Met Ala Met Leu Arg Asn Val Leu
385                 390                 395                 400

Val Leu Ile Asn Phe Leu Tyr Thr Val Val Leu Asn Tyr Ser Ser
                405                 410                 415

Val Gly Phe Met Val Leu Ser Leu His Glu Thr Leu Val Ala Phe Lys
            420                 425                 430

Ser Val Tyr Tyr Ile Gly Thr Val Ile Pro Ile Ala Val Leu Leu Leu
            435                 440                 445

Ser Tyr Leu Val Pro Val Lys Pro Val Arg Pro Lys Thr Arg Lys Glu
    450                 455                 460

Glu
465

<210> SEQ ID NO 76
<211> LENGTH: 213
<212> TYPE: PRT
<213> ORGANISM: Capsicum annuum

<400> SEQUENCE: 76

His Glu Lys Arg Leu Gly Tyr Gln Tyr Met Ala Gly Phe Thr Ala Arg
1               5                   10                  15

Trp Lys Tyr Tyr Phe Ile Trp Ser Ile Ser Glu Ala Ala Ile Ile Ile
            20                  25                  30

Ser Gly Leu Gly Phe Ser Gly Trp Thr Asp Ser Ser Pro Lys Pro
        35                  40                  45

Arg Trp Asp Arg Ala Lys Asn Val Asp Val Leu Gly Val Glu Leu Ala
50                  55                  60

Lys Ser Ser Val Gln Leu Pro Ala Val Trp Asn Ile Gln Val Ser Thr
65                  70                  75                  80

Trp Leu Arg His Tyr Val Tyr Glu Arg Leu Ile Gln Lys Gly Arg Lys
                85                  90                  95

Pro Gly Phe Phe Gln Leu Leu Ala Thr Gln Thr Val Ser Ala Val Trp
            100                 105                 110

His Gly Leu Tyr Pro Gly Tyr Ile Ile Phe Phe Val Gln Ser Ala Leu
        115                 120                 125

Met Ile Ala Gly Ser Arg Val Leu Tyr Arg Trp Gln Gln Ala Ala Lys
130                 135                 140

Gly Ser Met Phe Glu Lys Ile Leu Val Ala Met Asn Phe Ala Tyr Thr
145                 150                 155                 160

Leu Leu Val Leu Asn Tyr Ser Ala Val Gly Phe Met Val Leu Ser Leu
                165                 170                 175

His Glu Thr Leu Thr Ala Tyr Gly Ser Val Tyr Tyr Val Gly Thr Ile
            180                 185                 190

Ile Pro Ile Ala Leu Ile Leu Leu Ser Lys Val Ile Lys Pro Pro Arg
        195                 200                 205

Pro Cys Thr Ser Lys
    210

<210> SEQ ID NO 77
<211> LENGTH: 244
<212> TYPE: PRT
<213> ORGANISM: Tomato

<400> SEQUENCE: 77
```

```
Gly Met Gly Leu Tyr Leu Tyr Leu Val Pro Gln Phe Pro Leu Ser Arg
1               5                   10                  15

Phe Thr Glu Ser Val Tyr His Glu Trp Gly Phe Phe Lys Arg Leu Gly
            20                  25                  30

Tyr Gln Tyr Met Ala Gly Phe Thr Ala Arg Trp Lys Tyr Tyr Phe Ile
            35                  40                  45

Trp Ser Ile Ser Glu Ala Ser Ile Ile Ile Ser Gly Leu Gly Phe Ser
        50                  55                  60

Gly Trp Thr Asn Ser Ser Pro Pro Lys Pro Arg Trp Asp Arg Ala Lys
65                  70                  75                  80

Asn Val Asp Val Leu Gly Val Glu Leu Ala Lys Ser Ser Val Gln Leu
                85                  90                  95

Pro Leu Val Trp Asn Ile Gln Val Ser Thr Trp Leu Arg His Tyr Val
                100                 105                 110

Tyr Glu Arg Leu Val Gln Lys Gly Arg Lys Pro Gly Phe Phe Gln Leu
            115                 120                 125

Leu Ala Thr Gln Thr Val Ser Ala Val Trp His Gly Leu Tyr Pro Gly
130                 135                 140

Tyr Ile Ile Phe Phe Val Gln Ser Ala Leu Met Ile Ala Gly Ser Arg
145                 150                 155                 160

Val Ile Tyr Arg Trp Gln Gln Ala Thr Lys Gly Thr Met Phe Glu Lys
                165                 170                 175

Ile Leu Ile Ala Met Asn Phe Ala Tyr Thr Leu Leu Val Leu Asn Tyr
                180                 185                 190

Ser Ala Val Gly Phe Met Val Leu Ser Leu His Glu Thr Leu Thr Ala
            195                 200                 205

Tyr Gly Ser Val Tyr Tyr Ile Gly Thr Ile Val Pro Ile Leu Leu Ile
            210                 215                 220

Leu Leu Ser Lys Val Ile Lys Pro Pro Arg Pro Ala Thr Ser Lys Ala
225                 230                 235                 240

Arg Lys Ala Glu

<210> SEQ ID NO 78
<211> LENGTH: 235
<212> TYPE: PRT
<213> ORGANISM: Snapdragon

<400> SEQUENCE: 78

Ile Asn Tyr Asn Asp Gly Leu Leu Lys Lys Glu Asp Leu Arg Glu Pro
1               5                   10                  15

Gln Lys Lys Asn Arg Leu Leu Lys Met Pro Ser Leu Leu Glu Tyr Ile
            20                  25                  30

Gly Tyr Cys Leu Cys Cys Gly Ser His Phe Ala Gly Pro Val Tyr Glu
            35                  40                  45

Met Lys Asp Tyr Leu Glu Trp Thr Glu Arg Lys Gly Ile Trp Gln His
        50                  55                  60

Thr Thr Lys Gly Pro Lys Pro Ser Pro Tyr Trp Ala Thr Leu Arg Ala
65                  70                  75                  80

Ile Leu Gln Ala Ala Ile Cys Met Gly Leu Tyr Leu Tyr Leu Val Pro
                85                  90                  95

His Tyr Pro Leu Ser Arg Phe Thr Glu Pro Glu Tyr Gln Glu Tyr Gly
                100                 105                 110

Phe Trp Lys Arg Leu Ser Tyr Gln Tyr Met Ser Gly Phe Thr Ala Arg
            115                 120                 125
```

```
Trp Lys Tyr Tyr Phe Ile Trp Ser Ile Ser Glu Ala Ser Ile Ile Ile
            130                 135                 140
Ser Gly Leu Gly Phe Ser Gly Trp Thr Asp Ser Asp Pro Pro Lys Ala
145                 150                 155                 160
Leu Trp Asp Arg Ala Lys Asn Val Asp Val Leu Gly Val Glu Leu Ala
                165                 170                 175
Lys Ser Ser Val Gln Leu Pro Leu Val Trp Asn Ile Gln Val Ser Thr
            180                 185                 190
Trp Leu Lys His Tyr Val Tyr Glu Arg Leu Val Gln Lys Gly Lys Lys
        195                 200                 205
Pro Gly Phe Phe Gln Leu Ala Thr Gln Thr Val Ser Ala Val Trp
    210                 215                 220
His Gly Leu Tyr Pro Gly Tyr Ile Ile Phe Phe
225                 230                 235

<210> SEQ ID NO 79
<211> LENGTH: 252
<212> TYPE: PRT
<213> ORGANISM: Castor Bean

<400> SEQUENCE: 79

Ile His Leu Tyr Leu Val Pro His Tyr Pro Leu Ser Arg Phe Thr Asp
1               5                   10                  15
Pro Val Tyr Gln Glu Trp Gly Phe Trp Lys Arg Leu Thr Tyr Gln Tyr
            20                  25                  30
Met Ser Gly Leu Thr Ala Arg Trp Lys Tyr Tyr Phe Ile Trp Ser Ile
        35                  40                  45
Ser Glu Ala Ser Ile Ile Ile Ser Gly Leu Gly Phe Ser Gly Trp Thr
50                  55                  60
Asp Thr Ser Pro Pro Lys Pro Gln Trp Asp Arg Ala Arg Asn Val Asp
65                  70                  75                  80
Ile Leu Gly Val Glu Phe Ala Lys Ser Ala Ala Glu Leu Pro Leu Val
                85                  90                  95
Trp Asn Ile Gln Val Ser Thr Trp Leu Arg His Tyr Val Tyr Asp Arg
            100                 105                 110
Leu Val Pro Lys Gly Lys Lys Ala Gly Phe Leu Gln Leu Leu Ala Thr
        115                 120                 125
Gln Thr Thr Ser Ala Val Trp His Gly Leu Tyr Pro Gly Tyr Ile Ile
130                 135                 140
Phe Phe Val Gln Ser Ala Leu Met Ile Ala Gly Ser Lys Val Ile Tyr
145                 150                 155                 160
Arg Trp Gln Gln Ala Ile Pro Ser Asn Lys Ala Leu Glu Lys Lys Ile
                165                 170                 175
Leu Val Phe Met Asn Phe Ala Tyr Thr Val Leu Val Leu Asn Tyr Ser
            180                 185                 190
Cys Val Gly Phe Met Val Leu Ser Leu His Glu Thr Ile Ala Ala Tyr
        195                 200                 205
Gly Ser Val Tyr Phe Ile Gly Thr Ile Val Pro Val Phe Phe Leu
    210                 215                 220
Leu Gly Phe Ile Ile Lys Pro Ala Arg Pro Ser Arg Ser Lys His Gly
225                 230                 235                 240
Thr Met Ser Glu Val Glu Thr Val Phe Leu Leu Leu
                245                 250

<210> SEQ ID NO 80
<211> LENGTH: 288
```

```
<212> TYPE: PRT
<213> ORGANISM: Sunflower

<400> SEQUENCE: 80
```

| | | | | | | | | | | | | | | |
|---|---|---|---|---|---|---|---|---|---|---|---|---|---|---|
| Glu | Asn | Arg | Ile | Leu | Lys | Leu | Pro | Ser | Leu | Ile | Glu | Tyr | Val | Gly | Tyr |
| 1 | | | | 5 | | | | | 10 | | | | | 15 | |

| Cys | Leu | Cys | Cys | Gly | Ser | His | Phe | Ala | Gly | Pro | Val | Tyr | Glu | Ile | Lys |
|---|---|---|---|---|---|---|---|---|---|---|---|---|---|---|---|
| | | | 20 | | | | | 25 | | | | | 30 | | |

| Asp | Tyr | Leu | Asp | Trp | Thr | Glu | Arg | Lys | Gly | Ile | Trp | Thr | Lys | Ser | Glu |
|---|---|---|---|---|---|---|---|---|---|---|---|---|---|---|---|
| | | 35 | | | | | 40 | | | | | 45 | | | |

| Lys | Gly | Thr | Pro | Ser | Pro | Phe | Leu | Pro | Thr | Leu | Arg | Ala | Ile | Leu | Gln |
|---|---|---|---|---|---|---|---|---|---|---|---|---|---|---|---|
| 50 | | | | | 55 | | | | | 60 | | | | | |

| Ala | Gly | Phe | Cys | Met | Gly | Leu | Tyr | Leu | Tyr | Leu | Ser | Pro | Ser | Tyr | Pro |
|---|---|---|---|---|---|---|---|---|---|---|---|---|---|---|---|
| 65 | | | | | 70 | | | | | 75 | | | | | 80 |

| Leu | Ser | Arg | Phe | Ser | Glu | Pro | Ile | Tyr | Gln | Glu | Trp | Gly | Phe | Val | Lys |
|---|---|---|---|---|---|---|---|---|---|---|---|---|---|---|---|
| | | | | 85 | | | | | 90 | | | | | 95 | |

| Arg | Leu | Thr | Val | Gln | Tyr | Met | Ser | Gly | Phe | Thr | Ala | Arg | Trp | Lys | Tyr |
|---|---|---|---|---|---|---|---|---|---|---|---|---|---|---|---|
| | | | 100 | | | | | 105 | | | | | 110 | | |

| Tyr | Phe | Ile | Trp | Ser | Ile | Ser | Glu | Ala | Ser | Ile | Ile | Ile | Ser | Gly | Phe |
|---|---|---|---|---|---|---|---|---|---|---|---|---|---|---|---|
| | | 115 | | | | | 120 | | | | | 125 | | | |

| Gly | Phe | Ser | Gly | Trp | Thr | Asp | Ser | Ser | Pro | Pro | Lys | Ala | Arg | Trp | Asp |
|---|---|---|---|---|---|---|---|---|---|---|---|---|---|---|---|
| 130 | | | | | 135 | | | | | 140 | | | | | |

| Arg | Ala | Lys | Asn | Val | Asp | Val | Leu | Gly | Val | Glu | Phe | Ala | Lys | Ser | Ser |
|---|---|---|---|---|---|---|---|---|---|---|---|---|---|---|---|
| 145 | | | | | 150 | | | | | 155 | | | | | 160 |

| Val | Glu | Leu | Pro | Leu | Val | Trp | Asn | Ile | Gln | Val | Ser | Thr | Trp | Leu | Arg |
|---|---|---|---|---|---|---|---|---|---|---|---|---|---|---|---|
| | | | | 165 | | | | | 170 | | | | | 175 | |

| His | Tyr | Val | Tyr | Asp | Arg | Leu | Val | Gln | Lys | Gly | Lys | Lys | Pro | Gly | Phe |
|---|---|---|---|---|---|---|---|---|---|---|---|---|---|---|---|
| | | | 180 | | | | | 185 | | | | | 190 | | |

| Phe | Gln | Leu | Leu | Ala | Thr | Gln | Thr | Val | Ser | Ala | Val | Trp | His | Gly | Leu |
|---|---|---|---|---|---|---|---|---|---|---|---|---|---|---|---|
| | | 195 | | | | | 200 | | | | | 205 | | | |

| Tyr | Pro | Gly | Tyr | Leu | Ile | Phe | Phe | Val | Gln | Ser | Ala | Leu | Met | Ile | Ser |
|---|---|---|---|---|---|---|---|---|---|---|---|---|---|---|---|
| 210 | | | | | 215 | | | | | 220 | | | | | |

| Gly | Ser | Arg | Ala | Ile | Tyr | Arg | Trp | Gln | Gln | Ala | Val | Pro | Pro | Thr | Val |
|---|---|---|---|---|---|---|---|---|---|---|---|---|---|---|---|
| 225 | | | | | 230 | | | | | 235 | | | | | 240 |

| Lys | Lys | Phe | Leu | Met | Leu | Met | Asn | Phe | Ala | Tyr | Thr | Leu | Leu | Val | Leu |
|---|---|---|---|---|---|---|---|---|---|---|---|---|---|---|---|
| | | | | 245 | | | | | 250 | | | | | 255 | |

| Asn | Tyr | Ser | Cys | Ile | Gly | Phe | Met | Val | Leu | Ser | Leu | His | Glu | Thr | Leu |
|---|---|---|---|---|---|---|---|---|---|---|---|---|---|---|---|
| | | | 260 | | | | | 265 | | | | | 270 | | |

| Ala | Ala | Tyr | Gly | Ser | Val | Tyr | Tyr | Val | Gly | Asn | Ile | Ile | Pro | Val | Ala |
|---|---|---|---|---|---|---|---|---|---|---|---|---|---|---|---|
| | | 275 | | | | | 280 | | | | | 285 | | | |

```
<210> SEQ ID NO 81
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(4)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be Ile or Leu
<220> FEATURE:
<221> NAME/KEY: MISC_FEATURE
<222> LOCATION: (9)..(9)
<223> OTHER INFORMATION: X can be any amino acid
<220> FEATURE:
<221> NAME/KEY: MISC_FEATURE
```

```
<222> LOCATION: (12)..(12)
<223> OTHER INFORMATION: X can be Ser or Thr

<400> SEQUENCE: 81

Glu Ala Xaa Xaa Ile Xaa Ser Gly Xaa Gly Phe Xaa Gly Trp
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (5)..(5)
<223> OTHER INFORMATION: X can be any amino acid

<400> SEQUENCE: 82

Trp Asp Arg Ala Xaa Asn Val Asp
1               5

<210> SEQ ID NO 83
<211> LENGTH: 14
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (10)..(11)
<223> OTHER INFORMATION: X can be any amino acid

<400> SEQUENCE: 83

Trp Asn Ile Gln Val Ser Thr Trp Leu Xaa Xaa Tyr Val Tyr
1               5                   10

<210> SEQ ID NO 84
<211> LENGTH: 22
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be any amino acid
<220> FEATURE:
<221> NAME/KEY: MISC_FEATURE
<222> LOCATION: (11)..(11)
<223> OTHER INFORMATION: X can be any amino acid
<220> FEATURE:
<221> NAME/KEY: MISC_FEATURE
<222> LOCATION: (14)..(14)
<223> OTHER INFORMATION: X can be any amino acid

<400> SEQUENCE: 84

Gly Phe Xaa Gln Leu Leu Xaa Thr Gln Thr Xaa Ser Ala Xaa Trp His
1               5                   10                  15

Gly Leu Tyr Pro Gly Tyr
            20

<210> SEQ ID NO 85
<211> LENGTH: 487
<212> TYPE: PRT
<213> ORGANISM: Homo Sapiens
```

<400> SEQUENCE: 85

```
Met Ala Ser Ser Ala Glu Gly Asp Glu Gly Thr Val Val Ala Leu Ala
1               5                   10                  15

Gly Val Leu Gln Ser Gly Phe Gln Glu Leu Ser Leu Asn Lys Leu Ala
            20                  25                  30

Thr Ser Leu Gly Ala Ser Glu Gln Ala Leu Arg Leu Ile Ile Ser Ile
        35                  40                  45

Phe Leu Gly Tyr Pro Phe Ala Leu Phe Tyr Arg His Tyr Leu Phe Tyr
    50                  55                  60

Lys Glu Thr Tyr Leu Ile His Leu Phe His Thr Phe Thr Gly Leu Ser
65                  70                  75                  80

Ile Ala Tyr Phe Asn Phe Gly Asn Gln Leu Tyr His Ser Leu Leu Cys
                85                  90                  95

Ile Val Leu Gln Phe Leu Ile Leu Arg Leu Met Gly Arg Thr Ile Thr
            100                 105                 110

Ala Val Leu Thr Thr Phe Cys Phe Gln Met Ala Tyr Leu Leu Ala Gly
        115                 120                 125

Tyr Tyr Tyr Thr Ala Thr Gly Asn Tyr Asp Ile Lys Trp Thr Met Pro
    130                 135                 140

His Cys Val Leu Thr Leu Lys Leu Ile Gly Leu Ala Val Asp Tyr Phe
145                 150                 155                 160

Asp Gly Gly Lys Asp Gln Asn Ser Leu Ser Ser Glu Gln Lys Tyr
                165                 170                 175

Ala Ile Arg Gly Val Pro Ser Leu Leu Glu Val Ala Gly Phe Ser Tyr
            180                 185                 190

Phe Tyr Gly Ala Phe Leu Val Gly Pro Gln Phe Ser Met Asn His Tyr
    195                 200                 205

Met Lys Leu Val Gln Gly Glu Leu Ile Asp Ile Pro Gly Lys Ile Pro
210                 215                 220

Asn Ser Ile Ile Pro Ala Leu Lys Arg Leu Ser Leu Gly Leu Phe Tyr
225                 230                 235                 240

Leu Val Gly Tyr Thr Leu Leu Ser Pro His Ile Thr Glu Asp Tyr Leu
            245                 250                 255

Leu Thr Glu Asp Tyr Asp Asn His Pro Phe Trp Phe Arg Cys Met Tyr
        260                 265                 270

Met Leu Ile Trp Gly Lys Phe Val Leu Tyr Lys Tyr Val Thr Cys Trp
    275                 280                 285

Leu Val Thr Glu Gly Val Cys Ile Leu Thr Gly Leu Gly Phe Asn Gly
    290                 295                 300

Phe Glu Glu Lys Gly Lys Ala Lys Trp Asp Ala Cys Ala Asn Met Lys
305                 310                 315                 320

Val Trp Leu Phe Glu Thr Asn Pro Arg Phe Thr Gly Thr Ile Ala Ser
                325                 330                 335

Phe Asn Ile Asn Thr Asn Ala Trp Val Ala Arg Tyr Ile Phe Lys Arg
            340                 345                 350

Leu Lys Phe Leu Gly Asn Lys Glu Leu Ser Gln Gly Leu Ser Leu Leu
        355                 360                 365

Phe Leu Ala Leu Trp His Gly Leu His Ser Gly Tyr Leu Val Cys Phe
    370                 375                 380

Gln Met Glu Phe Leu Ile Val Ile Val Glu Arg Gln Ala Ala Arg Leu
385                 390                 395                 400

Ile Gln Glu Ser Pro Thr Leu Ser Lys Leu Ala Ala Ile Thr Val Leu
            405                 410                 415
```

```
Gln Pro Phe Tyr Tyr Leu Val Gln Gln Thr Ile His Trp Leu Phe Met
            420                 425                 430

Gly Tyr Ser Met Thr Ala Phe Cys Leu Phe Thr Trp Asp Lys Trp Leu
            435                 440                 445

Lys Val Tyr Lys Ser Ile Tyr Phe Leu Gly His Ile Phe Phe Leu Ser
            450                 455                 460

Leu Leu Phe Ile Leu Pro Tyr Ile His Lys Ala Met Val Pro Arg Lys
465                 470                 475                 480

Glu Lys Leu Lys Lys Met Glu
                485

<210> SEQ ID NO 86
<211> LENGTH: 495
<212> TYPE: PRT
<213> ORGANISM: Homo Sapiens

<400> SEQUENCE: 86

Met Ala Ala Glu Pro Gln Pro Ser Ser Leu Ser Tyr Arg Thr Thr Gly
1               5                   10                  15

Ser Thr Tyr Leu His Pro Leu Ser Glu Leu Leu Gly Ile Pro Leu Asp
            20                  25                  30

Gln Val Asn Phe Val Val Cys Gln Leu Val Ala Leu Phe Ala Ala Phe
            35                  40                  45

Trp Phe Arg Ile Tyr Leu Arg Pro Gly Thr Thr Ser Ser Asp Val Arg
    50                  55                  60

His Ala Val Ala Thr Ile Phe Gly Ile Tyr Phe Val Ile Phe Cys Phe
65                  70                  75                  80

Gly Trp Tyr Ser Val His Leu Phe Val Leu Val Leu Met Cys Tyr Ala
                85                  90                  95

Ile Met Val Thr Ala Ser Val Ser Asn Ile His Arg Tyr Ser Phe Phe
            100                 105                 110

Val Ala Met Gly Tyr Leu Thr Ile Cys His Ile Ser Arg Ile Tyr Ile
            115                 120                 125

Phe His Tyr Gly Ile Leu Thr Thr Asp Phe Ser Gly Pro Leu Met Ile
    130                 135                 140

Val Thr Gln Lys Ile Thr Thr Leu Ala Phe Gln Val His Asp Gly Leu
145                 150                 155                 160

Gly Arg Arg Ala Glu Asp Leu Ser Ala Glu Gln His Arg Leu Ala Ile
                165                 170                 175

Lys Val Lys Pro Ser Phe Leu Glu Tyr Leu Ser Tyr Leu Leu Asn Phe
            180                 185                 190

Met Ser Val Ile Ala Gly Pro Cys Asn Asn Phe Lys Asp Tyr Ile Ala
            195                 200                 205

Phe Ile Glu Gly Lys His Ile His Met Lys Leu Leu Glu Val Asn Trp
    210                 215                 220

Lys Arg Lys Gly Phe His Ser Leu Pro Glu Pro Ser Pro Thr Gly Ala
225                 230                 235                 240

Val Ile His Lys Leu Gly Ile Thr Leu Val Ser Leu Leu Phe Leu
                245                 250                 255

Thr Leu Thr Lys Thr Phe Pro Val Thr Cys Leu Val Asp Asp Trp Phe
            260                 265                 270

Val His Lys Ala Ser Phe Pro Ala Arg Leu Cys Tyr Leu Tyr Val Val
    275                 280                 285

Met Gln Ala Ser Lys Pro Lys Tyr Tyr Phe Ala Trp Thr Leu Ala Asp
    290                 295                 300
```

```
Ala Val Asn Asn Ala Ala Gly Phe Gly Phe Ser Gly Val Asp Lys Asn
305                 310                 315                 320

Gly Asn Phe Cys Trp Asp Leu Leu Ser Asn Leu Asn Ile Trp Lys Ile
                325                 330                 335

Glu Thr Ala Thr Ser Phe Lys Met Tyr Leu Glu Asn Trp Asn Ile Gln
            340                 345                 350

Thr Ala Thr Trp Leu Lys Cys Val Cys Tyr Gln Arg Val Pro Trp Tyr
        355                 360                 365

Pro Thr Val Leu Thr Phe Ile Leu Ser Ala Leu Trp His Gly Val Tyr
    370                 375                 380

Pro Gly Tyr Tyr Phe Thr Phe Leu Thr Gly Ile Leu Val Thr Leu Ala
385                 390                 395                 400

Ala Arg Ala Val Arg Asn Asn Tyr Arg His Tyr Phe Leu Ser Ser Arg
                405                 410                 415

Ala Leu Lys Ala Val Tyr Asp Ala Gly Thr Trp Ala Val Thr Gln Leu
            420                 425                 430

Ala Val Ser Tyr Thr Val Ala Pro Phe Val Met Leu Ala Val Glu Pro
        435                 440                 445

Thr Ile Ser Leu Tyr Lys Ser Met Tyr Phe Tyr Leu His Ile Ile Ser
    450                 455                 460

Leu Leu Ile Ile Leu Phe Leu Pro Met Lys Pro Gln Ala His Thr Gln
465                 470                 475                 480

Arg Arg Pro Gln Thr Leu Asn Ser Ile Asn Lys Arg Lys Thr Asp
                485                 490                 495

<210> SEQ ID NO 87
<211> LENGTH: 810
<212> TYPE: PRT
<213> ORGANISM: Homo Sapiens

<400> SEQUENCE: 87

Met Val Met Met Met Met Lys Val Leu Leu Leu Met Lys Gln
1               5                   10                  15

Arg Gly Ala Gly Leu Pro Ala Pro Ala Gly Val Glu Pro Arg Pro Ser
                20                  25                  30

Ser His His Pro Lys Ala Arg Val Arg Leu Gln Gly Asp Glu Ser Val
            35                  40                  45

Arg Pro Arg Gly Cys Ser Gln Leu Trp Ala Phe Thr Arg His Ser Pro
        50                  55                  60

Arg Gln Arg Gly Phe Ser Ala Arg Ser Leu Phe Trp Val Val Leu
65                  70                  75                  80

Pro Ala Pro Thr Phe Val Pro Asn Phe Pro Trp Arg Trp Leu Gly Gly
                85                  90                  95

Val Pro His Ile Val Pro Pro Ala Ala Thr Pro Gly Pro Phe Val Val
            100                 105                 110

Cys Arg Leu Ser Gln Arg Gly Val Gly Arg Asp Ile Pro Gly Arg
        115                 120                 125

Arg Asn Arg Gly Val Arg Gly Lys Asp Ala Leu Pro Cys Ser His Pro
130                 135                 140

Arg Ser Ala Pro His Asp Ala Gly Gln Pro Phe Ser Gly Asp Ala Arg
145                 150                 155                 160

His Pro Arg Ala Glu Arg Val Gly Arg Ala Leu Leu Pro Ala Thr
                165                 170                 175

Ala Pro Gly Glu Gly Arg Met Gly Val Arg Val Cys Met Arg Ser
            180                 185                 190
```

-continued

```
Leu Pro Phe Ala Ala Ala Ala Leu Gly Ser Gly Gly Arg Val Pro Glu
        195                 200                 205
Gln Pro Pro Val Arg Met Asp Arg Val Val Glu Arg Val Arg Lys Ala
        210                 215                 220
Ala Leu Trp Gly Ala Trp Arg Gly Ala Ala Cys Pro Ala Arg Ala Ser
225                 230                 235                 240
Glu Arg Pro Pro Glu Arg Leu Met His Gly Ser Gly Asp Gly Leu Leu
                245                 250                 255
Gly Phe Ser Phe Val Arg Ala Ser Leu Thr Val Phe Gly Glu Glu Ala
                260                 265                 270
Gly Pro Ser Phe Leu Leu Ala Val Leu Cys Ala Val Val Trp Gly Gly
            275                 280                 285
Arg Gly Glu Asp Val Val Ser Asp Val Gln Ala Cys Pro Ala Glu Gln
        290                 295                 300
Gly Phe Leu Leu Ala Glu Pro Ser Val Phe Gly Val Asn Phe Val Val
305                 310                 315                 320
Cys Gln Leu Phe Ala Leu Leu Ala Ala Ile Trp Phe Arg Thr Tyr Leu
                325                 330                 335
His Ser Ser Lys Thr Ser Ser Phe Ile Arg His Val Val Ala Thr Leu
                340                 345                 350
Leu Gly Leu Tyr Leu Ala Leu Phe Cys Phe Gly Trp Tyr Ala Leu His
            355                 360                 365
Phe Leu Val Gln Ser Gly Ile Ser Tyr Cys Ile Met Ile Ile Ile Gly
370                 375                 380
Val Glu Asn Met His Asn Tyr Cys Phe Val Phe Ala Leu Gly Tyr Leu
385                 390                 395                 400
Thr Val Cys Gln Val Thr Arg Val Tyr Ile Phe Asp Tyr Gly Gln Tyr
                405                 410                 415
Ser Ala Asp Phe Ser Gly Pro Met Met Ile Ile Thr Gln Lys Ile Thr
                420                 425                 430
Ser Leu Ala Cys Glu Ile His Asp Gly Met Phe Arg Lys Asp Glu Glu
            435                 440                 445
Leu Thr Ser Ser Gln Arg Asp Leu Ala Val Arg Arg Met Pro Ser Leu
        450                 455                 460
Leu Glu Tyr Leu Ser Tyr Asn Cys Asn Phe Met Gly Ile Leu Ala Gly
465                 470                 475                 480
Pro Leu Cys Ser Tyr Lys Asp Tyr Ile Thr Phe Ile Glu Gly Arg Ser
                485                 490                 495
Tyr His Ile Thr Gln Ser Gly Glu Asn Gly Lys Glu Thr Gln Tyr
                500                 505                 510
Glu Arg Thr Glu Pro Ser Pro Asn Thr Ala Val Val Gln Lys Leu Leu
            515                 520                 525
Val Cys Gly Leu Ser Leu Leu Phe His Leu Thr Ile Cys Thr Thr Leu
530                 535                 540
Pro Val Glu Tyr Asn Ile Asp Glu His Phe Gln Ala Thr Ala Ser Trp
545                 550                 555                 560
Pro Thr Lys Ile Ile Tyr Leu Tyr Ile Ser Leu Leu Ala Ala Arg Pro
                565                 570                 575
Lys Tyr Tyr Phe Ala Trp Thr Leu Ala Asp Ala Ile Asn Asn Ala Ala
                580                 585                 590
Gly Phe Gly Phe Arg Gly Tyr Asp Glu Asn Gly Ala Ala Arg Trp Asp
            595                 600                 605
Leu Ile Ser Asn Leu Arg Ile Gln Gln Ile Glu Met Ser Thr Ser Phe
610                 615                 620
```

```
Lys Met Phe Leu Asp Asn Trp Asn Ile Gln Thr Ala Leu Trp Leu Lys
625                 630                 635                 640

Arg Val Cys Tyr Glu Arg Thr Ser Phe Ser Pro Thr Ile Gln Thr Phe
                645                 650                 655

Ile Leu Ser Ala Ile Trp His Gly Val Tyr Pro Gly Tyr Tyr Leu Thr
                660                 665                 670

Phe Leu Thr Gly Val Leu Met Thr Leu Ala Ala Arg Ala Met Arg Asn
                675                 680                 685

Asn Phe Arg His Tyr Phe Ile Glu Pro Ser Gln Leu Lys Leu Phe Tyr
            690                 695                 700

Asp Val Ile Thr Trp Ile Val Thr Gln Val Ala Ile Ser Tyr Thr Val
705                 710                 715                 720

Val Pro Phe Val Leu Leu Ser Ile Lys Pro Ser Leu Thr Phe Tyr Ser
                725                 730                 735

Ser Trp Tyr Tyr Cys Leu His Ile Leu Gly Ile Leu Val Leu Leu Leu
                740                 745                 750

Leu Pro Val Lys Lys Thr Gln Arg Arg Lys Asn Thr His Glu Asn Ile
                755                 760                 765

Gln Leu Ser Gln Ser Lys Lys Phe Asp Glu Gly Glu Asn Ser Leu Gly
            770                 775                 780

Gln Asn Ser Phe Ser Thr Thr Asn Asn Val Cys Asn Gln Asn Gln Glu
785                 790                 795                 800

Ile Ala Ser Arg His Ser Ser Leu Lys Gln
                805                 810

<210> SEQ ID NO 88
<211> LENGTH: 463
<212> TYPE: PRT
<213> ORGANISM: Homo Sapiens

<400> SEQUENCE: 88

Met Val Asn Phe Val Val Cys Gln Leu Val Ala Leu Phe Ala Ala Phe
1               5                   10                  15

Trp Phe Arg Ile Tyr Leu Arg Pro Gly Thr Thr Ser Ser Asp Val Arg
                20                  25                  30

His Ala Val Ala Thr Ile Phe Gly Ile Tyr Phe Val Ile Phe Cys Phe
            35                  40                  45

Gly Trp Tyr Ser Val His Leu Phe Val Leu Val Leu Met Cys Tyr Ala
    50                  55                  60

Ile Met Val Thr Ala Ser Val Ser Asn Ile His Arg Tyr Ser Phe Phe
65                  70                  75                  80

Val Ala Met Gly Tyr Leu Thr Ile Cys His Ile Ser Arg Ile Tyr Ile
                85                  90                  95

Phe His Tyr Gly Ile Leu Thr Thr Asp Phe Ser Gly Pro Leu Met Ile
            100                 105                 110

Val Thr Gln Lys Ile Thr Thr Leu Ala Phe Gln Val His Asp Gly Leu
        115                 120                 125

Gly Arg Arg Ala Glu Asp Leu Ser Ala Glu Gln His Arg Leu Ala Ile
    130                 135                 140

Lys Val Lys Pro Ser Phe Leu Glu Tyr Leu Ser Tyr Leu Leu Asn Phe
145                 150                 155                 160

Met Ser Val Ile Ala Gly Pro Cys Asn Asn Phe Lys Asp Tyr Ile Ala
                165                 170                 175

Phe Ile Glu Gly Lys His Ile His Met Lys Leu Leu Glu Val Asn Trp
            180                 185                 190
```

```
Lys Arg Lys Gly Phe His Ser Leu Pro Glu Pro Ser Pro Thr Gly Ala
        195                 200                 205

Val Ile His Lys Leu Gly Ile Thr Leu Val Ser Leu Leu Leu Phe Leu
    210                 215                 220

Thr Leu Thr Lys Thr Phe Pro Val Thr Cys Leu Val Asp Asp Trp Phe
225                 230                 235                 240

Val His Lys Ala Ser Phe Pro Ala Arg Leu Cys Tyr Leu Tyr Val Val
                245                 250                 255

Met Gln Ala Ser Lys Pro Lys Tyr Tyr Phe Ala Trp Thr Leu Ala Asp
                260                 265                 270

Ala Val Asn Asn Ala Ala Gly Phe Gly Phe Ser Gly Val Asp Lys Asn
            275                 280                 285

Gly Asn Phe Cys Trp Asp Leu Leu Ser Asn Leu Asn Ile Trp Lys Ile
        290                 295                 300

Glu Thr Ala Thr Ser Phe Lys Met Tyr Leu Glu Asn Trp Asn Ile Gln
305                 310                 315                 320

Thr Ala Thr Trp Leu Lys Cys Val Cys Tyr Gln Arg Val Pro Trp Tyr
                325                 330                 335

Pro Thr Val Leu Thr Phe Ile Leu Ser Ala Leu Trp His Gly Val Tyr
                340                 345                 350

Pro Gly Tyr Tyr Phe Thr Phe Leu Thr Gly Ile Leu Val Thr Leu Ala
            355                 360                 365

Ala Arg Ala Val Arg Asn Asn Tyr Arg His Tyr Phe Leu Ser Ser Arg
        370                 375                 380

Ala Leu Lys Ala Val Tyr Asp Ala Gly Thr Trp Ala Val Thr Gln Leu
385                 390                 395                 400

Ala Val Ser Tyr Thr Val Ala Pro Phe Val Met Leu Ala Val Glu Pro
                405                 410                 415

Thr Ile Ser Leu Tyr Lys Ser Met Tyr Phe Tyr Leu His Ile Ile Ser
                420                 425                 430

Leu Leu Ile Ile Leu Phe Leu Pro Met Lys Pro Gln Ala His Thr Gln
            435                 440                 445

Arg Arg Pro Gln Thr Leu Asn Ser Ile Asn Lys Arg Lys Thr Asp
        450                 455                 460

<210> SEQ ID NO 89
<211> LENGTH: 24
<212> TYPE: DNA
<213> ORGANISM: Thalassiosira pseudonana

<400> SEQUENCE: 89
ggtatgctca tctgctaccc cctc                                              24

<210> SEQ ID NO 90
<211> LENGTH: 26
<212> TYPE: DNA
<213> ORGANISM: Thalassiosira pseudonana

<400> SEQUENCE: 90
ttaagtctcc ttcgtctttg gtgtag                                            26
```

What is claimed is:

1. A method for increasing fatty acid production in a cell, the method comprising:
   transfecting a cell with a nucleic acid molecule encoding a lyso-phosphatidylcholine acyltransferase comprising a peptide having at least 60% sequence homology with SEQ ID NO: 6; and
   growing the cell under conditions wherein the lyso-phosphatidylcholine acyltransferase is expressed; and
   selecting a transfected cell having increased fatty acid production compared to a non-transfected cell.

2. The method according to claim 1, further comprising isolating the fatty acid.

3. The method according to claim 1, wherein the peptide has at least 70% homology to SEQ ID NO:6.

4. The method according to claim 1, wherein the peptide comprises SEQ ID NO:6.

5. A seed produced by a plant that has been genetically manipulated to have modified lyso-phosphatidylcholine acyltransferase activity by including into the plant a nucleic acid molecule encoding a lyso-phosphatidylcholine acyltransferase comprising a peptide having at least 60% sequence homology with SEQ ID NO: 6.

6. A process for obtaining oil comprising enhanced levels of fatty acids, the process comprising:
   extracting oil from the seed of claim 5.

7. The seed of claim 5, wherein the peptide has at least 70% homology to SEQ ID NO:6.

8. The seed of claim 5, wherein the peptide comprises SEQ ID NO:6.

* * * * *